United States Patent
Bertram et al.

(10) Patent No.: US 10,077,442 B2
(45) Date of Patent: Sep. 18, 2018

(54) BIOACTIVE RENAL CELLS

(75) Inventors: Timothy A. Bertram, George Town (KY); Roger M. Ilagan, Burlington, NC (US); Russell W. Kelley, Winston-Salem, NC (US); Sharon C. Presnell, Lewisville, NC (US); Sumana Choudhury, Kernersville, NC (US); Andrew T. Bruce, Lexington, NC (US); Christopher W. Genheimer, Colfax, NC (US); Bryan R. Cox, Winston-Salem, NC (US); Kelly I. Guthrie, Winston-Salem, NC (US); Joydeep Basu, Winston-Salem, NC (US); Shay M. Wallace, Winston-Salem, NC (US); Eric Werdin, Lewisville, TX (US); Oluwatoyin A. Knight, Winston-Salem, NC (US); Namrata D. Sangha, Winston-Salem, NC (US); John W. Ludlow, Carrboro, NC (US); Craig R. Halberstadt, Clemmons, NC (US); Richard Payne, Winston-Salem, NC (US); Neil F. Robins, Winston-Salem, NC (US); Darell McCoy, Clemmons, NC (US); Deepak Jain, Winston-Salem, NC (US); Manuel J. Jayo, Winston-Salem, NC (US); Elias A. Rivera, Oak Ridge, NC (US); Thomas Spencer, Winston-Salem, NC (US); Benjamin Watts, King, NC (US)

(73) Assignee: inRegen, Camana Bay, Grand Cayman (KY)

( * ) Notice: Subject to any disclaimer, the term of this patent is extended or adjusted under 35 U.S.C. 154(b) by 152 days.

(21) Appl. No.: 13/697,206

(22) PCT Filed: May 12, 2011

(86) PCT No.: PCT/US2011/036347
§ 371 (c)(1),
(2), (4) Date: Jun. 17, 2013

(87) PCT Pub. No.: WO2011/143499
PCT Pub. Date: Nov. 17, 2011

(65) Prior Publication Data
US 2016/0244751 A1    Aug. 25, 2016

Related U.S. Application Data

(60) Provisional application No. 61/473,111, filed on Apr. 7, 2011, provisional application No. 61/441,423, filed on Feb. 10, 2011, provisional application No. 61/412,933, filed on Nov. 12, 2010, provisional application No. 61/413,382, filed on Nov. 12, 2010, provisional application No. 61/388,765, filed on Oct. 1, 2010, provisional application No. 61/376,586, filed on Aug. 24, 2010, provisional application No. 61/372,077, filed on Aug. 9, 2010, provisional application No. 61/371,888, filed on Aug. 9, 2010, provisional application No. 61/353,895, filed on Jun. 11, 2010, provisional application No. 61/334,032, filed on May 12, 2010.

(51) Int. Cl.
C07H 21/02 (2006.01)
C07H 21/04 (2006.01)
A61K 48/00 (2006.01)
C12N 15/113 (2010.01)
C12N 5/071 (2010.01)
C12Q 1/6883 (2018.01)

(52) U.S. Cl.
CPC .......... *C12N 15/113* (2013.01); *C12N 5/0686* (2013.01); *C12Q 1/6883* (2013.01); *C12N 2310/141* (2013.01); *C12N 2320/30* (2013.01); *C12N 2320/32* (2013.01); *C12Q 2600/106* (2013.01); *C12Q 2600/178* (2013.01)

(58) Field of Classification Search
CPC ..... A61K 48/00; A61K 31/713; C12N 15/111
See application file for complete search history.

(56) References Cited

U.S. PATENT DOCUMENTS

| | | | |
|---|---|---|---|
| 6,224,893 B1 | 5/2001 | Langer et al. |
| 6,283,761 B1 | 9/2001 | Joao |
| 6,794,154 B1 | 9/2004 | Yamanouchi et al. |
| 8,318,484 B2 | 11/2012 | Presnell et al. |
| 2007/0128174 A1 | 6/2007 | Lkeinsek et al. |
| 2007/0184033 A1 | 8/2007 | Sevrain et al. |
| 2007/0276507 A1 | 11/2007 | Bertram et al. |
| 2008/0112939 A1 | 5/2008 | Colter et al. |
| 2008/0305146 A1 | 12/2008 | Atala et al. |

(Continued)

FOREIGN PATENT DOCUMENTS

| | | |
|---|---|---|
| CN | 1044496 | 8/1990 |
| JP | 2004309186 | 11/2004 |

(Continued)

OTHER PUBLICATIONS

Aboushwareb et al. "Erythropoietin producing cells for potential cell therapy", World J. Urol. 26(4):295-300, 2008.
Amann et al. "Cardiac remodelling in experimental renal failure—an immunohistochemical study", Nephrol Dial Transplant 13(8):1958-1966, 1998.
Birn et al. "Renal albumin absorption in physiology and pathology", Kidney Intl. 69(3):440-449, 2006.
Brenner, BM. "Nephron adaptation to renal injury or ablation", Am J Physiol. 249:F324-F337, 1985.
Bugelski et al. "Pharmacodynamics of recombinant human erythropoietin in murine bone marrow", Pharm Res. 25(2):369-378, 2008.
Campeau et al. "Mesenchymal stromal cells engineered to express erythropoietin induce anti-erythropoietin antibodies and anemia in allorecipients", Mol Ther. 17(2):369-372, 2009.

(Continued)

*Primary Examiner* — Amy Hudson Bowman
(74) *Attorney, Agent, or Firm* — Mintz Levin Cohn Ferris Glovsky and Popeo, P.C.

(57) ABSTRACT

The present invention concerns bioactive renal cell populations, renal cell constructs, and methods of making and using the same.

17 Claims, 49 Drawing Sheets

Specification includes a Sequence Listing.

(56) References Cited

U.S. PATENT DOCUMENTS

| | | |
|---|---|---|
| 2009/0186004 A1 | 7/2009 | Fukui et al. |
| 2010/0104544 A1 | 4/2010 | Atala et al. |
| 2010/0112062 A1 | 5/2010 | Atala et al. |
| 2011/0033523 A1 | 2/2011 | Cantaluppi et al. |
| 2011/0144038 A1 | 6/2011 | Camussi et al. |
| 2011/0256111 A1 | 10/2011 | Camussi et al. |
| 2012/0135433 A1 | 5/2012 | Sugaya et al. |
| 2012/0251489 A1 | 10/2012 | Sanchez et al. |
| 2012/0321723 A1 | 12/2012 | Bruno et al. |
| 2014/0134264 A1 | 5/2014 | Cantaluppi et al. |
| 2016/0312189 A1 | 10/2016 | Tetta et al. |
| 2017/0348356 A1 | 12/2017 | Bruno et al. |

FOREIGN PATENT DOCUMENTS

| | | |
|---|---|---|
| KR | 2001-0026239 | 4/2001 |
| WO | 1990/002796 | 3/1990 |
| WO | 1990/012604 | 11/1990 |
| WO | 1993/07913 | 4/1993 |
| WO | 1995/11048 | 4/1995 |
| WO | 1996/40175 | 12/1996 |
| WO | 2002/061053 | 8/2002 |
| WO | 2003/043674 | 5/2003 |
| WO | 2007/035843 | 3/2007 |
| WO | 2008/045498 | 4/2008 |
| WO | 2008/061213 | 5/2008 |
| WO | 2008/066498 | 6/2008 |
| WO | 2008/153970 | 12/2008 |
| WO | WO 2008/153970 A1 | 12/2008 |
| WO | WO 2009/057165 A8 | 5/2009 |
| WO | WO 2009/071486 A1 | 6/2009 |
| WO | PCT/US00/33891 | 2/2010 |
| WO | PCT/US09/64421 | 2/2010 |
| WO | 2010/057013 | 5/2010 |
| WO | 2010/057015 | 5/2010 |
| WO | WO 2010/052192 A1 | 5/2010 |
| WO | WO 2010/056328 | 5/2010 |
| WO | WO 2011/070001 A1 | 6/2011 |
| WO | WO 2011/107437 A1 | 9/2011 |
| WO | 2011/143499 | 11/2011 |
| WO | 2012/064369 | 5/2012 |
| WO | WO 2015/091493 A1 | 6/2015 |
| WO | WO 2017/178472 A1 | 10/2017 |
| WO | WO 2017/191234 A1 | 11/2017 |

OTHER PUBLICATIONS

Castrop, H. "Mediators of tubuloglomerular feedback regulation of glomerular filtration: ATP and adenosine", Acta Physiol (Oxf) 189(1):3-14, 2007.

Chade et al. "Endothelial progenitor cells restore renal function in chronic experimental renovascular disease", Circulation 119(4):547-557, 2009.

Chen et al. "Regulation of angiogenesis through a micro RNA (miR-130a) that down-regulates antiangiogenic homeobox genes GAX and HOXA5", Blood 111(3):1217-1226, 2008.

Chironi et al. "Endothelial microparticles in diseases", Cell and Tissue Research 335(1):143-151, 2008.

Choi et al. "The role of mesenchymal stem cells in the functional improvement of chronic renal failure", Stem Cells Dev. 18(3):521-529, 2009.

de Zeeuw et al. "Proteinuria, a target for renoprotection in patients with Type 2 diabetic nephropathy: lessons from RENAAL", Kidney International 65(6):2309-2320, 2004.

Ding et al. "The bioartificial kidney and bioengineered membranes in acute kidney injury", Nephron Exp Nephrol. 109(4):e118-e122, 2008.

Duarte et a. "Cardiovascular effects of captopril and enalapril in obese Zucker rats", Eur J Pharmacol. 365:225-232, 1999.

Dudas et al. "BMP-7 fails to attenuate TGF-betal-induced epithelial to mesenchymal transition in human proxinal tubule epithelial cells", Nephrol Dial Transplant 24(5):1406-1416, 2009.

Eckardt et al. "Distribution of erythropoietin producing cells in rat kidneys during hypoxic hypoxia", Kidney Int. 43(4):815-823,1993.

Eliopoulos et al. "Erythropoietin delivery by genetically engineered bone marrow stromal cells for correction of anemia in mice with chronic renal failure", J Am Soc Nephrol. 17(6):1576-1584, 2006.

Foley et al. "Clinical and echocardiographic disease in patients starting end-stage rena disease therapy", Kidney Int. 47(1):186-192,1995.

Ganzoni et al. "Red cell aging in vivo", J Clin Invest. 50:1373-1378, 1971.

Gnecchi et al. "Paracrine mechanisms in adult stem cell signaling and therapy", Circ Res. 103(11):1204-1219, 2008.

Gesek et al. "Improved separation method for rat proximal and distal renal tubules", Am J Physiol. 253:F358-F365,1987.

Greene et al. "Role of aldosterone in the remnant kidney model in the rat", J Clin Invest. 98(4): 1063-1068, 1996.

Griffin et al. "Dynamic blood pressure load and nephropathy in the ZSF1 (fa/fa cp) model of type 2 diabetes", Am J. Physiol Renal Physiol. 293(5):F1605-F1613, 2007.

Hammerman, M.R. "Growing kidneys", Curr. Opin. Nephrol. Hypertens. 10(1):13-17, 2001.

Hills et al. "C-peptide reverses TGF-betal-induced changes in renal proximal tubular cells: implifications for treatment of diabetic nephropathy", Am J Physiol Renal Physiol 296(3):F614-F621; 2009.

Hopkins et al. "Stem cell options for kidney diseases", J Pathology 217(2):265-281, 2009.

Hoy et al. "Nephron number, hypertension, renal disease, and renal failure", J Am Soc Nephrol. 16(9):2557-2564, 2005.

Humes et al. "Replacement of renal function in uremic animals with a tissue-engineered kidney", Nature Biotechnology 17(5):451-455, 1999.

Humes et al. "Initial clinical results of the bioartificial kidney containing human cells in ICU patients with acute renal failure", Kidney International 66(4):1578-1588, 2004.

Humphreys et al. "Mesenchymal stem cells in acute kidney injury", Annu. Rev. Med 59:311-325, 2008.

Jackson et al. "A(1) receptor blockade induces natriuresis with a favorable renal hemodynamic profile in SHHF/Mcc-fa(cp) rats chronically treated with salt and furosemide", J Pharmacology and Experimental Therapeutics 299(3):978-987, 2001.

Jarad et al. "Update on the glomerular filtration barrier", Curr Opin Nephrol Hypertens 18(3): 226-232, 2009.

Joraku et al. "In vitro generation of three-dimensional renal structures", Methods 47(2):129-133, 2009.

Joshi et al. "TRC4186, a novel AGE-breaker, improves diabetic cardiomyopathy and nephropathy in Ob-ZSF1 model of type 2 diabetes", J Cardiovasc Pharmacol. 54(1):72-81, 2009.

Jovanovic et al. "Transfer of tolerance to heart and kidney allografts in the rat model", EP Society for Organ Transplantation 21:199-206, 2008.

Kasiske et al. "Pharmacologic treatment of hyperlipidemia reduces glomerular injury in rat 5/6 nephrectomy model of chronic renal failure", Circ Res. 62(2):367-374, 1988.

Kato et al. "MicroRNA-192 in diabetic kidney glomeruli and its function in TGF-beta-induced collagen expression via inhibition of E-box repressors", Proc. Natl. Sci USA 104(9):3432-3437, 2007.

Kaufman et al. "Compensatory adaptation of structure and function following progressive renal ablation", Kidney Int. 6(1):10-17, 1974.

Keller et al. "Nephron number in patients with primary hypertension", New England Journal of Medicine 348(2):101-108, 2003.

Kelley et al. "Tubular cell-enriched subpopulation of primary renal cells improves survival and augments kidney function in rodent model of chronic kidney disease", American J. Physiol. Renal Physiol. 299(5):F1026-F1039, 2010.

Khan et al. "Regulation of the renal thiazide-sensitive Na—CI cotransporter, blood pressure, and natriuresis in obese Zucker rats treated with rosiglitazone", Am J Physiol Renal Physiol. 289:F442-F450, 2005.

Kim et al. "Kidney tissue reconstruction by fetal kidney cell transplantation: effect of gestation stage o fetal kidney cells", Stem Cells 25(6):1393-1401, 2007.

(56) References Cited

OTHER PUBLICATIONS

Kim et al. "Improvement of kidney failure with fetal kidney precursor cell transplantation", Transplantation 83(9):1249-1258, 2007.
Koshiba et al. "Clinical, immunological and pathological aspects of operational tolerance after pediatric living-donor liver transplantation", Transpl Immunol. 17(2):94-97, 2007.
Kucic et al. "Mesenchymal stromal cells genetically engineered to overexpress IGF-I enhance cell-based gene therapy of renal failure-induced anemia", Am J Physiol Renal Physiol, 295(2): F488-F496, 2008.
Marshall et al. "Increasing renal mass improves survival in anephric rats following metanephros transplantation", Exp Physiol. 92(1):263-271, 2007.
Marquez et al. "MicroRNA-21 is upregulated during the proliferative phase of liver regeneration, targets Pelino-1, and inhibits NF-κB signaling", Am J Physiol Gastrointest Liver Physiol. 298:G535-G541, 2010.
Maxwell et al. "The interstitial response to renal injury: fibroblast-like cells show phenotypic changes and have reduced potential for erythropoietin gene expression", Kidney Int. 52(3):715-724, 1997.
Maxwell et al. "HIF-1: an oxygen response system with special relevance to the kidney", J Am Soc Nephrol 14(11):2712-2722, 2003.
McLaren et al. "Isolation and characterisation of human proximal tubular cells derived from kidney cortical segments", Hum Exp Toxicol 14(11):916-922, 1995.
Mizuno et al. "The effect of angiotensin II receptor blockade on an end-stage renal failure model of type 2 diabetes", Cardiovasc Pharmacol. 48(4):135-142, 2006.
Mujais et al. "Erythropoietin is produced by tubular cells of the rat kidney", Cell Biochem Biophys 30(1):153-166, 1999.
Nangaku et al. "Pathogenesis of renal anemia", Semin Nephrol 26(4):261-268, 2006.
Obara et al. "Repression via the GATA box is essential for tissue-specific erythropoietin gene expression", Blood 111(10):5223-5232, 2008.
Ormrod et al. "Experimental uremia description of a model producing varying degrees of stable uremia", Nephron 26(5):249-254, 1980.
Patschan et al. "Therapeutic use of stem and endothelial progenitor cells in acute renal injury: ca ira.", Curr Opin Pharmacol. 6(2):176-183, 2006.
Pirot et al. "Mediators and mechanisms of pancreatic beta-cell death in type 1 diabetes", Arq Bras Endocrinol Metabol 52(2):156-165, 2008.
Platt et al. "Experimental renal failure", Department of Medicine, University of Manchester 11(3):217-231, 1952.
Powe et al. "Public health surveillance of CKD: principles, steps, and challenges", Am J Kidney Dis 53:S37-S45, 2009.
Presnell et al. "Isolation, characterization and expansion methods for defined primary renal cell populations from rodent, canine, and human normal and diseased kidneys", Tissue Eng Part C Methods 17(3):261-273, 2011.
Prodromidi et al. "Bone marrow-derived cells contribute to podocyte regenration and amelioration of renal disease in a mouse model of alport syndrome", Stem Cells 24(11):2448-2455, 2006.
Qi et al. "Isolation, propaganation and characterization of primary tubule cell culture from human kidney", Nephrology 12(2):155-159, 2007.
Rafikova et al. "Renal and metabolic effects of tempol in obese ZSF1 rats—distinct role for superoxide and hydrogen peroxide in diabetic renal injury", Metabolism 57(10):1434-1444, 2008.
Rangan et al. "NF-kappaB signaling in chronic kidney disease", Front Bioscience 14:3496-3522, 2009.
Renaud et al. "Long-term protection of obese zucker rat kidneys from fibrosis and renal failure with an angiotensin-converting enzyme inhibitor/diuretic combination", Fundam Clin Pharmacol. 18(4):437-447, 2004.
Rogler et al. "MicroRNA-23b cluster microRNAs regulate transforming growth factor-beta/bone morphogenetic protein signaling and liver stem cell differentiation by targeting Smads", Hepatology 50(2):575-584, 2009.
Sanz et al. "NF-kappaB in renal inflammation", J Am Soc Nephrol 21:1254-1262, 2010.
Sequeira-Lopez et al. "The microRNA-processing enzyme dicer maintains juxtaglomerular cells", J American Society Nephrology 21(3):460-467, 2010.
Seo et al. "Positive feedback loop between plasminogen activator inhibitor-1 and transforming growth factor-beta1 during renal fibrosis in diabetes", Am J Nephrol 30(6):481-490, 2009.
Silberberg et al. "Impact of left ventricular hypertrophy on survival in end-stage renal disease", Kidney Int. 36(2):286-290, 1989.
Sugimoto et al. "Bone-marrow-derived stem cells repair basement membrane collagen defects and reverse genetic kidney disease", Proc Natl. Acad. Sci USA 103(19):7321-7326, 2006.
Taganov et al. "NF-kappaB-dependent induction of microRNA miR-146, an inhibitor targeted to signaling proteins of innate immune responses", Proc Natl. Acad, Sci, USA 103(33):12481-12486, 2006.
Tan et al. "Therapeutic role and potential mechanisms of active vitamin D in renal interstitial fibrosis", J Steroid Biochem Mol Biol. 103:491-496, 2007.
Thery et al. "Membrane vesicles as conveyors of immune responses", Nat. Rev. Immunol. 9(8):581-593, 2010.
Tofovic et al. "Rat models of the metabolic syndrome", Methods Mol Med. 86:29-46, 2003.
Tofovic et al. "Renal and metabolic effects of caffeine in obese (fa/fa(cp), diabetic, hypertensive ZSF1 rats", Ren Fail. 23(2):159-173, 2001.
Tofovic et al. "Renal function and structure in diabetic, hypertensive, obese ZDFxSHHF-hybrid rats", Ren Fail. 22(4):387-406, 2000.
Togel et al. "Administered mesenchymal stem cells protect against ischemic acute renal failure through differentiation-independent mechanisms", Am J Physiol Renal Physiol 289(1):F31-F42, 2005.
Togel et al. "Vasculotropic, paracrine actions of infused mesenchymal stem cells are important to the recovery from acute kidney injury", Am J Physiol Renal Physiol 292:F1626-F1635, 2007.
Tumlin et al. "Efficacy and safety of renal tubule cell therapy for acute renal failure", J Am Soc Nephrol 19(5):1034-1040, 2008.
Uhlenius et al. "Renoprotective mechanisms of angiotensin II antagonism in experimental chronic renal failure", Kidney Blood Press Res. 25(2):71-79, 2002.
Vora et al. "Evolution of metabolic and renal changes in the ZDF/Drt-fa rat model of type II diabetes", J Am Soc. Nephrol. 7(1):113-117 ,1996.
Woo et al. "Phannacokinetic and pharmacodynamic modeling of recombinant human erythropoietin after intravenous and subcutaneous administration in rats", J Pharmacol Exp Ther. 319(3):1297-1306,2006.
Yang, H.C. "Tailoring tacrolimus-based immunotherapy in renal transplantation", Nephrol Dial Transplant 18:i16-i20, 2003.
Yokoo et al. "Generation of a transplatable erythropoietin-producer derived from human mesenchymal stem cells", Transplantation 85:1654-1658, 2008.
Yokoo et al. "Xenobiotic kidney organogenesis from human nesenchymal stem cells using a growing rodent embryo", J Am Soc Nephrol. 17:1026-1034, 2006.
Zeisberg et al. "Bone morphogenic protein-7 inhibits progression of chronic renal fibrosis associated with two genetic mouse models", Am J Physiol Renal Physiol. 285(6):F1060-F1067, 2003.
Zeisberg et al. "BMP-7 counteracts TGF-beta1-induced epithelial-to-mesenchymal transition and reverses chronic renal injury", Nat Med. 9:964-968, 2003.
Zolty et al. "Severe left ventricular systolic dysfunction may reverse with renal transplantation: uremic cardiomyopathy and cardiorenal syndrome", Am J Transplant 8(11):2219-2224, 2008.
Brown, et al., "Characterisation of human tubular cell monolayers as a model of proximal tubular xenobiotic handling," Tox. Appl. Pharm., vol. 233, No. 3, Oct. 1, 2008, pp. 428-438.

(56) References Cited

OTHER PUBLICATIONS

Gobe, et al., "Bcl-2 genes and growth factors in the pathology of ischaemic acute renal failure," Immunol. Cell Biol., Jun. 1999, vol. 77, No. 3, pp. 279-286.
Kreisberg, et al. "Separation of proximal tubule cells from suspensions of rat kidney cells in density gradients of Ficoll in tissue culture medium," Am. J. Pathol., Mar. 1977, vol. 86, No. 3, pp. 591-602.
Miranda, et al., "Nucleic acids within urinary exosomes/microvesicles are potential biomarkers for renal disease," Kidney International, Jul. 2010, vol. 78, No. 2, pp. 191-199.
Saal, et al., "MicroRNAs and the kidney: coming of age," Current Opinion Nephrological Hypertension, Jul. 2009, vol. 18, No. 4, pp. 317-323.
Sahai, et al., "Mechanisms of chronic hypoxia-induced renal cell growth," Kidney International, 1999, vol. 56, pp. 1277-1281.
Anglani et al. "The renal stem cell system in kidney repair and regeneration", Frontiers in Bioscience, 2008, 13:6395-6405.
Ben-Ze'ev, et al., "Cell-cell and cell-matrix interactions differently regulate the expression of hepatic and cytoskeletal genes in primary cultures of rat hepatocytes", PNAS, 1998, vol. 85, pp. 2161-2165.
Daley, et al., "Realistic prospects for stem cell therapeutics", Hematology, 2003, 1:398-418.
Donnelly, "New insights into renal anemia", Canadian J of Diabetes, 2003, 27(2):176-181.
Fisher, et al., "Erythropoietin: physiology and pharmacology update", Experimental Biology and Medicine, 2003, 228:1-14.
Fontaine, et al., "Transplantation of genetically altered hepatocytes using cell-polymer constructs", Transplantation Proceedings, 1993, vol. 25, No. 1, pp. 1002-1004.
Genestie, et al., "Polarity and Transport Properties of Rabbit Kidney Proximal Tubule Cells on Collagen IV-coated Porous Membranes", (ABST) Am. J. Physiol., 1995, 269(1): pt 2, f22-30.
Guo, et al., "Cellular maintenance and repair of the kidney", Annu. Rev. Physiol., 2010, 72:357-376.
Held, et al., "In vivo genetic selection of renal proximal tubules", Molecular Therapy, 2006, vol. 13, No. 1, pp. 49-58.
Kim, et al, "Kidney tissue reconstruction by fetal kidney cell transplantation: Effect of gestation stage of fetal kidney cells", Stem cells, 2007, 25:1393-1401.
Krantz, Erythropoietin, Blood, Feb. 1991, 77(3):419-434.
Kreisberg, et al. "Separation of proximal tubule cells from suspensions of Rat Kidney cells in density gradients of ficoll in tissue culture medium". Am J. Pathol., 1977, 86:591-602.
Kurtz, et al., "Renal mesangial cell cultures as a model for study of erythropoietin production", Proc. Natl. Acad. Sci. USA, 1983, 80:4008-4011.
Lin, et al., "Intrarenal cells, not bone marrow-derived cells, are the major source for regeneration in postischemic kidney", The Journal of Clinical Investigation, 2005, vol. 115, No. 7, pp. 1756-1764.
Nangaku, "Chronic hypoxia and tubulointerstitial injury: a final common pathway to end-stage renal failure", J Am Soc Nephrol, 2006, 17:17-25.
Newsome, "Yet another role for mesenchmyal stem cells", Transplantation, 2008, vol. 85, No. 11, pp. 1548-1549.
Ormrod, et al., "Experimental uremia: description of a model producing varying degrees of stable uremia", Nephron, 1980, 26:249-254.
Plotkin et al., "Mesenchymal cells from adult kidney support angiogenesis and differentiate into multiple interstitial cell types including erythropoietin-producing fibroblasts", 2006, Am J Physiol Renal Physiol, 291:F902-F912.
Rinsch, et al., "Delivery of erythropoietin by encapsulated myoblasts in a genetic model of severe anemia", Kidney Intl, 2002, 62:1395-1401.
Rossert, et al., "Anemia management and the delay of chronic renal failure progression", J Am Soc Nephrol, 2003, 14:S173-S177.
Rudikoff, et al. "Single Amino Acid Substitution Altering Antigen-Binding Specificity" Proc. Natl. Acad. Sci. Mar. 1982. vol. 79, pp. 1979-83.
Satchell, et al., "Conditionally immortalized human glomerular endothelial cells expressing fenestrations in response to VEGF", Kidney International, 2006, 69:1633-1640.
Bussolati B. et al., Renal CD133+/CD73+Progenitors Produce Erythropoietin under Hypoxia and Prolyl Hydroxylase Inhibition. *J Am Soc. Nephrol.*, 2013, 24(8):1234-1241.
Bussolati B. et al., New Insights into the Renal Progenitor Cells and Kidney Diseases by Studying CD133. *Advances in Experimental Medicine and Biology*, 2013;777, 113-123.
Bussolati B. et al., Hypoxia modulates the undifferentiated phenotype of human renal inner medullary CD133+ progenitors through Oct. 4/miR-145 balance, Am J Physiol Renal Physiol, First Published 2011, 302(1):F116-F128.
Camussi G. et al., Role of stem-cell-derived microvesicles in the paracrine action of stem cells, *Biochem. Soc. Trans.*, 2013; 41(1):283-287.
Cantaluppi V. et al., Microvesicles derived from endothelial progenitor cells protect the kidney from ischemia-reperfusion injury by microRNA-dependent reprogramming of resident renal cells, *Kidney Int.* 2012; 82(4):412-427
Tsurkan M.V. et al., Growth factor delivery from hydrogel particle aggregates to promote tubular regeneration after acute kidney injury, *Journal of Control Release*, 2013;167(3):248-255.
Chen et al., Mesenchymal stem cell secretes microparticles enriched in pre-microRNAs. Nucleic Acids Research, 38(1): 215-224, 2010.
Dursun et al., The relationship between circulating endothelial microparticles and arterial stiffness and atherosclerosis in children with chronic kidney disease, Nephrol Dial Transplant, 24: 2511-2518, 2009.
Martinez and Andriantsitohaina, Microparticles in Angiogenesis: Therapeutic Potential, Circ Res, 109(1):110-119, 2011.
Stoorvogel et al., The biogenesis and functions of exosomes. Traffic, 3(5):321-330, 2002.
Sahoo et al., Exosomes from human CD34(+) stem cells mediate their proangiogenic paracrine activity. Circ Res, 109(7):724-728, 2011.
Camussi et al., Exosome/microvesicles as a Mechanism of cell-to cell communication, Kidney Int., 78(9):838-48, 2010.
Baer et al., Conditioned medium from renal tubular epithelial cells initiates differentiation of human mesenchymal stem cells. Cell Prolif. 2009, 42(1):29-37, 2009.
Nieuwland and Sturk, Why do cells release vesicles? Thrombosis Research, 125, S-49-S51, 2010.
Simons and Raposo, Exosomes-vasicular carriers for intercellular communication, Current Opinion in Cell Biology, 21:575-581, 2009.

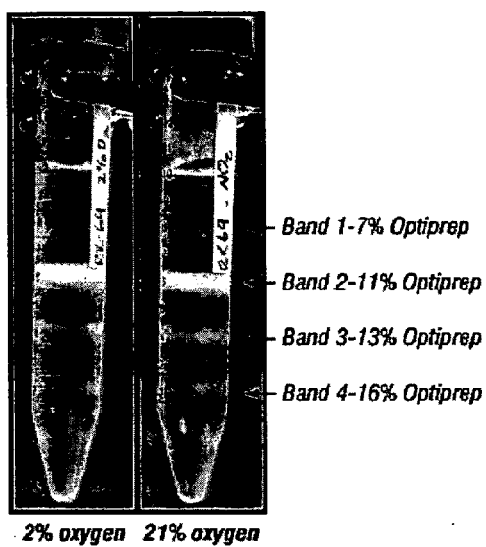 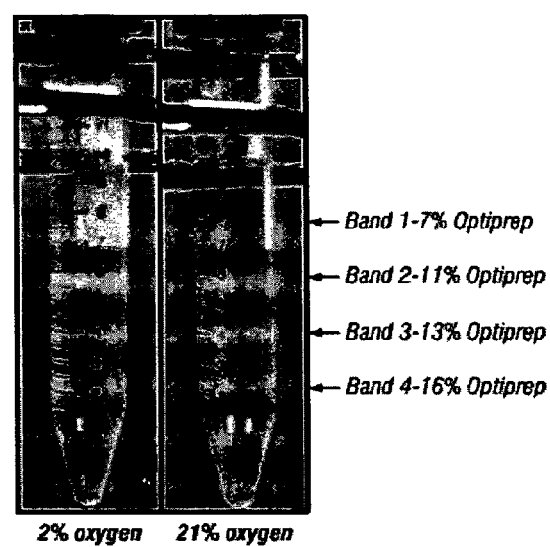
Figure 2
Figure 3

Non-CKD (HK17)
CKD (HK19)
Figure 4

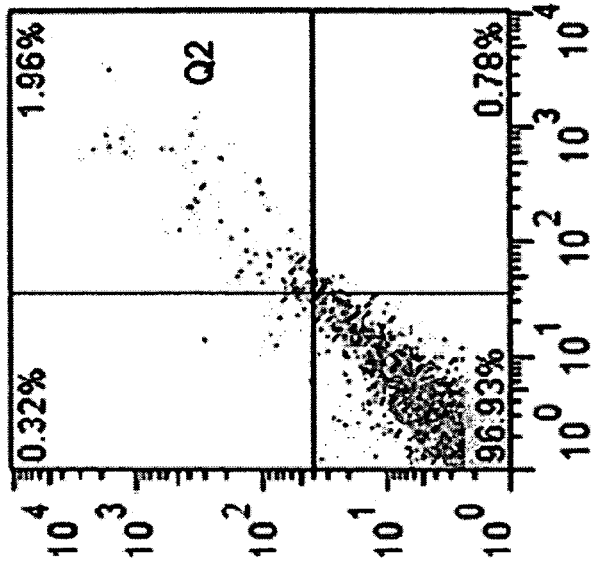
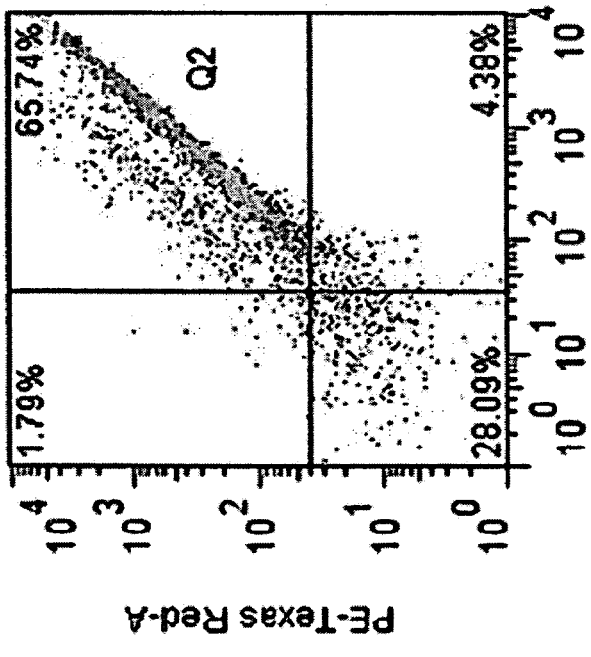
Figure 15B

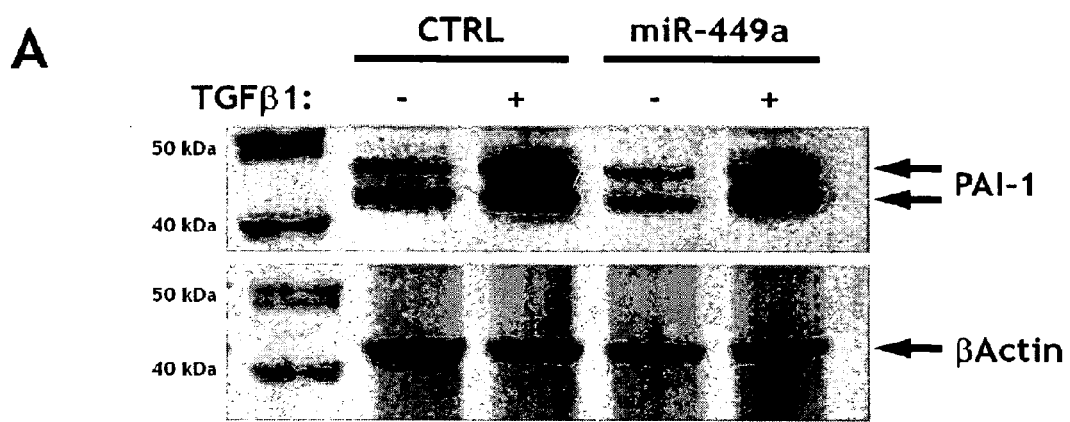
Figure 16A-B

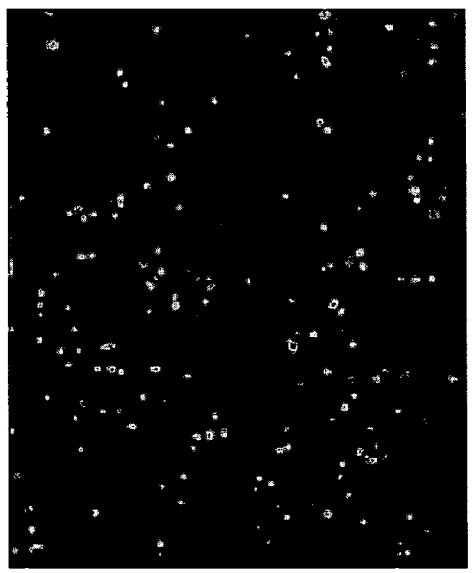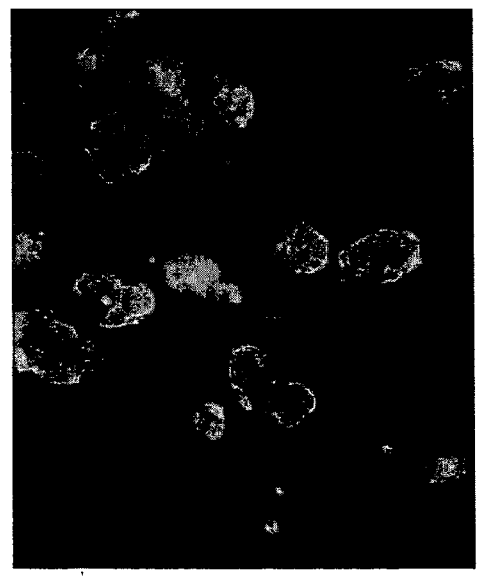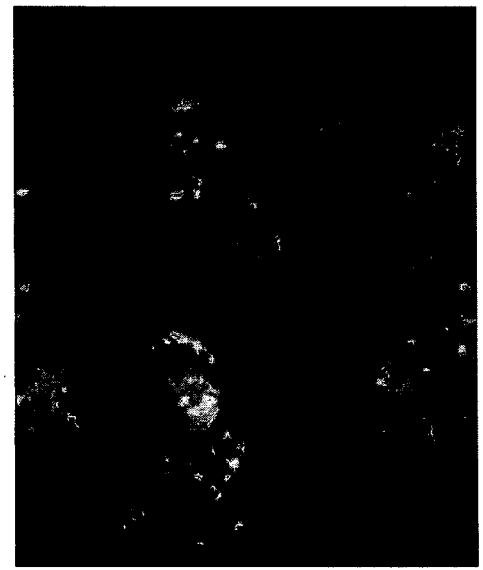
Figure 20

Figure 23A

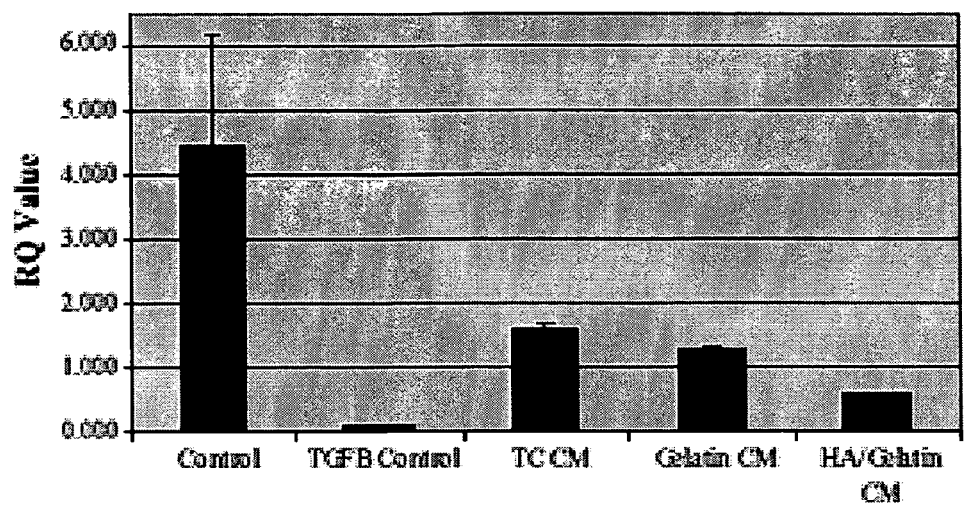
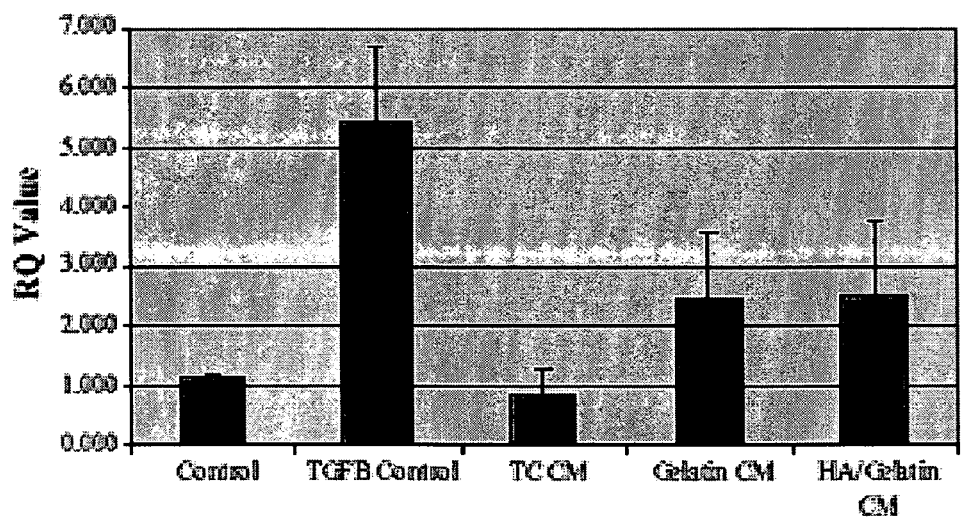
Figure 26

1. Label cells with fluorescent dyes
     2%O$_2$
     21%O$_2$
     HK2 Tubular Monolayer (wounded)
2. Wound tubular cell monolayer
    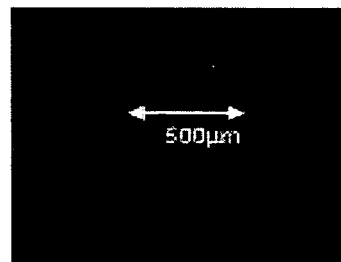
3. Add oxygen-exposed labeled cells
    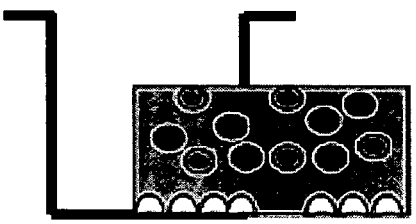
4. Quantify cells that repair wound
Figure 29A red circles = cells cultured 2%O2, blue circles= 21%O2

1. Label cells with fluorescent dyes
2. Establish tubular cell monolayer on bottom of 8μm pore size transwell insert and wound
3. Add 2% and 21% oxygen exposed labeled cells
4. Quantify cells that migrate and repair wound
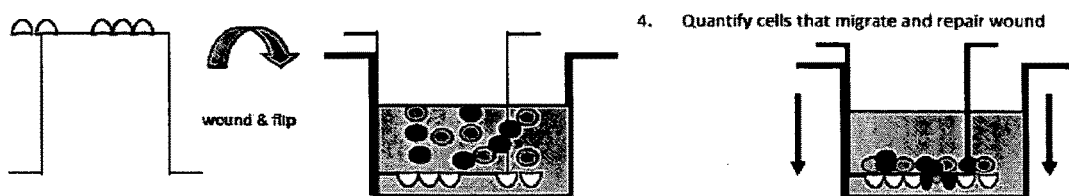
Figure 30A
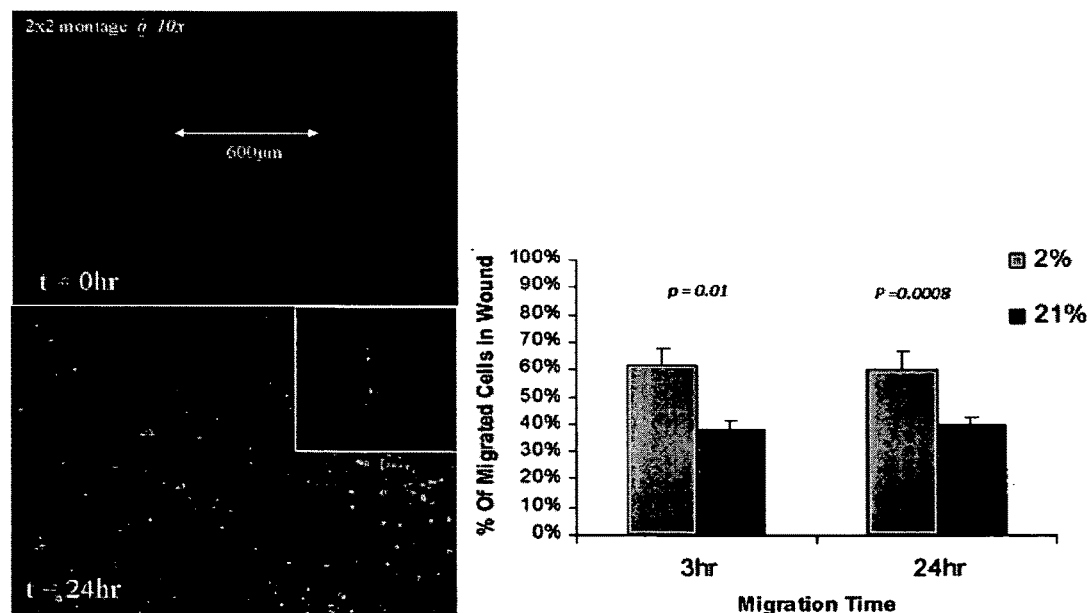
Figure 30B
Figure 30C Osteopontin Immunocytochemistry: Hoechst nuclear stain (blue), Osteopontin (Red), 10x

SEQUENCE LISTING

<160> NUMBER OF SEQ ID NOS: 3

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cgacucacau ccuacaaaug u                                              21

<210> SEQ ID NO 2
<211> LENGTH: 26
<212> TYPE: DNA
<213> ORGANISM: Rattus sp.

<400> SEQUENCE: 2
ttcagagtgt agatgacttg tttaca                                         26

<210> SEQ ID NO 3
<211> LENGTH: 27
<212> TYPE: DNA
<213> ORGANISM: Homo sapiens

<400> SEQUENCE: 3
ttttggagtg taggtgactt gtttact                                        27

BIOACTIVE RENAL CELLS

RELATED APPLICATIONS

This application is a US National Stage application claiming the benefit under 35 USC § 371 of PCT/US2011/36347 filed May 12, 2011, which claims the benefit under 35 USC § 119 of U.S. Provisional Application No. 61/473,111 filed Apr. 7, 2011; U.S. Provisional Application No. 61/441,423 filed Feb. 10, 2011; U.S. Provisional Application No. 61/413,382 filed Nov. 12, 2010; U.S. Provisional Application No. 61/412,933 Nov. 12, 2010; U.S. Provisional Application No. 61/388,765 filed Oct. 1, 2010; U.S. Provisional Application No. 61/376,586 filed Aug. 24, 2010; U.S. Provisional Application No. 61/371,888 Aug. 9, 2010; U.S. Provisional Application No. 61/372,077 filed Aug. 9, 2010; U.S. Provisional Application No. 61/353,895 filed Jun. 11, 2010; and U.S. Provisional Application No. 61/334,032 filed May 12, 2010. The disclosures of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 22, 2016, is named RMX-1020-US_SL.txt and is 1,149 bytes in size.

FIELD OF THE INVENTION

The present invention relates to bioactive renal cell populations or fractions that lack cellular components as compared to a healthy individual yet retain therapeutic properties, and methods of isolating and culturing the same, as well as methods of treating a subject in need with the cell populations. In addition, the present invention relates to methods of providing regenerative effects to a native kidney using bioactive renal cell populations.

BACKGROUND OF THE INVENTION

Chronic Kidney Disease (CKD) affects over 19 million people in the United States and is frequently a consequence of metabolic disorders involving obesity, diabetes, and hypertension. Examination of the data reveals that the rate of increase is due to the development of renal failure secondary to hypertension and non-insulin dependent diabetes mellitus (NIDDM) (United States Renal Data System: Costs of CKD and ESRD. ed. Bethesda, Md., National Institutes of Health, National Institute of Diabetes and Digestive and Kidney Diseases, 2007 pp 223-238)—two diseases that are also on the rise worldwide. Obesity, hypertension, and poor glycemic control have all been shown to be independent risk factors for kidney damage, causing glomerular and tubular lesions and leading to proteinuria and other systemically-detectable alterations in renal filtration function (Aboushwareb, et al., World J Urol, 26: 295-300, 2008; Amann, K. et al., Nephrol Dial Transplant, 13: 1958-66, 1998). CKD patients in stages 1-3 of progression are managed by lifestyle changes and pharmacological interventions aimed at controlling the underlying disease state(s), while patients in stages 4-5 are managed by dialysis and a drug regimen that typically includes anti-hypertensive agents, erythropoiesis stimulating agents (ESAs), iron and vitamin D supplementation. Regenerative medicine technologies may provide next-generation therapeutic options for CKD. Presnell et al. WO/2010/056328 describe isolated renal cells, including tubular and erythropoietin (EPO)-producing kidney cell populations, and methods of isolating and culturing the same, as well as methods of treating a subject in need with the cell populations. There is a need for new treatment paradigms that provide substantial and durable augmentation of kidney functions, to slow progression and improve quality of life in this patient population.

SUMMARY OF THE INVENTION

In one aspect, the present invention provides a method for providing a regenerative effect to a native kidney. In one embodiment, the method includes the step of in vivo contacting the native kidney with products secreted by an enriched renal cell population. In another embodiment, the products are secreted by an enriched renal cell population that is not part of a construct, as described herein, e.g., the cell population is not seeded on a scaffold. In one other embodiment, the products are secreted from a renal cell construct comprising an enriched renal cell population directly seeded on or in a scaffold. In another embodiment, the secretion of the products is bioresponsive to oxygen levels. Secretion may be induced by a less than atmospheric oxygen level. In one other embodiment, the lower oxygen level is less than about 5% oxygen.

In one embodiment, the regenerative effect is a reduction in epithelial-mesenchymal transition (EMT). The reduction in EMT may be achieved via attenuation of TGF-β signalling and/or attenuation of Plasminogen Activator Inhibitor-1 (PAI-1) signalling. In another embodiment, the regenerative effect is a reduction in renal fibrosis and/or a reduction in renal inflammation. In some embodiments, the reduction in inflammation may be mediated by NFκB. In one other embodiment, the regenerative effect is characterized by differential expression of a stem cell marker in the native kidney. The expression may be an upregulation of marker expression in the in vivo contacted native kidney relative to expression in a non-contacted native kidney.

In one aspect, the enriched renal cell population includes one or more cell populations, i.e., an admixture, as described herein. In one embodiment, the population includes a first cell population, B2, that contains an enriched population of tubular cells. In another embodiment, the population includes an admixture of human renal cells having a first cell population, B2, and a second cell population, which contains one or more of erythropoietin (EPO)-producing cells, glomerular cells and vascular cells. In one other embodiment, the second cell population is a B4 cell population. In yet another embodiment, the second cell population is a B3 cell population.

In one embodiment, the admixture further includes a third cell population having one or more of erythropoietin (EPO)-producing cells, glomerular cells and vascular cells. In another embodiment, the third cell population is a B4 cell population. In one other embodiment, the third cell population is a B3 cell population.

In all embodiments, the B2 cell population has a density between about 1.045 g/mL and about 1.052 g/mL. In all embodiments, the B4 cell population has a density between about 1.063 g/mL and about 1.091 g/mL. In all embodiments, the B3 cell population has a density between about 1.052 g/ml and about 1.063 g/ml.

In all embodiments, the enriched renal cell population may be non-autologous to the native kidney. In all embodiments, the enriched renal cell population may be autologous to the native kidney.

In all embodiments, the products include paracrine factors, endocrine factors, juxtacrine factors, RNA, vesicles, microvesicles, exosomes, and any combination thereof. In one other embodiment, the vesicles include one or more secreted products selected from the group consisting of paracrine factors, endocrine factors, juxtacrine factors, and RNA. In another embodiment, the products are secreted from a renal cell construct comprising an enriched renal cell population directly seeded on or in a scaffold.

In all embodiments, the scaffold may contain a biocompatible material. In all embodiments, the biocompatible material may be a hydrogel.

In one embodiment, the present invention provides methods of assessing whether a kidney disease (KD) patient is responsive to treatment with a therapeutic. The method may include the step of determining or detecting the amount of vesicles or their luminal contents in a test sample obtained from a KD patient treated with the therapeutic, as compared to or relative to the amount of vesicles in a control sample, wherein a higher or lower amount of vesicles or their luminal contents in the test sample as compared to the amount of vesicles or their luminal contents in the control sample is indicative of the treated patient's responsiveness to treatment with the therapeutic. The vesicles may be kidney derived vesicles. The test sample may contain urine. The vesicles may contain a biomarker, which may be miRNA. The therapeutic may contain an enriched population of renal cells.

BRIEF DESCRIPTION OF THE DRAWINGS

FIG. 2 shows step gradients of "normoxic" (21% oxygen) and "hypoxic" (2% oxygen) rodent cultures that were harvested separately and applied side-by-side to identical step gradients.

FIG. 3 shows step gradients of "normoxic" (21% oxygen) and "hypoxic" (2% oxygen) canine cultures that were harvested separately and applied side-by-side to identical step gradients.

FIG. 4 shows histopathologic features of the HK17 and HK19 samples.

FIG. 13A shows that UNFX-conditioned media attenuates TNF-a mediated activation of NF-kB. FIG. 13B shows that UNFX-conditioned media increases proangiogenic behavior of HUVEC cell cultures. FIG. 13C shows that UNFX-conditioned media attenuates fibrosis pathways in epithelial cells.

FIG. 15A-C shows that the conditioned media from UNFX contains secreted vesicles. FIG. 15A depicts secreted vesicles, which are bilipid structures (red) that encompass cytoplasm-derived internal components (green). FIG. 15B-C shows FACS sorting.

FIG. 16A shows a Western blot in which total protein was prepared and assayed for PAI-1 and bActin. FIG. 16B depicts the microRNA, miR-30b-5p (SEQ ID NOS 1-3, respectively, in order of appearance).

FIG. 20A-D shows live/dead staining of NKA constructs.

FIG. 23A-C shows confocal microscopy of NKA Constructs.

FIG. 26 shows conditioned medium from NKA Constructs attenuates TGF-β induced EMT in HK2 cells in vitro.

FIG. 29A depicts an assay developed to observe repair of tubular monolayers in vitro.

FIG. 30A depicts an assay developed to observe repair of tubular monolayers in vitro. FIG. 30B shows that the induction of cells with 2% Oxygen enhanced the migration and wound repair compared to un-induced (21% oxygen). FIG. 30C plots the % of migrated cells against migration time.

DETAILED DESCRIPTION OF THE INVENTION

Figure 1:
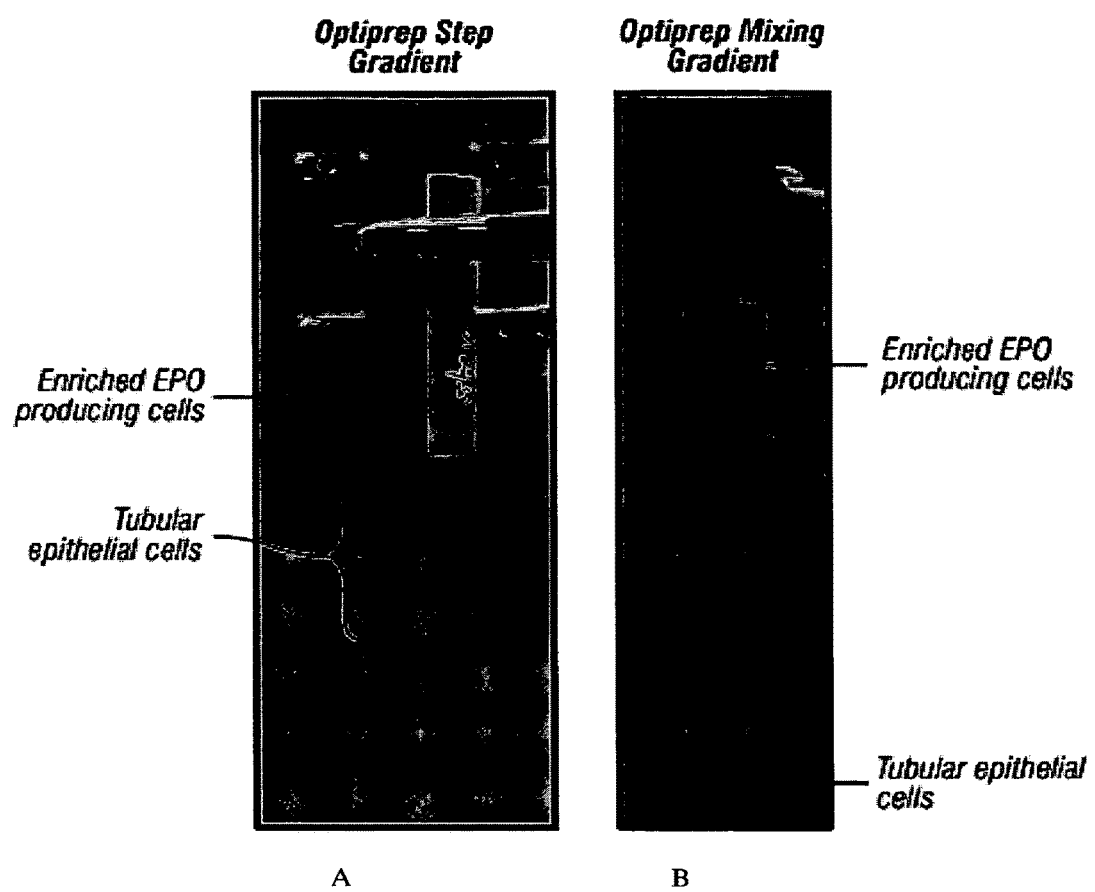
FIG. 1 shows enrichment of epo-producing cell fraction from freshly-dissociated kidney tissue using a multi-layered step gradient technique (A—left panel) or a single-layer mixing gradient technique (B—right panel). Both methods result in the partial depletion of non epo-producing cell components (predominantly tubular cells) from the epo band, which appears between 1.025 g/mL and 1.035 g/mL.

The present invention is directed to heterogenous mixtures or fractions of bioactive renal cells (BRCs) and methods of isolating and culturing the same, as well as methods of treating a subject in need with BRCs and/or BRC-containing constructs formed from a scaffold seeded with BRCs as described herein. The bioactive renal cells may be isolated renal cells including tubular and erythropoietin (EPO)-producing kidney cells. The BRC cell populations may include enriched tubular and EPO-producing cell populations. The BRCs may be derived from or are themselves renal cell fractions from healthy individuals. In addition, the present invention provides renal cell fractions obtained from an unhealthy individual may lack certain cellular components when compared to the corresponding renal cell fractions of a healthy individual, yet still retain therapeutic properties. The present invention also provides therapeutically-active cell populations lacking cellular components compared to a healthy individual, which cell populations can be, in one embodiment, isolated and expanded from autologous sources in various disease states.

The present invention also relates methods of providing a regenerative effect to a native kidney by in vivo contacting the native kidney with products secreted by renal cells, as well as methods of preparing the secreted products. The present invention further relates to the use of markers to determine the presence of renal regeneration following treatment with a method described herein.

Definitions

Unless defined otherwise, technical and scientific terms used herein have the same meaning as commonly understood by one of ordinary skill in the art to which this invention belongs. *Principles of Tissue Engineering*, $3^{rd}$ Ed. (Edited by R Lanza, R Langer, & J Vacanti), 2007 provides one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "cell population" as used herein refers to a number of cells obtained by isolation directly from a suitable tissue source, usually from a mammal. The isolated cell population may be subsequently cultured in vitro. Those of ordinary skill in the art will appreciate that various methods for isolating and culturing cell populations for use with the present invention and various numbers of cells in a cell population that are suitable for use in the present invention. A cell population may be an unfractionated, heterogeneous cell population derived from the kidney. For example, a heterogeneous cell population may be isolated from a kidney biopsy or from whole kidney tissue. Alternatively, the heterogeneous cell population may be derived from in vitro cultures of mammalian cells, established from kidney biopsies or whole kidney tissue. An unfractionated heterogeneous cell population may also be referred to as a non-enriched cell population.

The term "native kidney" shall mean the kidney of a living subject. The subject may be healthy or un-healthy. An unhealthy subject may have a kidney disease.

The term "regenerative effect" shall mean an effect which provides a benefit to a native kidney. The effect may include, without limitation, a reduction in the degree of injury to a native kidney or an improvement in, restoration of, or stabilization of a native kidney function. Renal injury may be in the form of fibrosis, inflammation, glomerular hypertrophy, etc. and related to kidney disease in the subject.

The term "admixture" as used herein refers to a combination of two or more isolated, enriched cell populations derived from an unfractionated, heterogeneous cell population. According to certain embodiments, the cell populations of the present invention are renal cell populations.

An "enriched" cell population or preparation refers to a cell population derived from a starting kidney cell population (e.g., an unfractionated, heterogeneous cell population) that contains a greater percentage of a specific cell type than the percentage of that cell type in the starting population. For example, a starting kidney cell population can be enriched for a first, a second, a third, a fourth, a fifth, and so on, cell population of interest. As used herein, the terms "cell population", "cell preparation" and "cell prototype" are used interchangeably.

In one aspect, the term "enriched" cell population as used herein refers to a cell population derived from a starting kidney cell population (e.g., a cell suspension from a kidney biopsy or cultured mammalian kidney cells) that contains a percentage of cells capable of producing EPO that is greater than the percentage of cells capable of producing EPO in the starting population. For example, the term "B4" is a cell population derived from a starting kidney cell population that contains a greater percentage of EPO-producing cells, glomerular cells, and vascular cells as compared to the starting population. The cell populations of the present invention may be enriched for one or more cell types and depleted of one or more other cell types. For example, an enriched EPO-producing cell population may be enriched for interstitial fibroblasts and depleted of tubular cells and collecting duct epithelial cells relative to the interstitial fibroblasts and tubular cells in a non-enriched cell population, i.e. the starting cell population from which the enriched cell population is derived. In all embodiments citing EPO-enriched or "B4" populations, the enriched cell populations are heterogeneous populations of cells containing cells that can produce EPO in an oxygen-regulated manner, as demonstrated by oxygen-tunable EPO expression from the endogenous native EPO gene.

In another aspect, an enriched cell population, which contains a greater percentage of a specific cell type, e.g., vascular, glomerular, or endocrine cells, than the percentage of that cell type in the starting population, may also lack or be deficient in one or more specific cell types, e.g., vascular, glomerular, or endocrine cells, as compared to a starting kidney cell population derived from a healthy individual or subject. For example, the term "B4'," or B4 prime," in one aspect, is a cell population derived from a starting kidney cell population that lacks or is deficient in one or more cell types, e.g., vascular, glomerular or endocrine, depending on the disease state of the starting specimen, as compared to a healthy individual. In one embodiment, the B4' cell population is derived from a subject having chronic kidney disease. In one embodiment, the B4' cell population is derived from a subject having focal segmental glomerulosclerosis (FSGS). In another embodiment, the B4' cell population is derived from a subject having autoimmune glomerulonephritis. In another aspect, B4' is a cell population derived from a starting cell population including all cell types, e.g., vascular, glomerular, or endocrine cells, which is later depleted of or made deficient in one or more cell types, e.g., vascular, glomerular, or endocrine cells. In yet another aspect, B4' is a cell population derived from a starting cell population including all cell types, e.g., vascular, glomerular, or endocrine cells, in which one or more specific cell types e.g., vascular, glomerular, or endocrine cells, is later enriched. For example, in one embodiment, a B4' cell population may be enriched for vascular cells but depleted of glomerular and/or endocrine cells. In another embodiment, a B4' cell population may be enriched for glomerular cells but depleted of vascular and/or endocrine cells. In another embodiment, a B4' cell population may be enriched for endocrine cells but depleted of vascular and/or glomerular cells. In another embodiment, a B4' cell population may be enriched for vascular and endocrine cells but depleted of glomerular cells. In preferred embodiments, the B4' cell population, alone or admixed with another enriched cell population, e.g., B2 and/or B3, retains therapeutic properties. A B4' cell population, for example, is described herein in the Examples, e.g., Examples 7-9.

In another aspect, an enriched cell population may also refer to a cell population derived from a starting kidney cell population as discussed above that contains a percentage of cells expressing one or more tubular cell markers that is greater than the percentage of cells expressing one or more tubular cell markers in the starting population. For example, the term "B2" refers to a cell population derived from a starting kidney cell population that contains a greater percentage of tubular cells as compared to the starting population. In addition, a cell population enriched for cells that express one or more tubular cell markers (or "B2") may contain some epithelial cells from the collecting duct system. Although the cell population enriched for cells that express one or more tubular cell markers (or "B2") is relatively depleted of EPO-producing cells, glomerular cells, and vascular cells, the enriched population may contain a smaller percentage of these cells (EPO-producing, glomerular, and vascular) in comparison to the starting population. In general, a heterogeneous cell population is depleted of one or more cell types such that the depleted cell population contains a lesser proportion of the cell type(s) relative to the proportion of the cell type(s) contained in the heterogeneous cell population prior to depletion. The cell types that may be depleted are any type of kidney cell. For example, in certain embodiments, the cell types that may be depleted include cells with large granularity of the collecting duct and tubular system having a density of <about 1.045 g/ml, referred to as "B1". In certain other embodiments, the cell types that may be depleted include debris and small cells of low granularity and viability having a density of >about 1.095 g/ml, referred to as "B5". In some embodiments, the cell population enriched for tubular cells is relatively depleted of all of the following: "B1", "B5", oxygen-tunable EPO-expressing cells, glomerular cells, and vascular cells.

The term "hypoxic" culture conditions as used herein refers to culture conditions in which cells are subjected to a reduction in available oxygen levels in the culture system relative to standard culture conditions in which cells are cultured at atmospheric oxygen levels (about 21%). Non-hypoxic conditions are referred to herein as normal or normoxic culture conditions.

The term "oxygen-tunable" as used herein refers to the ability of cells to modulate gene expression (up or down) based on the amount of oxygen available to the cells. "Hypoxia-inducible" refers to the upregulation of gene expression in response to a reduction in oxygen tension (regardless of the pre-induction or starting oxygen tension).

The term "biomaterial" as used here refers to a natural or synthetic biocompatible material that is suitable for introduction into living tissue. A natural biomaterial is a material that is made by a living system. Synthetic biomaterials are materials which are not made by a living system. The biomaterials disclosed herein may be a combination of natural and synthetic biocompatible materials. As used herein, biomaterials include, for example, polymeric matrices and scaffolds. Those of ordinary skill in the art will appreciate that the biomaterial(s) may be configured in various forms, for example, as liquid hydrogel suspensions, porous foam, and may comprise one or more natural or synthetic biocompatible materials.

The term "anemia" as used herein refers to a deficit in red blood cell number and/or hemoglobin levels due to inadequate production of functional EPO protein by the EPO-producing cells of a subject, and/or inadequate release of EPO protein into systemic circulation, and/or the inability of erythroblasts in the bone marrow to respond to EPO protein. A subject with anemia is unable to maintain erythroid homeostasis. In general, anemia can occur with a decline or loss of kidney function (e.g., chronic renal failure), anemia associated with relative EPO deficiency, anemia associated with congestive heart failure, anemia associated with myelosuppressive therapy such as chemotherapy or anti-viral therapy (e.g., AZT), anemia associated with non-myeloid cancers, anemia associated with viral infections such as HIV, and anemia of chronic diseases such as autoimmune diseases (e.g., rheumatoid arthritis), liver disease, and multi-organ system failure.

The term "EPO-deficiency" refers to any condition or disorder that is treatable with an erythropoietin receptor agonist (e.g., recombinant EPO or EPO analogs), including anemia.

The term "kidney disease" as used herein refers to disorders associated with any stage or degree of acute or chronic renal failure that results in a loss of the kidney's ability to perform the function of blood filtration and elimination of excess fluid, electrolytes, and wastes from the blood. Kidney disease also includes endocrine dysfunctions such as anemia (erythropoietin-deficiency), and mineral imbalance (Vitamin D deficiency). Kidney disease may originate in the kidney or may be secondary to a variety of conditions, including (but not limited to) heart failure, hypertension, diabetes, autoimmune disease, or liver disease. Kidney disease may be a condition of chronic renal failure that develops after an acute injury to the kidney. For example, injury to the kidney by ischemia and/or exposure to toxicants may cause acute renal failure; incomplete recovery after acute kidney injury may lead to the development of chronic renal failure.

The term "treatment" refers to both therapeutic treatment and prophylactic or preventative measures for kidney disease, anemia, EPO deficiency, tubular transport deficiency, or glomerular filtration deficiency wherein the object is to reverse, prevent or slow down (lessen) the targeted disorder. Those in need of treatment include those already having a kidney disease, anemia, EPO deficiency, tubular transport deficiency, or glomerular filtration deficiency as well as those prone to having a kidney disease, anemia, EPO deficiency, tubular transport deficiency, or glomerular filtration deficiency or those in whom the kidney disease, anemia, EPO deficiency, tubular transport deficiency, or glomerular filtration deficiency is to be prevented. The term "treatment" as used herein includes the stabilization and/or improvement of kidney function.

The term "in vivo contacting" as used herein refers to direct contact in vivo between products secreted by an enriched population of renal cells (or an admixture or construct containing renal cells/renal cell fractions) and a native kidney. The direct in vivo contacting may be paracrine, endocrine, or juxtacrine in nature. The products secreted may be a heterogeneous population of different products described herein.

The term "ribonucleic acid" or "RNA" as used herein refers to a chain of nucleotide units where each unit is made up of a nitrogenous base, a ribose sugar, and a phosphate. The RNA may be in single or double stranded form. The RNA may be part of, within, or associated with a vesicle. The vesicle may be an exosome. RNA includes, without limitation, mRNAs, rRNA, small RNAs, snRNAs, snoRNAs, microRNAs (miRNAs), small interfering RNAs (siRNAs), and noncoding RNAs. The RNA is preferably human RNA.

The term "construct" refers to one or more cell populations deposited on or in a surface of a scaffold or matrix made up of one or more synthetic or naturally-occurring biocompatible materials. The one or more cell populations may be coated with, deposited on, embedded in, attached to, seeded, or entrapped in a biomaterial made up of one or more synthetic or naturally-occurring biocompatible polymers, proteins, or peptides. The one or more cell populations may be combined with a biomaterial or scaffold or matrix in vitro or in vivo. In general, the one or more biocompatible materials used to form the scaffold/biomaterial is selected to direct, facilitate, or permit the formation of multicellular, three-dimensional, organization of at least one of the cell populations deposited thereon. The one or more biomaterials used to generate the construct may also be selected to direct, facilitate, or permit dispersion and/or integration of the construct or cellular components of the construct with the endogenous host tissue, or to direct, facilitate, or permit the survival, engraftment, tolerance, or functional performance of the construct or cellular components of the construct.

The term "marker" or "biomarker" refers generally to a DNA, RNA, protein, carbohydrate, or glycolipid-based molecular marker, the expression or presence of which in a cultured cell population can be detected by standard methods (or methods disclosed herein) and is consistent with one or more cells in the cultured cell population being a particular type of cell. The marker may be a polypeptide expressed by the cell or an identifiable physical location on a chromosome, such as a gene, a restriction endonuclease recognition site or a nucleic acid encoding a polypeptide (e.g., an mRNA) expressed by the native cell. The marker may be an expressed region of a gene referred to as a "gene expression marker", or some segment of DNA with no known coding function. The biomarkers may be cell-derived, e.g., secreted, products.

The terms "differentially expressed gene," "differential gene expression" and their synonyms, which are used interchangeably, refer to a gene whose expression is activated to a higher or lower level in a first cell or cell population, relative to its expression in a second cell or cell population. The terms also include genes whose expression is activated to a higher or lower level at different stages over time during passage of the first or second cell in culture. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between the first cell and the second cell. Differential expression includes both quantitative, as well as qualitative, differences in the temporal or cellular expression pattern in a gene or its expression products among, for example, the first cell and the second cell. For the purpose of this invention, "differential gene expression" is considered to be present when there is a difference between the expression of a given gene in the first cell and the second cell. The differential expression of a marker may be in cells from a patient before administration of a cell population, admixture, or construct (the first cell) relative to expression in cells from the patient after administration (the second cell).

The terms "inhibit", "down-regulate", "under-express" and "reduce" are used interchangeably and mean that the expression of a gene, or level of RNA molecules or equivalent RNA molecules encoding one or more proteins or protein subunits, or activity of one or more proteins or protein subunits, is reduced relative to one or more controls, such as, for example, one or more positive and/or negative controls. The under-expression may be in cells from a patient before administration of a cell population, admixture, or construct relative to cells from the patient after administration.

The term "up-regulate" or "over-express" is used to mean that the expression of a gene, or level of RNA molecules or equivalent RNA molecules encoding one or more proteins or protein subunits, or activity of one or more proteins or protein subunits, is elevated relative to one or more controls, such as, for example, one or more positive and/or negative controls. The over-expression may be in cells from a patient after administration of a cell population, admixture, or construct relative to cells from the patient before administration.

The term "subject" shall mean any single human subject, including a patient, eligible for treatment, who is experiencing or has experienced one or more signs, symptoms, or other indicators of a kidney disease, anemia, or EPO deficiency. Such subjects include without limitation subjects who are newly diagnosed or previously diagnosed and are now experiencing a recurrence or relapse, or are at risk for a kidney disease, anemia, or EPO deficiency, no matter the cause. The subject may have been previously treated for a kidney disease, anemia, or EPO deficiency, or not so treated.

The term "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "sample" or "patient sample" or "biological sample" shall generally mean any biological sample obtained from a subject or patient, body fluid, body tissue, cell line, tissue culture, or other source. The term includes tissue biopsies such as, for example, kidney biopsies. The term includes cultured cells such as, for example, cultured mammalian kidney cells. Methods for obtaining tissue biopsies and cultured cells from mammals are well known in the art. If the term "sample" is used alone, it shall still mean that the "sample" is a "biological sample" or "patient sample", i.e., the terms are used interchangeably.

The term "test sample" refers to a sample from a subject that has been treated by a method of the present invention. The test sample may originate from various sources in the mammalian subject including, without limitation, blood, semen, serum, urine, bone marrow, mucosa, tissue, etc.

The term "control" or "control sample" refers a negative or positive control in which a negative or positive result is expected to help correlate a result in the test sample. Controls that are suitable for the present invention include, without limitation, a sample known to exhibit indicators characteristic of normal erythroid homeostasis, a sample known to exhibit indicators characteristic of anemia, a sample obtained from a subject known not to be anemic, and a sample obtained from a subject known to be anemic. Additional controls suitable for use in the methods of the present invention include, without limitation, samples derived from subjects that have been treated with pharmacological agents known to modulate erythropoiesis (e.g., recombinant EPO or EPO analogs). In addition, the control may be a sample obtained from a subject prior to being treated by a method of the present invention. An additional suitable control may be a test sample obtained from a subject known to have any type or stage of kidney disease, and a sample from a subject known not to have any type or stage of kidney disease. A control may be a normal healthy matched control. Those of skill in the art will appreciate other controls suitable for use in the present invention.

"Regeneration prognosis", "regenerative prognosis", or "prognostic for regeneration" generally refers to a forecast or prediction of the probable regenerative course or outcome of the administration or implantation of a cell population, admixture or construct described herein. For a regeneration prognosis, the forecast or prediction may be informed by one or more of the following: improvement of a functional kidney after implantation or administration, development of a functional kidney after implantation or administration, development of improved kidney function or capacity after implantation or administration, and expression of certain markers by the native kidney following implantation or administration.

"Regenerated kidney" refers to a native kidney after implantation or administration of a cell population, admixture, or construct as described herein. The regenerated kidney is characterized by various indicators including, without limitation, development of function or capacity in the native kidney, improvement of function or capacity in the native kidney, and the expression of certain markers in the native kidney. Those of ordinary skill in the art will appreciate that other indicators may be suitable for characterizing a regenerated kidney.

Cell Populations

Isolated, heterogeneous populations of kidney cells, and admixtures thereof, enriched for specific bioactive components or cell types and/or depleted of specific inactive or undesired components or cell types for use in the treatment of kidney disease, i.e., providing stabilization and/or improvement and/or regeneration of kidney function, were previously described in U.S. application Ser. No. 12/617,721 filed Nov. 12, 2009, the entire contents of which is incorporated herein by reference. The present invention provides isolated renal cell fractions that lack cellular components as compared to a healthy individual yet retain therapeutic properties, i.e., provide stabilization and/or improvement and/or regeneration of kidney function. The cell populations, cell fractions, and/or admixtures of cells described herein may be derived from healthy individuals, individuals with a kidney disease, or subjects as described herein.

Bioactive Cell Populations

In one aspect, the present invention is based on the surprising finding that certain subfractions of a heterogeneous population of renal cells, enriched for bioactive components and depleted of inactive or undesired components, provide superior therapeutic and regenerative outcomes than the starting population. For example, bioactive components of the invention, e.g., B2, B4, and B3, which are depleted of inactive or undesired components, e.g., B1 and B5, alone or admixed, provide unexpected stabilization and/or improvement and/or regeneration of kidney function.

In another aspect, the present invention is based on the surprising finding that a specific subfraction, B4, depleted of or deficient in one or more cell types, e.g., vascular, endocrine, or endothelial, i.e., B4', retains therapeutic properties, e.g., stabilization and/or improvement and/or regeneration of kidney function, alone or when admixed with other bioactive subfractions, e.g., B2 and/or B3. In a preferred embodiment, the bioactive cell population is B2. In certain embodiments, the B2 cell population is admixed with B4 or B4'. In other embodiments, the B2 cell population is admixed with B3. In other embodiments, the B2 cell population is admixed with both B3 and B4, or specific cellular components of B3 and/or B4.

The B2 cell population is characterized by expression of a tubular cell marker selected from the group consisting of one or more of the following: megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8), and collecting duct marker Aquaporin-4 (Aqp4). B2 is larger and more granulated than B3 and/or B4 and thus having a buoyant density between about 1.045 g/ml and about 1.063 g/ml (rodent), between about 1.045 g/ml and about 1.052 g/ml (human), and between about 1.045 g/ml and about 1.058 g/ml (canine).

The B3 cell population is characterized by the expression of vascular, glomerular and proximal tubular markers with some EPO-producing cells, being of an intermediate size and granularity in comparison to B2 and B4, and thus having a buoyant density between about 1.063 g/ml and about 1.073 g/ml (rodent), between about 1.052 g/ml and about 1.063 g/ml (human), and between about 1.058 g/ml and about 1.063 g/ml (canine). B3 is characterized by expression of markers selected from the group consisting of one or more of the following: aquaporin 7 (Aqp7), FXYD domain-containing ion transport regulator 2 (Fxyd2), solute carrier family 17 (sodium phosphate), member 3 (Slc17a3), solute carrier family 3, member 1 (Slc3a1), claudin 2 (Cldn2), napsin A aspartic peptidase (Napsa), solute carrier family 2 (facilitated glucose transporter), member 2 (Slc2a2), alanyl (membrane) aminopeptidase (Anpep), transmembrane protein 27 (Tmem27), acyl-CoA synthetase medium-chain family member 2 (Acsm2), glutathione peroxidase 3 (Gpx3), fructose-1,6-biphosphatase 1 (Fbp1), and alanine-glyoxylate aminotransferase 2 (Agxt2). B3 is also characterized by the vascular expression marker Platelet endothelial cell adhesion molecule (Pecam) and the glomerular expression marker podocin (Podn).

The B4 cell population is characterized by the expression of a vascular marker set containing one or more of the following: PECAM, VEGF, KDR, HIF1a, CD31, CD146; a glomerular marker set containing one or more of the following: Podocin (Podn), and Nephrin (Neph); and an oxygen-tunable EPO enriched population compared to unfractionated (UNFX), B2 and B3. B4 is also characterized by the expression of one or more of the following markers: chemokine (C-X-C motif) receptor 4 (Cxcr4), endothelin receptor type B (Ednrb), collagen, type V, alpha 2 (Col5a2), Cadherin 5 (Cdh5), plasminogen activator, tissue (Plat), angiopoietin 2 (Angpt2), kinase insert domain protein receptor (Kdr), secreted protein, acidic, cysteine-rich (osteonectin) (Sparc), serglycin (Srgn), TIMP metallopeptidase inhibitor 3 (Timp3), Wilms tumor 1 (Wt1), wingless-type MMTV integration site family, member 4 (Wnt4), regulator of G-protein signaling 4 (Rgs4), Platelet endothelial cell adhesion molecule (Pecam), and Erythropoietin (Epo). B4 is also characterized by smaller, less granulated cells compared to either B2 or B3, with a buoyant density between about 1.073 g/ml and about 1.091 g/ml (rodent), between about 1.063 g/ml and about 1.091 g/mL (human and canine).

The B4' cell population is defined as having a buoyant density of between 1.063 g/mL and 1.091 g/mL and expressing one or more of the following markers: PECAM, vEGF, KDR, HIF1a, podocin, nephrin, EPO, CK7, CK8/18/19. In one embodiment, the B4' cell population is characterized by the expression of a vascular marker set containing one or more of the following: PECAM, vEGF, KDR, HIF1a, CD31, CD146. In another embodiment, the B4' cell population is characterized by the expression of an endocrine marker EPO. In one embodiment, the B4' cell population is characterized by the expression of a glomerular marker set containing one or more of the following: Podocin (Podn), and Nephrin (Neph). In certain embodiments, the B4' cell population is characterized by the expression of a vascular marker set containing one or more of the following: PECAM, vEGF, KDR, HIF1a and by the expression of an endocrine marker EPO. In another embodiment, B4' is also characterized by smaller, less granulated cells compared to either B2 or B3, with a buoyant density between about 1.073 g/ml and about 1.091 g/ml (rodent), between about 1.063 g/ml and about 1.091 g/ml (human and canine).

In one aspect, the present invention provides an isolated, enriched B4' population of human renal cells comprising at least one of erythropoietin (EPO)-producing cells, vascular cells, and glomerular cells having a density between 1.063 g/mL and 1.091 g/mL. In one embodiment, the B4' cell population is characterized by expression of a vascular marker. In certain embodiments, the B4' cell population is not characterized by expression of a glomerular marker. In some embodiments, the B4' cell population is capable of oxygen-tunable erythropoietin (EPO) expression.

In one embodiment, the B4' cell population does not include a B2 cell population comprising tubular cells having a density between 1.045 g/mL and 1.052 g/mL. In another embodiment, the B4' cell population does not include a B1 cell population comprising large granular cells of the collecting duct and tubular system having a density of <1.045 g/ml. In yet another embodiment, the B4' cell population does not include a B5 cell population comprising debris and small cells of low granularity and viability with a density >1.091 g/ml.

In one embodiment, the B4' cell population does not include a B2 cell population comprising tubular cells having a density between 1.045 g/mL and 1.052 g/mL; a B1 cell population comprising large granular cells of the collecting duct and tubular system having a density of <1.045 g/ml; and a B5 cell population comprising debris and small cells of low granularity and viability with a density >1.091 g/ml. In some embodiments, the B4' cell population may be derived from a subject having kidney disease.

In one aspect, the present invention provides an admixture of human renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between about 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiment, the B4' cell population is characterized by expression of a vascular marker. In one embodiment, the B4' cell population is not characterized by expression of a glomerular marker. In certain embodiments, B2 further comprises collecting duct epithelial cells. In one embodiment, the admixture of cells is capable of receptor-mediated albumin uptake. In another embodiment, the admixture of cells is capable of oxygen-tunable erythropoietin (EPO) expression. In one embodiment, the admixture contains HAS-2-expressing cells capable of producing and/or stimulating the production of high-molecular weight species of hyaluronic acid (HA) both in vitro and in vivo. In all embodiments, the first and second cell populations may be derived from kidney tissue or cultured kidney cells.

In one embodiment, the admixture is capable of providing a regenerative stimulus upon in vivo delivery. In other embodiments, the admixture is capable of reducing the decline of, stabilizing, or improving glomerular filtration, tubular resorption, urine production, and/or endocrine function upon in vivo delivery. In one embodiment, the B4' cell population is derived from a subject having kidney disease.

In one aspect, the present invention provides an isolated, enriched B4' population of human renal cells comprising at least one of erythropoietin (EPO)-producing cells, vascular cells, and glomerular cells having a density between 1.063 g/mL and 1.091 g/mL. In one embodiment, the B4' cell population is characterized by expression of a vascular marker. In certain embodiments, the B4' cell population is not characterized by expression of a glomerular marker. The glomerular marker that is not expressed may be podocin (see Example 7). In some embodiments, the B4' cell population is capable of oxygen-tunable erythropoietin (EPO) expression.

In one embodiment, the B4' cell population does not include a B2 cell population comprising tubular cells having a density between 1.045 g/mL and 1.052 g/mL. In another embodiment, the B4' cell population does not include a B1 cell population comprising large granular cells of the collecting duct and tubular system having a density of <1.045 g/ml. In yet another embodiment, the B4' cell population does not include a B5 cell population comprising debris and small cells of low granularity and viability with a density >1.091 g/ml.

In one embodiment, the B4' cell population does not include a B2 cell population comprising tubular cells having a density between 1.045 g/mL and 1.052 g/mL; a B1 cell population comprising large granular cells of the collecting duct and tubular system having a density of <1.045 g/ml; and a B5 cell population comprising debris and small cells of low granularity and viability with a density >1.091 g/ml.

In some embodiments, the B4' cell population may be derived from a subject having kidney disease. In one aspect, the present invention provides an admixture of human renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between about 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiment, the B4' cell population is characterized by expression of a vascular marker. In one embodiment, the B4' cell population is not characterized by expression of a glomerular marker. In certain embodiments, B2 further comprises collecting duct epithelial cells. In one embodiment, the admixture of cells is capable of receptor-mediated albumin uptake. In another embodiment, the admixture of cells is capable of oxygen-tunable erythropoietin (EPO) expression. In one embodiment, the admixture contains HAS-2-expressing cells capable of producing and/or stimulating the production of high-molecular weight species of hyaluronic acid (HA) both in vitro and in vivo. In all embodiments, the first and second cell populations may be derived from kidney tissue or cultured kidney cells.

In one embodiment, the admixture is capable of providing a regenerative stimulus upon in vivo delivery. In other embodiments, the admixture is capable of reducing the decline of, stabilizing, or improving glomerular filtration, tubular resorption, urine production, and/or endocrine function upon in vivo delivery. In one embodiment, the B4' cell population is derived from a subject having kidney disease.

In a preferred embodiment, the admixture comprises B2 in combination with B3 and/or B4. In another preferred embodiment, the admixture comprises B2 in combination with B3 and/or B4'. In other preferred embodiments, the admixture consists of or consists essentially of (i) B2 in combination with B3 and/or B4; or (ii) B2 in combination with B3 and/or B4'.

The admixtures that contain a B4' cell population may contain B2 and/or B3 cell populations that are also obtained from a non-healthy subject. The non-healthy subject may be the same subject from which the B4' fraction was obtained.

In contrast to the B4' cell population, the B2 and B3 cell populations obtained from non-healthy subjects are typically not deficient in one or more specific cell types as compared to a starting kidney cell population derived from a healthy individual.

Hyaluronic Acid Production by B2 and B4

Hyaluronan (also called hyaluronic acid or hyaluronate) is a glycosaminoglycan (GAG), which consists of a regular repeating sequence of non-sulfated disaccharide units, specifically N-acetylglucosamine and glucuronic acid. Its molecular weight can range from 400 daltons (the disaccharide) to over a million daltons. It is found in variable amounts in all tissues, such as the skin, cartilage, and eye, and in most if not all fluids in adult animals. It is especially abundant in early embryos. Space created by hyaluronan, and indeed GAGs in general, permit it to play a role in cell migration, cell attachment, during wound repair, organogenesis, immune cell adhesion, activation of intracellular signalling, as well as tumour metastasis. These roles are mediated by specific protein and proteoglycan binding to Hyaluronan. Cell motility and immune cell adhesion is mediated by the cell surface receptor RHAMM (Receptor for Hyaluronan-Mediated Motility; Hardwick et al., 1992) and CD44 (Jalkenan et al., 1987; Miyake et al., 1990). Hyaluronan is synthesized directly at the inner membrane of the cell surface with the growing polymer extruded through the membrane to the outside of the cell as it is being synthesized. Synthesis is mediated by a single protein enzyme, hyaluronan synthetase (HAS) whose gene family consists of at least 3 members.

It has recently been shown that hyaluronic acid interacts with CD44, and such interactions may, among other actions, recruit non-resident cells (such as mesenchymal stem cells (MSCs)) to injured renal tissue and enhance renal regeneration (*Kidney International* (2007) 72, 430-441).

Unexpectedly, it has been found that the B2 and B4 cell preparations are capable of expressing higher molecular weight species of hyaluronic acid (HA) both in vitro and in vivo, through the actions of hyaluronic acid synthase-2 (HAS-2)—a marker that is enriched more specifically in the B2 cell population. Treatment with B2 in a 5/6 Nx model was shown to reduce fibrosis, concomitant with strong expression HAS-2 expression in vivo and the expected production of high-molecular-weight HA within the treated tissue. Notably, the 5/6 Nx model left untreated resulted in fibrosis with limited detection of HAS-2 and little production of high-molecular-weight HA. Without wishing to be bound by theory, it is hypothesized that this anti-inflammatory high-molecular weight species of HA produced predominantly by B2 (and to some degree by B4) acts synergystically with the cell preparations in the reduction of renal fibrosis and in the aid of renal regeneration. Accordingly, the instant invention includes delivery of the cellular prototypes of the invention in a biomaterial comprising hyaluronic acid. Also comtemplated by the instant invention is the provision of a biomaterial component of the regenerative stimulus via direct production or stimulation of production by the implanted cells.

In one aspect, the present invention provides isolated, heterogeneous populations of EPO-producing kidney cells for use in the treatment of kidney disease, anemia and/or EPO deficiency in a subject in need. In one embodiment, the cell populations are derived from a kidney biopsy. In another embodiment, the cell populations are derived from whole kidney tissue. In one other embodiment, the cell populations are derived from in vitro cultures of mammalian kidney cells, established from kidney biopsies or whole kidney tissue. In all embodiments, these populations are unfractionated cell populations, also referred to herein as non-enriched cell populations.

In another aspect, the present invention provides isolated populations of erythropoietin (EPO)-producing kidney cells that are further enriched such that the proportion of EPO-producing cells in the enriched subpopulation is greater relative to the proportion of EPO-producing cells in the starting or initial cell population. In one embodiment, the enriched EPO-producing cell fraction contains a greater proportion of interstitial fibroblasts and a lesser proportion of tubular cells relative to the interstitial fibroblasts and tubular cells contained in the unenriched initial population. In certain embodiments, the enriched EPO-producing cell fraction contains a greater proportion of glomerular cells and vascular cells and a lesser proportion of collecting duct cells relative to the glomerular cells, vascular cells and collecting duct cells contained in the unenriched initial population. In such embodiments, these populations are referred to herein as the "B4" cell population.

In another aspect, the present invention provides an EPO-producing kidney cell population that is admixed with one or more additional kidney cell populations. In one embodiment, the EPO-producing cell population is a first cell population enriched for EPO-producing cells, e.g., B4. In another embodiment, the EPO-producing cell population is a first cell population that is not enriched for EPO-producing cells, e.g., B2. In another embodiment, the first cell population is admixed with a second kidney cell population. In some embodiments, the second cell population is enriched for tubular cells, which may be demonstrated by the presence of a tubular cell phenotype. In another embodiment, the tubular cell phenotype may be indicated by the presence of one tubular cell marker. In another embodiment, the tubular cell phenotype may be indicated by the presence of one or more tubular cell markers. The tubular cell markers include, without limitation, megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8). In another embodiment, the first cell population is admixed with at least one of several types of kidney cells including, without limitation, interstitium-derived cells, tubular cells, collecting duct-derived cells, glomerulus-derived cells, and/or cells derived from the blood or vasculature. The EPO-producing kidney cell population may contain B4 or B4' in the form of an admixture with B2 and/or B3, or in the form of an enriched cell population, e.g., B2+B3+B4/B4'.

In one aspect, the EPO-producing kidney cell populations of the present invention are characterized by EPO expression and bioresponsiveness to oxygen, such that a reduction in the oxygen tension of the culture system results in an induction in the expression of EPO. In one embodiment, the EPO-producing cell populations are enriched for EPO-producing cells. In one embodiment, the EPO expression is induced when the cell population is cultured under conditions where the cells are subjected to a reduction in available oxygen levels in the culture system as compared to a cell population cultured at normal atmospheric (~21%) levels of available oxygen. In one embodiment, EPO-producing cells cultured in lower oxygen conditions express greater levels of EPO relative to EPO-producing cells cultured at normal oxygen conditions. In general, the culturing of cells at reduced levels of available oxygen (also referred to as hypoxic culture conditions) means that the level of reduced oxygen is reduced relative to the culturing of cells at normal atmospheric levels of available oxygen (also referred to as normal or normoxic culture conditions). In one embodiment, hypoxic cell culture conditions include culturing cells at about less than 1% oxygen, about less than 2% oxygen, about less than 3% oxygen, about less than 4% oxygen, or about less than 5% oxygen. In another embodiment, normal or normoxic culture conditions include culturing cells at about 10% oxygen, about 12% oxygen, about 13% oxygen, about 14% oxygen, about 15% oxygen, about 16% oxygen, about 17% oxygen, about 18% oxygen, about 19% oxygen, about 20% oxygen, or about 21% oxygen.

In one other embodiment, the induction or increased expression of EPO is obtained and can be observed by culturing cells at about less than 5% available oxygen and comparing EPO expression levels to cells cultured at atmospheric (about 21%) oxygen. In another embodiment, the induction of EPO is obtained in a culture of cells capable of expressing EPO by a method that includes a first culture phase in which the culture of cells is cultivated at atmospheric oxygen (about 21%) for some period of time and a second culture phase in which the available oxygen levels are reduced and the same cells are cultured at about less than 5% available oxygen. In another embodiment, the EPO expression that is responsive to hypoxic conditions is regulated by HIF1α. Those of ordinary skill in the art will appreciate that other oxygen manipulation culture conditions known in the art may be used for the cells described herein.

In one aspect, the enriched populations of EPO-producing mammalian cells are characterized by bio-responsiveness (e.g., EPO expression) to perfusion conditions. In one embodiment, the perfusion conditions include transient, intermittent, or continuous fluid flow (perfusion). In one embodiment, the EPO expression is mechanically-induced when the media in which the cells are cultured is intermittently or continuously circulated or agitated in such a manner that dynamic forces are transferred to the cells via the flow. In one embodiment, the cells subjected to the transient, intermittent, or continuous fluid flow are cultured in such a manner that they are present as three-dimensional structures in or on a material that provides framework and/or space for such three-dimensional structures to form. In one embodiment, the cells are cultured on porous beads and subjected to intermittent or continuous fluid flow by means of a rocking platform, orbiting platform, or spinner flask. In another embodiment, the cells are cultured on three-dimensional scaffolding and placed into a device whereby the scaffold is stationary and fluid flows directionally through or across the scaffolding. Those of ordinary skill in the art will appreciate that other perfusion culture conditions known in the art may be used for the cells described herein.

Inactive Cell Populations

As described herein, the present invention is based, in part, on the surprising finding that certain subfractions of a heterogeneous population of renal cells, enriched for bioactive components and depleted of inactive or undesired components, provide superior therapeutic and regenerative outcomes than the starting population. In preferred embodiments, the cellular populations of the instant invention are depleted of B1 and/or B5 cell populations. For instance, the following may be depleted of B1 and/or B5: admixtures of two or more of B2, B3, and B4'; an enriched cell population of B2, B3, and B4'.

The B1 cell population comprises large, granular cells of the collecting duct and tubular system, with the cells of the population having a buoyant density less than about 1.045 g/m. The B5 cell population is comprised of debris and small cells of low granularity and viability and having a buoyant density greater than about 1.091 g/ml.

Methods of Isolating and Culturing Cell Populations

The present invention, in one aspect, provides methods for separating and isolating renal cellular components, e.g., enriched cell populations, for therapeutic use, including the treatment of kidney disease, anemia, EPO deficiency, tubular transport deficiency, and glomerular filtration deficiency. In one embodiment, the cell populations are isolated from freshly digested, i.e., mechanically or enzymatically digested, kidney tissue or from heterogeneous in vitro cultures of mammalian kidney cells.

It has unexpectedly been discovered that culturing heterogeneous mixtures of renal cells in hypoxic culture conditions prior to separation on a density gradient provides for enhanced distribution and composition of cells in both B4, including B4', and B2 and/or B3 fractions. The enrichment of oxygen-dependent cells in B4 from B2 was observed for renal cells isolated from both diseased and non-diseased kidneys. Without wishing to be bound by theory, this may be due to one or more of the following phenomena: 1) selective survival, death, or proliferation of specific cellular components during the hypoxic culture period; 2) alterations in cell granularity and/or size in response to the hypoxic culture, thereby effecting alterations in buoyant density and subsequent localization during density gradient separation; and 3) alterations in cell gene/protein expression in response to the hypoxic culture period, thereby resulting in differential characteristics of the cells within any given fraction of the gradient. Thus, in one embodiment, the cell populations enriched for tubular cells, e.g., B2, are hypoxia-resistant.

Exemplary techniques for separating and isolating the cell populations of the invention include separation on a density gradient based on the differential specific gravity of different cell types contained within the population of interest. The specific gravity of any given cell type can be influenced by the degree of granularity within the cells, the intracellular volume of water, and other factors. In one aspect, the present invention provides optimal gradient conditions for isolation of the cell preparations of the instant invention, e.g., B2 and B4, including B4', across multiple species including, but not limited to, human, canine, and rodent. In a preferred embodiment, a density gradient is used to obtain a novel enriched population of tubular cells fraction, i.e., B2 cell population, derived from a heterogeneous population of renal cells. In one embodiment, a density gradient is used to obtain a novel enriched population of EPO-producing cells fraction, i.e., B4 cell population, derived from a heterogeneous population of renal cells. In other embodiments, a density gradient is used to obtain enriched subpopulations of tubular cells, glomerular cells, and endothelial cells of the kidney. In one embodiment, both the EPO-producing and the tubular cells are separated from the red blood cells and cellular debris. In one embodiment, the EPO-producing, glomerular, and vascular cells are separated from other cell types and from red blood cells and cellular debris, while a subpopulation of tubular cells and collecting duct cells are concomitantly separated from other cell types and from red blood cells and cellular debris. In one other embodiment, the endocrine, glomerular, and/or vascular cells are separated from other cell types and from red blood cells and cellular debris, while a subpopulation of tubular cells and collecting duct cells are concomitantly separated from other cell types and from red blood cells and cellular debris.

The instant invention generated the novel cell populations by using, in part, the OPTIPREP® (Axis-Shield) density gradient medium, comprising 60% nonionic iodinated compound iodixanol in water, based on certain key features described below. One of skill in the art, however, will recognize that any density gradient or other means, e.g., immunological separation using cell surface markers known in the art, comprising necessary features for isolating the cell populations of the instant invention may be used in accordance with the invention. It should also be recognized by one skilled in the art that the same cellular features that contribute to separation of cellular subpopulations via density gradients (size and granularity) can be exploited to separate cellular subpopulations via flow cytometry (forward scatter=a reflection of size via flow cytometry, and side scatter=a reflection of granularity). Importantly, the density gradient medium should have low toxicity towards the specific cells of interest. While the density gradient medium should have low toxicity toward the specific cells of interest, the instant invention contemplates the use of gradient mediums which play a role in the selection process of the cells of interest. Without wishing to be bound by theory, it appears that the cell populations of the instant invention recovered by the gradient comprising iodixanol are iodixanol-resistant, as there is an appreciable loss of cells between the loading and recovery steps, suggesting that exposure to iodixanol under the conditions of the gradient leads to elimination of certain cells. The cells appearing in the specific bands after the iodixanol gradient are resistant to any untoward effects of iodixanol and/or density gradient exposure. Accordingly, the present invention also contemplates the use of additional contrast medias which are mild to moderate nephrotoxins in the isolation and/or selection of the cell populations of the instant invention. In addition, the density gradient medium should also not bind to proteins in human plasma or adversely affect key functions of the cells of interest.

In another aspect, the present invention provides methods of enriching and/or depleting kidney cell types using fluorescent activated cell sorting (FACS). In one embodiment, kidney cell types may be enriched and/or depleted using BD FACSAria™ or equivalent.

In another aspect, the present invention provides methods of enriching and/or depleting kidney cell types using magnetic cell sorting. In one embodiment, kidney cell types may be enriched and/or depleted using the Miltenyi autoMACS® system or equivalent.

In another aspect, the present invention provides methods of three-dimensional culturing of the renal cell populations. In one aspect, the present invention provides methods of culturing the cell populations via continuous perfusion. In one embodiment, the cell populations cultured via three-dimensional culturing and continuous perfusion demonstrate greater cellularity and interconnectivity when compared to cell populations cultured statically. In another embodiment, the cell populations cultured via three dimensional culturing and continuous perfusion demonstrate greater expression of EPO, as well as enhanced expression of renal tubule-associate genes such as e-cadherin when compared to static cultures of such cell populations.

In yet another embodiment, the cell populations cultured via continuous perfusion demonstrate greater levels of glucose and glutamine consumption when compared to cell populations cultured statically.

As described herein (including Example 3), low or hypoxic oxygen conditions may be used in the methods to prepare the cell populations of the present invention. However, the methods of the present invention may be used without the step of low oxygen conditioning. In one embodiment, normoxic conditions may be used.

Those of ordinary skill in the art will appreciate that other methods of isolation and culturing known in the art may be used for the cells described herein.

Biomaterials (Polymeric Matrices or Scaffolds)

As described in Bertram et al. U.S. Published Application 20070276507 (incorporated herein by reference in its entirety), polymeric matrices or scaffolds may be shaped into any number of desirable configurations to satisfy any number of overall system, geometry or space restrictions. In one embodiment, the matrices or scaffolds of the present invention may be three-dimensional and shaped to conform to the dimensions and shapes of an organ or tissue structure. For example, in the use of the polymeric scaffold for treating kidney disease, anemia, EPO deficiency, tubular transport deficiency, or glomerular filtration deficiency, a three-dimensional (3-D) matrix may be used. A variety of differently shaped 3-D scaffolds may be used. Naturally, the polymeric matrix may be shaped in different sizes and shapes to conform to differently sized patients. The polymeric matrix may also be shaped in other ways to accommodate the special needs of the patient. In another embodiment, the polymeric matrix or scaffold may be a biocompatible, porous polymeric scaffold. The scaffolds may be formed from a variety of synthetic or naturally-occurring materials including, but not limited to, open-cell polylactic acid (OPLA®), cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, collagens, laminins, fibronectin, silk, elastin, alginate, hyaluronic acid, agarose, or copolymers or physical blends thereof. Scaffolding configurations may range from liquid hydrogel suspensions to soft porous scaffolds to rigid, shape-holding porous scaffolds.

Hydrogels may be formed from a variety of polymeric materials and are useful in a variety of biomedical applications. Hydrogels can be described physically as three-dimensional networks of hydrophilic polymers. Depending on the type of hydrogel, they contain varying percentages of water, but altogether do not dissolve in water. Despite their high water content, hydrogels are capable of additionally binding great volumes of liquid due to the presence of hydrophilic residues. Hydrogels swell extensively without changing their gelatinous structure. The basic physical features of hydrogel can be specifically modified, according to the properties of the polymers used and the additional special equipments of the products.

Preferably, the hydrogel is made of a polymer, a biologically derived material, a synthetically derived material or combinations thereof, that is biologically inert and physiologically compatible with mammalian tissues. The hydrogel material preferably does not induce an inflammatory response. Examples of other materials which can be used to form a hydrogel include (a) modified alginates, (b) polysaccharides (e.g. gellan gum and carrageenans) which gel by exposure to monovalent cations, (c) polysaccharides (e.g., hyaluronic acid) that are very viscous liquids or are thixotropic and form a gel over time by the slow evolution of structure, and (d) polymeric hydrogel precursors (e.g., polyethylene oxide-polypropylene glycol block copolymers and proteins). U.S. Pat. No. 6,224,893 B1 provides a detailed description of the various polymers, and the chemical properties of such polymers, that are suitable for making hydrogels in accordance with the present invention.

Scaffolding or biomaterial characteristics may enable cells to attach and interact with the scaffolding or biomaterial material, and/or may provide porous spaces into which cells can be entrapped. In one embodiment, the porous scaffolds or biomaterials of the present invention allow for the addition or deposition of one or more populations or admixtures of cells on a biomaterial configured as a porous scaffold (e.g., by attachment of the cells) and/or within the pores of the scaffold (e.g., by entrapment of the cells). In another embodiment, the scaffolds or biomaterials allow or promote for cell:cell and/or cell:biomaterial interactions within the scaffold to form constructs as described herein.

In one embodiment, the biomaterial used in accordance with the present invention is comprised of hyaluronic acid (HA) in hydrogel form, containing HA molecules ranging in size from 5.1 kDA to $>2\times10^6$ kDa. In another embodiment, the biomaterial used in accordance with the present invention is comprised of hyaluronic acid in porous foam form, also containing HA molecules ranging in size from 5.1 kDA to $>2\times10^6$ kDa. In yet another embodiment, the biomaterial used in accordance with the present invention is comprised of a poly-lactic acid (PLA)-based foam, having an open-cell structure and pore size of about 50 microns to about 300 microns. In yet another embodiment, the specific cell populations, preferentially B2 but also B4, provide directly and/or stimulate synthesis of high molecular weight Hyaluronic Acid through Hyaluronic Acid Synthase-2 (HAS-2), especially after intra-renal implantation.

Those of ordinary skill in the art will appreciate that other types of synthetic or naturally-occurring materials known in the art may be used to form scaffolds as described herein.

In one aspect, the present invention provides constructs as described herein made from the above-referenced scaffolds or biomaterials.

Constructs

In one aspect, the invention provides implantable constructs having one or more of the cell populations described herein for the treatment of kidney disease, anemia, or EPO deficiency in a subject in need. In one embodiment, the construct is made up of a biocompatible material or biomaterial, scaffold or matrix composed of one or more synthetic or naturally-occurring biocompatible materials and one or more cell populations or admixtures of cells described herein deposited on or embedded in a surface of the scaffold by attachment and/or entrapment. In certain embodiments, the construct is made up of a biomaterial and one or more cell populations or admixtures of cells described herein coated with, deposited on, deposited in, attached to, entrapped in, embedded in, or combined with the biomaterial component(s). Any of the cell populations described herein, including enriched cell populations or admixtures thereof, may be used in combination with a matrix to form a construct.

In another embodiment, the deposited cell population or cellular component of the construct is a first kidney cell population enriched for oxygen-tunable EPO-producing cells. In another embodiment, the first kidney cell population contains glomerular and vascular cells in addition to the oxygen-tunable EPO-producing cells. In one embodiment, the first kidney cell population is a B4' cell population. In one other embodiment, the deposited cell population or cellular component(s) of the construct includes both the first enriched renal cell population and a second renal cell population. In some embodiments, the second cell population is not enriched for oxygen-tunable EPO producing cells. In another embodiment, the second cell population is enriched for renal tubular cells. In another embodiment, the second cell population is enriched for renal tubular cells and contains collecting duct epithelial cells. In other embodiments, the renal tubular cells are characterized by the expression of one or more tubular cell markers that may include, without limitation, megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8).

In one embodiment, the cell populations deposited on or combined with biomaterials or scaffolds to form constructs of the present invention are derived from a variety of sources, such as autologous sources. Non-autologous sources are also suitable for use, including without limitation, allogeneic, or syngeneic (autogeneic or isogeneic) sources.

Those of ordinary skill in the art will appreciate there are several suitable methods for depositing or otherwise combining cell populations with biomaterials to form a construct.

In one aspect, the constructs of the present invention are suitable for use in the methods of use described herein. In one embodiment, the constructs are suitable for administration to a subject in need of treatment for a kidney disease of any etiology, anemia, or EPO deficiency of any etiology. In other embodiments, the constructs are suitable for administration to a subject in need of an improvement in or restoration of erythroid homeostasis. In another embodiment, the constructs are suitable for administration to a subject in need of improved kidney function.

In yet another aspect, the present invention provides a construct for implantation into a subject in need of improved kidney function comprising: a) a biomaterial comprising one or more biocompatible synthetic polymers or naturally-occurring proteins or peptides; and b) an admixture of mammalian renal cells derived from a subject having kidney disease comprising a first cell population, B2, comprising an isolated, enriched population of tubular cells having a density between 1.045 g/mL and 1.052 g/mL and a second cell population, B4', comprising erythropoietin (EPO)-producing cells and vascular cells but depleted of glomerular cells having a density between 1.063 g/mL and 1.091 g/mL, coated with, deposited on or in, entrapped in, suspended in, embedded in and/or otherwise combined with the biomaterial. In certain embodiments, the admixture does not include a B1 cell population comprising large granular cells of the collecting duct and tubular system having a density of <1.045 g/ml, or a B5 cell population comprising debris and small cells of low granularity and viability with a density >1.091 g/ml.

In one embodiment, the construct includes a B4' cell population which is characterized by expression of a vascular marker. In some embodiments, the B4' cell population is not characterized by expression of a glomerular marker. In certain embodiments, the admixture is capable of oxygen-tunable erythropoietin (EPO) expression. In all embodiments, the admixture may be derived from mammalian kidney tissue or cultured kidney cells.

In one embodiment, the construct includes a biomaterial configured as a three-dimensional (3-D) porous biomaterial suitable for entrapment and/or attachment of the admixture. In another embodiment, the construct includes a biomaterial configured as a liquid or semi-liquid gel suitable for embedding, attaching, suspending, or coating mammalian cells. In yet another embodiment, the construct includes a biomaterial configured comprised of a predominantly high-molecular weight species of hyaluronic acid (HA) in hydrogel form. In another embodiment, the construct includes a biomaterial comprised of a predominantly high-molecular weight species of hyaluronic acid in porous foam form. In yet another embodiment, the construct includes a biomaterial comprised of a poly-lactic acid-based foam having pores of between about 50 microns to about 300 microns. In still another embodiment, the construct includes one or more cell populations that may be derived from a kidney sample that is autologous to the subject in need of improved kidney function. In certain embodiments, the sample is a kidney biopsy. In some embodiments, the subject has a kidney disease. In yet other embodiments, the cell population is derived from a non-autologous kidney sample. In one embodiment, the construct provides erythroid homeostasis.

Secreted Products

In one other aspect, the present invention concerns products secreted from an enriched renal cell population or admixture of enriched renal cell populations, as described herein. In one embodiment, the products include one or more of the following: paracrine factors, endocrine factors, juxtacrine factors, and vesicles. The vesicles may include one or more of the following: paracrine factors, endocrine factors, juxtacrine factors, microvesicles, exosomes, and RNA. The secreted products may also include products that are not within microvesicles including, without limitation, paracrine factors, endocrine factors, juxtacrine factors, and RNA. For example, extracellular miRNAs have been detected externally to vesicles (Wang et al., *Nuc Acids Res* 2010, 1-12 doi:10.1093/nar/gkq601, Jul. 7, 2010). The secreted products may also be referred to as cell-derived products, e.g., cell-derived vesicles.

In one other embodiment, the secreted products may be part of a vesicle derived from renal cells. The vesicles may be capable of delivering the factors to other destinations. In one embodiment, the vesicles are secreted vesicles. Several types of secreted vesicles are contemplated including, without limitation, exosomes, microvesicles, ectosomes, membrane particles, exosome-like vesicles, and apoptotic vesicles (Thery et al. 2010. Nat. Rev. Immunol. 9:581-593). In one embodiment, the secreted vesicles are exosomes. In one other embodiment, the secreted vesicles are microvesicles. In one other embodiment, the secreted vesicles contain or comprise one or more cellular components. The components may be one or more of the following: membrane lipids, RNA, proteins, metabolites, cytosolic components, and any combination thereof. In a preferred embodiment, the secreted vesicles comprise, consist of, or consist essentially of microRNAs. Preferably, the miRNAs are human miRNAs. In one embodiment, one or more miRNAs are selected from the group consisting of miR-30b-5p, miR-449a, miR-146a, miR-130a, miR-23b, miR-21, miR-124, and miR-151. In one other embodiment, one or more miRNAs may be selected from the group consisting of let-7a-1; let-7a-2; let-7a-3; let-7b; let-7c; let-7d; let-7e; let-7f-1; let-7f-2; let-7g; let-7i; mir-1-1; mir-1-2; mir-7-1; mir-7-2; mir-7-3; mir-9-1; mir-9-2; mir-9-3; mir-10a; mir-10b; mir-15a; mir-15b; mir-16-1; mir-16-2; mir-17; mir-18a; mir-18b; mir-19a; mir-19b-1; mir-19b-2; mir-20a; mir-20b; mir-21; mir-22; mir-23a; mir-23b; mir-23c; mir-24-1; mir-24-2; mir-25; mir-26a-1; mir-26a-2; mir-26b; mir-27a; mir-27b; mir-28; mir-29a; mir-29b-1; mir-29b-2; mir-29c; mir-30a; mir-30b; mir-30c-1; mir-30c-2; mir-30d; mir-30e; mir-31; mir-32; mir-33a; mir-33b; mir-34a; mir-34b; mir-34c; mir-92a-1; mir-92a-2; mir-92b; mir-93; mir-95; mir-96; mir-98; mir-99a mir-99b; mir-100; mir-101-1; mir-101-2; mir-103-1; mir-103-1-as; mir-103-2; mir-103-2-as; mir-105-1; mir-105-2; mir-106a; mir-106b; mir-107; mir-122; mir-124-1; mir-124-2; mir-124-3; mir-125a; mir-125b-1; mir-125b-2; mir-126; mir-127; mir-128-1; mir-128-2; mir-129-1; mir-129-2; mir-130a; mir-130b; mir-132; mir-132; mir-133a-1; mir-133a-2; mir-133b; mir-134; mir-135a-1; mir-135a-2; mir-135b; mir-136 MI101351120; mir-137; mir-138-1; mir-138-2; mir-139; mir-140; mir-141; mir-142; mir-143; mir-144; mir-145; mir-146a; mir-146b; mir-147; mir-147b; mir-148a; mir-148b; mir-149; mir-150; mir-151; mir-152; mir-153-1; mir-153-2; mir-154; mir-155; mir-181a-1; mir-181a-2; mir-181b-1; mir-181b-2; mir-181c; mir-181d; mir-182; mir-183; mir-184; mir-185; mir-186; mir-187; mir-188; mir-190; mir-190b; mir-191; mir-192; mir-193a; mir-193b; mir-194-1; mir-194-2; mir-195; mir-196a-1; mir-196a-2; mir-196b; mir-197; mir-198; mir-199a-1; mir-199a-2; mir-199b; mir-200a; mir-200b; mir-200c; mir-202; mir-203; mir-204; mir-205; mir-206; mir-208a; mir-208b; mir-210; mir-211; mir-212; mir-214; mir-215; mir-216a; mir-216b; mir-217; mir-218-1; mir-218-2; mir-219-1; mir-219-2; mir-221; mir-222; mir-223; mir-224; mir-296; mir-297; mir-298; mir-299; mir-300; mir-301a; mir-301b; mir-302a; mir-302b; mir-302c; mir-302d; mir-302e; mir-302f; mir-320a; mir-320b-1; mir-320b-2; mir-320c-1; mir-320c-2; mir-320d-1; mir-320d-2; mir-320e; mir-323; mir-323b; mir-324; mir-325; mir-326; mir-328; mir-329-1; mir-329-2; mir-330; mir-331; mir-335; mir-337; mir-338; mir-339; mir-340; mir-342; mir-345; mir-346; mir-361; mir-362; mir-363; mir-365-1; mir-365-2; mir-367; mir-369; mir-370; mir-37; mir-372; mir-373; mir-374a; mir-374b; mir-374c; mir-375; mir-376a-1; mir-376a-2; mir-376b; mir-376c; mir-377; mir-378; mir-378b; mir-378c; mir-379; mir-380; mir-381; mir-382; mir-383; mir-384; mir-409; mir-410; mir-411; mir-412; mir-421; mir-422a; mir-423; mir-424; mir-425; mir-429; mir-431; mir-432; mir-433; mir-448; mir-449a; mir-449b; mir-449c; mir-450a-1; mir-450a-2; mir-450b; mir-451; mir-452; mir-454; mir-455; mir-466; mir-483; mir-484; mir-485; mir-486; mir-487a; mir-487b; mir-488; mir-489; mir-490; mir-491; mir-492; mir-493; mir-494; mir-495; mir-496; mir-497; mir-498; mir-499; mir-500a; mir-500b; mir-501; mir-502; mir-503; mir-504; mir-505; mir-506; mir-507; mir-508; mir-509-1; mir-509-2; mir-509-3; mir-510; mir-511-1; mir-511-2; mir-512-1; mir-512-2; mir-513a-1; mir-513a-2; mir-513b; mir-513c; mir-514-1; mir-514-2; mir-514-3; mir-514b; mir-515-1; mir-515-2; mir-516a-1; mir-516a-2; mir-516b-1; mir-516b-2; mir-517a; mir-517b; mir-517c; mir-518a-1; mir-518a-2; mir-518b; mir-518c; mir-518d; mir-518e; mir-518f; mir-519a-1; mir-519a-2; mir-519b; mir-519c; mir-519d; mir-519e; mir-520a; mir-520b; mir-520c; mir-520d; mir-520e; mir-520f; mir-520g; mir-520h; mir-521-1; mir-521-2; mir-522; mir-523; mir-524; mir-525; mir-526a-1; mir-526a-2; mir-526b; mir-527; mir-532; mir-539; mir-541; mir-542; mir-543; mir-544; mir-544b; mir-545; mir-548a-1; mir-548a-2; mir-548a-3; mir-548ah-1; mir-548ah-2; mir-548b; mir-548c; mir-548d-1; mir-548d-2; mir-548e; mir-548f-1; mir-548f-2; mir-548f-3; mir-548f-4; mir-548f-5; mir-548g; mir-548h-1; mir-548h-2; mir-548h-3; mir-548h-4; mir-548i-1; mir-548i-2; mir-548i-3; mir-548i-4; mir-548j; mir-548k; mir-548l; mir-548m; mir-548n; mir-548o; mir-548p; mir-548s; mir-548t; mir-548u; mir-548v; mir-548w; mir-548x; mir-548y; mir-548z; mir-549; mir-550a-1; mir-550a-2; mir-550b-1; mir-550b-2; mir-551a; mir-551b; mir-552; mir-553; mir-554; mir-555; mir-556; mir-557; mir-558; mir-559; mir-561; mir-562; mir-563; mir-564; mir-566; mir-567; mir-568; mir-569; mir-570; mir-571; mir-572; mir-573; mir-574; mir-575; mir-576; mir-577; mir-578; mir-579; mir-580; mir-581; mir-582; mir-583; mir-584; mir-585; mir-586; mir-587; mir-588; mir-589; mir-590; mir-591; mir-592; mir-593; mir-595; mir-596; mir-597; mir-598; mir-599; mir-600; mir-601; mir-602; mir-603; mir-604; mir-605; mir-606; mir-607; mir-608; mir-609; mir-610; mir-611; mir-612; mir-613; mir-614; mir-615; mir-616; mir-617; mir-618; mir-619; mir-620; mir-621; mir-622; mir-623; mir-624; mir-625; mir-626; mir-627; mir-628; mir-629; mir-630; mir-631; mir-632; mir-633; mir-634; mir-635; mir-636; mir-637; mir-638; mir-639; mir-640; mir-641; mir-642a; mir-642b; mir-643; mir-644; mir-645; mir-646; mir-647; mir-648; mir-649; mir-650; mir-651; mir-652; mir-653; mir-654; mir-655; mir-656; mir-657; mir-658; mir-659; mir-660; mir-661; mir-662; mir-663; mir-663b; mir-664; mir-665; mir-668; mir-670; mir-671; mir-675; mir-676; mir-708; mir-711; mir-718; mir-720; mir-744; mir-758; mir-759; mir-760; mir-761; mir-762; mir-764; mir-765; mir-766; mir-767; mir-769; mir-770; mir-802; mir-873; mir-874; mir-875; mir-876; mir-877; mir-885; mir-887; mir-888; mir-889; mir-890; mir-891a; mir-891b; mir-892a; mir-892b; mir-920; mir-921; mir-922; mir-924; mir-933; mir-934; mir-935; mir-936; mir-937; mir-938; mir-939; mir-940; mir-941-1; mir-941-2; mir-941-3; mir-941-4; mir-942; mir-942; mir-943; mir-944; mir-1178; mir-1179; mir-1180; mir-1181; mir-1182; mir-1183; mir-1184-1; mir-1184-2; mir-1184-3; mir-1185-1; mir-1185-2; mir-1193; mir-1197; mir-1200; mir-1202; mir-1203; mir-1204; mir-1205; mir-1206; mir-1207; mir-1208; mir-1224; mir-1225; mir-1226; mir-1227; mir-1228; mir-1229; mir-1231; mir-1233-1; mir-1233-2; mir-1234; mir-1236; mir-1237; mir-1238; mir-1243; mir-1244-1; mir-1244-2; mir-1244-3; mir-1245; mir-1246; mir-1247; mir-1248; mir-1249; mir-1250; mir-1251; mir-1252; mir-1253; mir-1254; mir-1255a; mir-1255b-1; mir-1255b-2; mir-1256; mir-1257; mir-1258; mir-1260; mir-1260b; mir-1261; mir-1262; mir-1263; mir-1264; mir-1265; mir-1266; mir-1267; mir-1268; mir-1269; mir-1270-1; mir-1270-2; mir-1271; mir-1272; mir-1273; mir-1273c; mir-1273d; mir-1273e; mir-1274a; mir-1274b; mir-1275; mir-1276; mir-1277; mir-1278; mir-1279; mir-1280; mir-1281; mir-1282; mir-1283-1; mir-1283-2; mir-1284; mir-1285-1; mir-1285-2; mir-1286; mir-1287; mir-1288; mir-1289-1; mir-1289-2; mir-1290; mir-1291; mir-1292; mir-1293; mir-1294; mir-1295; mir-1296; mir-1297; mir-1298; mir-1299; mir-1301; mir-1302-1; mir-1302-10; mir-1302-11; mir-1302-2; mir-1302-3; mir-1302-4; mir-1302-5; mir-1302-6; mir-1302-7; mir-1302-8; mir-1302-9; mir-1303; mir-1304; mir-1305; mir-1306; mir-1307; mir-1321; mir-1322; mir-1323; mir-1324; mir-1468; mir-1469; mir-1470; mir-1471; mir-1537; mir-1538; mir-1539; mir-1825; mir-1827; mir-1908; mir-1909; mir-1910; mir-1911; mir-1912; mir-1913; mir-1914; mir-1915; mir-1972-1; mir-1972-2; mir-1973; mir-1976; mir-2052; mir-2053; mir-2054; mir-2110; mir-2113; mir-2114; mir-2115; mir-2116; mir-2117; mir-2276; mir-2277; mir-2278; mir-2355; mir-2861; mir-2909; mir-3065; mir- 3074; mir-3115; mir-3116-1; mir-3116-2; mir-3117; mir-3118-1; mir-3118-2; mir-3118-3; mir-3118-4; mir-3118-5; mir-3118-6; mir-3119-1; mir-3119-2; mir-3120; mir-3121; mir-3122; mir-3123; mir-3124; mir-3125; mir-3126; mir-3127; mir-3128; mir-3129; mir-3130-1; mir-3130-2; mir-3131; mir-3132; mir-3133; mir-3134; mir-3135; mir-3136; mir-3137; mir-3138; mir-3139; mir-3140; mir-3141; mir-3142; mir-3143; mir-3144; mir-3145; mir-3146; mir-3147; mir-3148; mir-3149; mir-3150; mir-3151; mir-3152; mir-3153; mir-3154; mir-3155; mir-3156-1; mir-3156-2; mir-3156-3; mir-3157; mir-3158-1; mir-3158-2; mir-3159; mir-3160-1; mir-3160-2; mir-3161; mir-3162; mir-3163; mir-3164; mir-3165; mir-3166; mir-3167; mir-3168; mir-3169; mir-3170; mir-3171; mir-3173; mir-3174; mir-3175; mir-3176; mir-3177; mir-3178; mir-3179-1; mir-3179-2; mir-3179-3; mir-3180-1; mir-3180-2; mir-3180-3; mir-3180-4; mir-3180-5; mir-3181; mir-3182; mir-3183; mir-3184; mir-3185; mir-3186; mir-3187; mir-3188; mir-3189; mir-3190; mir-3191; mir-3192; mir-3193; mir-3194; mir-3195; mir-3196; mir-3197; mir-3198; mir-3199-1; mir-3199-2; mir-3200; mir-3201; mir-3202-1; mir-3202-2; mir-3605; mir-3606; mir-3607; mir-3609; mir-3610; mir-3611; mir-3612; mir-3613; mir-3614; mir-3615; mir-3616; mir-3617; mir-3618; mir-3619; mir-3620; mir-3621; mir-3622a; mir-3622b; mir-3646; mir-3647; mir-3648; mir-3649; mir-3650; mir-3651; mir-3652; mir-3653; mir-3654; mir-3655; mir-3656mir-3657; mir-3658; mir-3659; mir-3660; mir-3661; mir-3662; mir-3663; mir-3664; mir-3665; mir-3666; mir-3667; mir-3668; mir-3669; mir-3670; mir-3670; mir-3671; mir-3671; mir-3673; mir-3673; mir-3675; mir-3675; mir-3676; mir-3663; mir-3677; mir-3678; mir-3679; mir-3680; mir-3681; mir-3682; mir-3683; mir-3684; mir-3685; mir-3686; mir-3687; mir-3688; mir-3689a; mir-3689b; mir-3690; mir-3691; mir-3692; mir-3713; mir-3714; mir-3907; mir-3908; mir-3909; mir-3910-1; mir-3910-2; mir-3911; mir-3912; mir-3913-1; mir-3913-2; mir-3914-1; mir-3914-2; mir-3915; mir-3916; mir-3917; mir-3918; mir-3919; mir-3920; mir-3921; mir-3922; mir-3923; mir-3924; mir-3925; mir-3926-1; mir-3926-2; mir-3927; mir-3928; mir-3929; mir-3934; mir-3935; mir-3936; mir-3937; mir-3938; mir-3939; mir-3940; mir-3941; mir-3942; mir-3943; mir-3944; mir-3945; mir-4251; mir-4252; mir-4253; mir-4254; mir-4255; mir-4256; mir-4257; mir-4258; mir-4259; mir-4260; mir-4261; mir-4262; mir-4263; mir-4264; mir-4265; mir-4266; mir-4267; mir-4268; mir-4269; mir-4270; mir-4271; mir-4272; mir-4273; mir-4274; mir-4275; mir-4276; mir-4277; mir-4278; mir-4279; mir-4280; mir-4281; mir-4282; mir-4283-1; mir-4283-2; mir-4284; mir-4285; mir-4286; mir-4287; mir-4288; mir-4289; mir-4290; mir-4291; mir-4292; mir-4293; mir-4294; mir-4295; mir-4296; mir-4297; mir-4298; mir-4299; mir-4300; mir-4301; mir-4302; mir-4303; mir-4304; mir-4305; mir-4306; mir-4307; mir-4308; mir-4309; mir-4310; mir-4311; mir-4312; mir-4313; mir-4314; mir-4315-1; mir-4315-2; mir-4316; mir-4317; mir-4318; mir-4319; mir-4320; mir-4321; mir-4322; mir-4323; mir-4324; mir-4325; mir-4326; mir-4327; mir-4328; mir-4329; mir-4329; and mir-4330.

The present invention relates to cell-derived or secreted miRNAs obtainable from the cell populations or constructs described herein. In one embodiment, one or more of the individual miRNAs may be used to provide a regenerative effect to a native kidney. Combinations of the individual miRNAs may be suitable for providing such an effect. Exemplary combinations include two or more of the following: miR-21; miR-23a; miR-30c; miR-1224; miR-23b; miR-92a; miR-100; miR-125b-5p; miR-195; miR-10a-5p; and any combination thereof. Another exemplary combination includes two or more of the following: miR-30b-5p, miR-449a, miR-146a, miR-130a, miR-23b, miR-21, miR-124, miR-151, and any combination thereof. In one embodiment, the combination of miRNAs may include 2, 3, 4, 5, 6, 7, 8, 9, 10, or more individual miRNAs. Those of ordinary skill in the are will appreciate that other miRNAs and combinations of mirRNAs may be suitable for use in the present invention. Sources of additional miRNAs include miRBase at http://mirbase.org, which is hosted and maintained in the Faculty of Life Sciences at the University of Manchester.

In one embodiment, the secreted products comprise paracrine factors. In general, paracrine factors are molecules synthesized by a cell that can diffuse over small distances to induce or effect changes in a neighboring cell, i.e., a paracrine interaction. The diffusable molecules are referred to as paracrine factors.

In yet another embodiment, the present invention concerns a composition of one or more isolated renal-cell derived secreted vesicles, as described herein. Those of ordinary skill in the art will appreciate that various types of compositions containing the secreted vesicles will be suitable.

In another aspect, the present invention provides methods of preparing renal cell secreted products, e.g., vesicles. In one embodiment, the method includes the steps of providing a renal cell population, including admixtures of one or more enriched renal cell populations. In another embodiment, the method further includes the step of culturing the population under suitable conditions. The conditions may be low oxygen conditions. In another embodiment, the method further includes the step of isolating the secreted products from the renal cell population. The secreted vesicles may be obtained from the cell culture media of the cell population. In one other embodiment, the renal cells are characterized by vesicle production and/or secretion that is bioresponsive to oxygen levels, such that a reduction in the oxygen tension of the culture system results in an induction of vesicle production and/or secretion. In one embodiment, the vesicle production and/or secretion is induced when the cell population is cultured under conditions where the cells are subjected to a reduction in available oxygen levels in the culture system as compared to a cell population cultured at normal atmospheric (~21%) levels of available oxygen. In one embodiment, the cell populations cultured in lower oxygen conditions produce and/or secrete greater levels of vesicles relative to cell populations cultured at normal oxygen conditions. In general, the culturing of cells at reduced levels of available oxygen (also referred to as hypoxic culture conditions) means that the level of reduced oxygen is reduced relative to the culturing of cells at normal atmospheric levels of available oxygen (also referred to as normal or normoxic culture conditions). In one embodiment, hypoxic cell culture conditions include culturing cells at about less than 1% oxygen, about less than 2% oxygen, about less than 3% oxygen, about less than 4% oxygen, or about less than 5% oxygen. In another embodiment, normal or normoxic culture conditions include culturing cells at about 10% oxygen, about 12% oxygen, about 13% oxygen, about 14% oxygen, about 15% oxygen, about 16% oxygen, about 17% oxygen, about 18% oxygen, about 19% oxygen, about 20% oxygen, or about 21% oxygen. In a preferred embodiment, the method provides for the isolation of exosomes and/or microvesicles from renal cells.

In one embodiment, the products are secreted from renal cells. The products may be secreted from renal cells that are not on a scaffold, e.g., the cells are not part of a construct as described herein.

In another embodiment, the products are secreted by renal cells that have been seeded on a scaffold, e.g., a construct. The construct includes one or more enriched renal cell populations or an admixture thereof that are directly seeded on or in a scaffold.

In another aspect, the present invention provides in vitro methods for screening/optimizing/monitoring the biotherapeutic efficacy of one or more enriched renal cell populations, and admixtures or constructs containing the same. In one embodiment, the method includes the step of providing one or more test populations, test admixture or test construct (the "test article"). In another embodiment, the method includes the step of culturing the test article under suitable conditions, as described herein. In one other embodiment, the method includes the step of collecting cell culture media from the cultured test article. This media may be referred to as "conditioned media" and it is expected to contain products secreted by the renal cells of the test article.

In one other aspect, the conditioned media may be used to conduct one or more in vitro assays in order to test the biotherapeutic efficacy of the test article. In one embodiment, the conditioned media is subjected to an epithelial-mesenchymal transition (EMT) assay. The assay may test for EMT induced by TGFβ1. Example 15 provides an exemplary protocol for this assay.

In another embodiment, the conditioned media is subjected to the detection of RNAs, e.g., via PCR-based assays, and/or vesicles or exosomes, e.g., via FACS. In one other embodiment, the conditioned media is subjected to a signaling pathway assay, e.g., immune response (e.g., NFκB), fibrotic response (PAI-1), and angiogenesis. Examples 12-14 provides exemplary protocols for these assays.

Methods of Use

In one aspect, the present invention provides methods for the treatment of a kidney disease, anemia, or EPO deficiency in a subject in need with the kidney cell populations and admixtures of kidney cells described herein. In one embodiment, the method comprises administering to the subject a composition that includes a first kidney cell population enriched for EPO-producing cells. In another embodiment, the first cell population is enriched for EPO-producing cells, glomerular cells, and vascular cells. In one embodiment, the first kidney cell population is a B4' cell population. In another embodiment, the composition may further include one or more additional kidney cell populations. In one embodiment, the additional cell population is a second cell population not enriched for EPO-producing cells. In another embodiment, the additional cell population is a second cell population not enriched for EPO-producing cells, glomerular cells, or vascular cells. In another embodiment, the composition also includes a kidney cell population or admixture of kidney cells deposited in, deposited on, embedded in, coated with, or entrapped in a biomaterial to form an implantable construct, as described herein, for the treatment of a disease or disorder described herein. In one embodiment, the cell populations are used alone or in combination with other cells or biomaterials, e.g., hydrogels, porous scaffolds, or native or synthetic peptides or proteins, to stimulate regeneration in acute or chronic disease states.

In another aspect, the effective treatment of a kidney disease, anemia, or EPO deficiency in a subject by the methods of the present invention can be observed through various indicators of erythropoiesis and/or kidney function.

In one embodiment, the indicators of erythroid homeostasis include, without limitation, hematocrit (HCT), hemoglobin (HB), mean corpuscular hemoglobin (MCH), red blood cell count (RBC), reticulocyte number, reticulocyte %, mean corpuscular volume (MCV), and red blood cell distribution width (RDW). In one other embodiment, the indicators of kidney function include, without limitation, serum albumin, albumin to globulin ratio (A/G ratio), serum phosphorous, serum sodium, kidney size (measurable by ultrasound), serum calcium, phosphorous:calcium ratio, serum potassium, proteinuria, urine creatinine, serum creatinine, blood nitrogen urea (BUN), cholesterol levels, triglyceride levels and glomerular filtration rate (GFR). Furthermore, several indicators of general health and well-being include, without limitation, weight gain or loss, survival, blood pressure (mean systemic blood pressure, diastolic blood pressure, or systolic blood pressure), and physical endurance performance.

In another embodiment, an effective treatment is evidenced by stabilization of one or more indicators of kidney function. The stabilization of kidney function is demonstrated by the observation of a change in an indicator in a subject treated by a method of the present invention as compared to the same indicator in a subject that has not been treated by a method of the present invention. Alternatively, the stabilization of kidney function may be demonstrated by the observation of a change in an indicator in a subject treated by a method of the present invention as compared to the same indicator in the same subject prior to treatment. The change in the first indicator may be an increase or a decrease in value. In one embodiment, the treatment provided by the present invention may include stabilization of blood urea nitrogen (BUN) levels in a subject where the BUN levels observed in the subject are lower as compared to a subject with a similar disease state who has not been treated by the methods of the present invention. In one other embodiment, the treatment may include stabilization of serum creatinine levels in a subject where the serum creatinine levels observed in the subject are lower as compared to a subject with a similar disease state who has not been treated by the methods of the present invention. In another embodiment, the treatment may include stabilization of hematocrit (HCT) levels in a subject where the HCT levels observed in the subject are higher as compared to a subject with a similar disease state who has not been treated by the methods of the present invention. In another embodiment, the treatment may include stabilization of red blood cell (RBC) levels in a subject where the RBC levels observed in the subject are higher as compared to a subject with a similar disease state who has not been treated by the methods of the present invention. Those of ordinary skill in the art will appreciate that one or more additional indicators described herein or known in the art may be measured to determine the effective treatment of a kidney disease in the subject.

In another aspect, the present invention concerns a method of providing erythroid homeostasis in a subject in need. In one embodiment, the method includes the step of (a) administering to the subject a renal cell population, e.g., B2 or B4', or admixture of renal cells, e.g., B2/B4' and/or B2/B3, as described herein; and (b) determining, in a biological sample from the subject, that the level of an erythropoiesis indicator is different relative to the indicator level in a control, wherein the difference in indicator level (i) indicates the subject is responsive to the administering step (a), or (ii) is indicative of erythroid homeostasis in the subject. In another embodiment, the method includes the step of (a) administering to the subject a composition comprising a renal cell population or admixture of renal cells as described herein; and (b) determining, in a biological sample from the subject, that the level of an erythropoiesis indicator is different relative to the indicator level in a control, wherein the difference in indicator level (i) indicates the subject is responsive to the administering step (s), or (ii) is indicative of erythroid homeostasis in the subject. In another embodiment, the method includes the step of (a) providing a biomaterial or biocompatible polymeric scaffold; (b) depositing a renal cell population or admixture of renal cells of the present invention on or within the biomaterial or scaffold in a manner described herein to form an implantable construct; (c) implanting the construct into the subject; and (d) determining, in a biological sample from the subject, that the level of an erythropoiesis indicator is different relative to the indicator level in a control, wherein the difference in indicator level (i) indicates the subject is responsive to the administering step (a), or (ii) is indicative of erythroid homeostasis in the subject.

In another aspect, the present invention concerns a method of providing both stabilization of kidney function and restoration of erythroid homeostasis to a subject in need, said subject having both a deficit in kidney function and an anemia and/or EPO-deficiency. In one embodiment, the method includes the step of administering a renal cell population or admixture of renal cells as described herein that contain at least one of the following cell types: tubular-derived cells, glomerulus-derived cells, interstitium-derived cells, collecting duct-derived cells, stromal tissue-derived cells, or cells derived from the vasculature. In another embodiment, the population or admixture contains both EPO-producing cells and tubular epithelial cells, the tubular cells having been identified by at least one of the following markers: megalin, cubilin, hyaluronic acid synthase 2 (HAS2), Vitamin D3 25-Hydroxylase (CYP2D25), N-cadherin (Ncad), E-cadherin (Ecad), Aquaporin-1 (Aqp1), Aquaporin-2 (Aqp2), RAB17, member RAS oncogene family (Rab17), GATA binding protein 3 (Gata3), FXYD domain-containing ion transport regulator 4 (Fxyd4), solute carrier family 9 (sodium/hydrogen exchanger), member 4 (Slc9a4), aldehyde dehydrogenase 3 family, member B1 (Aldh3b1), aldehyde dehydrogenase 1 family, member A3 (Aldh1a3), and Calpain-8 (Capn8). In this embodiment, treatment of the subject would be demonstrated by an improvement in at least one indicator of kidney function concomitant with improvement in at least one indicator of erythropoiesis, compared to either an untreated subject or to the subject's pre-treatment indicators.

In one aspect, the present invention provides methods of (i) treating a kidney disease, anemia, or an EPO-deficiency; (ii) stabilizing kidney function, (iii) restoring erythroid homeostasis, or (iv) any combination of thereof by administering a renal cell population enriched for EPO-producing cells or admixture of renal cells containing a cell population enriched for EPO-producing cells as described herein, wherein the beneficial effects of the administration are greater than the effects of administering a cell population not enriched for EPO-producing cells. In another embodiment, the enriched cell population provides an improved level of serum blood urea nitrogen (BUN). In another embodiment, the enriched cell population provides an improved retention of protein in the serum. In another embodiment, the enriched cell population provides improved levels of serum cholesterol and/or triglycerides. In another embodiment, the enriched cell population provides an improved level of Vitamin D. In one embodiment, the enriched cell population provides an improved phosphorus:calcium ratio as compared to a non-enriched cell population. In another embodiment, the enriched cell population provides an improved level of hemoglobin as compared to a non-enriched cell population. In a further embodiment, the enriched cell population provides an improved level of serum creatinine as compared to a non-enriched cell population. In yet another embodiment, the enriched cell population provides an improved level of hematocrit as compared to a non-enriched cell population. In a further embodiment, the enriched cell population provides an improved level of red blood cell number (RBC#) as compared to a non-enriched cell population. In one embodiment, the improved level of hematocrit is restored to 95% normal healthy level. In a further embodiment, the enriched cell population provides an improved reticulocyte number as compared to a non-enriched cell population. In other embodiments, the enriched cell population provides an improved reticulocyte percentage as compared to a non-enriched cell population. In yet other embodiments, the enriched cell population provides an improved level of red blood cell volume distribution width (RDW) as compared to a non-enriched cell population. In yet another embodiment, the enriched cell population provides an improved level of hemoglobin as compared to a non-enriched cell population. In yet another embodiment, the enriched cell population provides an erythroietic response in the bone marrow, such that the marrow cellularity is near-normal and the myeloid:erythroid ratio is near normal.

In another aspect, the present invention provides methods of (i) treating a kidney disease, anemia, or an EPO-deficiency; (ii) stabilizing kidney function, (iii) restoring erythroid homeostasis, or (iv) any combination of thereof by administering an enriched cell population, wherein the beneficial effects of administering a renal cell population or admixture of renal cell populations described herein are characterized by improved erythroid homeostasis when compared to the beneficial effects provided by the administering of recombinant EPO (rEPO). In one embodiment, the population or admixture, when administered to a subject in need provides improved erythroid homeostasis (as determined by hematocrit, hemoglobin, or RBC#) when compared to the administration of recombinant EPO protein. In one embodiment, the population or admixture, when administered provides an improved level of hematocrit, RBC, or hemoglobin as compared to recombinant EPO, being no greater than about 10% lower or higher than hematocrit in a control. In a further embodiment, a single dose or delivery of the population or admixture, when administered provides improvement in erythroid homeostasis (as determined by increase in hematocrit, hemoglobin, or RBC#) in the treated subject for a period of time that significantly exceeds the period of time that a single dose or delivery of the recombinant EPO protein provides improvement in erythroid homeostasis. In another embodiment, the population or admixture, when administered at a dose described herein does not result in hematocrit, hemoglobin, or RBC# greater than about 110% of normal levels in matched healthy controls. In a further embodiment, the population or admixture, when administered at a dose described herein provides superior erythroid homeostasis (as determined by hematocrit, hemoglobin, or RBC#) compared to recombinant EPO protein delivered at a dose described herein. In another embodiment, the recombinant EPO is delivered at a dose of about 100 IU/kg, about 200 IU/kg, about 300 IU/kg, about 400 IU/kg, or about 500 IU/kg. Those of ordinary skill in the art will appreciate that other dosages of recombinant EPO known in the art may be suitable.

Another embodiment of the present invention is directed to the use of at least one cell population, including enriched cell populations and admixtures thereof, described herein, or an implantable construct described herein, or secreted products as described herein, for the preparation of a medicament useful in the treatment of a kidney disease, anemia, or EPO deficiency in a subject in need, the providing of erythroid homeostasis in a subject in need, the improvement of kidney function in a subject in need, or providing a regenerative effect to a native kidney.

Another embodiment of the present invention is directed to the use of specific enriched cell population(s) (described herein) for the treatment of a kidney disease of a specific etiology, based on selection of specific cell subpopulation(s) based on specific verified therapeutic attributes.

In yet another aspect, the present invention provides a method of treating a kidney disease in a subject in need, comprising: administering to the subject a composition comprising an admixture of mammalian renal cells comprising a first cell population, B2, comprising an isolated, enriched population of tubular cells having a density between 1.045 g/mL and 1.052 g/mL, and a second cell population, B4', comprising erythropoietin (EPO)-producing cells and vascular cells but depleted of glomerular cells having a density between 1.063 g/mL and 1.091 g/mL, wherein the admixture does not include a B1 cell population comprising large granular cells of the collecting duct and tubular system having a density of <1.045 g/ml, or a B5 cell population comprising debris and small cells of low granularity and viability with a density >1.091 g/ml. In certain embodiments, the method includes determining in a test sample from the subject that the level of a kidney function indicator is different relative to the indicator level in a control, wherein the difference in indicator level is indicative of a reduction in decline, a stabilization, or an improvement of one or more kidney functions in the subject. In one embodiment, the B4' cell population used in the method is characterized by expression of a vascular marker. In certain embodiments, the B4' cell population used in the method is not characterized by expression of a glomerular marker. In one embodiment, the admixture of cells used in the method is capable of oxygen-tunable erythropoietin (EPO) expression. In certain embodiments, the kidney disease to be treated by the methods of the invention is accompanied by an erythropoietin (EPO) deficiency. In certain embodiments, the EPO deficiency is anemia. In some embodiments, the EPO deficiency or anemia occurs secondary to renal failure in the subject. In some other embodiments, the EPO deficiency or anemia occurs secondary to a disorder selected from the group consisting of chronic renal failure, primary EPO deficiency, chemotherapy or anti-viral therapy, non-myeloid cancer, HIV infection, liver disease, cardiac failure, rheumatoid arthritis, or multi-organ system failure. In certain embodiments, the composition used in the method further comprises a biomaterial comprising one or more biocompatible synthetic polymers and/or naturally-occurring proteins or peptides, wherein the admixture is coated with, deposited on or in, entrapped in, suspended in, embedded in and/or otherwise combined with the biomaterial. In certain embodiments, the admixture used in the methods of the invention is derived from mammalian kidney tissue or cultured mammalian kidney cells. In other embodiments, the admixture is derived from a kidney sample that is autologous to the subject in need. In one embodiment, the sample is a kidney biopsy. In other embodiments, the admixture used in the methods of the invention is derived from a non-autologous kidney sample.

In yet another aspect, the invention provides a use of the cell preparations and admixtures thereof or an implantable construct of the instant invention for the preparation of a medicament useful in the treatment of a kidney disease, anemia or EPO deficiency in a subject in need thereof.

In another aspect, the present invention provides methods for the regeneration of a native kidney in a subject in need thereof. In one embodiment, the method includes the step of administering or implanting a cell population, admixture, or construct described herein to the subject. A regenerated native kidney may be characterized by a number of indicators including, without limitation, development of function or capacity in the native kidney, improvement of function or capacity in the native kidney, and the expression of certain markers in the native kidney. In one embodiment, the developed or improved function or capacity may be observed based on the various indicators of erythroid homeostasis and kidney function described above. In another embodiment, the regenerated kidney is characterized by differential expression of one or more stem cell markers. The stem cell marker may be one or more of the following: SRY (sex determining region Y)-box 2 (Sox2); Undifferentiated Embryonic Cell Transcription Factor (UTF1); Nodal Homolog from Mouse (NODAL); Prominin 1 (PROM1) or CD133 (CD133); CD24; and any combination thereof. In another embodiment, the expression of the stem cell marker(s) is upregulated compared to a control.

The cell populations described herein, including enriched cell populations and admixtures thereof as well as constructs containing the same, may be used to provide a regenerative effect to a native kidney. The effect may be provided by the cells themselves and/or by products secreted from the cells. The regenerative effect may be characterized by one or more of the following: a reduction in epithelial-mesenchymal transition (which may be via attenuation of TGF-β signalling); a reduction in renal fibrosis; a reduction in renal inflammation; differential expression of a stem cell marker in the native kidney; migration of implanted cells and/or native cells to a site of renal injury, e.g., tubular injury, engraftment of implanted cells at a site of renal injury, e.g., tubular injury; stabilization of one or more indicators of kidney function (as described herein); restoration of erythroid homeostasis (as described herein); and any combination thereof.

Methods of Monitoring Regeneration

In another aspect, the present invention provides a prognostic method for monitoring regeneration of a native kidney following administration or implantation of a cell population, admixture, or construct described herein to the subject. In one embodiment, the method includes the step of detecting the level of marker expression in a test sample obtained from the subject and in a control sample, wherein a higher level of expression of the marker in the test sample, as compared to the control sample, is prognostic for regeneration of the native kidney in the subject. In another embodiment, the method includes the detection of expression of one or more stem cell markers in the sample. The stem cell marker may be selected from Sox2; UTF1; NODAL; CD133; CD24; and any combination thereof. The detecting step may include determining that expression of the stem cell marker(s) is upregulated or higher in the test sample relative to a control sample, wherein the higher level of expression is prognostic for regeneration of the subject's native kidney. In one other embodiment, mRNA expression of the stem cell marker(s) is detected. In other embodiments, the detection of mRNA expression may be via a PCR-based method, e.g., qRT-PCR. In situ hybridization may also be used for the detection of mRNA expression.

In one other embodiment, polypeptide expression of the stem cell marker(s) is detected. In another embodiment, polypeptide expression is detected using an anti-stem cell marker agent. In one other embodiment, the agent is an antibody against the marker. In another embodiment, stem cell marker polypeptide expression is detected using immunohistochemistry or a Western Blot.

Those of ordinary skill in the art will appreciate other methods for detecting mRNA and/or polypeptide expression of markers.

In one embodiment, the detecting step is preceded by the step of obtaining the test sample from the subject. In another embodiment, the test sample is kidney tissue.

In one other aspect, the present invention provides the use of markers, such as stem cell markers, as a surrogate marker for regeneration of the native kidney. Such a marker could be used independent of or in conjunction with an assessment of regeneration based on whether function or capacity has been developed or improved (e.g., indicators of erythroid homeostasis and kidney function). Monitoring a surrogate marker over the time course of regeneration may also serve as a prognostic indicator of regeneration.

In another aspect, the invention provides methods for prognostic evaluation of a patient following implantation or administration of a cell population, admixture, or construct described herein. In one embodiment, the method includes the step of detecting the level of marker expression in a test sample obtained from said subject; (b) determining the expression level in the test sample relative to the level of marker expression relative to a control sample (or a control reference value); and (c) predicting regenerative prognosis of the patient based on the determination of marker expression levels, wherein a higher level of expression of marker in the test sample, as compared to the control sample (or a control reference value), is prognostic for regeneration in the subject.

In another aspect, the invention provides methods for prognostic evaluation of a patient following implantation or administration of a cell population, admixture, or construct described herein. In one embodiment, the method includes the steps of (a) obtaining a patient biological sample; and (b) detecting stem cell marker expression in the biological sample, wherein stem cell marker expression is prognostic for regeneration of the native kidney in the patient. In some embodiments, increased stem cell marker expression in the patient biological sample relative to a control sample (or a control reference value) is prognostic for regeneration in the subject. In some embodiments, decreased stem cell marker expression in the patient sample relative to the control sample (or control reference value) is not prognostic for regeneration in the subject. The patient sample may be a test sample comprising a biopsy. The patient sample may be a bodily fluid, such as blood or urine.

In one other aspect, the present invention provides prognostic methods for monitoring regeneration of a native kidney following administration or implantation of a cell population, admixture, or construct described herein to the subject, in which a non-invasive method is used. As an alternative to a tissue biopsy, a regenerative outcome in the subject receiving treatment can be assessed from examination of a bodily fluid, e.g., urine. It has been discovered that microvesicles obtained from subject-derived urine sources contain certain components including, without limitation, specific proteins and miRNAs that are ultimately derived from the renal cell populations impacted by treatment with the cell populations of the present invention. These components may include factors involved in stem cell replication and differentiation, apoptosis, inflammation and immunomodulation. A temporal analysis of microvesicle-associated miRNA/protein expression patterns allows for continuous monitoring of regenerative outcomes within the kidney of subjects receiving the cell populations, admixtures, or constructs of the present invention. Example 17 describes exemplary protocols for analysis of the urine of subjects.

These kidney-derived vesicles and/or the luminal contents of kidney derived vesicles shed into the urine of a subject may be analyzed for biomarkers indicative of regenerative outcome.

In one embodiment, the present invention provides methods of assessing whether a kidney disease (KD) patient is responsive to treatment with a therapeutic. The method may include the step of determining or detecting the amount of vesicles or their luminal contents in a test sample obtained from a KD patient treated with the therapeutic, as compared to or relative to the amount of vesicles in a control sample, wherein a higher or lower amount of vesicles or their luminal contents in the test sample as compared to the amount of vesicles or their luminal contents in the control sample is indicative of the treated patient's responsiveness to treatment with the therapeutic.

The present invention also provides a method of monitoring the efficacy of treatment with a therapeutic in a KD patient. In one embodiment, the method includes the step of determining or detecting the amount of vesicles in a test sample obtained from a KD patient treated with the therapeutic, as compared to or relative to the amount of vesicles or their luminal contents in a control sample, wherein a higher or lower amount of vesicles or their luminal contents in the test sample as compared to the amount of vesicles or their luminal contents in the control sample is indicative of the efficacy of treatment with the therapeutic in the KD patient.

The present invention also provides a method of identifying an agent as a therapeutic effective to treat kidney disease (KD) in a patient subpopulation. In one embodiment, the method includes the step of determining a correlation between efficacy of the agent and the presence of an amount of vesicles in samples from the patient subpopulation as compared to the amount of vesicles or their luminal contents in a sample obtained from a control sample, wherein a higher or lower amount of vesicles or their luminal contents in the samples from the patient subpopulation as compared to the amount of vesicles or their luminal contents in the control sample is indicative that the agent is effective to treat KD in the patient subpopulation.

The present invention provides a method of identifying a patient subpopulation for which an agent is effective to treat kidney disease (KD). In one embodiment, the method includes the step of determining a correlation between efficacy of the agent and the presence of an amount of vesicles or their luminal contents in samples from the patient subpopulation as compared to the amount of vesicles or their luminal contents in a sample obtained from a control sample, wherein a higher or lower amount of vesicles in the samples from the patient subpopulation as compared to the amount of vesicles or their luminal contents in the control sample is indicative that the agent is effective to treat KD in the patient subpopulation.

The determining or detecting step may include analyzing the amount of miRNA or other secreted products that may exist in the test sample (see Example 17).

The non-invasive prognostic methods may include the step of obtaining a urine sample from the subject before and/or after administration or implantation of a cell population, admixture, or construct described herein. Vesicles and other secreted products may be isolated from the urine samples using standard techniques including without limitation, centrifugation to remove unwanted debris (Zhou et al. 2008. Kidney Int. 74(5):613-621; Skog et al. U.S. Published Patent Application No. 20110053157, each of which is incorporated herein by reference in its entirety).

The present invention relates to non-invasive methods to detect regenerative outcome in a subject following treatment. The methods involve detection of vesicles or their luminal contents in urine from a treated subject. The luminal contents may be one or more miRNAs. The detection of combinations or panels of the individual miRNAs may be suitable for such prognostic methods. Exemplary combinations include two or more of the following: miR-24; miR-195; miR-871; miR-30b-5p; miR-19b; miR-99a; miR-429; let-7f; miR-200a; miR-324-5p; miR-10a-5p; and any combination thereof. In one embodiment, the combination of miRNAs may include 2, 3, 4, 5, 6, 7, 8, 9, 10, 11, or more individual miRNAs. Those of ordinary skill in the art will appreciate that other miRNAs and combinations of miRNAs may be suitable for use in such prognostic methods. Sources of additional miRNAs include miRBase at http://mirbase.org, which is hosted and maintained in the Faculty of Life Sciences at the University of Manchester.

Those of skill in the art will appreciate that the prognostic methods for detecting regeneration may be suitable for subjects treated with other therapeutics known in the art, apart from the cell populations and constructs described herein.

In some embodiments, the determining step comprises the use of a software program executed by a suitable processor for the purpose of (i) measuring the differential level of marker expression (or vesicles/vesicle contents) in a test sample and a control; and/or (ii) analyzing the data obtained from measuring differential level of marker expression in a test sample and a control. Suitable software and processors are well known in the art and are commercially available. The program may be embodied in software stored on a tangible medium such as CD-ROM, a floppy disk, a hard drive, a DVD, or a memory associated with the processor, but persons of ordinary skill in the art will readily appreciate that the entire program or parts thereof could alternatively be executed by a device other than a processor, and/or embodied in firmware and/or dedicated hardware in a well known manner.

Following the determining step, the measurement results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. In some embodiments, the assays will be performed or the assay results analyzed in a country or jurisdiction which differs from the country or jurisdiction to which the results or diagnoses are communicated.

In a preferred embodiment, a prognosis, prediction and/or treatment recommendation based on the level of marker expression measured in a test subject having a differential level of marker expression is communicated to the subject as soon as possible after the assay is completed and the prognosis and/or prediction is generated. The results and/or related information may be communicated to the subject by the subject's treating physician. Alternatively, the results may be communicated directly to a test subject by any means of communication, including writing, electronic forms of communication, such as email, or telephone. Communication may be facilitated by use of a computer, such as in case of email communications. In certain embodiments, the communication containing results of a prognostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, prognosis and/or prediction of regeneration, and communicating of assay results or prognoses, may be carried out in diverse (e.g., foreign) jurisdictions.

In another aspect, the prognostic methods described herein provide information to an interested party concerning the regenerative success of the implantation or administration.

In all embodiments, the methods of providing a regenerated kidney to a subject in need of such treatment as described herein may include the post-implantation step of prognostic evaluation of regeneration as described above.

Methods and Routes of Administration

The cell preparations and/or constructs of the instant invention can be administered alone or in combination with other bioactive components.

The therapeutically effective amount of the renal cell populations or admixtures of renal cell populations described herein can range from the maximum number of cells that is safely received by the subject to the minimum number of cells necessary for treatment of kidney disease, e.g., stabilization, reduced rate-of-decline, or improvement of one or more kidney functions. In certain embodiments, the methods of the present invention provide the administration of renal cell populations or admixtures of renal cell populations described herein at a dosage of about 10,000 cells/kg, about 20,000 cells/kg, about 30,000 cells/kg, about 40,000 cells/kg, about 50,000 cells/kg, about 100,000 cells/kg, about 200,000 cells/kg, about 300,000 cells/kg, about 400,000 cells/kg, about 500,000 cells/kg, about 600,000 cells/kg, about 700,000 cells/kg, about 800,000 cells/kg, about 900,000 cells/kg, about $1.1 \times 10^6$ cells/kg, about $1.2 \times 10^6$ cells/kg, about $1.3 \times 10^6$ cells/kg, about $1.4 \times 10^6$ cells/kg, about $1.5 \times 10^6$ cells/kg, about $1.6 \times 10^6$ cells/kg, about $1.7 \times 10^6$ cells/kg, about $1.8 \times 10^6$ cells/kg, about $1.9 \times 10^6$ cells/kg, about $2.1 \times 10^6$ cells/kg, about $2.1 \times 10^6$ cells/kg, about $1.2 \times 10^6$ cells/kg, about $2.3 \times 10^6$ cells/kg, about $2.4 \times 10^6$ cells/kg, about $2.5 \times 10^6$ cells/kg, about $2.6 \times 10^6$ cells/kg, about $2.7 \times 10^6$ cells/kg, about $2.8 \times 10^6$ cells/kg, about $2.9 \times 10^6$ cells/kg, about $3 \times 10^6$ cells/kg, about $3.1 \times 10^6$ cells/kg, about $3.2 \times 10^6$ cells/kg, about $3.3 \times 10^6$ cells/kg, about $3.4 \times 10^6$ cells/kg, about $3.5 \times 10^6$ cells/kg, about $3.6 \times 10^6$ cells/kg, about $3.7 \times 10^6$ cells/kg, about $3.8 \times 10^6$ cells/kg, about $3.9 \times 10^6$ cells/kg, about $4 \times 10^6$ cells/kg, about $4.1 \times 10^6$ cells/kg, about $4.2 \times 10^6$ cells/kg, about $4.3 \times 10^6$ cells/kg, about $4.4 \times 10^6$ cells/kg, about $4.5 \times 10^6$ cells/kg, about $4.6 \times 10^6$ cells/kg, about $4.7 \times 10^6$ cells/kg, about $4.8 \times 10^6$ cells/kg, about $4.9 \times 10^6$ cells/kg, or about $5 \times 10^6$ cells/kg. In another embodiment, the dosage of cells to a subject may be a single dosage or a single dosage plus additional dosages. In other embodiments, the dosages may be provided by way of a construct as described herein. In other embodiments, the dosage of cells to a subject may be calculated based on the estimated renal mass or functional renal mass.

The therapeutically effective amount of the renal cell populations or admixtures thereof described herein can be suspended in a pharmaceutically acceptable carrier or excipient. Such a carrier includes, but is not limited to basal culture medium plus 1% serum albumin, saline, buffered saline, dextrose, water, collagen, alginate, hyaluronic acid, fibrin glue, polyethyleneglycol, polyvinylalcohol, carboxymethylcellulose and combinations thereof. The formulation should suit the mode of administration. Accordingly, the invention provides a use of renal cell populations or admixtures thereof, for example, the B2 cell population alone or admixed with the B3 and/or B4 or B4' cell population, for the manufacture of a medicament to treat kidney disease in a subject. In some embodiments, the medicament further comprises recombinant polypeptides, such as growth factors, chemokines or cytokines. In further embodiments, the medicaments comprise a human kidney-derived cell population. The cells used to manufacture the medicaments can be isolated, derived, or enriched using any of the variations provided for the methods described herein.

The renal cell preparation(s), or admixtures thereof, or compositions are formulated in accordance with routine procedures as a pharmaceutical composition adapted for administration to human beings. Typically, compositions for intravenous administration, intra-arterial administration or administration within the kidney capsule, for example, are solutions in sterile isotonic aqueous buffer. Where necessary, the composition can also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. When the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Pharmaceutically acceptable carriers are determined in part by the particular composition being administered, as well as by the particular method used to administer the composition. Accordingly, there are a wide variety of suitable formulations of pharmaceutical compositions (see, e.g., Alfonso R Gennaro (ed), Remington: The Science and Practice of Pharmacy, formerly Remington's Pharmaceutical Sciences 20th ed., Lippincott, Williams & Wilkins, 2003, incorporated herein by reference in its entirety). The pharmaceutical compositions are generally formulated as sterile, substantially isotonic and in full compliance with all Good Manufacturing Practice (GMP) regulations of the U.S. Food and Drug Administration.

One aspect of the invention further provides a pharmaceutical formulation, comprising a renal cell preparation of the invention, for example, the B2 cell preparation alone or incombination with the B3 and/or B4 or B4' cell preparation, and a pharmaceutically acceptable carrier. In some embodiments, the formulation comprises from $10^4$ to $10^9$ mammalian kidney-derived cells.

In one aspect, the present invention provides methods of providing one or more of the cell populations described herein, including admixtures, to a subject in need. In one embodiment, the source of the cell population(s) may be autologous or allogeneic, syngeneic (autogeneic or isogeneic), and any combination thereof. In instances where the source is not autologous, the methods may include the administration of an immunosuppressant agent. Suitable immunosuppressant drugs include, without limitation, azathioprine, cyclophosphamide, mizoribine, ciclosporin, tacrolimus hydrate, chlorambucil, lobenzarit disodium, auranofin, alprostadil, gusperimus hydrochloride, biosynsorb, muromonab, alefacept, pentostatin, daclizumab, sirolimus, mycophenolate mofetil, leflonomide, basiliximab, dornase a, bindarid, cladribine, pimecrolimus, ilodecakin, cedelizumab, efalizumab, everolimus, anisperimus, gavilimomab, faralimomab, clofarabine, rapamycin, siplizumab, saireito, LDP-03, CD4, SR-43551, SK&F-106615, IDEC-114, DEC-131, FTY-720, TSK-204, LF-080299, A-86281, A-802715, GVH-313, HMR-1279, ZD-7349, IPL-423323, CBP-1011, MT-1345, CNI-1493, CBP-2011, J-695, LJP-920, L-732531, ABX-RB2, AP-1903, IDPS, BMS-205820, BMS-224818, CTLA4-1g, ER-49890, ER-38925, ISAtx-247, RDP-58, PNU-156804, LJP-1082, TMC-95A, TV-4710, PTR-262-MG, and AGI-1096 (see U.S. Pat. No. 7,563,822). Those of ordinary skill in the art will appreciate other suitable immunosuppressant drugs.

The treatment methods of the subject invention involve the delivery of an isolated renal cell population, or admixture thereof, into individuals. In one embodiment, direct administration of cells to the site of intended benefit is preferred. In one embodiment, the cell preparations, or admixtures thereof, of the instant invention are delivered to an individual in a delivery vehicle.

A subject in need may also be treated by in vivo contacting of a native kidney with products secreted from one or more enriched renal cell populations, and/or an admixture or construct containing the same. The step of contacting a native kidney in vivo with secreted products may be accomplished through the use/administration of a population of secreted products from cell culture media, e.g., conditioned media, or by implantation of an enriched cell population, and admixture, or a construct capable of secreting the products in vivo. The step of in vivo contacting provides a regenerative effect to the native kidney.

A variety of means for administering cells and/or secreted products to subjects will, in view of this specification, be apparent to those of skill in the art. Such methods include injection of the cells into a target site in a subject. Cells and/or secreted products can be inserted into a delivery device or vehicle, which facilitates introduction by injection or implantation into the subjects. In certain embodiments, the delivery vehicle can include natural materials. In certain other embodiments, the delivery vehicle can include synthetic materials. In one embodiment, the delivery vehicle provides a structure to mimic or appropriately fit into the organ's architecture. In other embodiments, the delivery vehicle is fluid-like in nature. Such delivery devices can include tubes, e.g., catheters, for injecting cells and fluids into the body of a recipient subject. In a preferred embodiment, the tubes additionally have a needle, e.g., a syringe, through which the cells of the invention can be introduced into the subject at a desired location. In some embodiments, mammalian kidney-derived cell populations are formulated for administration into a blood vessel via a catheter (where the term "catheter" is intended to include any of the various tube-like systems for delivery of substances to a blood vessel). Alternatively, the cells can be inserted into or onto a biomaterial or scaffold, including but not limited to textiles, such as weaves, knits, braids, meshes, and non-wovens, perforated films, sponges and foams, and beads, such as solid or porous beads, microparticles, nanoparticles, and the like (e.g., Cultispher-S gelatin beads—Sigma). The cells can be prepared for delivery in a variety of different forms. For example, the cells can be suspended in a solution or gel. Cells can be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. One of skill in the art will appreciate that the delivery vehicle used in the delivery of the cell populations and admixtures thereof of the instant invention can include combinations of the above-mentioned characteristics.

Modes of administration of the isolated renal cell population(s), for example, the B2 cell population alone or admixed with B4' and/or B3, include, but are not limited to, systemic, intra-renal (e.g., parenchymal), intravenous or intra-arterial injection and injection directly into the tissue at the intended site of activity. Additional modes of administration to be used in accordance with the present invention include single or multiple injection(s) via direct laparotomy, via direct laparoscopy, transabdominal, or percutaneous. Still yet additional modes of administration to be used in accordance with the present invention include, for example, retrograde and ureteropelvic infusion. Surgical means of administration include one-step procedures such as, but not limited to, partial nephrectomy and construct implantation, partial nephrectomy, partial pyelectomy, vascularization with omentum±peritoneum, multifocal biopsy needle tracks, cone or pyramidal, to cylinder, and renal pole-like replacement, as well as two-step procedures including, for example, organoid-internal bioreactor for replanting. In one embodiment, the admixtures of cells are delivered via the same route at the same time. In another embodiment, each of the cell compositions comprising the controlled admixture are delivered separately to specific locations or via specific methodologies, either simultaneously or in a temporally-controlled manner, by one or more of the methods described herein.

The appropriate cell implantation dosage in humans can be determined from existing information relating to either the activity of the cells, for example EPO production, or extrapolated from dosing studies conducted in preclinical studies. From in vitro culture and in vivo animal experiments, the amount of cells can be quantified and used in calculating an appropriate dosage of implanted material. Additionally, the patient can be monitored to determine if additional implantation can be made or implanted material reduced accordingly.

One or more other components can be added to the cell populations and admixtures thereof of the instant invention, including selected extracellular matrix components, such as one or more types of collagen or hyaluronic acid known in the art, and/or growth factors, platelet-rich plasma and drugs.

Those of ordinary skill in the art will appreciate the various formulations and methods of administration suitable for the secreted products described herein.

Kits

The instant invention further includes kits comprising the polymeric matrices and scaffolds of the invention and related materials, and/or cell culture media and instructions for use. The instructions for use may contain, for example, instructions for culture of the cells or administration of the cells and/or cell products. In one embodiment, the present invention provides a kit comprising a scaffold as described herein and instructions. In yet another embodiment, the kit includes an agent for detection of marker expression, reagents for use of the agent, and instructions for use. This kit may be used for the purpose of determining the regenerative prognosis of a native kidney in a subject following the implantation or administration of a cell population, an admixture, or a construct described herein. The kit may also be used to determine the biotherapeutic efficacy of a cell population, admixture, or construct described herein.

Reports

The methods of this invention, when practiced for commercial purposes generally produce a report or summary of the regenerative prognosis. The methods of this invention will produce a report comprising a prediction of the probable course or outcome of regeneration before and after any administration or implantation of a cell population, an admixture, or a construct described herein. The report may include information on any indicator pertinent to the prognosis. The methods and reports of this invention can further include storing the report in a database. Alternatively, the method can further create a record in a database for the subject and populate the record with data. In one embodiment the report is a paper report, in another embodiment the report is an auditory report, in another embodiment the report is an electronic record. It is contemplated that the report is provided to a physician and/or the patient. The receiving of the report can further include establishing a network connection to a server computer that includes the data and report and requesting the data and report from the server computer. The methods provided by the present invention may also be automated in whole or in part.

All patents, patent applications, and literature references cited in the present specification are hereby incorporated by reference in their entirety.

The following examples are offered for illustrative purposes only, and are not intended to limit the scope of the present invention in any way.

EXAMPLES

Example 1—Isolation & Characterization of Bioresponsive Renal Cells

A case of idiopathic progressive chronic kidney disease (CKD) with anemia in an adult male swine (*Sus scrofa*) provided fresh diseased kidney tissue for the assessment of cellular composition and characterization with direct comparison to age-matched normal swine kidney tissue. Histological examination of the kidney tissue at the time of harvest confirmed renal disease characterized by severe diffuse chronic interstitial fibrosis and crescentic glomerulonephritis with multifocal fibrosis. Clinical chemistry confirmed azotemia (elevation of blood urea nitrogen and serum creatinine), and mild anemia (mild reduction in hematocrit and depressed hemoglobin levels). Cells were isolated, expanded, and characterized from both diseased and normal kidney tissue. As shown in FIG. 1 of Presnell et al. WO/2010/056328 (incorporated herein by reference in its entirety), a Gomori's Trichrome stain highlighs the fibrosis (blue staining indicated by arrows) in the diseased kidney tissue compared to the normal kidney tissue. Functional tubular cells, expressing cubulin:megalin and capable of receptor-mediated albumin transport, were propagated from both normal and diseased kidney tissue. Erythropoietin (EPO)-expressing cells were also present in the cultures and were retained through multiple passages and freeze/thaw cycles. Furthermore, molecular analyses confirmed that the EPO-expressing cells from both normal and diseased tissue responded to hypoxic conditions in vitro with HIF1α-driven induction of EPO and other hypoxia-regulated gene targets, including vEGF. Cells were isolated from the porcine kidney tissue via enzymatic digestion with collagenase+dispase, and were also isolated in separate experiments by performing simple mechanical digestion and explant culture. At passage two, explant-derived cell cultures containing epo-expressing cells were subjected to both atmospheric (21%) and varying hypoxic (<5%) culture conditions to determine whether exposure to hypoxia culminated in upregulation of EPO gene expression. As noted with rodent cultures (see Example 3), the normal pig displayed oxygen-dependent expression and regulation of the EPO gene. Surprisingly, despite the uremic/anemic state of the CKD pig (Hematocrit <34, Creatinine >9.0) EPO expressing cells were easily isolated and propagated from the tissue and expression of the EPO gene remained hypoxia regulated, as shown in FIG. 2 of Presnell et al. WO/2010/056328 (incorporated herein by reference in its entirety). As shown in FIG. 3 of Presnell et al. WO/2010/056328 (incorporated herein by reference in its entirety), cells in the propagated cultures demonstrated the ability to self-organize into tubule-like structures. As shown in FIG. 4 of Presnell et al. WO/2010/056328 (incorporated herein by reference in its entirety), the presence of functional tubular cells in the culture (at passage 3) was confirmed by observing receptor-mediated uptake of FITC-conjugated Albumin by the cultured cells. The green dots (indicated by thin white arrows) represent endocytosed fluorescein-conjugated albumin which is mediated by tubular cell-specific receptors, Megalin and Cubilin, indicating protein reabsorption by functional tubular cells. The blue staining (indicated by thick white arrows) is Hoescht-stained nuclei. Taken together, these data suggest that functional tubular and endocrine cells can be isolated and propagated from porcine renal tissues, even in renal tissues that have been severely compromised with CKD. Furthermore, these findings support the advancement of autologous cell-based therapeutic products for the treatment of CKD.

Figure 5:
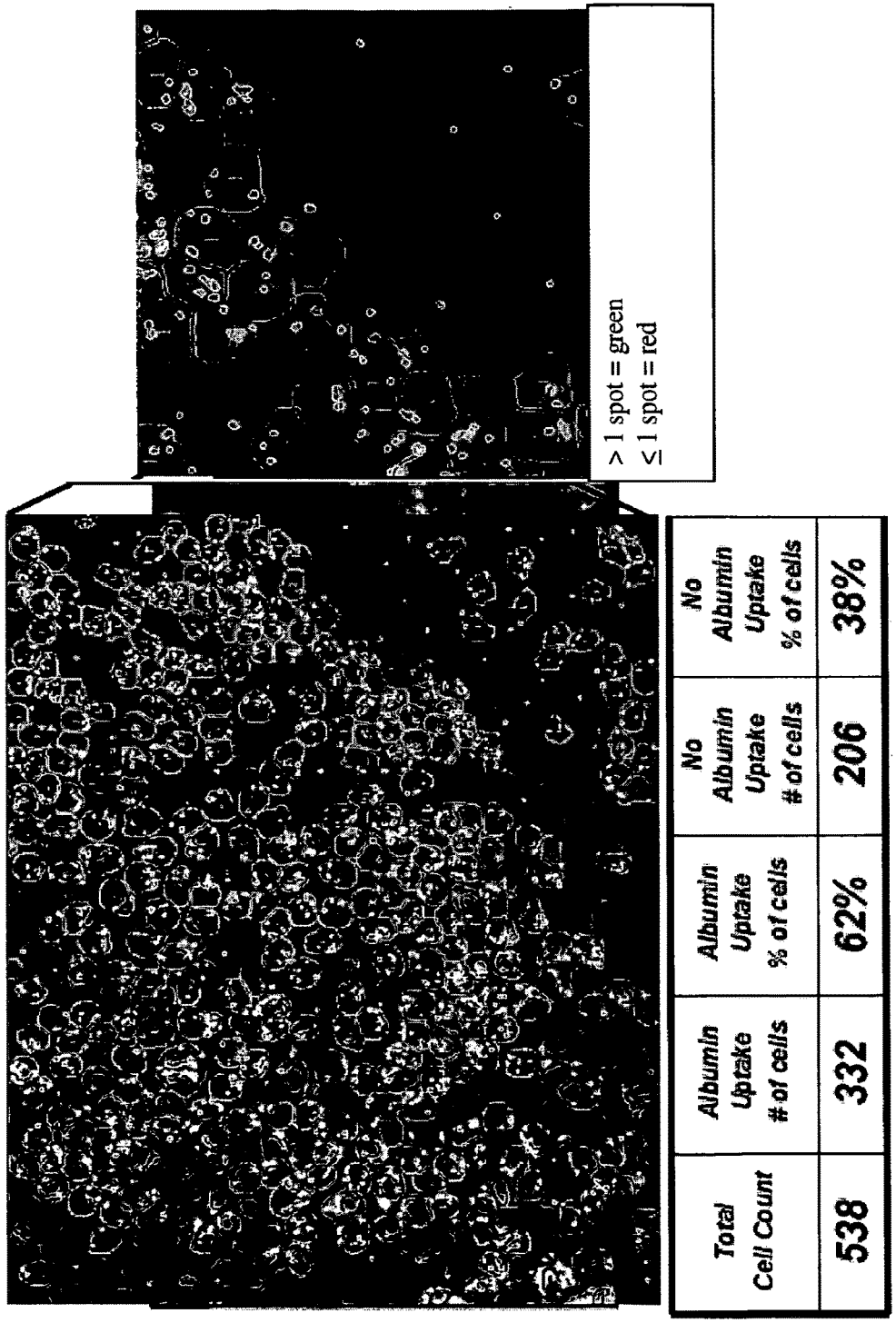
FIG. 5 shows high content analysis (HCA) of albumin transport in human NKA cells defining regions of interest (ROI).
Figure 6:
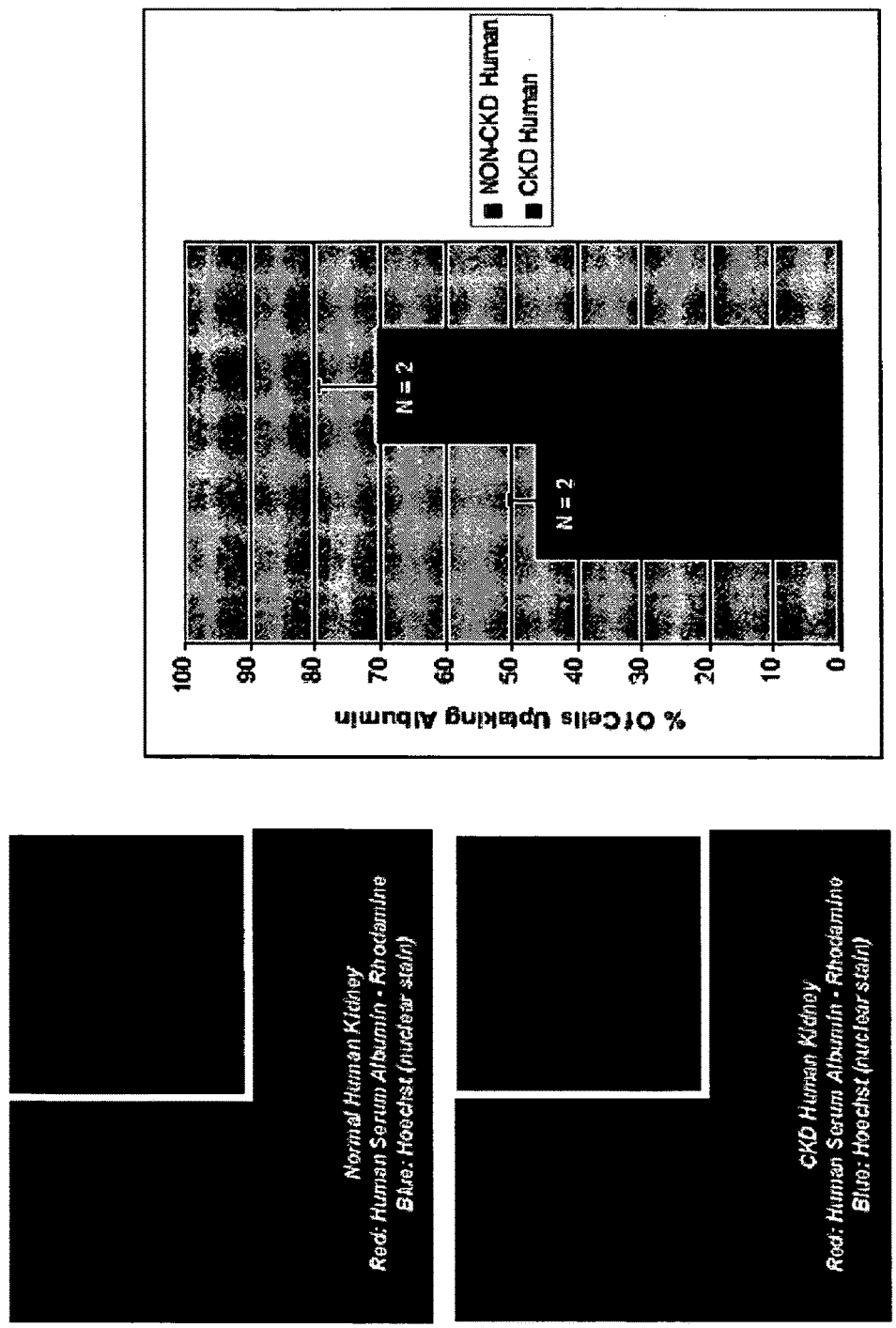
FIG. 6 shows quantitative comparison of albumin transport in NKA cells derived from non-CKD and CKD kidney.

In addition, EPO-producing cells were isolated enzymatically from normal adult human kidney (as described above in Example 1). As shown in FIG. 5 of Presnell et al. WO/2010/056328 (incorporated herein by reference in its entirety), the isolation procedure resulted in more relative EPO expression after isolation than in the initial tissue. As shown in FIG. 6 of Presnell et al. WO/2010/056328 (incorporated herein by reference in its entirety), it is possible to maintain the human EPO producing cells in culture with retention of EPO gene expression. Human cells were cultured/propagated on plain tissue-culture treated plastic or plastic that had been coated with some extracellular matrix, such as, for instance, fibronectin or collagen, and all were found to support EPO expression over time.

Example 2—Isolation & Enrichment of Specific Bioreactive Renal Cells

Kidney Cell Isolation:

Briefly, batches of 10, 2-week-old male Lewis rat kidneys were obtained from a commercial supplier (Hilltop Lab Animals Inc.) and shipped overnight in Viaspan preservation medium at a temperature around 4° C. All steps described herein were carried out in a biological safety cabinet (BSC) to preserve sterility. The kidneys were washed in Hank's balanced salt solution (HBSS) 3 times to rinse out the Viaspan preservation medium. After the third wash the remaining kidney capsules were removed as well as any remaining stromaltissue. The major calyx was also removed using micro dissection techniques. The kidneys were then finely minced into a slurry using a sterile scalpel. The slurry was then transferred into a 50 ml conical centrifuge tube and weighed. A small sample was collected for RNA and placed into an RNAse-free sterile 1.5 ml micro-centrifuge tube and snap frozen in liquid nitrogen. Once frozen, it was then transferred to the −80 degree freezer until analysis. The tissue weight of 10 juvenile kidneys equaled approximately 1 gram. Based on the weight of the batch, the digestion medium was adjusted to deliver 20 mls of digestion medium per 1 gram of tissue. Digestion buffer for this procedure contained 4 Units of Dispase 1 (Stem Cell Tech) in HBSS, 300 Units/ml of Collagenase type IV (Worthington) with 5 mM $CaCl_2$ (Sigma).

The appropriate volume of pre-warmed digestion buffer was added to the tube, which was then sealed and placed on a rocker in a 37° C. incubator for 20 minutes. This first digestion step removes many red blood cells and enhances the digestion of the remaining tissue. After 20 minutes, the tube was removed and placed in the BSC. The tissue was allowed to settle at the bottom of the tube and then the supernatant was removed. The remaining tissue was then supplemented with fresh digestion buffer equaling the starting volume. The tube was again placed on a rocker in a 37° C. incubator for an additional 30 minutes.

After 30 minutes the digestion mixture was pipetted through a 70 μm cell strainer (BD Falcon) into an equal volume of neutralization buffer (DMEM w/10% FBS) to stop the digestion reaction. The cell suspension was then washed by centrifugation at 300×g for 5 min. After centrifugation, the pellet was then re-suspended in 20 mls KSFM medium and a sample acquired for cell counting and viability assessment using trypan blue exclusion. Once the cell count was calculated, 1 million cells were collected for RNA, washed in PBS, and snap frozen in liquid nitrogen. The remaining cell suspension was brought up to 50 mls with KSFM medium and washed again by centrifugation at 300×g for 5 minutes. After washing, the cell pellet was re-suspended in a concentration of 15 million cells per ml of KSFM.

Five milliliters of kidney cell suspension were then added to 5 mls of 30% (w/v) Optiprep® in 15 ml conical centrifuge tubes (BD Falcon) and mixed by inversion 6 times. This formed a final mixture of 15% (w/v) of Optiprep®. Post inversion, tubes were carefully layered with 1 mL PBS. The tubes were centrifuged at 800×g for 15 minutes without brake. After centrifugation, the tubes were removed and a cell band was formed at the top of the mixing gradient. There was also a pellet containing red blood cells, dead cells, and a small population of live cells that included some small less granular cells, some epo-producing cells, some tubular cells, and some endothelial cells. The band was carefully removed using a pipette and transferred to another 15 ml conical tube. The gradient medium was removed by aspiration and the pellet was collected by re-suspension in 1 ml KSFM. The band cells and pellet cells were then recombined and re-suspended in at least 3 dilutions of the collected band volume using KSFM and washed by centrifugation at 300×g for 5 minutes. Post washing, the cells were re-suspended in 20 mls of KSFM and a sample for cell counting was collected. Once the cell count was calculated using trypan blue exclusion, 1 million cells were collected for an RNA sample, washed in PBS, and snap frozen in liquid nitrogen.

Pre-Culture 'Clean-Up' to Enhance Viability and Culture Performance of Specific Bioactive Renal Cells Using Density Gradient Separation:

To yield a clean, viable population of cells for culture, a cell suspension was first generated as described above in "Kidney Cell Isolation". As an optional step and as a means of cleaning up the initial preparation, up to 100 million total cells, suspended in sterile isotonic buffer were mixed thoroughly 1:1 with an equal volume of 30% Optiprep® prepared at room temperature from stock 60% (w/v) iodixanol (thus yielding a final 15% w/v Optiprep solution) and mixed thoroughly by inversion six times. After mixing, 1 ml PBS buffer was carefully layered on top of the mixed cell suspension. The gradient tubes were then carefully loaded into the centrifuge, ensuring appropriate balance. The gradient tubes were centrifuged at 800×g for 15 minutes at 25° C. without brake. The cleaned-up cell population (containing viable and functional collecting duct, tubular, endocrine, glomerular, and vascular cells) segmented between 6% and 8% (w/v) Optiprep®, corresponding to a density between 1.025-1.045 g/mL. Other cells and debris pelleted to the bottom of the tube.

Kidney Cell Culture:

The combined cell band and pellet were then plated in tissue culture treated triple flasks (Nunc T500) or equivalent at a cell concentration of 30,000 cells per cm2 in 150 mls of a 50:50 mixture of DMEM(high glucose)/KSFM containing 5% (v/v) FBS, 2.5 µg EGF, 25 mg BPE, 1×ITS (insulin/transferrin/sodium selenite medium supplement) with antibiotic/antimycotic. The cells were cultured in a humidified 5% CO2 incubator for 2-3 days, providing a 21% atmospheric oxygen level for the cells. After two days, the medium was changed and the cultures were placed in 2% oxygen-level environment provided by a CO2/Nitrogen gas multigas humidified incubator (Sanyo) for 24 hrs. Following the 24 hr incubation, the cells were washed with 60 mls of 1×PBS and then removed using 40 mls 0.25% (w/v) trypsin/EDTA (Gibco). Upon removal, the cell suspension was neutralized with an equal volume of KSFM containing 10% FBS. The cells were then washed by centrifugation 300×g for 10 minutes. After washing, the cells were re-suspended in 20 mls of KSFM and transferred to a 50 ml conical tube and a sample was collected for cell counting. Once the viable cell count was determined using trypan blue exclusion, 1 million cells were collected for an RNA sample, washed in PBS, and snap frozen in liquid nitrogen. The cells were washed again in PBS and collected by centrifugation at 300×g for 5 minutes. The washed cell pellet was re-suspended in KSFM at a concentration of 37.5 million cells/ml.

Enriching for Specific Bioactive Renal Cells Using Density Step Gradient Separation:

Cultured kidney cells, predominantly composed of renal tubular cells but containing small subpopulations of other cell types (collecting duct, glomerular, vascular, and endocrine) were separated into their component subpopulations using a density step gradient made from multiple concentrations w/v of iodixanol (Optiprep). The cultures were placed into a hypoxic environment for up to 24 hours prior to harvest and application to the gradient. A stepped gradient was created by layering four different density mediums on top of each other in a sterile 15 mL conical tube, placing the solution with the highest density on the bottom and layering to the least dense solution on the top. Cells were applied to the top of the step gradient and centrifuged, which resulted in segregation of the population into multiple bands based on size and granularity.

Briefly, densities of 7, 11, 13, and 16% Optiprep (60% w/v Iodixanol) were made using KFSM medium as diluents. For example: for 50 mls of 7% (w/v) Optiprep®, 5.83 mls of stock 60% (w/v) Iodixanol was added to 44.17 mls of KSFM medium and mixed well by inversion. A peristaltic pump (Master Flex L/S) loaded with sterile L/S 16 Tygon tubing connected to sterile capillary tubes was set to a flow rate of 2 ml per minute, and 2 mL of each of the four solutions was loaded into a sterile conical 15 mL tube, beginning with the 16% solution, followed by the 13% solution, the 11% solution, and the 7% solution. Finally, 2 mL of cell suspension containing 75 million cultured rodent kidney cells was loaded atop the step gradient (suspensions having been generated as described above in 'Kidney cell Culture'). Importantly, as the pump was started to deliver the gradient solutions to the tube, care was taken to allow the fluid to flow slowly down the side of the tube at a 45° angle to insure that a proper interface formed between each layer of the gradient. The step gradients, loaded with cells, were then centrifuged at 800×g for 20 minutes without brake. After centrifugation, the tubes were carefully removed so as not to disturb each interface. Five distinct cell fractions resulted (4 bands and a pellet) (B1-B4, +Pellet) (see FIG. 1A, left conical tube). Each fraction was collected using either a sterile disposable bulb pipette or a 5 ml pipette and characterized phenotypically and functionally (See Example 10 of Presnell et al. WO/2010/056328). When rodent kidney cell suspensions are subjected to step-gradient fractionation immediately after isolation, the fraction enriched for tubular cells (and containing some cells from the collecting duct) segments to a density between 1.062-1.088 g/mL. In contrast, when density gradient separation was performed after ex vivo culture, the fraction enriched for tubular cells (and containing some cells from the collecting duct) segmented to a density between 1.051-1.062 g/mL. Similarly, when rodent kidney cell suspensions are subjected to step-gradient fractionation immediately after isolation, the fraction enriched for epo-producing cells, glomerular podocytes, and vascular cells ("B4") segregates at a density between 1.025-1.035 g/mL. In contrast, when density gradient separation was performed after ex vivo culture, the fraction enriched for epo-producing cells, glomerular podocytes, and vascular cells ("B4") segregated at a density between 1.073-1.091 g/mL. Importantly, the post-culture distribution of cells into both the "B2" and the "B4" fractions was enhanced by exposure (for a period of about 1 hour to a period of about 24 hours) of the cultures to a hypoxic culture environment (hypoxia being defined as <21% (atmospheric) oxygen levels prior to harvest and step-gradient procedures (additional details regarding hypoxia-effects on band distribution are provided in Example 3).

Each band was washed by diluting with 3× the volume of KSFM, mixed well, and centrifuged for 5 minutes at 300×g. Pellets were re-suspended in 2 mls of KSFM and viable cells were counted using trypan blue exclusion and a hemacytometer. 1 million cells were collected for an RNA sample, washed in PBS, and snap frozen in liquid nitrogen. The cells from B2 and B4 were used for transplantation studies into uremic and anemic female rats, generated via a two-step 5/6 nephrectomy procedure at Charles River Laboratories. Characteristics of B4 were confirmed by quantitative real-time PCR, including oxygen-regulated expression of erythropoietin and vEGF, expression of glomerular markers (nephrin, podocin), and expression of vascular markers (PECAM).

Phenotype of the 'B2' fraction was confirmed via expression of E-Cadherin, N-Cadherin, and Aquaporin-2. See FIGS. 49a and 49b of Presnell et al. WO/2010/056328.

Thus, use of the step gradient strategy allows not only the enrichment for a rare population of epo-producing cells (B4), but also a means to generate relatively enriched fractions of functional tubular cells (B2) (see FIGS. 50 & 51 of Presnell et al. WO/2010/056328). The step gradient strategy also allows EPO-producing and tubular cells to be separated from red blood cells, cellular debris, and other potentially undesirable cell types, such as large cell aggregates and certain types of immune cells.

The step gradient procedure may require tuning with regard to specific densities employed to provide good separation of cellular components. The preferred approach to tuning the gradient involves 1) running a continuous density gradient where from a high density at the bottom of the gradient (16-21% Optiprep, for example) to a relatively low density at the top of the gradient (5-10%, for example). Continuous gradients can be prepared with any standard density gradient solution (Ficoll, Percoll, Sucrose, iodixanol) according to standard methods (Axis Shield). Cells of interest are loaded onto the continuous gradient and centrifuged at 800×G for 20 minutes without brake. Cells of similar size and granularity tend to segregate together in the gradients, such that the relative position in the gradient can be measured, and the specific gravity of the solution at that position also measured. Thus, subsequently, a defined step gradient can be derived that focuses isolation of particular cell populations based on their ability to transverse the density gradient under specific conditions. Such optimization may need to be employed when isolating cells from unhealthy vs. healthy tissue, or when isolating specific cells from different species. For example, optimization was conducted on both canine and human renal cell cultures, to insure that the specific B2 and B4 subpopulations that were identified in the rat were isolatable from the other species. The optimal gradient for isolation of rodent B2 and B4 subpopulations consists of (w/v) of 7%, 11%, 13%, and 16% Optiprep. The optimal gradient for isolation of canine B2 and B4 subpopulations consists of (w/v) of 7%, 10%, 11%, and 16% Optiprep. The optimal gradient for isolation of human B2 and B4 subpopulations consists of (w/v) 7%, 9%, 11%, 16%. Thus, the density range for localization of B2 and B4 from cultured rodent, canine, and human renal cells is provided in Table 2.1.

TABLE 2.1

| Step Gradient Band | Species Density Ranges g/ml | | |
|---|---|---|---|
| | Rodent | Canine | Human |
| B2 | 1.045-1.063 g/ml | 1.045-1.058 g/ml | 1.045-1.052 g/ml |
| B4 | 1.073-1.091 g/ml | 1.063-1.091 g/ml | 1.063-1.091 g/ml |

Example 3—Low-Oxygen Culture Prior to Gradient Affects Band Distribution, Composition, and Gene Expression To determine the effect of oxygen conditions on distribution and composition of prototypes B2 and B4, neokidney cell preparations from different species were exposed to different oxygen conditions prior to the gradient step. A rodent neo-kidney augmentation (NKA) cell preparation (RK069) was established using standard procedures for rat cell isolation and culture initiation, as described supra. All flasks were cultured for 2-3 days in 21% (atmospheric) oxygen conditions. Media was changed and half of the flasks were then relocated to an oxygen-controlled incubator set to 2% oxygen, while the remaining flasks were kept at the 21% oxygen conditions, for an additional 24 hours. Cells were then harvested from each set of conditions using standard enzymatic harvesting procedures described supra. Step gradients were prepared according to standard procedures and the "normoxic" (21% oxygen) and "hypoxic" (2% oxygen) cultures were harvested separately and applied side-by-side to identical step gradients. (FIG. 2). While 4 bands and a pellet were generated in both conditions, the distribution of the cells throughout the gradient was different in 21% and 2% oxygen-cultured batches (Table 1). Specifically, the yield of B2 was increased with hypoxia, with a concomitant decrease in B3. Furthermore, the expression of B4-specific genes (such as erythropoietin) was enhanced in the resulting gradient generated from the hypoxic-cultured cells (FIG. 73 of Presnell et al. WO/2010/056328).

A canine NKA cell preparation (DK008) was established using standard procedures for dog cell isolation and culture (analogous to rodent isolation and culture procedures), as described supra. All flasks were cultured for 4 days in 21% (atmospheric) oxygen conditions, then a subset of flasks were transferred to hypoxia (2%) for 24 hours while a subset of the flasks were maintained at 21%. Subsequently, each set of flasks was harvested and subjected to identical step gradients (FIG. 3). Similar to the rat results (Example 1), the hypoxic-cultured dog cells distributed throughout the gradient differently than the atmospheric oxygen-cultured dog cells (Table 3.1). Again, the yield of B2 was increased with hypoxic exposure prior to gradient, along with a concomitant decrease in distribution into B3.

TABLE 3.1

| | Rat (RK069) | | Dog (DK008) | |
|---|---|---|---|---|
| | 2% O2 | 21% O2 | 2% O2 | 21% O2 |
| B1 | 0.77% | 0.24% | 1.20% | 0.70% |
| B2 | 88.50% | 79.90% | 64.80% | 36.70% |
| B3 | 10.50% | 19.80% | 29.10% | 40.20% |
| B4 | 0.23% | 0.17% | 4.40% | 21.90% |

The above data show that pre-gradient exposure to hypoxia enhances composition of B2 as well as the distribution of specific specialized cells (erythropoietin-producing cells, vascular cells, and glomerular cells) into B4. Thus, hypoxic culture, followed by density-gradient separation as described supra, is an effective way to generate 'B2' and 'B4' cell populations, across species.

Example 4—Isolation of Tubular/Glomerular Cells from Human Kidney

Tubular and glomerular cells were isolated and propagated from normal human kidney tissue by the enzymatic isolation methods described throughout. By the gradient method described above, the tubular cell fraction was enriched ex vivo and after culture. As shown in FIG. 68 of Presnell et al. WO/2010/056328 (incorporated herein by reference in its entirety), phenotypic attributes were maintained in isolation and propagation. Tubular cell function, assessed via uptake of labeled albumin, was also retained after repeated passage and cryopreservation. FIG. 69 of Presnell et al. WO/2010/056328 (incorporated herein by reference in its entirety) shows that when tubular-enriched and tubular-depleted populations were cultured in 3D dynamic culture, a marked increase in expression of tubular marker, cadherin, was expressed in the tubular-enriched population. This confirms that the enrichment of tubular cells can be maintained beyond the initial enrichment when the cells are cultured in a 3D dynamic environment.

Example 5—Further Separation of EPO-Producing Cells Via Flow Cytometry

The same cultured population of kidney cells described above in Example 2 was subjected to flow cytometric analysis to examine forward scatter and side scatter. The small, less granular EPO-producing cell population was discernable (8.15%) and was separated via positive selection of the small, less granular population using the sorting capability of a flow cytometer (see FIG. 70 of Presnell et al. WO/2010/056328 (incorporated herein by reference in its entirety)).

Example 6—Characterization of an Unfractionated Mixture of Renal Cells Isolated from an Autoimmune Glomerulonephritis Patient Sample An unfractionated mixture of renal cells was isolated, as described above, from an autoimmune glomerulonephritis patient sample. To determine the unbiased genotypic composition of specific subpopulations of renal cells isolated and expanded from kidney tissue, quantitative real time PCR (qrtpcr) analysis (Brunskill et al., supra 2008) was employed to identify differential cell-type-specific and pathway-specific gene expression patterns among the cell subfractions. As shown in Table 6.1, HK20 is an autoimmune glomerulonephritis patient sample. Table 6.2 shows that cells generated from HK20 are lacking glomerular cells, as determined by qRTPCR.

Example 7—Genetic Profiling of Therapeutically Relevant Renal Bioactive Cell Populations Isolated from a Case of Focal Segmental Glomerulosclerosis To determine the unbiased genotypic composition of specific subpopulations of renal cells isolated and expanded from kidney tissue, quantitative real time PCR (qrtpcr) analysis (Brunskill et al., supra 2008) was employed to identify differential cell-type-specific and pathway-specific gene expression patterns among the cell subfractions. Human preparation HK023, derived from a case of focal segmental glomerulosclerosis (FSGS) in which a large portion of glomeruli had been destroyed, was evaluated for presence of glomerular cells in the B4 fraction at the time of harvest. In brief, unfractionated (UNFX) cultures were generated (Aboushwareb et al., supra 2008) and maintained independently from each of (4) core biopsies taken from the kidney using standard biopsy procedures. After (2) passages of UNFX ex vivo, cells were harvested and subjected to density gradient methods (as in Example 8) to generate subfractions, including subfraction B4, which is known to be enriched for endocrine, vascular, and glomerular cells based on work conducted in rodent, dog, and other human specimens.

TABLE 6.1

| Sample ID | Species | Age/Gender | Etiology of Renal Disease | Cause of Death (D) or Kidney Removal (KR) | BUN (mg/dL) | sCreat (mg/dL) |
|---|---|---|---|---|---|---|
| PK001 | Swine | <1 yr/M | Idiopathic nephropathy | (D) Renal Failure | 75 | 9.5 |
| PK002 | Swine | >1 yr/M | no renal disease | (D) Sacrifice | na | na |
| DK001 | Canine | <11 yr/M | age-related renal degeneration with fatty metaplasis of flomeruli | (D) Sacrifice | 24 | 1/1 |
| DK002 | Canine | <2 yr/M | chronic glomerulonephritis | (D) Sacrifice | 20 | 0.8 |
| HK016 | Human | 2 mo/F | no renal disease | (D) Head Trauma | 13 | 0.4 |
| HK017 | Human | 35 yr/F | Petechial hemorrhage secondary to DIC | (D) CVA | 12 | 2.9 |
| HK018 | Human | 48 yr/F | secondary to hypertension, NIDDM, and heart disease | (D) CV/ Renal Failure | 40 | 8.6 |
| HK019 | Human | 52 yr/F | secondary to hypertension, NIDDM, and heart disease | (D) CV/ Renal Failure | 127 | 5.7 |
| HK020 | Human | 54 yr/F | auto-immune glomerulonephritis | (D) CV/ Stroke | 94 | 16.6 |
| HK022 | Human | 60 yr/M | secondary to hypertension, NIDDM, and heart disease | (D) CVA/ Intracranial hemorrhage | 53 | 3.3 |

TABLE 6.1-continued

| Sample ID | Species | Age/Sex | Condition | Outcome | (col 6) | (col 7) |
|---|---|---|---|---|---|---|
| HK023 | Human | 18 yr/M | focal segmental glomerulosclerosis, nephrotic syndrome, hypertension | (KR) failed kidneys removed prior to transplant | 28 | 6.4 |
| CKD Rats (5/6Nx) n = 16 | Rat (Lewis) | 4-6 mo/F | renal mass insufficiency | (D) Renal Failure | 96.5 ± 14* | 2.4 ± 0.2* |
| Healthy rats (age-matched; n = 16) | Rat (Lewis) | 4-6 mo/F | None | (D) Sacrifice | 16.9 ± 0.6* | 0.4 ± 0.02* |
| Diabetic Nephropathy Rats (Ob/Ob ZSF1); n = 10 | Rat (ZSF1) | 9 mo/M | obesity, diabeties | (D) Sacrifice | 30.9 ± 4.8* | 0.6 ± 0.5* |
| Lean ZSF1 Rat (Age-Matched); n = 10 | Rat (ZSF1) | 9 mo/M | None | (D) Sacrifice | 18.9 ± 2.9* | 0.4 ± 0.05* |

| Sample ID | Creatinine Clearance (CC)/GFR/eGFR | HCT (%) | NB (mg/dL) | sPHOS (mg/dL) | uPRO | Key Histopathologic Features |
|---|---|---|---|---|---|---|
| PK001 | na | 34.1 | 10.6 | 6.3 | na | marked fibrosis; glomerular hypertrophy with focal sclerosis; tubular dilatation with protein casts |
| PK002 | na | na | na | na | na | normal kidney histology |
| DK001 | ma | 40.1 | 13.5 | 6.6 | 0 | diffuse glomerular lipidosis with focal segmental glomerular sclerosis |
| DK002 | na | 47 | 15.9 | 3.6 | >3.0 | chronic glomerulonephritis with chronic inflammation, glomerular sclerosis, and moderate fibrosis |
| HK016 | na | 26.6 | 9.6 | 8.6 | trace | normal neonatal kidney histology |
| HK017 | na | 26 | 8.8 | 6.3 | trace | normal tubular histology; no fibrosis; fibrin thrombi throughout glomerular capillaries |
| HK018 | 8.06 (CC) | 24.6 | 8.1 | 6.7 | na (anuric) | marked fibrosis; glomerular sclerosis; tubular dilatation with protein casts |
| HK019 | 14.5 (CC) | 23.7 | 8.4 | 12.4 | >300 | diffuse moderate glomerular obsolescence with thickening of Bowman's capsule; peri-glomerulas fibrosis; moderate tubular injury with diffuse tubulo-interstilial fibrosis, tubular dilatation with protein casts. |
| HK020 | 4.35 (CC) | 29 | 9.6 | 5.4 | na (anuric) | Severe end-stage renal disease; no functional |

TABLE 6.1-continued

| | | | | | | |
|---|---|---|---|---|---|---|
| | | | | | | glomeruli observed; severe glomerular sclerosis and interstitial fibrosis with chronic inflammation, tubular congestion with protein casts. |
| HK021 | 73.4 (CC) | 29 | 10.3 | 3.4 | trace | normal kidney histology |
| HK022 | 17 (GFR) | 31.1 | 10 | 1.8 | 100 | Severe end-stage renal disease; diffuse severe glomerulosclerosis, interstitial fibrosis and tubular atrophy with protein casts. |
| HK023 | 13.8 (GFR) | 36 | 11.8 | 6.4 | na | focal segmental glomerulosclerosis (10-15% of glomeruli sclerosed), associated with diffuse mesangial hypercellularity; diffuse, locally accentuated moderate to marked interstitial fibrosis and tubular atrophy; marked chronic active interstitial nephritis |
| CKD Rats (5/6Nx) n = 16 | 0.48 0.48 ± 0.3* (eGFR) | 39.3 ± 1.8* | 13.2 ± 0.6* | 10.2 ± 1.2* | 1420 ± 535* | interstitial fibrosis; glomerular atrophy and sclerosis; tubular degeneration and dilatation |
| Healthy rats (age-matched; n = 16) | 1.7 ± 0.1* (eGFR) | 46.1 ± 0.6* | 14.7 ± 0.3* | 6.8 ± 0.3* | 36 ± 13* | normal adult kidney histology |
| Diabetic Nephropathy Rats (Ob/Ob ZSF1); n =10 | 3.8 ± 0.3* (eGFR) | na | na | 5.3 ± 0.4* | 931 ± 0.4* | arteriolar thickening, severe tubular degeneration, dilation, and atrophy, and protein casts in the Bowman's space and tubular lumens (REF: Prabhakar, 2007 JASN); at 20 weeks of age |
| Lean ZSF1 Rat (Age-Matched); n = 10 | 6.4 ± 1.2* (eGFR) | na | na | 4.6 ± 0.5* | 296 ± 69* | moderate arteriolar thickening; normal tubular and glomerular structures (REF: Prabhakar 2007 JASN); at 20 weeks of age |

TABLE 6.2

Compartmental analysis of cultured human, swine, and rat renal cells.

| Sample ID | TUBULAR | | | | | | GLOMERULAR | | DUCTULAR | OTHER | | | | |
|---|---|---|---|---|---|---|---|---|---|---|---|---|---|---|
| | E-CAD | N-CAD | AQP-1 | CUB | CYP24 | ALB-U | NEPH | PODO | AQP-2 | EPO | vEGF | KDR | CD31 | SSC/FSC |
| PK001 | + | nd | nd | nd | nd | ++ | nd | nd | nd | +R | + | nd | nd | + |
| PK002 | + | nd | nd | nd | nd | + | nd | nd | nd | +R | + | nd | nd | + |
| HK016 | 3.03 | 0.83 | 0.0001 | 0.0006 | 0.055 | + | 0.0004 | 0.0050 | 0.0001 | 0.020 R | 0.85 | 0.001 | trace | + |
| HK017 | 0.66 | 0.83 | 0.0009 | 0.0002 | 0.046 | ++ | trace | 0.0001 | 0.0003 | 0.032 R | 0.36 | 0.002 | 0.0003 | + |
| HK018 | 0.61 | 1.59 | 0.0001 | 0.0003 | 0.059 | + | 0.0002 | – | – | 0.004 R | 0.36 | 0.003 | trace | + |
| HK019 | 0.62 | 2.19 | 0.026 | 0.0008 | 0.068 | +/– | 0.0009 | 0.0003 | 0.0020 | 0.076 R | 0.40 | 0.002 | 0.0040 | + |
| HK020 | 0.07 | 1.65 | 0.0003 | 0.0007 | 0.060 | +++ | – | – | – | 0.011 R | 0.40 | 0.002 | – | + |
| Healthy Lewis Rat (male) | + | + | + | + | + | + | + | + | + | +R | + | + | + | + |
| Rat CKD model (5/6 NX Lewis) | + | + | + | + | nd | nd | + | + | nd | +R | nd | nd | nd | + |

The B4 fractions were collected separately from each independent UNFX sample of HK023, appearing as distinct bands of cells with buoyant density between 1.063-1.091 g/mL. RNA was isolated from each sample and examined for expression of Podocin (glomerular cell marker) and PECAM (endothelial cell marker) by quantitative real-time PCR. As expected from a biopsy-generated sample from a case of severe FSGS, the presence of podocin(+) glomerular cells in B4 fractions was inconsistent, with podocin undetectable in 2/4 of the samples. In contrast, PECAM+ vascular cells were consistently present in the B4 fractions of 4/4 of the biopsy-initiated cultures. Thus, the B4 fraction can be isolated at the 1.063-1.091 g/mL density range, even from human kidneys with severe disease states.

TABLE 7.1

Expression of Podocin and PECAM for detection of glomerular and vascular cells in subfraction B4 isolated from a case of FSGS.

| HK023/ Biopsy | RQ (Podocin)/B4 | RQ (PECAM)/B4 |
|---|---|---|
| #1/p2 | 0.188 | 0.003 |
| #2/p2 | ND | 0.02 |
| #3/p2 | 40.1 | 0.001 |
| #4/p2 | ND | 0.003 |

Further, as shown in Table 7.2, human sample (HK018) displayed undetected Podocin (glomerular marker) by qRT-PCR after density gradient centrifugation.

TABLE 7.2

HK018 Post-Gradient gene expression characterization of B2 & B4'

| Gene | RQ(Unfx) | RQ(B2) | RQ(B4) | B2/B4 |
|---|---|---|---|---|
| Podocin | 1 | ND | ND | — |
| VegF | 1 | 1.43 | 1.62 | 0.9 |
| Aqp1 | 1 | 1.7 | 1.2 | 1.4 |
| Epo | 1 | 0.9 | 0.5 | 1.8 |
| Cubilin | 1 | 1.2 | 0.7 | 1.7 |
| Cyp | 1 | 1.2 | 1.4 | 0.85 |
| Ecad | 1 | 1.15 | 0.5 | 2.3 |
| Ncad | 1 | 1.02 | 0.72 | 1.4 |

Example 8—Enrichment/Depletion of Viable Kidney Cell Types Using Fluorescent Activated Cell Sorting (FACS)

One or more isolated kidney cells may be enriched, and/or one or more specific kidney cell types may be depleted from isolated primary kidney tissue using fluorescent activated cell sorting (FACS).

Reagents:

70% ethanol; Wash buffer (PBS); 50:50 Kidney cell medium (50% DMEM high glucose): 50% Keratinocyte-SFM; Trypan Blue 0.4%; Primary antibodies to target kidney cell population such as CD31 for kidney endothelial cells and Nephrin for kidney glomerular cells. Matched isotype specific fluorescent secondary antibodies; Staining buffer (0.05% BSA in PBS)

Procedure:

Following standard procedures for cleaning the biological safety cabinet (BSC), a single cell suspension of kidney cells from either primary isolation or cultured cells may be obtained from a T500 TIC treated flask and resuspend in kidney cell medium and place on ice. Cell count and viability is then determined using trypan blue exclusion method. For kidney cell enrichment/depletion of, for example, glomerular cells or endothelial cells from a heterogeneous population, between 10 and 50e6 live cells with a viability of at least 70% are obtained. The heterogeneous population of kidney cells is then stained with primary antibody specific for target cell type at a starting concentration of 1 µg/0.1 ml of staining buffer/1×10$^6$ cells (titer if necessary). Target antibody can be conjugated such as CD31 PE (specific for kidney endothelial cells) or un-conjugated such as Nephrin (specific for kidney glomerular cells).

Cells are then stained for 30 minutes on ice or at 4° C. protected from light. After 30 minutes of incubation, cells are washed by centrifugation at 300×g for 5 min. The pellet is then resuspended in either PBS or staining buffer depending on whether a conjugated isotype specific secondary antibody is required. If cells are labeled with a fluorochrome conjugated primary antibody, cells are resuspended in 2 mls of PBS per 10e7 cells and proceed to FACS aria or equivalent cell sorter. If cells are not labeled with a fluorochrome conjugated antibody, then cells are labeled with an isotype specific fluorochrome conjugated secondary antibody at a starting concentration of 1 ug/0.1 ml/1 e6 cells.

Cells are then stained for 30 min. on ice or at 4° C. protected from light. After 30 minutes of incubation, cells are washed by centrifugation at 300×g for 5 min. After centrifugation, the pellet is resuspended in PBS at a concentration of 5e6/ml of PBS and then 4 mls per 12×75 mm is transferred to a sterile tube.

FACs Aria is prepared for live cell sterile sorting per manufacturer's instructions (BD FACs Aria User Manual). The sample tube is loaded into the FACs Aria and PMT voltages are adjusted after acquisition begins. The gates are drawn to select kidney specific cells types using fluorescent intensity using a specific wavelength. Another gate is drawn to select the negative population. Once the desired gates have been drawn to encapsulate the positive target population and the negative population, the cells are sorted using manufacturer's instructions.

The positive target population is collected in one 15 ml conical tube and the negative population in another 15 ml conical tube filled with 1 ml of kidney cell medium. After collection, a sample from each tube is analyzed by flow cytometry to determine purity. Collected cells are washed by centrifugation at 300×g for 5 min. and the pellet is resuspended in kidney cell medium for further analysis and experimentation.

Example 9—Enrichment/Depletion of Kidney Cell Types Using Magnetic Cell Sorting

One or more isolated kidney cells may be enriched and/or one or more specific kidney cell types may be depleted from isolated primary kidney tissue.
Reagents:
70% ethanol, Wash buffer (PBS), 50:50 Kidney cell medium (50% DMEM high glucose): 50% Keratinocyte-SFM, Trypan Blue 0.4%, Running Buffer (PBS, 2 mM EDTA, 0.5% BSA), Rinsing Buffer (PBS, 2 mM EDTA), Cleaning Solution (70% v/v ethanol), Miltenyi FCR Blocking reagent, Miltenyi microbeads specific for either IgG isotype, target antibody such as CD31(PECAM) or Nephrin, or secondary antibody.
Procedure:
Following standard procedures for cleaning the biological safety cabinet (BSC), a single cell suspension of kidney cells from either primary isolation or culture is obtained and resuspended in kidney cell medium. Cell count and viability is determined using trypan blue exclusion method.

For kidney cell enrichment/depletion of, for example, glomerular cells or endothelial cells from a heterogeneous population, at least 10e6 up to 4e9 live cells with a viability of at least 70% is obtained.

The best separation for enrichment/depletion approach is determined based on target cell of interest. For enrichment of a target frequency of less than 10%, for example, glomerular cells using Nephrin antibody, the Miltenyi autoMACS, or equivalent, instrument program POSSELDS (double positive selection in sensitive mode) is used. For depletion of a target frequency of greater than 10%, the Miltenyi autoMACS, or equivalent, instrument program DEPLETES (depletion in sensitive mode) is used.

Live cells are labeled with target specific primary antibody, for example, Nephrin rb polyclonal antibody for glomerular cells, by adding 1 μg/10e6 cells/0.1 ml of PBS with 0.05% BSA in a 15 ml conical centrifuge tube, followed by incubation for 15 minutes at 4° C.

After labeling, cells are washed to remove unbound primary antibody by adding 1-2 ml of buffer per 10e7 cells followed by centrifugation at 300×g for 5 min. After washing, isotype specific secondary antibody, such as chicken anti-rabbit PE at 1 ug/10e6/0.1 ml of PBS with 0.05% BSA, is added, followed by incubation for 15 minutes at 4° C.

After incubation, cells are washed to remove unbound secondary antibody by adding 1-2 ml of buffer per 10e7 cells followed by centrifugation at 300×g for 5 min. The supernatant is removed, and the cell pellet is resuspended in 60 μl of buffer per 10e7 total cells followed by addition of 20 μl of FCR blocking reagent per 10e7 total cells, which is then mixed well.

Add 20 μl of direct MACS microbeads (such as anti-PE microbeads) and mix and then incubate for 15 min at 4° C.

After incubation, cells are washed by adding 10-20× the labeling volume of buffer and centrifuging the cell suspension at 300×g for 5 min. and resuspending the cell pellet in 500 μl-2 mls of buffer per 10e8 cells.

Per manufacturer's instructions, the autoMACS system is cleaned and primed in preparation for magnetic cell separation using autoMACS. New sterile collection tubes are placed under the outlet ports. The autoMACS cell separation program is chosen. For selection the POSSELDS program is chosen. For depletion the DEPLETES program is chosen.

The labeled cells are inserted at uptake port, then beginning the program.

After cell selection or depletion, samples are collected and placed on ice until use. Purity of the depleted or selected sample is verified by flow cytometry.

Example 10—Cells with Therapeutic Potential can be Isolated and Propagated from Normal and Chronically-Diseased Kidney Tissue The objective of the present study was to determine the functional characterization of human NKA cells through high content analysis (HCA). High-content imaging (HCI) provides simultaneous imaging of multiple sub-cellular events using two or more fluorescent probes (multiplexing) across a number of samples. High-content Analysis (HCA) provides simultaneous quantitative measurement of multiple cellular parameters captured in High-Content Images. In brief, unfractionated (UNFX) cultures were generated (Aboushwareb et al., supra 2008) and maintained independently from core biopsies taken from five human kidneys with advanced chronic kidney disease (CKD) and three non-CKD human kidneys using standard biopsy procedures. After (2) passages of UNFX ex vivo, cells were harvested and subjected to density gradient methods (as in Example 2) to generate subfractions, including subfractions B2, B3, and/or B4.

Figure 7:
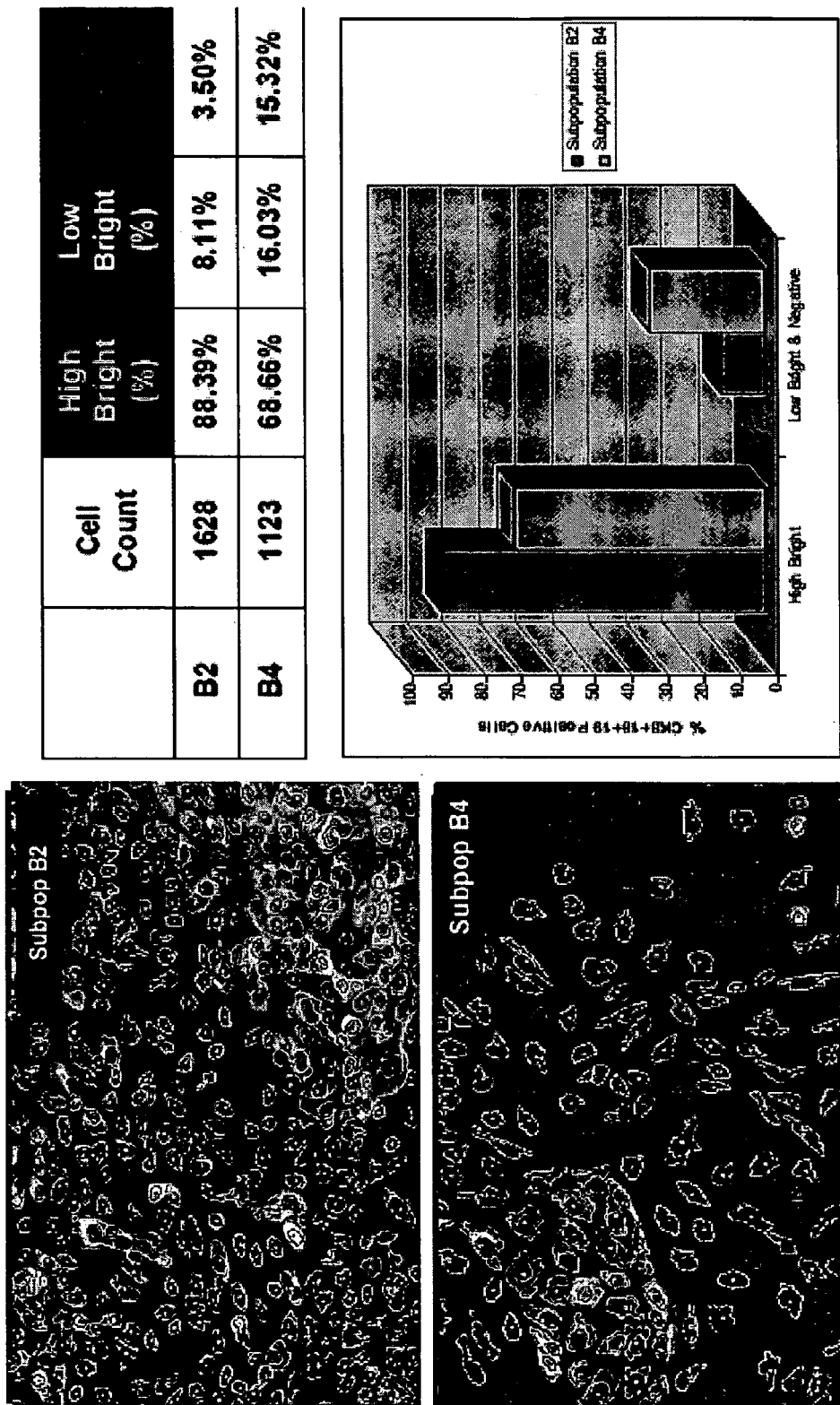
FIG. 7 depicts comparative analysis of marker expression between tubular-enriched B2 and tubular cell-depleted B4 subfractions.

Human kidney tissues were procured from non-CKD and CKD human donors as summarized in Table 10.1. FIG. 4 shows histopathologic features of the HK17 and HK19 samples. Ex vivo cultures were established from all non-CKD (3/3) and CKD (5/5) kidneys. High content analysis (HCA) of albumin transport in human NKA cells defining regions of interest (ROI) is shown in FIG. 5 (HCA of albumin transport in human NKA cells). Quantitative comparison of albumin transport in NKA cells derived from non-CKD and CKD kidney is shown in FIG. 6. As shown in FIG. 6, albumin transport is not compromised in CKD-derived NKA cultures. Comparative analysis of marker expression between tubular-enriched B2 and tubular cell-depleted B4 subfractions is shown in FIG. 7 (CK8/18/19).

TABLE 10.1

| Sample ID | Age/ Gender | Etiology of Renal Disease | Cause of Death (D) or Kidney Removal (KR) | BUN (mg/dL) | sCREAT (mg/dL) | Creatinine Clearance (CC)/ GFR/eGFR |
|---|---|---|---|---|---|---|
| HK016 | 2 mo/F | no renal disease | (D) Trauma | 13 | 0.4 | na |
| HK017 | 35 yr/F | Petechial hemorrhage secondary to DIC | (D) CVA | 12 | 2.9 | na |
| HK018 | 48 yr/F | secondary to hypertension, NIDDM, and heart disease | (D) CV/Renal Failure | 40 | 8.6 | 8.06 (CC) |
| HK019 | 52 yr/F | secondary to hypertension, NIDDM, and heart disease | (D) CV/Renal Failure | 127 | 5.7 | 14.5 (CC) |
| HK020 | 54 yr/F | auto-immune glomerulonephritis | (D) CV/Stroke | 94 | 16.6 | 4.35 (CC) |
| HK021 | 15 mo/M | no renal disease | (D) Trauma | 11 | 0.4 | 73.4 (CC) |
| HK022 | 60 yr/M | secondary to hypertension, NIDDM, and heart disease | (D) CVA/ intracranial hemorrhage | 53 | 3.3 | 17 (GFR) |
| HK023 | 18 yr/M | focal segmental glomerulosclerosis, nephrotic syndrome, hypertension | (KR) failed kidneys removed prior to transplant | 28 | 6.4 | 13.8 (GFR) |

| Sample ID | HCT (%) | HB (mg/dL) | sPHOS (mg/dL) | uPRO | Key Histopathologic Features |
|---|---|---|---|---|---|
| HK016 | 26.6 | 9.6 | 8.6 | trace | normal neonatal kidney histology |
| HK017 | 26 | 8.8 | 6.3 | trace | normal tubular histology; no fibrosis fibrin thrombi throughout glomerular capillaries |
| HK018 | 24.6 | 8.1 | 6.7 | na (anuric) | marked fibrosis; glomerular sclerosis; tubular dilatation with protein casts |
| HK019 | 23.7 | 8.4 | 12.4 | >300 | diffuse moderate glomerular obsolescence with thickening of Bowman's capsule; peri-glomerular fibrosis; moderate tubular injury with diffuse tubulo-interstilial fibrosis, tubular dilatation with protein casts. |
| HK020 | 29 | 9.6 | 5.4 | na (anuric) | Severe end-stage renal disease; no functional glomeruli observed; severe glomerular sclerosis observed interstitial fibrosis with chronic inflammation, tubular congestion with protein casts. |
| HK021 | 29 | 10.3 | 3.4 | trace | normal kidney histology |
| HK022 | 31.1 | 10 | 1.8 | 100 | Severe end-stage renal disease diffuse severe glomerulosclerosis interstitial fibrosis and tubular atrophy with protein casts |
| HK023 | 36 | 11.8 | 6.4 | na | focal segmental glomerulosclerosis (10-15% of glomeruli sclerosed) associated with diffuse mesangial hypercellularity; diffuse, focally accentuated moderate to marked interstitial fibrosis and tubular atrophy; marked chronic active interstitial nephritis |

Figure 8:
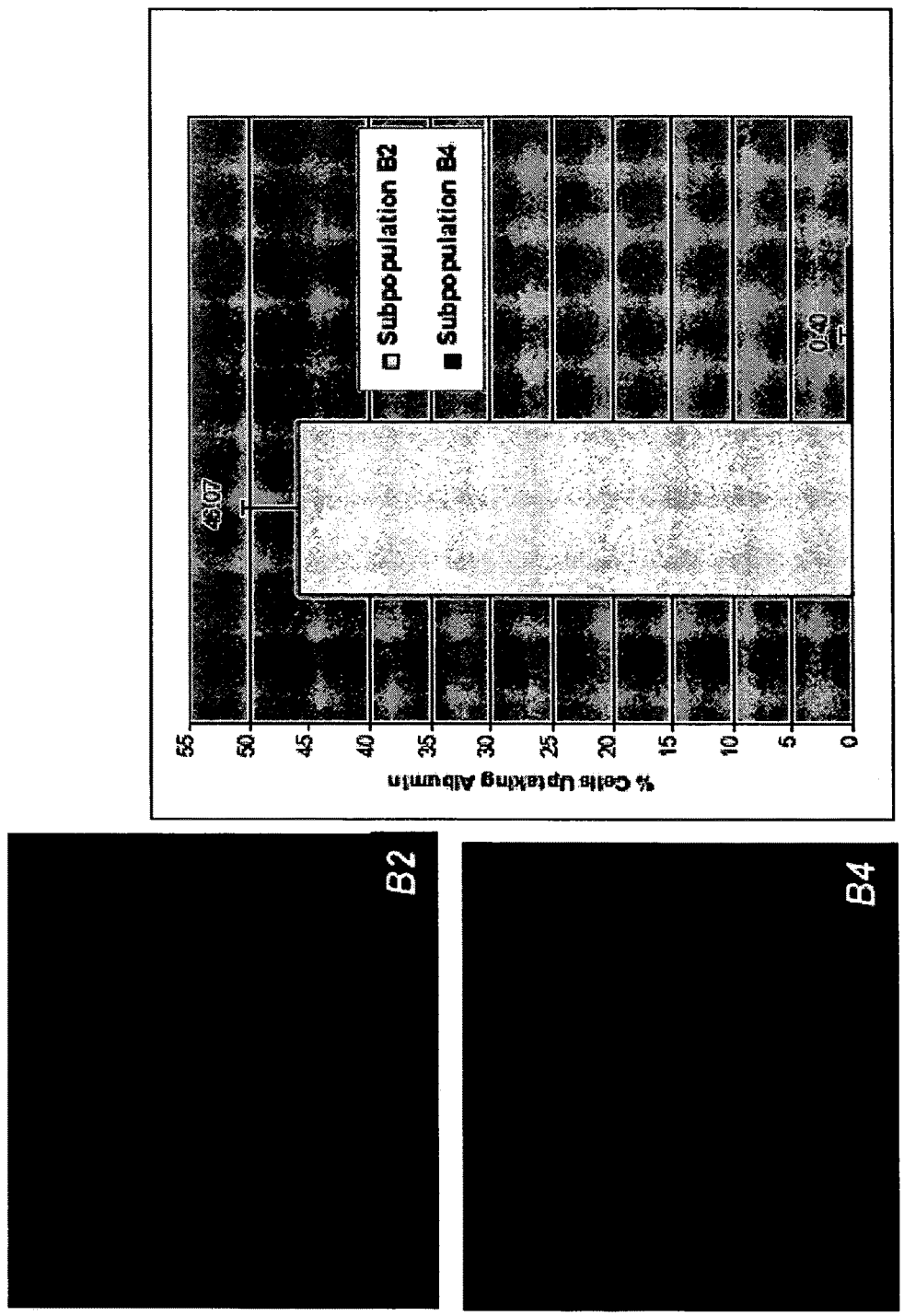
FIG. 8 depicts comparative functional analysis of albumin transport between tubular-enriched B2 and tubular cell-depleted B4 subfractions.

Comparative functional analysis of albumin transport between tubular-enriched B2 and tubular cell-depleted B4 subfractions is shown in FIG. 8. Subfraction B2 is enriched in proximal tubule cells and thus exhibits increased albumin-transport function.

Albumin Uptake:

Culture media of cells grown to confluency in 24-well, collagen IV plates (BD Biocoat™) was replaced for 18-24 hours with phenol red-free, serum-free, low-glucose DMEM (pr-/s-/lg DMEM) containing 1× antimycotic/antibiotic and 2 mM glutamine. Immediately prior to assay, cells were washed and incubated for 30 minutes with pr-/s-/lg DMEM+ 10 mM HEPES, 2 mM glutamine, 1.8 mM CaCl2, and 1 mM MgCl2. Cells were exposed to 25 μg/mL rhodamine-conjugated bovine albumin (Invitrogen) for 30 min, washed with ice cold PBS to stop endocytosis and fixed immediately with 2% paraformaldehyde containing 25 µg/mL Hoechst nuclear dye. For inhibition experiments, 1 µM receptor-associated protein (RAP) (Ray Biotech, Inc., Norcross Ga.) was added 10 minutes prior to albumin addition. Microscopic imaging and analysis was performed with a BD Pathway™855 High-Content BioImager (Becton Dickinson) (see Kelley et al. Am J Physiol Renal Physiol. 2010 November; 299(5): F1026-39. Epub Sep. 8, 2010).

In conclusion, HCA yields cellular level data and can reveal populations dynamics that are undetectable by other assays, i.e., gene or protein expression. A quantifiable ex-vivo HCA assay for measuring albumin transport (HCA-AT) function can be utilized to characterize human renal tubular cells as components of human NKA prototypes. HCA-AT enabled comparative evaluation of cellular function, showing that albumin transport-competent cells were retained in NKA cultures derived from human CKD kidneys. It was also shown that specific subfractions of NKA cultures, B2 and B4, were distinct in phenotype and function, with B2 representing a tubular cell-enriched fraction with enhanced albumin transport activity. The B2 cell subpopulation from human CKD are phenotypically and functionally analogous to rodent B2 cells that demonstrated efficacy in vivo (as shown above).

Example 11—Marker Expression as a Predictor of Renal Regeneration

This study concerns stem and progenitor marker expression as a predictor of renal regeneration in 5/6 nephrectomized rats treated with therapeutically bio-active primary renal cell sub-populations. The underlying mechanisms by which NKA treatment improved renal function are being characterized. Our studies on NKA treatment's mechanism of action concern cell-cell signalling, engraftment, and fibrotic pathways. The present work focused on how NKA treatment might increase the organ's intrinsic regenerative capacity—perhaps by mobilizing renal stem cells. We hypothesize that the extended survival and improvement in renal function observed in NKA-treated 5/6 NX rats is associated with molecular expression of specific stem cell markers.

Using a rat 5/6 nephrectomy model for CKD, this study employs molecular assays to evaluate the mobilization of resident stem and progenitor cells within the rat 5/6 nephrectomized kidney in response to direct injection with defined, therapeutically bio-active primary renal cell populations. It was observed that this cell-based therapy is specifically associated with up-regulation of the key stem cell markers CD24, CD133, UTF1, SOX2, LEFTY1, and NODAL at both transcript and protein levels. Up-regulation was detected by 1 week post-injection and peaked by 12 weeks post-injection. Activation of stem and progenitor cell markers was associated with increased survival and significant improvement of serum biomarkers relative to untreated nephrectomized controls.

Figure 9:
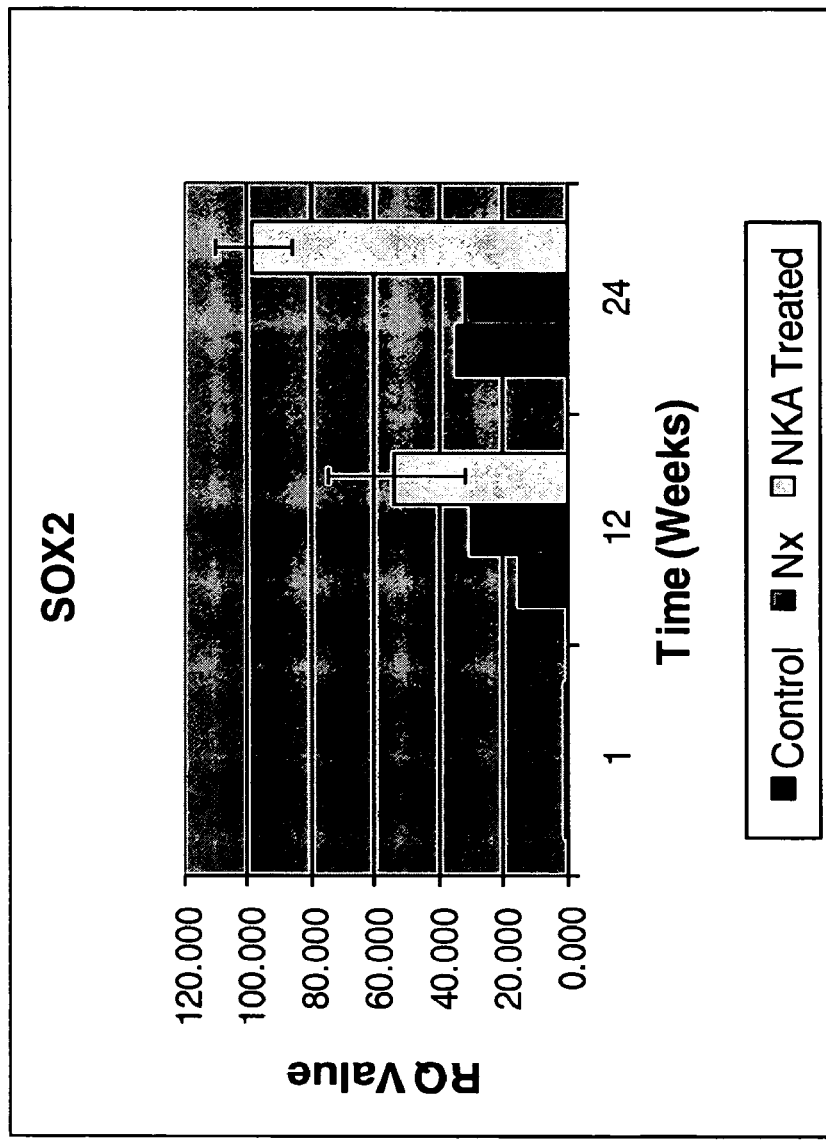
FIG. 9 shows expression of SOX2 mRNA in host tissue after treatment of 5/6 NX rats.
Figure 11:
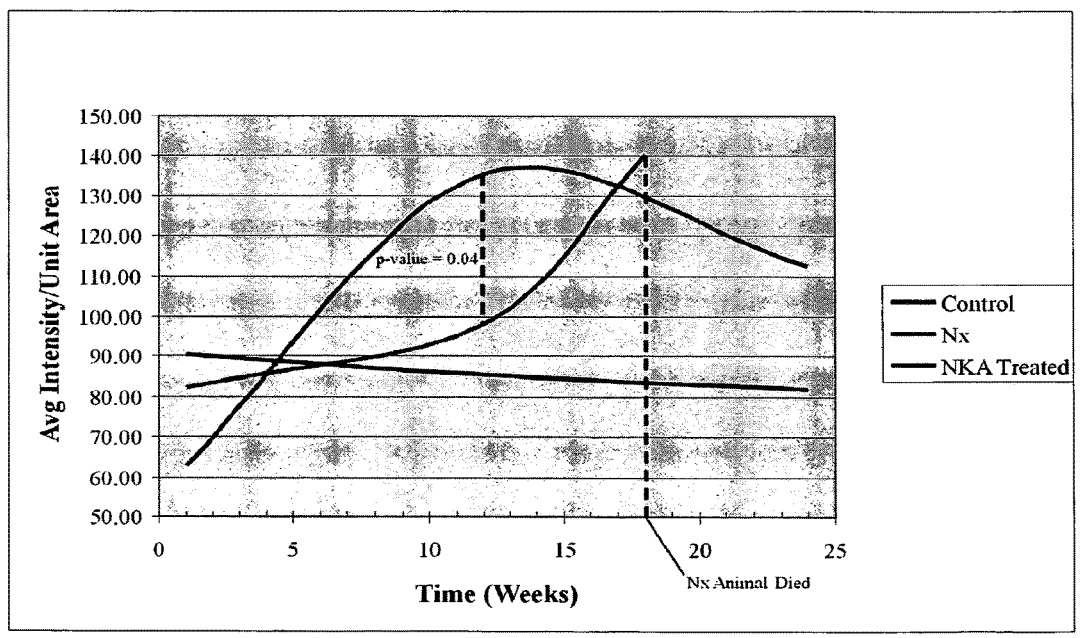
FIG. 11 depicts a time course of regenerative response index (RRI).

Materials and Methods
Isolation of Primary Renal Cell Populations from Rat.
Isolation of primary renal cell populations from rat were performed as previously described (Aboushwareb et al., supra 2008; Presnell et al., 2009 FASEB J 23: LB143).
In Vivo Study Design and Analysis.
Detailed descriptions of the isolation of primary renal cell populations (Presnell et al. Tissue Eng Part C Methods. 2010 Oct. 27. [Epub ahead of print]) and the in vivo studies that evaluated the bioactivity of primary renal cell sub-populations in the 5/6 nephrectomized rodent model of CKD (Kelley et al. supra 2010). A tubular cell-enriched subpopulation of primary renal cells improves survival and augments kidney function in a rodent model of chronic kidney disease were published elsewhere. In the current study, tissues were isolated at necropsy from rats treated with B2 (NKA #1) or a B2+B4 mixture (NKA #2) and compared to nephrectomized (Nx) and sham-operated, non-nephrectomized rats (Control). In FIGS. 9 and 11 and Table 11.1, data from NKA #1 and NKA #2 treated rats was pooled. Systemic data was obtained by analysis of blood samples drawn weekly and pre-necropsy from rats on study.

Table 11.1 shows survival data for sham treated animals (control), n=3; nx control (Nx), n+3; animals treated with B2 cells (NKA#1), n=7; B2+B4 cells (NKA#2); n=7. At the end of the study (23-24 weeks) none of the Nx animals remained. NKA treated animals had a superior survival rate compared to the untreated Nx control.

TABLE 11.1

| Treatment Group | Early 1 week | Midpoint 12-13 Week | End of Study [23-24 Week] |
| --- | --- | --- | --- |
| Control | 2/3* | 2/2 | 2/2 |
| NX | 2/3* | 1/2 | 0/1 |
| NKA #1 | 5/7** | 3/7** | 1/3** |
| NKA #2 | 5/7** | 3/7** | 3/3 |

*1 animal sacrificed at scheduled timepoint for tissue
**2 animals sacrificed at scheduled timepoint for tissue RNA Isolation, cDNA Synthesis and qRT-PCR.
RNA was isolated from tissues embedded in optimum cutting temperature (OCT) freezing media as follows: tissue blocks were placed at room temperature and excess OCT was removed, the tissues were then placed in PBS to allow complete thawing and removal of residual OCT, the tissues were washed three times in PBS and then coarsely chopped and aliquoted into microfuge tubes. The aliquoted tissues were then pulverized using a pestle and RNA was extracted using the RNeasy Plus Mini Kit (Qiagen, Valencia Calif.). RNA integrity was determined spectrophotomerically and cDNA was generated from a volume of RNA equal to 1.4 µg using the SuperScript® VILO™ cDNA Synthesis Kit (Invitrogen, Carlsbad Calif.). Following cDNA synthesis, each sample was diluted 1:6 by adding 200 µl of diH$_2$O to bring the final volume to 240 µl. The expression levels of target transcripts were examined via quantitative real-time PCR (qRT-PCR) using catalogued primers and probes from ABI and an ABI-Prism 7300 Real Time PCR System (Applied Biosystems, Foster City Calif.). Amplification was performed using the TaqMan® Gene Expression Master Mix (ABI, Cat #4369016) and peptidylprolyl isomerase B (PPIB) was utilized as the endogenous control. qRT-PCR Reaction: 10 µl Master Mix (2×), 1 µl Primer and Probe (20×), 9 µl cDNA, 20 µl Total Volume per Reaction. Each reaction was setup as follows using the TaqMan® primers and probes.

| Gene | Abbreviation | TaqMan primer |
| --- | --- | --- |
| SRY (sex determining region Y)-box 2 | Sox2 | Rn01286286_g1 |
| Undifferentiated Embryonic Cell Transcription Factor | UTF1 | Rn01498190_g1 |
| Nodal Homolog from Mouse | NODAL | Rn01433623_m1 |
| Prominin 1 | CD133 | Rn00572720_m1 |
| CD24 | CD24 | Rn00562598_m1 |
| LEFTY1 | | |

Western Blot.

Frozen whole kidney tissue embedded in OCT freezing media was utilized for protein sample collection. OCT was removed as described above and all tissues were lysed in a buffer consisting of 50 mM Tris (pH 8.0), 120 mM NaCl, 0.5% NP40, and protease inhibitor cocktail (Roche Applied Science, Indianapolis Ind.). Lysis proceeded for 15 minutes at room temperature with rocking followed by centrifugation for 10 minutes at 13,000 RPM. All supernatants were collected and protein concentrations were determined by Bradford Assay. SDS PAGE Gel was carried out by adding 30 μg of protein per sample to each well of NuPAGE® Novex 10% Bis-Tris Gels (Invitrogen). The gels were electrophoresed for 40 min at 200V in MES running buffer (Invitrogen). The proteins were then transferred to nitrocellulose membranes using the I-Blot system (Invitrogen), and blocked with 15 mL of 4% w/v low-fat milk dissolved in Tris Buffered Saline with 0.1% Tween-20 (TBS-T) (Sigma, St. Louis, Mo.) for 2 hours at room temperature. The membranes were probed overnight at room temperature with the following antibodies:each diluted in 5 mL TBS-T with 2% w/v low-fat milk. (Anti-Human Lefty-A Long & Short isoforms (R&D systems MAB7461); Anti-Human, Mouse & Rat CD133 (Abcam AB19898); Anti-Human & Mouse UTF1 (Millipore MAB4337); Anti-Human NODAL (Abcam AB55676); Anti-Human & Rat CDH11 (OB Cadherin) (Thermo Scientific MA1-06306); Anti-Rat CD24 (Becton Dickinson)). The membranes were washed 3 times/10 minutes each with TBS-T, then probed with the appropriate HRP-conjugated secondary antibody (Vector Labs PI-2000; PI-1000) diluted in TBS-T with 2% w/v low-fat milk (1:60, 000) for 1.5 hours at room temperature. The membranes were washed 3 times/10 minutes each in TBS-T, followed by two 10-minute washes in diH$_2$O. The blots were developed using ECL Advance chemiluminescent reagent (GE Healthcare Life Sciences, Piscataway N.J.) and visualized using the ChemiDoc™ XRS molecular imager and Quantity One® software (BioRad, Hercules Calif.).

Results.

Molecular assays to evaluate the mobilization of resident stem and progenitor cells in 5/6 NX rats were developed and used to investigate the temporal response of these markers to NKA treatment. It was observed that NKA treatment was specifically associated with up-regulation of the key stem cell markers CD24, CD133, UTF-1, SOX-2, LEFTY, and NODAL at mRNA transcript and protein levels. Up-regulation was detected by 1 week post-injection and had peaked by 12 weeks post-injection. Activation of stem and progenitor cell markers was associated with increased survival and significant improvement of serum biomarkers (i.e., improvement of renal filtration) relative to untreated 5/6 NX control animals.

FIG. 9 shows the expression of SOX2 mRNA in host tissue after treatment of 5/6 NX rats with NKA. Temporal analysis of SOX2 mRNA expression showed 1.8-fold increase in SOX2 mRNA within NKA treatment group over Nx control by 12 week post-implantation. A 2.7-fold increase in SOX2 mRNA expression was observed in NKA treatment group over Nx control by 24 weeks post-implantation. (1-week n=3 each for Control (sham), Nx (control), and NKA treated) (12 week n=1 each for Control (sham) and Nx (control); NKA treated n=4) (24 week n=1 each for Control (sham) and Nx (control); NKA treated n=4). *Indicates p-value=0.023 or <0.05.

Figure 10:
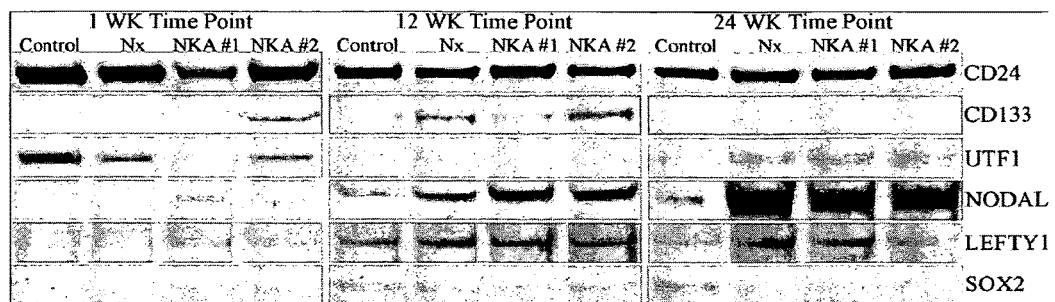
FIG. 10 Western blot showing time course of expression of CD24, CD133, UTF1, SOX2, NODAL and LEFTY.

FIG. 10—Western blot showing time course of expression of CD24, CD133, UTF1, SOX2, NODAL and LEFTY in sham control (Control), Nx control (Nx), and rats treated NKA #1 and NKA #2 at 1, 12 and 24 weeks post-treatment. Frozen whole kidney tissue (N=1 for each sample) embedded in OCT freezing media was utilized for protein sample collection. Lanes were normalized by total mass protein loaded. CD133, UTF1, NODAL, LEFTY and SOX2 protein levels in NKA-treated tissues were elevated relative to Control or Nx rats at all time points.

FIG. 11 depicts a time course of regenerative response index (RRI). A densitometric analysis of individual protein expression (FIG. 10) was used to generate a quantitative index of regenerative marker protein expression, or regenerative response index (RRI). Band intensity was calculated from each western blot using Image J v1.4 software (NIH) and values normalized per unit area for each protein. Average intensity was determined for sham, Nx, and NKA treatment groups by compiling the 5 markers used in the western blot analysis for each time point. Plot shows XY scatter with smoothed line fit generated from 1, 12, and 24 week time points. The average intensity for each group was plotted over time to highlight the trends in the host tissue response of stem cell marker protein expression. Statistical analysis was performed using standard two tailed Student's t-test assuming equal variance for each sample. Confidence interval of 95% (p-value<0.05) was used to determine statistical significance. (NKA treated group n=2; Control (sham) n=1; Nx (control) n=1). In sham control animals, RRI shows only a slight reduction from 90.47 at 1 week post-treatment to 81.89 at 24 weeks post treatment. In contrast, kidney from 5/6 Nx controls presents essentially the opposite response, with RRI increasing from 82.26 at 1 week post-treatment to 140.56 at 18 weeks post-treatment, at which point the animal died. In NKA-treated animals RRI increased sharply from 62.89 at 1 week post-treatment to 135.61 by 12 weeks post-treatment and fell to 112.61 by 24 weeks post-treatment.

NKA treatment was observed to be associated with up-regulation of the stem cell markers CD24, CD133, UTF-1, SOX-2 and NODAL at both transcript and protein levels in the host tissue. Up-regulation was detected by 1 week post-treatment and peaked by 12 weeks post-treatment. Overall activation of stem and progenitor cell markers in host tissues was associated with increased survival (1) and improvement of clinically-relevant serum biomarkers relative to untreated nephrectomized controls.

Mobilization of resident stem and progenitor cell populations in response to NKA treatment may contribute to the restoration of kidney function in 5/6 NX animals by regenerating damaged kidney tissue and organ architecture. The molecular assays used in this study might therefore provide a rapid, straightforward, and predictive assay of regenerative outcomes for evaluating tissue engineering and regenerative medicine treatments for CKD.

Example 12—Exosomes Derived from Primary Renal Cells Contain microRNAs

We sought to correlate specific exosome-derived miRNAs with functionally-relevant outcomes in target cells in vitro to inform the design of in vivo studies for elucidating mechanisms that yield regenerative outcomes.

Methods:

The effect of conditioned media on signaling pathways associated with regenerative healing responses was investigated using commercially available cells: HK-2 (human proximal tubule cell line), primary human renal mesangial cells (HRMC), and human umbilical cord endothelial cells (HUVEC). RNA content from exosomes in conditioned media from human and rat primary renal cell cultures (UNFX) was screened by PCR-based array designed to detect known miRNAs. Low oxygen has been reported to affect exosome shedding; therefore, a group of cultures was exposed to low oxygen (2% $O_2$) for 24 hours prior to media collection. Exosomes were separated from cellular debris by FACS.

Figure 12:
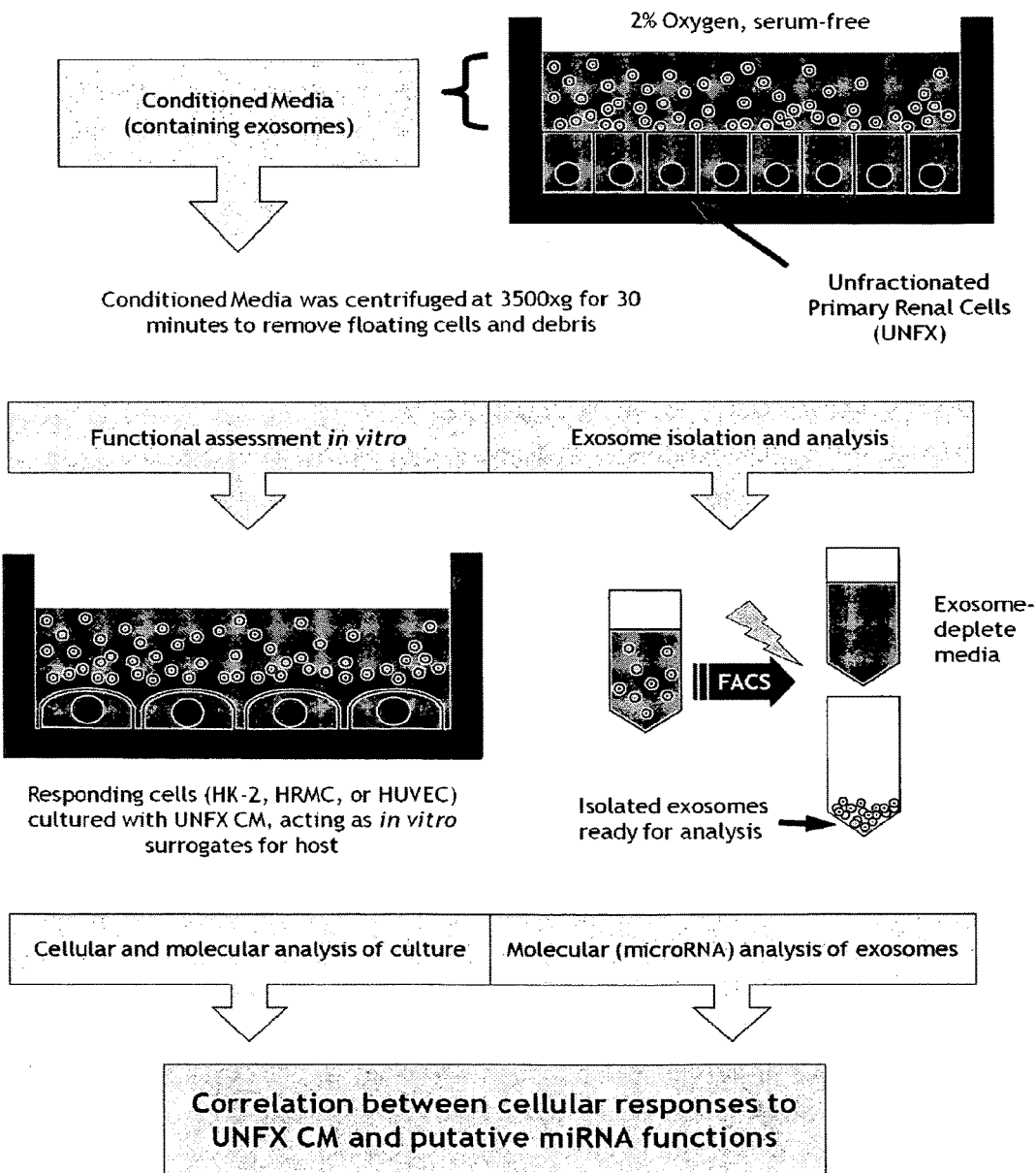
FIG. 12 provides a schematic for the preparation and analysis of UNFX conditioned media.

FIG. 12 provides a schematic for the preparation and analysis of UNFX conditioned media.

Results:

UNFX-conditioned media was found to affect signaling pathways associated with regenerative healing responses; these responses were not observed in controls using non-conditioned media. Specifically, NFκB (immune response) and epithelial-to-mesenchymal transition (fibrotic response) was attenuated in HK-2 cells, PAI-1 (fibrotic response) was attenuated in HRMC cells, and angiogenesis was promoted in HUVEC. Preliminary data from PCR array screening of exosome content from UNFX-conditioned media indicates that UNFX produces exosomes containing miRNA sequences consistent with the observed responses to UNFX-conditioned media.

Figure 13A:
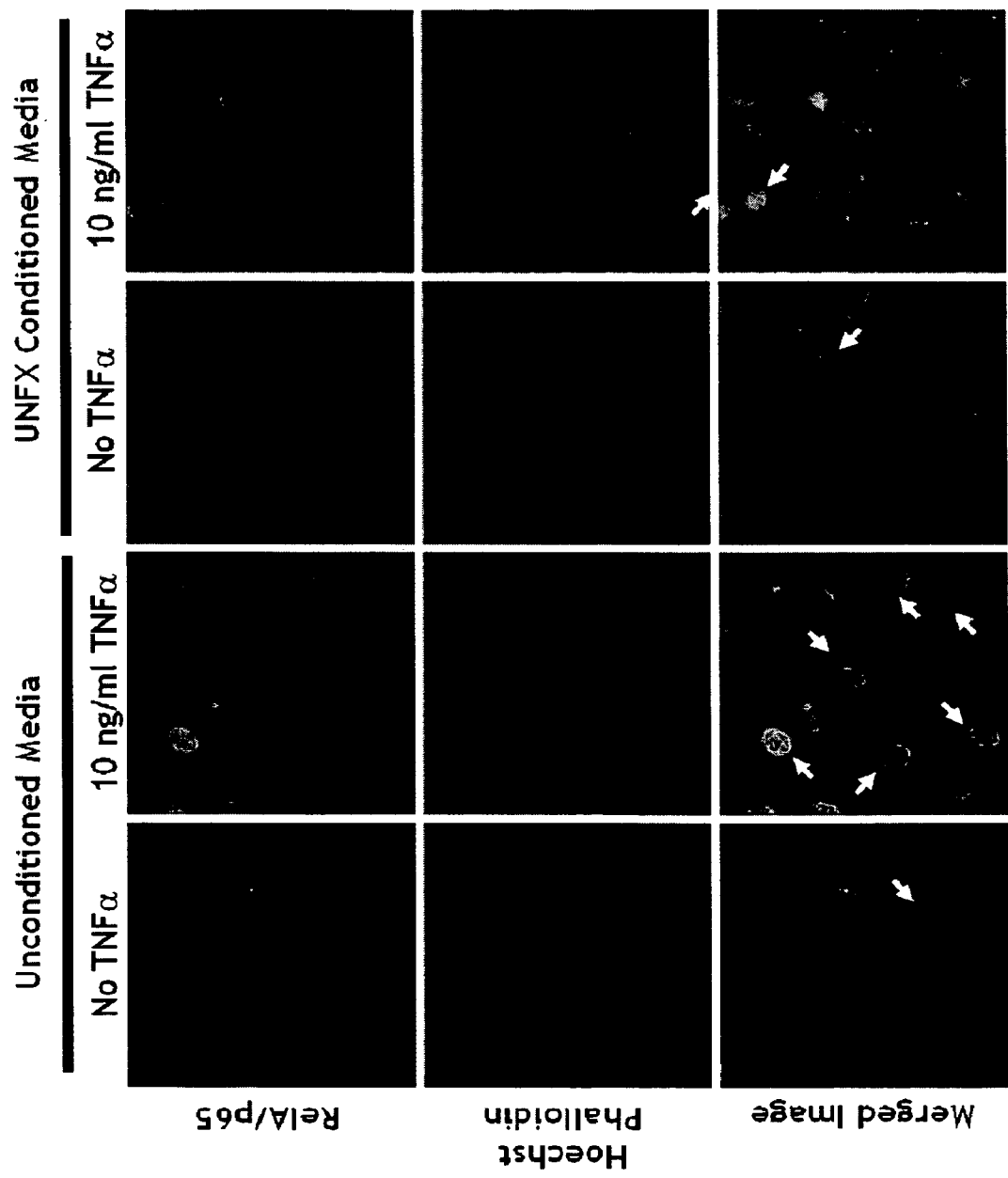
FIG. 13A-C shows that conditioned media from UNFX cultures affects multiple cellular processes in vitro that are potentially associated with regenerative outcomes.
Figure 13B:
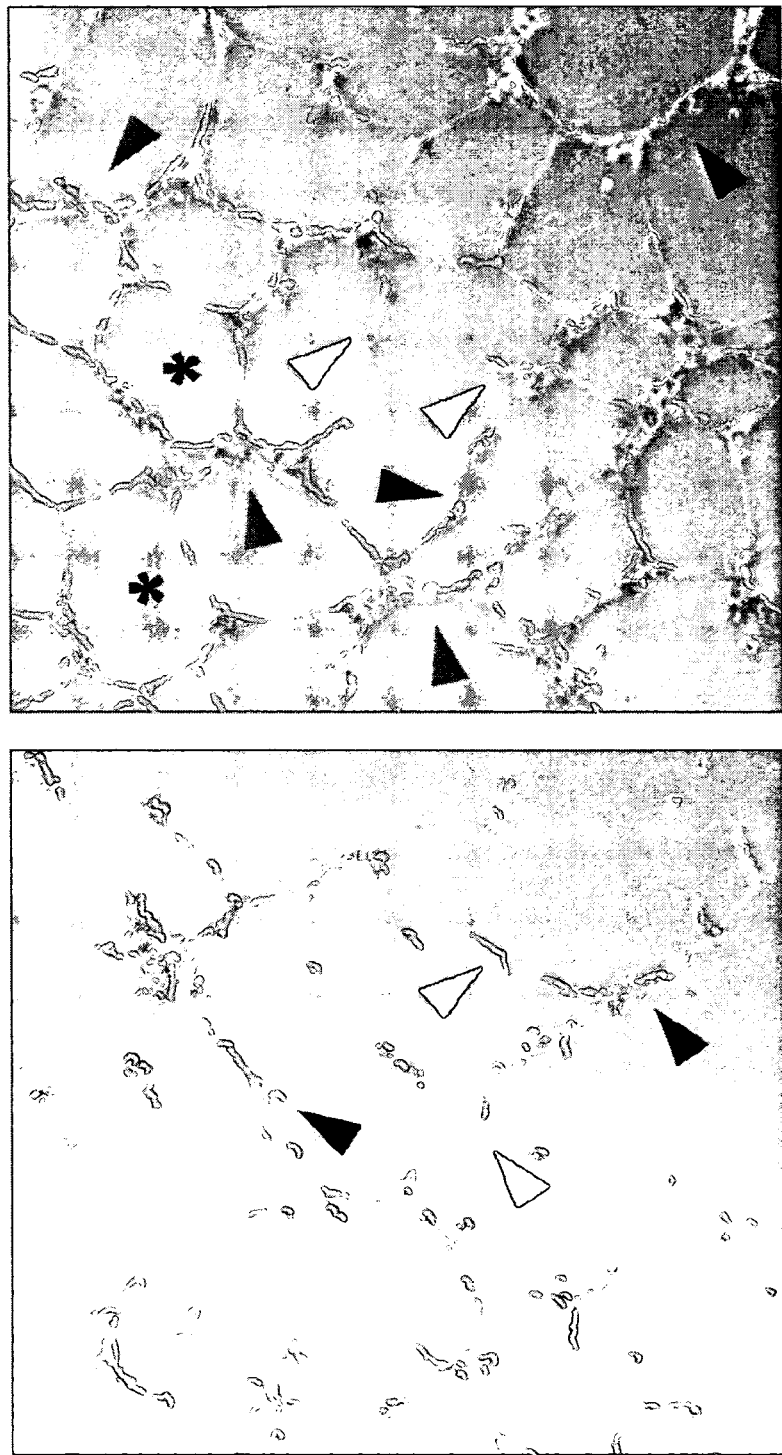
Figure 13C:
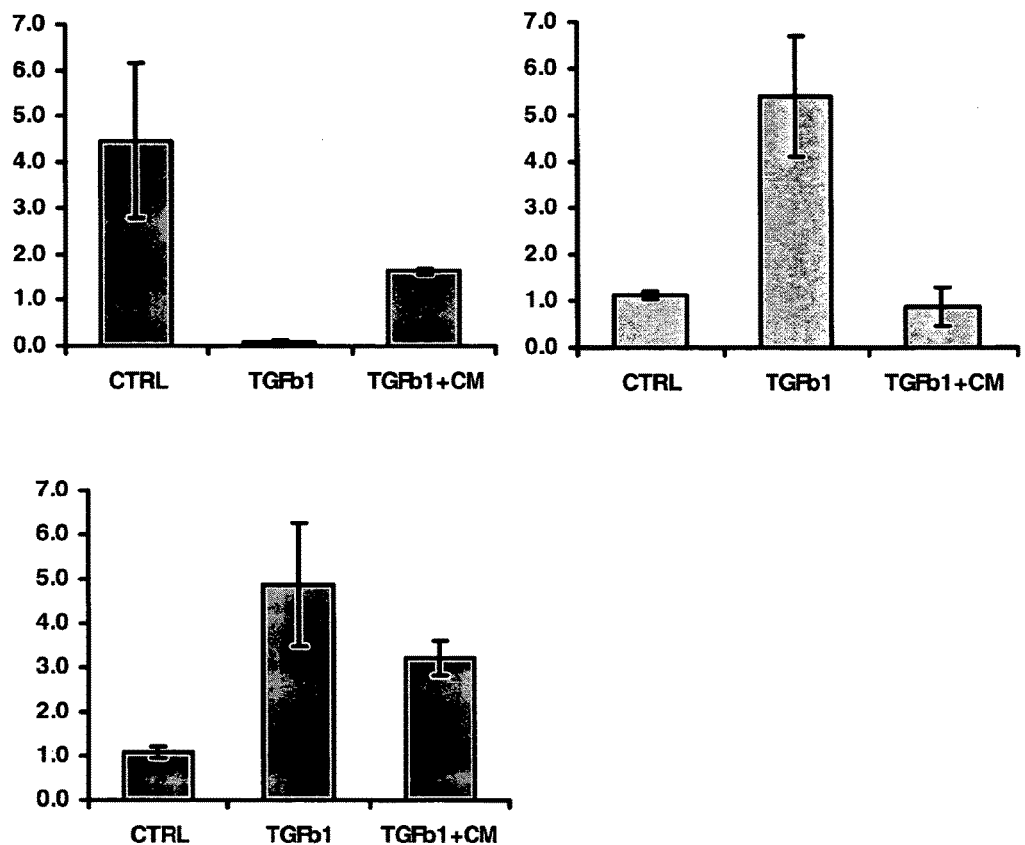

FIG. 13A-C shows that conditioned media from UNFX cultures affects multiple cellular processes in vitro that are potentially associated with regenerative outcomes. NFkB signaling is proposed as a key mediator of inflammatory processes in kidney diseases (Rangan et al., 2009. *Front Biosci* 12:3496-3522; Sanz et al., 2010. *J Am Soc Nephrol* 21:1254-1262), and can be activated by Tumor Necrosis Factors (TNF). HK-2 cells were preincubated with unconditioned media (left) or UNFX conditioned media (right) for 1 hour at 37° C., then activated with or without 10 ng/ml TNFa.

FIG. 13A shows that UNFX-conditioned media attenuates TNF-a mediated activation of NF-kB. NFkB activation was measured by RelA/p65 immunofluorescence staining (green). Hoechst-counter-stained nuclei (blue) and phalloidin-stained filamentous actin (red) facilitate assessment of RelA/p65 nuclear localization (white arrows).

FIG. 13B shows that UNFX-conditioned media increases proangiogenic behavior of HUVEC cell cultures. HUVEC cells (100,000 per well) were overlaid onto polymerized Matrigel in Media 200 plus 0.5% BSA. Unconditioned media (left) or UNFX-conditioned medium (right) was added and cellular organizational response was monitored visually for 3-6 hours with image capture. Cellular organization was scored for cell migration (white arrowheads), alignment (black arrowheads), tubule formation (red arrowheads), and formation of closed polygons (asterisks). UNFX conditioned media induced more tubules and closed polygons compared to unconditioned media, suggesting that proangiogenic factors are present in the media.

FIG. 13C shows that UNFX-conditioned media attenuates fibrosis pathways in epithelial cells. HK-2 cells lose epithelial characteristics, and acquire a mesenchymal phenotype when exposed to Transforming Growth Factors (TGF) in vitro, replicating the epithelial-to-mesenchymal transition (EMT) that is associated with progression of renal fibrosis (Zeisberg et al. 2003 *Nat Med* 9:964-968). HK-2 cells were cultured in unconditioned media (CTRL), unconditioned media containing 10 ng/ml TGFβ1 (TGFβ1), or UNFX conditioned media containing 10 ng/ml TGFβ1 (TGFβ1+CM) for 72 hours. Cells were assayed by quantitative RT-PCR for CDH1 (epithelial marker), CNN1 (mesenchymal marker) and MYH11 (mesenchymal marker). Conditioned media reduces the degree of TGFβ1-induced EMT as measured by CDH1, CNN1, and MYH11 gene expression. Error bars represent the standard error of the mean (SEM) of three experimental replicates.

Figure 13D:
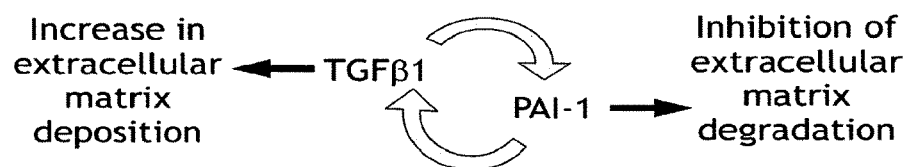
FIG. 13D depicts the positive feedback loop established by TGFβ1 and Plasminogen Activator Inhibitor-1 (PAI-1).

FIG. 13D depicts the positive feedback loop established by TGFβ1 and Plasminogen Activator Inhibitor-1 (PAI-1) that, when left unchecked, can lead to the progressive accumulation of extracellular matrix proteins (Seo et al., 2009. *Am J Nephrol* 30:481-490).

Figure 14:
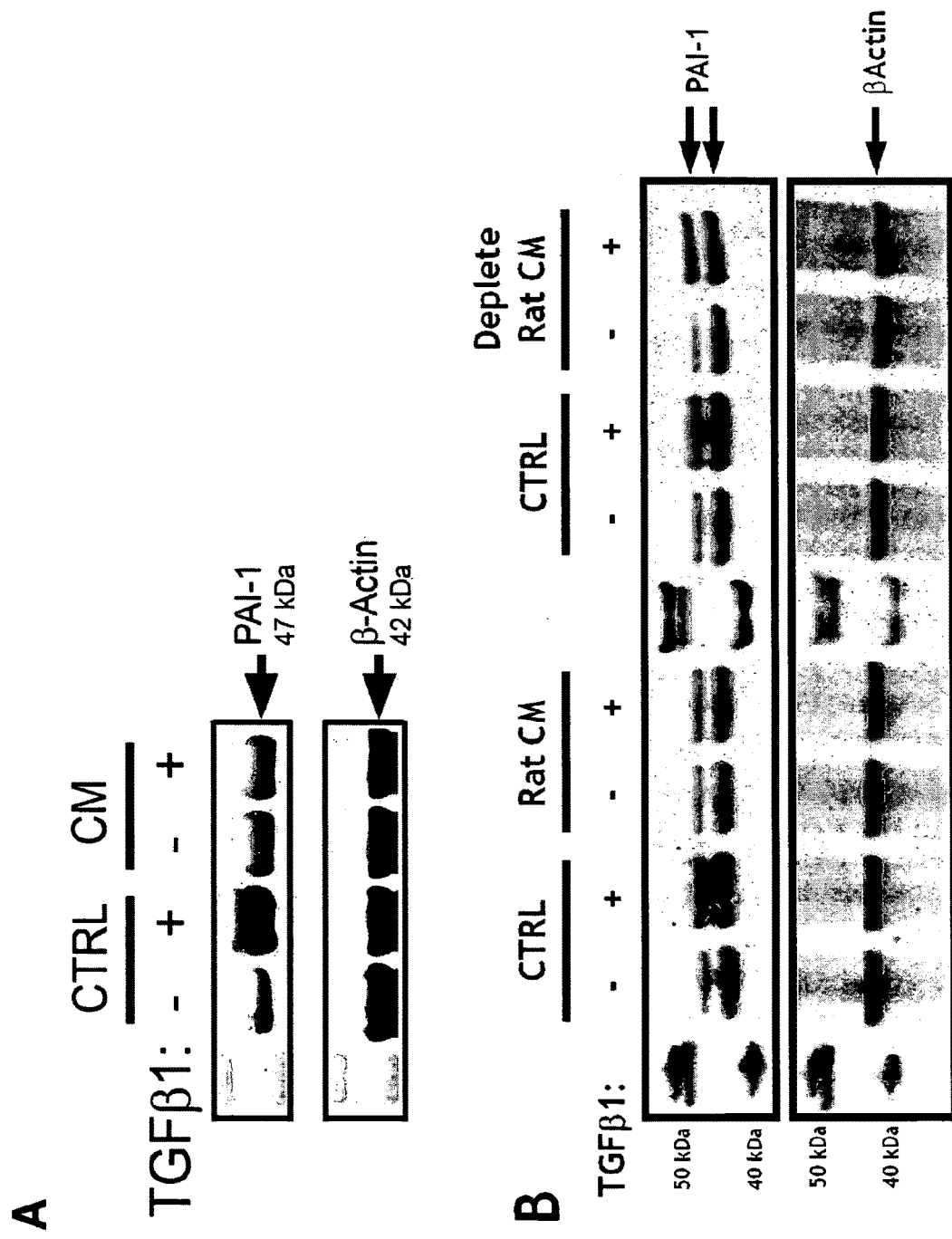
FIG. 14A-B shows a Western blot analysis demonstrating the attenuation of fibrosis pathways in mesangial cells.

FIG. 14A-B shows the attenuation of fibrosis pathways in mesangial cells. HRMC were cultured for 24 hours in control (CTRL) or UNFX conditioned media (UNFX CM) with (+) or without (−) the addition of 5 ng/ml TGFβ1. Western blot analysis for PAI-1 demonstrates that UNFX CM attenuates the TGFβ1-induced increase in PAI-1 protein levels. bActin is shown as a loading control. Human renal mesangial cells (HRMC) express increased levels of PAI-1 in the presence (+) of 5 ng/ml TGFb1. Co-culture with conditioned media (CM) derived from human bioactive kidney cells attenuates TGFb1-induced PAI-1 protein expression. PAI-1 expression at the mRNA level was unaltered by CM (data not shown).

FIG. 14B shows that CM from rat bioactive kidney cells had similar effect on cultured HRMC induced (+) and uninduced (−) with TGFb1. CM supernatant (Deplete Rat CM) collected after centrifugation was less effective at attenuating PAI-1 expression, suggesting that the CM component responsible for the observed attenuation of PAI-1 protein might be associated with vesicles secreted by the rat bioactive kidney cells.

Figure 15A:
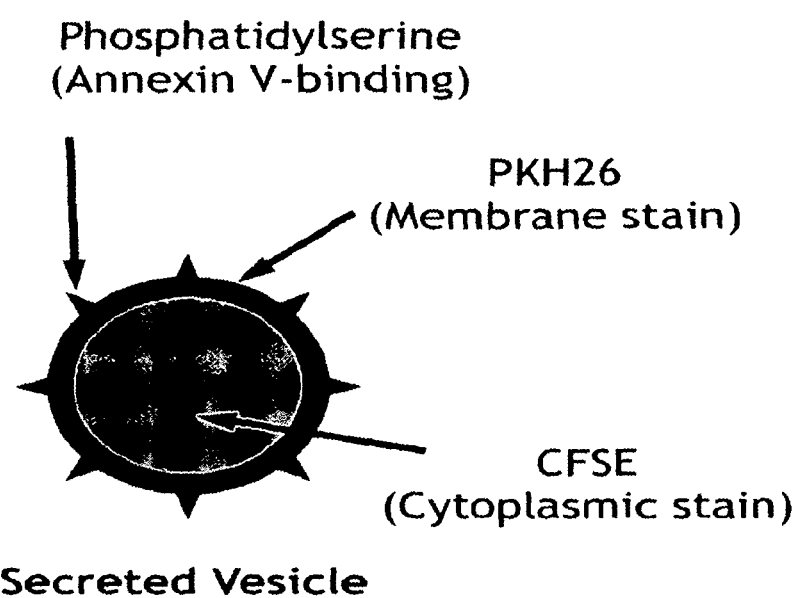

FIG. 15 shows that the conditioned media from UNFX contains secreted vesicles. FIG. 145A depicts secreted vesicles (including exosomes), which are bilipid structures (red) that encompass cytoplasm-derived internal components (green). Phosphatidylserines (blue triangles) are components of the membrane that are exposed to the extracellular space during vesicle biogenesis (Thery et al., 2010. *Nat Rev Immunol* 9:581-593).

PKH26 and CFSE label the lipid membrane and cytoplasm of secreted vesicles (Aliotta et al., 2010. *Exp Hematol* 38:233-245), respectively, while Annexin V binds phosphatidylserines.

Figure 15C:
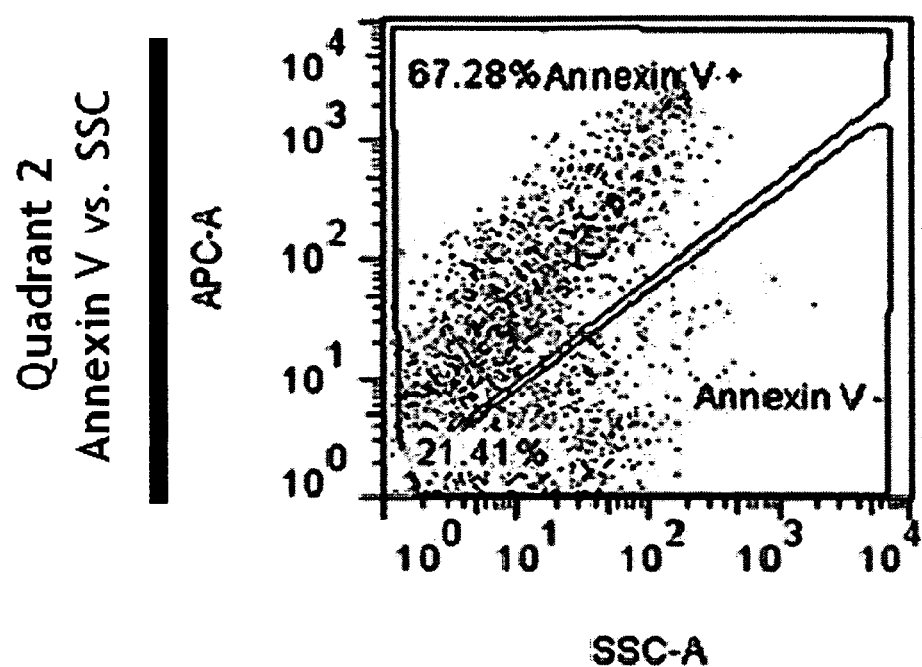

FIG. 15B-C shows FACS sorting. UNFX conditioned media was labeled with PKH26, CFSE, and APC-conjugated Annexin V, then sorted by fluorescence-assisted cell sorting (FACS). Triple-positive particles, representing secreted vesicles, were collected and total RNA was extracted using TRIZol reagent. microRNA content was screened for known sequences using commercially available RT-PCR-based arrays.

Table 12.1 shows that secreted vesicles contain microRNAs with predicted therapeutic outcomes. UNFX cells shed exosomes that contain known miRNA sequences. UNFX-conditioned media affects functionally-relevant regenerative responses in human cell lines. The cause and effect relationship between detected miRNAs and observed regenerative responses is under active investigation; however, the results achieved to date suggest that UNFX cells have the potential to produce therapeutically-relevant paracrine effects via exosome-mediated transfer of miRNAs to target cells and tissues.

TABLE 12.1

| miRNA in exosomes | Gene targets | Predicted effects |
|---|---|---|
| miR-146a | TRAF6, IRAK1* | Inhibits NFkB |
| miR-130a | GAX, HOXA5** | Promotes angiogenesis |

TABLE 12.1-continued

| miRNA in exosomes | Gene targets | Predicted effects |
|---|---|---|
| miR-23b | Smad 3/4/5*** | Inhibits TGFβ signal transduction (anti-fibrotic) |

*Taganov et al, 2006. Proc Natl Acad Sci USA 103: 12481-12486.
**Chen and Gorski, 2008. Blood 111: 1217-1226.
***Rogler et al., 2009. Hepatology 50: 575-584.

The data support the conclusion that excreted vesicles from bioactive renal cell cultures contain components that attenuate PAI-1 induced by the TGFb1/PAI-1 feedback loop.

Microarray and RT-PCR analysis. Unfractionated (UNFX) bioactive renal cells from Lewis rats were cultured in basal media (50:50 mix of DMEM and KSFM without serum or supplements) for 24 hours under low oxygen conditions (2% O2). Conditioned media was collected and ultracentrifuged at 100,000×g for 2 hours at 4 C to pellet secreted vesicles (e.g. microvesicles, exosomes). Total RNA was extracted from the resulting pellet, and assayed for known microRNA species by real time RT-PCR (Rat MicroRNA Genome V2.0 PCR Array; Qiagen #MAR-100A). The following miRNAs were detectable.

| | | |
|---|---|---|
| miR-21 | miR-92a | miR-370 |
| miR-23a | miR-100 | miR-24 |
| miR-30c | miR-125b-5p | miR-30a |
| miR-1224 | miR-195 | miR-16 |
| miR-23b | miR-10a-5p | miR-126* |
| miR-30b-5p | miR-29c | miR-652 |
| miR-27a | miR-200c | let-7d* |
| miR-20a | miR-151 | miR-503 |
| let-7c | miR-429 | miR-138 |
| miR-26a | miR-103 | miR-450a |
| miR-17-5p | let-7a | miR-365 |
| miR-30e | miR-322* | miR-874 |
| miR-25 | miR-15b | miR-345-5p |
| let-7b | miR-378 | miR-374 |
| miR-20b-5p | miR-127 | miR-872 |
| miR-29a | miR-199a-5p | miR-186 |
| let-7d | miR-181b | miR-130a |
| miR-22 | miR-106b | miR-140* |
| miR-322 | miR-196c | miR-28* |
| let-7e | miR-196b | miR-212 |
| miR-191 | miR-19a | miR-139-3p |
| miR-99b | miR-145 | miR-347 |
| miR-19b | let-7f | miR-151* |
| miR-10b | miR-181d | miR-328 |
| miR-27b | miR-181a | miR-185 |
| miR-125a-5p | miR-221 | miR-28 |
| miR-30d | miR-30a* | miR-192 |
| miR-31 | miR-351 | miR-92b |
| miR-93 | miR-218 | miR-672 |
| miR-182 | miR-210 | miR-150 |
| miR-99a | miR-98 | miR-425 |
| miR-320 | miR-18a | miR-146a |
| miR-664 | miR-342-3p | miR-107 |
| miR-30e* | miR-203 | miR-330* |
| let-7i | miR-352 | miR-409-3p |
| miR-196a | miR-181c | miR-877 |
| miR-26b | miR-222 | miR-760-3p |
| miR-200a | miR-219-1-3p | miR-770 |
| miR-126 | miR-708 | miR-152 |
| miR-106b* | miR-324-5p | miR-411 |
| miR-675 | miR-674-5p | miR-188 |
| miR-423 | miR-760-5p | miR-331 |
| miR-194 | miR-361 | miR-124 |
| miR-490 | miR-296 | miR-431 |
| miR-128 | miR-148b-3p | miR-154 |
| miR-497 | miR-542-3p | miR-30d* |
| miR-301a | miR-667 | miR-466c |
| miR-130b | miR-935 | miR-142-3p |
| miR-199a-3p | miR-24-2* | miR-7a* |
| miR-326 | miR-433 | miR-298 |
| miR-132 | miR-295 | let-7b* |
| miR-375 | miR-140 | miR-338 |
| miR-25* | miR-9 | miR-449a |
| miR-22* | miR-871 | miR-125b* |
| miR-96 | miR-29a* | miR-34c |
| miR-34a | miR-542-5p | miR-346 |
| miR-223 | miR-129 | miR-147 |
| miR-301b | miR-214 | miR-9* |
| miR-505 | miR-29c* | miR-146b |
| miR-532-3p | miR-489 | miR-219-5p |
| miR-7a | miR-141 | miR-653 |
| miR-451 | miR-500 | miR-340-3p |
| miR-34c* | miR-17-3p | miR-224 |
| miR-339-3p | miR-339-5p | miR-330 |
| miR-190 | miR-7b | miR-544 |
| miR-671 | miR-501 | miR-193 |
| miR-465 | miR-206 | miR-761 |
| miR-674-3p | miR-193* | miR-181a* |
| miR-21* | miR-350 | miR-27a* |
| miR-99b* | miR-466b | miR-34b |
| miR-125a-3p | miR-205 | miR-455 |
| miR-183 | miR-598-5p | miR-20a* |
| miR-143 | miR-532-5p | miR-488 |
| miR-26b* | miR-504 | miR-207 |
| miR-342-5p | let-7e* | miR-343 |
| miR-543 | miR-129* | miR-292-3p |
| miR-105 | miR-101b | miR-376a |
| miR-291a-5p | miR-122 | miR-540 |
| miR-138* | miR-539 | miR-336 |
| miR-190b | miR-30b-3p | miR-134 |
| let-7i* | miR-184 | miR-24-1* |
| miR-484 | miR-673 | miR-363 |
| miR-30c-2* | miR-463 | miR-329 |
| miR-125b-3p | miR-297 | miR-133b |
| miR-764 | miR-363* | miR-875 |
| miR-421 | miR-384-5p | miR-201 |
| miR-485 | miR-344-5p | miR-483 |
| miR-296* | miR-133a | miR-742 |
| miR-29b | miR-582 | miR-1 |
| miR-382 | miR-541 | miR-293 |
| miR-511 | miR-344-3p | miR-349 |
| miR-99a* | miR-345-3p | miR-30c-1* |
| miR-499 | miR-362 | miR-153 |
| miR-101a* | miR-380 | miR-743a |
| miR-20b-3p | miR-878 | miR-323 |
| miR-434 | miR-377 | miR-495 |
| miR-139-5p | miR-409-5p | miR-410 |
| miR-10a-3p | miR-216a | miR-137 |
| miR-148b-5p | miR-496 | miR-300-3p |
| miR-598-3p | miR-379 | miR-369-5p |
| miR-29b-2* | miR-711 | miR-376b-3p |
| miR-335 | miR-32 | miR-211 |
| miR-215 | miR-291a-3p | miR-33 |
| miR-219-2-3p | miR-487b | miR-758 |
| miR-327 | miR-23a* | miR-802 |
| miR-204 | miR-294 | |

Example 13—Paracrine Factors Derived from Bioactive Kidney Cells

In the present study, we employed in vitro cell-based assays to investigate potential paracrine mechanism(s) by which bioactive kidney cells could modulate fibrosis through mediators such as Plasminogen Activator Inhibitor-1 (PAI-1).

Materials and Methods:

Conditioned media was collected from rat and human cultures of bioactive kidney cells (Aboushwareb et al., World J Urol 26, 295, 2008; Presnell et al. 2010 supra) under serum- and supplement-free conditions and utilized for in vitro assays. Commercially available rat- and human-derived mesangial cells were used as surrogates for host-response tissues in the in vitro assays because mesangial cells are a source of PAI-1 production in injured or diseased kidneys (Rerolle et al., Kidney Int 58, 1841, 2000.). PAI-1 gene and protein expression were assayed by quantitative RT-PCR and Western blot, respectively. Vesicular particles shed by cells into the culture media (e.g., exosomes) were collected by high-speed centrifugation (Wang et al., *Nuc Acids Res* 2010, 1-12 doi:10.1093/nar/gkq601, Jul. 7, 2010) and total RNA extracted from the pellet with TRIzol reagent (Invitrogen). RNA content of the vesicles was screened using PCR-based arrays of known microRNA sequences (Qiagen).

Results:

Conditioned media from bioactive kidney cell cultures attenuated the TGFβ1-induced increase in PAI-1 steady-state protein levels in mesangial cells, but did not affect steady state mRNA levels; an observation that is consistent with the mechanism by which microRNAs modulate target genes. Based on the hypothesis that microRNAs can be transferred between cells through extracellular vesicle trafficking (Wang et al., supra 2010), we analyzed the conditioned media for microRNA content and confirmed the presence of microRNA 30b-5p (miR-30b-5p), a putative inhibitor of PAI-1.

The data presented here suggest that bioactive kidney cells may modulate fibrosis directly through cell-to-cell transfer of miR-30b-5p to target mesangial cells via exosomes. As a result of miR-30b-5p uptake by mesangial cells, TGFβ1-induced increases in steady-state PAI-1 protein levels are attenuated, a response that, in renal tissue, could ultimately reduce deposition of extracellular matrix within the glomerular space. Current work is underway to confirm that PAI-1 is indeed a direct target of miR-30b-5p.

FIG. 14A-B shows a western blot of PAI-1 and α-Actin (control) protein expression in human mesangial cells cultured for 24 hour in control (CTRL) or bioactive kidney cell conditioned media (CM) with (+) or without (−) TGFβ1 addition to the culture media. In CTRL cultures, TGFβ1 increased PAI-1 protein expression. In CM cultures, the TGFβ1-induced response was attenuated.

Secreted vesicles were analyzed for microRNAs that may be putative repressors of PAI-1. Secreted vesicles from human and rat bioactive kidney cell CM were collected by high-speed centrifugation and assayed for microRNA content using PCR-based arrays of known sequences. miR-449a, a putative regulator of PAI-1 (6), was identified. HRMC were transiently transfected with miR-449a or not (CTRL). 24 hours post-transfection cells were either exposed to 5 ng/ml TGFb1 (+) or not (−) for an additional 24 hours.

FIG. 16A shows a Western blot in which total protein was prepared and assayed for PAI-1 and bActin. miR-449a reduced steady-state PAI-1 protein levels (compare lane 1 to lane 3) and induced levels of PAI-1 protein were also lower in miR-449a transfected cultures (compare lane 2 to lane 4). The data support the conclusion that excreted vesicles contain miR-449a and uptake of miR-449a into mesangial cells reduces PAI-1 expression.

FIG. 16B depicts the microRNA, miR-30b-5p, which was also identified in the PCR-based array and is a putative regulator of PAI-1 based on predictive algorithms (http://mirbase.org—miRBase is hosted and maintained in the Faculty of Life Sciences at the University of Manchester).

PAI-1 protein levels in glomeruli were examined in vivo after treatment of CKD induced by 5/6 nephrectomy with bioactive renal cells.

Figure 17:
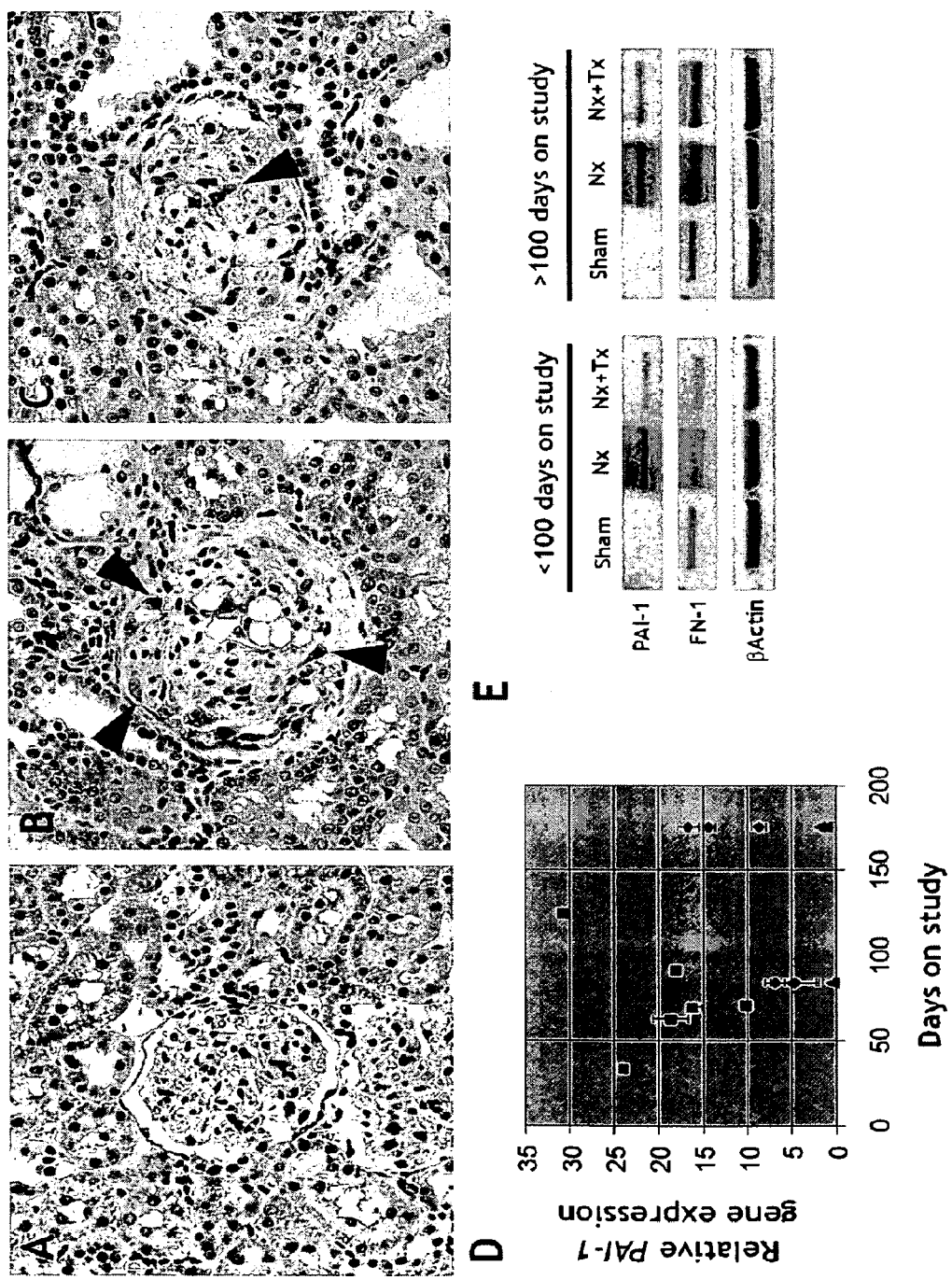
FIG. 17A-C shows representative immunohistochemistry images of PAI-1 in Lewis rat kidneys following delivery of bioactive kidney cells after undergoing a nephrectomy.
FIG. 17D shows a comparison of PAI-1 expression in untreated, nephrectomized rats (red squares), treated, nephrectomized rats (blue diamonds), and control animals (green triangles).
FIG. 17E shows representative Western blot analysis on kidney samples taken at 3 and 6 months post-treatment.
FIG. 17F shows a 2-hour exposure to NKA conditioned media reduces nuclear localization of NFκB p65.
FIG. 17G depicts the canonical activation of the NFkB pathway by TNFα.

FIG. 17A-C shows representative immunohistochemistry images of PAI-1 (A-C) in Lewis rat kidneys that have undergone unilateral nephrectomy (A), 5/6 nephrectomy (B), or 5/6 nephrectomy with intra-renal delivery of bioactive kidney cells (C). Accumulation of PAI-1 in the glomerulus (arrowheads) as a result of the 5/6 nephrectomy procedure (B) was reduced as a result of treatment (C).

In a separate study, qRT-PCR was conducted on kidney tissue harvested at necropsy and the relative gene expression values were plotted against days on study.

FIG. 17D shows that 5/6 nephrectomized rats (red squares) demonstrated more robust expression of PAI-1 relative to those treated with bioactive renal cells (blue diamonds) and sham-operated controls (green triangles).

FIG. 17E shows representative Western blot analysis on kidney samples taken at 3 and 6 months post-treatment. Treated tissues (Nx+Tx) of 5/6 nephrectomized rats (Nx) had reduced the accumulation of PAI-1 and Fibronectin (FN) protein (Kelley et al. 2010 supra).

The data support the conclusion that in vivo PAI-1 protein levels in glomeruli decrease after treatment of CKD induced by 5/6 nephrectomy with bioactive renal cells.

When taken together, Examples 12-13 support the hypothesis that one mechanism by which intra-renal delivery of bioactive kidney cells improves renal function might be via cell-cell transfer of components that modulate fibrotic pathways in resident kidney cells.

Example 14—Secreted Factors from Bioactive Kidney Cells Attenuate NFκB Signaling Pathways In this study, we investigated the role of NFκB pathways in the NKA-mediated attenuation of disease progression in the 5/6 nephrectomy model and to identify properties of the bioactive kidney cells that may contribute to regenerative outcomes through direct modulation of NFκB activation. FIG. 17G depicts the canonical activation of the NFkB pathway by TNFα.

Materials and Methods:

Remnant kidneys were harvested from Lewis rats in which a two-step 5/6 nephrectomy procedure was performed 6 weeks prior to being treated with B2+B4 in PBS (NKA prototype). NKA-treated (TX) or untreated (UNTX) tissues were assayed for NFκB activation by immunohistochemistry, RT-PCR, Western blot analysis, and electrophoresis mobility shift assays (EMSA). Conditioned media (CM) collected from ex vivo NKA cell cultures grown in serum- and supplement-free media was used for in vitro functional assays. The human proximal tubule cell line (HK-2) was used as target cell type for molecular and immunofluorescence-based assay readouts. Vesicular particles shed by cells into the culture media (exosomes) were collected by high-speed centrifugation. Total RNA isolated from exosomes was screened using PCR-based arrays of known microRNA sequences (Qiagen).

Results:

Nuclear localization of the NFκB subunit, RelA/p65, was observed in remnant kidneys from 5/6 nephrectomized rats, suggesting activation of inflammatory pathways in UNTX tissues. Preliminary comparison with TX tissues by RT-PCR showed a decrease in RelA gene expression, suggesting that NKA treatment may influence NFκB pathway activation through inhibition of RelA/p65 expression. This hypothesis is supported by the observation that CM attenuates TNFα-induced NFκB activation in vitro, as evidenced by the reduced nuclear localization of RelA/p65 in CM-exposed HK-2 cells (FIG. 17F) relative to that seen in response to Tumor Necrosis Factor-α(TNF α). Ongoing RT-PCR analyses of NKA exosome microRNAs are investigating whether sequences known to influence NFκB pathways are present.

Figure 17F:
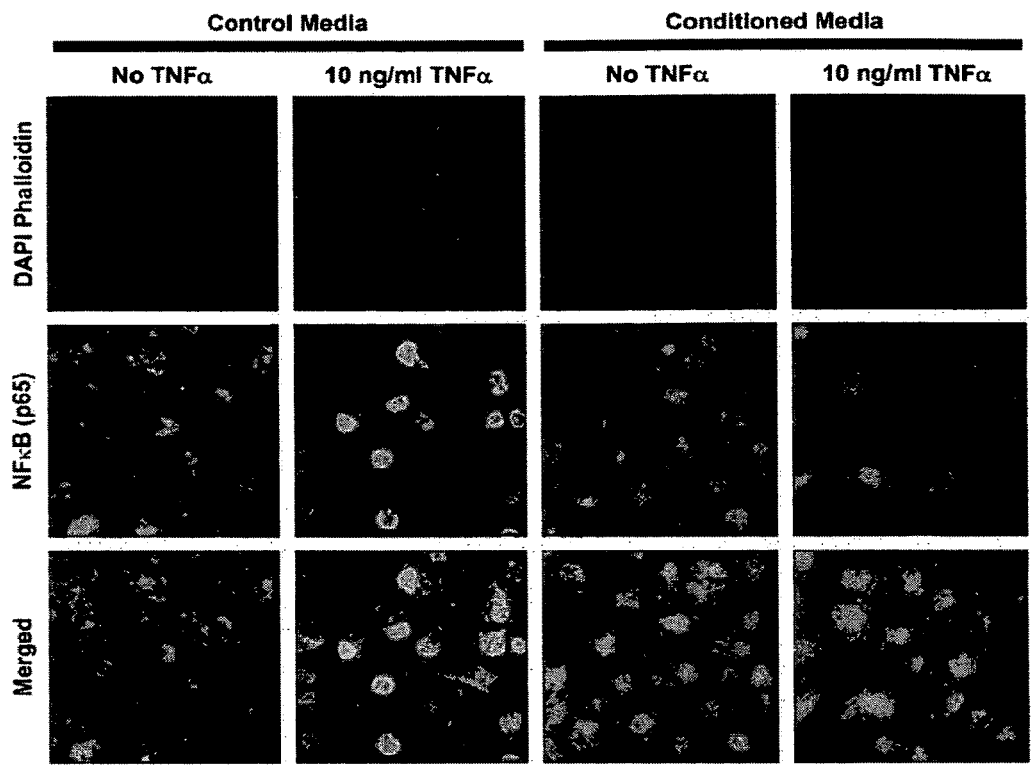
Figure 17G:
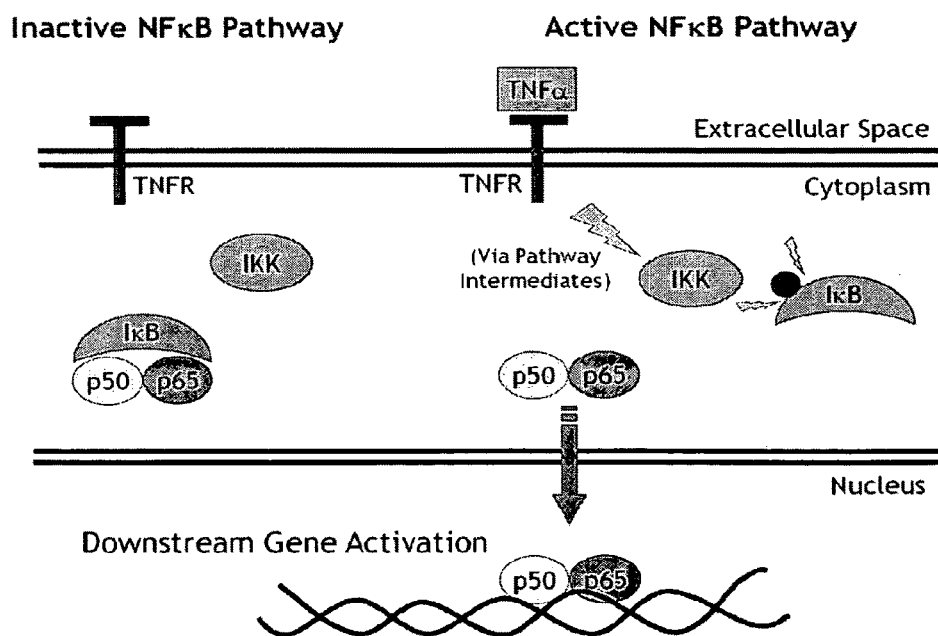

FIG. 17F shows a 2-hour exposure to NKA CM reduces nuclear localization of NFκB p65 (green) in HK-2 compared to that observed in control cultures pretreated with TNFα in immunofluorescent assays. In HK-2, NFkB p65 (green) localizes to the nucleus after a 30 minute exposure to TNFα(Control Media). However, pre-treatment of HK-2 cells with NKA Conditioned Media for 2 hours prior to TNFα addition attenuated the NFkB p65 nuclear localization response. Nuclei are stained with DAPI (blue) and filamentous actin is stained with Alexa594-phalloidin (red) to assist in qualitatively assessing the robustness of NFκB nuclear localization (note the slightly diminished phalloidin borders in TNFα-treated control cells in the merged panels in the bottom row). The counterstaining provide reference for the NFkB localization in the merged images.

Immunohistochemistry for the NFkB p65 subunit in kidney tissues of Lewis rats reveals that animals with progressive CKD initiated by 5/6 nephrectomy (panel B) have more robust nuclear localization of NFkB p65 subunit, particularly in tubular epithelial cells (black arrowheads) relative to the non-progressive renal insufficiency initiated by unilateral nephrectomy in control animals (panel A). Tissues harvested six weeks post-nephrectomy. Magnification at 200×.

Panel C:

Western blot analysis for NFkB p65 in the cytoplasmic ('C') and nuclear ('N') protein extracts of Lewis rat kidney tissue that have undergone the 5/6 nephrectomy. Comparing weeks 1 and 13, where gtubulin levels (loading control) are relatively consistent, nuclear NFkB p65 increases over time, consistent with the immunohistochemistry results.

Panel D:

Electrophoretic mobility shift assay (EMSA) on nuclear extracts confirms that the NFkB that localizes to the nucleus following 5/6 nephrectomy is activated for DNA binding. Lanes represent nuclear extracts prepared from two animals at each time point.

The NFkB pathway is progressively activated in the 5/6 nephrectomy model of chronic kidney disease. Immunohistochemistry for the NFkB p65 subunit in kidney tissues of Lewis rats was performed.

FIG. 18A-D reveals that animals with progressive CKD initiated by 5/6 nephrectomy (panel B) have more robust nuclear localization of NFkB p65 subunit, particularly in tubular epithelial cells (black arrowheads) relative to the non-progressive renal insufficiency initiated by unilateral nephrectomy in control animals (panel A). Tissues harvested six weeks post-nephrectomy. Magnification at 200×.

Figure 18:
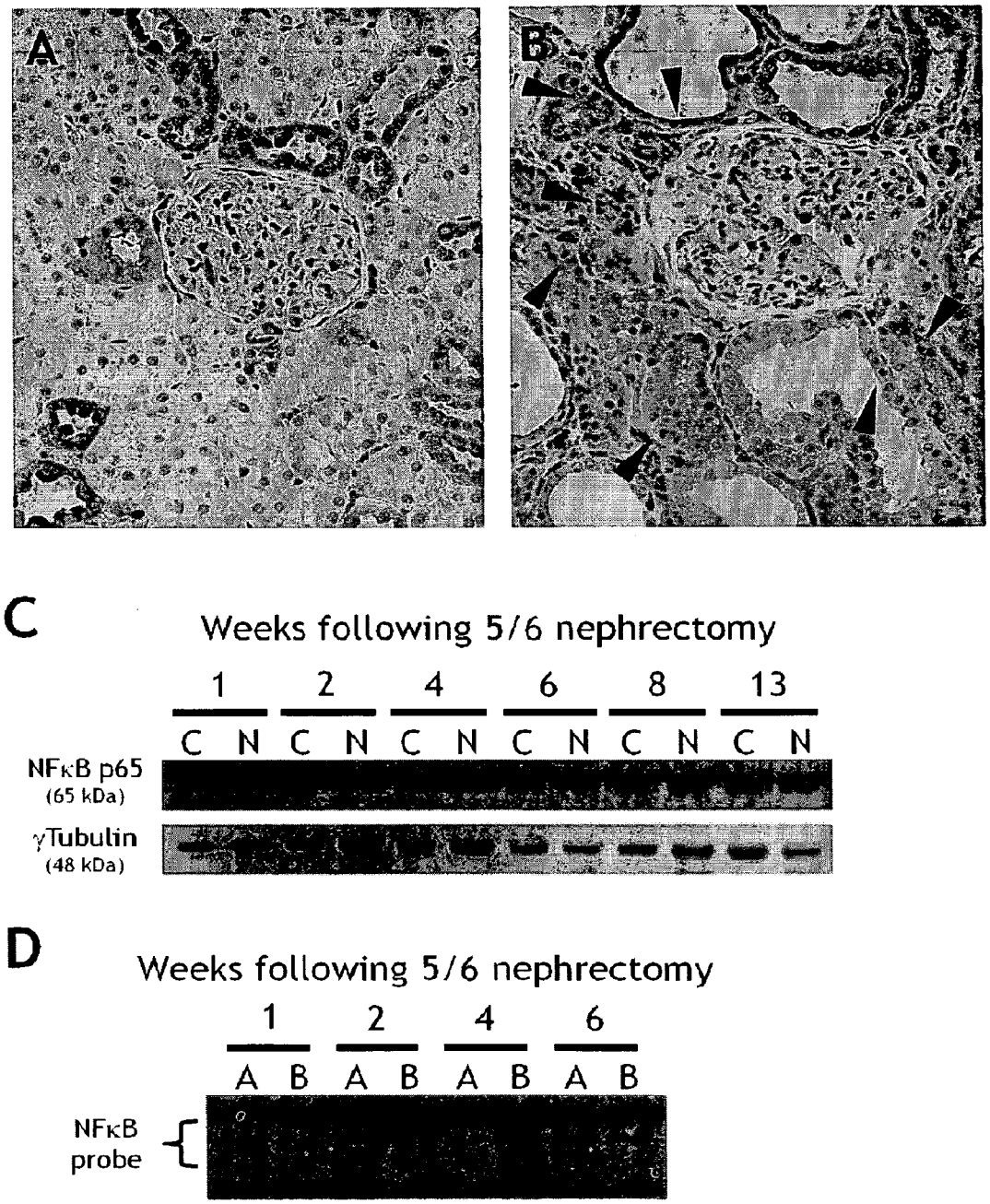
FIG. 18A-B shows the nuclear localization of NFkB p65 subunit in animals with (A) progressive CKD initiated by 5/6 nephrectomy and (B) non-progressive renal insufficiency initiated by unilateral nephrectomy.
FIG. 18C-D shows (C) a Western blot analysis for NFkB p65 in extracts of Lewis rat kidney tissue that have undergone the 5/6 nephrectomy; and (D) electrophoretic mobility shift assay (EMSA) on extracts.
FIG. 18E shows immunohistochemical detection of the NFκB p65 subunit in tissue obtained from Lewis rats with established CKD that received intra-renal injection of NKA (panel A) or non-bioactive renal cells (panel B).

FIG. 18C shows Western blot analysis for NFkB p65 in the cytoplasmic ('C') and nuclear ('N') protein extracts of Lewis rat kidney tissue that have undergone the 5/6 nephrectomy. Comparing weeks 1 and 13, where gtubulin levels (loading control) are relatively consistent, nuclear NFkB p65 increases over time, consistent with the immunohistochemistry results.

FIG. 18D shows an electrophoretic mobility shift assay (EMSA) on nuclear extracts and confirms that the NFkB that localizes to the nucleus following 5/6 nephrectomy is activated for DNA binding. Lanes represent nuclear extracts prepared from two animals at each time point. 1 mg of nuclear protein was incubated with 5 ng of NFkB DNA binding site, electrophoresed on a 6% DNA retardation gel, then subsequently stained with ethidium bromide.

Intra-Renal Delivery of NKA Cells Reduces NFkB Nuclear Localization.

Multiple defined subpopulations of renal cells have been isolated and assayed in vivo for bioactivity in improving renal function in the 5/6 nephrectomy model of CKD (Presnell et al. 2010 supra). NKA cells demonstrated bioactivity whereas other subpopulations did not (Kelley et al. 2010 supra).

Figure 18E:
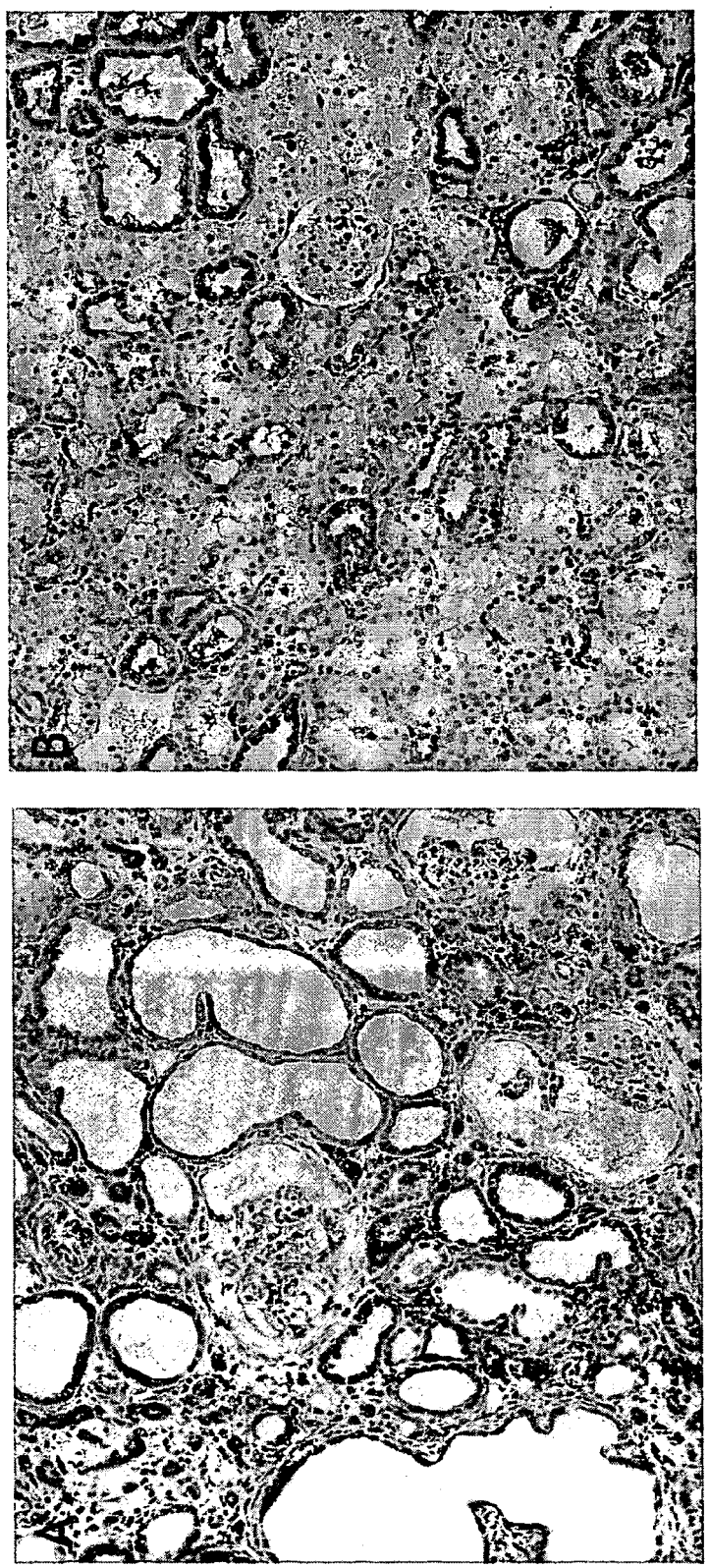

FIG. 18E shows that Lewis rats with established CKD that received intra-renal injection of NKA (A) or non-bioactive renal cells (B). Lewis rats with established CKD received intra-renal injection of NKA (A) or non-bioactive renal cells (B). At 6 months post-treatment, tissues were harvested and assayed by immunohistochemistry for the NFkB p65 subunit. Tissues from NKA-treated animals exhibited less nuclear localization of NFkB p65, particularly in the proximal tubules, compared to tissues from animals treated with non-bioactive renal cells, suggesting that the NKA treatment participated in attenuating the NFkB pathway activity in vivo.

Analysis of microRNA content of secreted vesicles isolated from human and rat NKA conditioned media by high-speed centrifugation using PCR-based arrays of known sequences identified several microRNA species that may influence immune responses via NFkB based on literature reports (Marquez R T et al. (2010) *Am J Physiol Gastrointest Liver Physiol* 298:G535; Taganov K D et al. (2006) *Proc Natl Acad Sci USA* 103:12481) or predictive algorithms (http://mirbase.org—miRBase is hosted and maintained in the Faculty of Life Sciences at the University of Manchester).

| microRNA in vesicles | Target mRNA |
| --- | --- |
| miR-21 | Pellino-1 (Marquez et al.) |
| miR-146a | IRAK1, TRAF6 (Taganov et al.) |
| miR-124, miR-151 | NFKB/RelA (miRBase) |

The in vivo and in vitro findings provide insight on how bioactive kidney cells (NKA) might improve renal function in chronically-diseased kidneys by modulating immune response pathways such as those affected by NFkB activation. Activated NFkB (p65 nuclear localization, particularly in proximal tubule cells) is associated with the establishment of chronic kidney disease in the 5/6 nephrectomy rodent model and was attenuated by NKA treatment. The in vitro response of proximal tubule cells (HK-2) to NKA conditioned medium mimics the in vivo attenuation of NFkB nuclear localization in response to NKA treatment. Putative mediators of cell-cell inhibition of NFkB activation (microRNAs) were identified in NKA conditioned medium. Taken together, these data support the hypothesis that one mechanism by which intra-renal delivery of bioactive kidney cells improves renal function might be via cell-cell transfer of components, e.g., RNA, that modulate immune responses in resident kidney cells.

Example 15—Functional Evaluation of NKA Constructs

Renal cell populations seeded onto gelatin or HA-based hydrogels were viable and maintained a tubular epithelial functional phenotype during an in vitro maturation of 3 days as measured by transcriptomic, proteomic, secretomic and confocal immunofluorescence assays. To investigate a potential mechanism by which NKA Constructs could impact a disease state, the effect of conditioned media on TGF-β signaling pathways related to tubulo-interstitial fibrosis associated with CKD progression was evaluated.

Conditioned medium was observed to attenuate TGF-β-induced epithelial-mesenchymal transition (EMT) in vitro in a human proximal tubular cell line (HK2).

Materials and Methods.

Biomaterials.

Biomaterials were prepared as beads (homogenous, spherical configuration) or as particles (heterogenous population with jagged edges). Gelatin beads (Cultispher S and Cultispher GL) manufactured by Percell Biolytica (Åstorp, Sweden) were purchased from Sigma-Aldrich (St. Louis, Mo.) and Fisher Scientific (Pittsburgh, Pa.), respectively. Crosslinked HA and HA/gelatin (HyStem™ and Extracel™ from Glycosan BioSystems, Salt Lake City, Utah) particles were formed from lyophilized sponges made according to the manufacturer's instructions. Gelatin (Sigma) particles were formed from crosslinked, lyophilized sponges.

PCL was purchased from Sigma-Aldrich (St. Louis, Mo.). PLGA 50:50 was purchased from Durect Corp. (Pelham, Ala.). PCL and PLGA beads were prepared using a modified double emulsion (W/O/W) solvent extraction method. PLGA particles were prepared using a solvent casting porogen leaching technique. All beads and particles were between 65 and 355 microns when measured in a dry state.

Cell Isolation, Preparation and Culture.

Cadaveric human kidneys were procured through National Disease Research Institute (NDRI) in compliance with all NIH guidelines governing the use of human tissues for research purposes. Canine kidneys were procured from a contract research organization (Integra). Rat kidneys (21 day old Lewis) were obtained from Charles River Labs (MI). The preparation of primary renal cell populations (UNFX) and defined sub-populations (B2) from whole rat, canine and human kidney has been previously described (Aboushwareb et al. World J Urol 26(4):295-300; 2008; Kelley et al. supra 2010; Presnell et al. WO/2010/056328). In brief, kidney tissue was dissociated enzymatically in a buffer containing 4.0 units/mL dispase (Stem Cell Technologies, Inc., Vancouver BC, Canada) and 300 units/ml collagenase IV (Worthington Biochemical, Lakewood N.J.), then red blood cells and debris were removed by centrifugation through 15% iodixanol (Optiprep®, Axis Shield, Norton, Mass.) to yield UNFX. UNFX cells were seeded onto tissue culture treated polystyrene plates (NUNC, Rochester N.Y.) and cultured in 50:50 media, a 1:1 mixture of high glucose DMEM:Keratinocyte Serum Free Medium (KSFM) containing 5% FBS, 2.5 μg EGF, 25 mg BPE, 1×ITS (insulin/transferrin/sodium selenite medium supplement), and antibiotic/antimycotic (all from Invitrogen, Carlsbad Calif.). B2 cells were isolated from UNFX cultures by centrifugation through a four-step iodixanol (OptiPrep; 60% w/v in unsupplemented KSFM) density gradient layered specifically for rodent (16%, 13%, 11%, and 7%), canine (16%, 11%, 10%, and 7%), or human (16%, 11%, 9%, and 7%) (Presnell et al. WO/2010/056328; Kelley et al. supra 2010). Gradients were centrifuged at 800×g for 20 minutes at room temperature (without brake). Bands of interest were removed via pipette and washed twice in sterile phosphate buffered saline (PBS).

Cell/Biomaterial Composites (NKA Constructs).

For in vitro analysis of cell functionality on biomaterials, a uniform layer of biomaterials (prepared as described above) was layered onto one well of a 6-well low attachment plate (Costar #3471, Corning). Human UNFX or B2 cells ($2.5 \times 10^5$ per well) were seeded directly onto the biomaterial. For studies of adherence of canine cells to biomaterials, $2.5 \times 10^6$ UNFX cells were seeded with 50 μl packed volume of biomaterials in a non-adherent 24-well plate (Costar #3473, Corning). After 4 hours on a rocking platform, canine NKA Constructs were matured overnight at 37° C. in a 5% $CO_2$ incubator. The next day, live/dead staining was performed using a live/dead staining assay kit (Invitrogen) according to the manufacturer's instructions. Rat NKA Constructs were prepared in a 60 cc syringe on a roller bottle apparatus with a rotational speed of 1 RPM.

For the transcriptomic, secretomic, and proteomic analyses described below, NKA Constructs were matured for 3 days. Cells were then harvested for transcriptomic or proteomic analyses and conditioned media was collected for secretomic profiling.

Functional Analysis of Tubular Cell Associated Enzyme Activity.

Canine NKA Constructs (10 μl loose packed volume) in 24-well plates were evaluated using an assay for leucine aminopeptidase (LAP) activity adapted from a previously published method (Tate et al. Methods Enzymol 113:400-419; 1985). Briefly, 0.5 ml of 0.3 mM L-leucine p-nitroanalide (Sigma) in PBS was added to NKA Constructs for 1 hour at room temperature. Wells were sampled in duplicate and absorbance at 405 nm recorded as a measure of LAP activity. LLC-PK1 cell lysate (American Type Culture Collection, or ATCC) served as the positive control.

Transcriptomic Profiling.

Poly-adenylated RNA was extracted using the RNeasy Plus Mini Kit (Qiagen, CA). Concentration and integrity was determined by UV spectrophotometry. cDNA was generated from 1.4 μg isolated RNA using the SuperScript VILO cDNA Synthesis Kit (Invitrogen). Expression levels of target transcripts were examined by quantitative real-time polymerase chain reaction (qRT-PCR) using commercially available primers and probes (Table 15.1) and an ABI-Prism 7300 Real Time PCR System (Applied Biosystems, CA). Amplification was performed using TaqMan Gene Expression Master Mix (ABI, Cat #4369016) and TATA Box Binding Protein gene (TBP) served as the endogenous control. Each reaction consisted of 10 μl Master Mix (2×), 1 μl Primer and Probe (20×) and 9 μl cDNA. Samples were run in triplicate.

TABLE 15.1

Human TaqMan Primers/Probes

| Gene | Abbrv. | Marker | TaqMan Cat # |
| --- | --- | --- | --- |
| Aquaporin 2 | AQP2 | Distal Collecting Duct Tubule | Hs00166640_m1 |
| Epithelial Cadherin/Cadherin 1, Type 1 | CDH1/ECAD | Distal Tubule | Hs00170423_m1 |
| Neuronal Cadherin/Cadherin 2, Type 1 | CDH2/NCAD | Proximal Tubule | Hs00169953_m1 |
| Cubilin, Intrinsic Factor-Cobalamin Receptor | CUBN | Proximal Tubule | Hs00153607_m1 |
| Nephrin | NPHS1 | Glomerular/Podocyte | Hs00190466_m1 |
| Podocin | NPHS2 | Glomerular/Podocyte | Hs00922492_m1 |
| Erthropoietin | EPO | Kidney Interstitum | Hs01071097_m1 |
| Cytochrome P450, Family 24, Subfamily A, Polypeptide 1/ | CYP2R1 | Proximal Tubule | Hs01379776_m1 |

TABLE 15.1-continued

Human TaqMan Primers/Probes

| Gene | Abbrv. | Marker | TaqMan Cat # |
|---|---|---|---|
| Vitamin D 24-Hydroxylase | | | |
| Vascular Endothelial Growth Factor A | VEGFA | Endothelial/Vascular | Hs00900055_m1 |
| Platelet/Endothelial Cell Adhesion Molecule | PECAM1 | Endothelial/Vascular | Hs00169777_m1 |
| Smooth Muscle Myosin Heavy Chain | MYH11/SMMHC | Smooth Muscle | Hs00224610_m1 |
| Calponin | CNN1 | Smooth Muscle | Hs00154543_m1 |
| TATA Box Binding Protein | TBP | Endogenous Control | Hs99999910_m1 |

Secretomic Profiling.

Conditioned medium from human NKA Constructs was collected and frozen at −80° C. Samples were evaluated for biomarker concentration quantitation. The results for a given biomarker concentration in conditioned media were normalized relative to the concentration of the same biomarker in conditioned media from control cultures (2D culture without biomaterial) and expressed as a unitless ratio.

Proteomic Profiling.

Protein from three independent replicates was extracted from cell/biomaterial composites and pooled for analysis by 2D gel electrophoresis. All reagents were from Invitrogen. Isoelectric focusing (IEF) was conducted by adding 30 μg of protein resuspended in 200 μl of ZOOM 2D protein solubilizer #1 (Cat #ZS10001), ZOOM carrier ampholytes pH 4-7 (Cat #ZM0022), and 2M DTT (Cat #15508-013) to pH 4-7 ZOOM IEF Strips (Cat #ZM0012). Following electrophoresis for 18 hours at 500V, IEF strips were loaded onto NuPAGE Novex 4-12% Bis-Tris ZOOM IPG well gels (Cat #NP0330BOX) for SDS-PAGE separation and electrophoresed for 45 min at 200V in MES buffer (Cat #NP0002). Proteins were visualized using SYPRO Ruby protein gel stain (Cat #S-12000) according to the manufacturer's instructions.

Confocal Microscopy.

NKA Constructs prepared from human or rat UNFX or B2 cells were matured for 3 days and then fixed in 2% paraformaldehyde for 30 minutes. Fixed NKA Constructs were blocked and permeabilized by incubation in 10% goat serum (Invitrogen) in D-PBS (Invitrogen)+0.2% Triton X-100 (Sigma) for 1 hour at room temperature (RT). For immunofluorescence, NKA Constructs were labeled with primary antibodies (Table 15.2) at a final concentration of 5 μg/ml overnight at RT. Labeled NKA constructs were washed twice with 2% goat serum/D-PBS+0/2% Triton X-100 and incubated with goat or rabbit TRITC conjugated anti-mouse IgG2A (Invitrogen) secondary antibody at 5 μg/mi. For double labeling with DBA (Dolichos biflorus agglutinin), NKA construct candidates were further incubated with FITC conjugated DBA (Vector Labs) diluted to 2 mg/ml in 2% goat serum/D-PBS+0.2% Triton X-100 for 2 hrs at RT.

TABLE 15.2

| Antibody | Source | Manufacturer | Catalog# | Target |
|---|---|---|---|---|
| IgG1 Ctrl | Mouse | BD | 557273 | Background control |
| IgG ctrl | goat | Invitrogen | 026202 | Background control |
| IgG ctrl | rabbit | Invitrogen | 026102 | Background control |
| N-Cadherin | Mouse | BD | 610920 | Proximal tubules |
| E-Cadherin | Mouse | BD | 610182 | Distal tubules |
| Cubilin (A-20) | goat | Santa Cruz | Sc-20609 | Proximal tubules |
| GGT-1 | Rabbit | Santa Cruz | Sc-20638 | Tubular epithelial |
| Megalin | Rabbit | Santa Cruz | Sc-25470 | Proximal tubules |

Samples were washed twice with D-PBS and optically sectioned using a Zeiss LSM510 laser scanning confocal system (Cellular Imaging Core, Wake Forest Baptist Medical Center) running LSM Image software (Zeiss) or with a Pathway 855 confocal microscope (BD Biosciences).

Analysis of TGF-β Mediated EMT in HK2 Cells.

HK2 cells (ATCC) were cultured in 50:50 media in fibronectin or collagen (IV) coated culture dishes (BD Biosciences). For EMT assays, HK2 cells were seeded in 24-well collagen (IV) coated plates at 70-80% confluency with 50:50 media or conditioned media collected from either two dimensional (2D) human UNFX cultures or NKA Constructs made with human UNFX that were matured for 3 days prior to media collection. TGF-β induction was initiated by adding 10 ng/ml to the culture media 3 days prior to isolating RNA from the cells for the EMT assay. EMT was monitored by qRT-PCR by analyzing the relative expression of E-cadherin (an epithelial marker) and calponin (mesenchymal marker) at the end of the three day incubation period. RNA was prepared from harvested HK2 cells for TaqMan qRT-PCR analysis as described above. Statistical analysis was done using standard two tailed Student's t-test assuming equal variance for each sample. Confidence intervals of 95% (p-value<0.05) and 99% (p-value<0.01) were used to determine statistical significance.

In Vivo Implantation of Acellular Biomaterials and NKA Constructs.

Lewis rats (6 to 8 weeks old) were purchased from Charles River (Kalamazoo, Mich.). All experimental procedures were performed under PHS and IACUC guidelines of the Carolinas Medical Center. Under isoflurane anesthesia, female Lewis rats (approximately 2 to 3 months old) underwent a midline incision, and the left kidney was exposed. 35 μl of packed biomaterials (acellular biomaterial or NKA Construct) were introduced by microinjection into the renal parenchyma. Two injection trajectories were used: (i) from each pole toward the cortex (referred to as cortical injection), or (ii) from the renal midline toward the pelvis (referred to as medullary injection). Rats were sacrificed at 1, 4, or 8 weeks post-injection. No early deaths occurred. Study design for the acellular implantation study is presented in Table 15.3 (ND=not done).

Renal Histology.

Representative kidney samples were collected and placed in 10% buffer formalin for 24 hours. Sections were dehydrated in ascending grades of ethanol and embedded in paraffin. Sections (5 μm) were cut, mounted on charged slides, and processed for hematoxylin and eosin (H&E), Masson's trichrome and Periodic Acid Schiff (PAS) staining in accordance with standard staining protocols (Prophet et al., Armed Forces Institute of Pathology: Laboratory methods in histotechnology. Washington, D.C.: American Registry of Pathology; 1992). Digital microphotographs were captured at total magnification of ×40, ×100 and ×400 using a Nikon Eclipse 50i microscope fitted with a Digital Sight (DS-U1) camera. Renal morphology changes were assessed by commonly used (Shackelford et al. Toxicol Pathol 30(1): 93-96; 2002) severity grade schemes (grades 1, 2, 3, 4), to which descriptive terms (minimal, mild, moderate, marked/severe) were applied to describe the degree of glomerulosclerosis, tubular atrophy and dilatation, tubular casts, and interstitial fibrosis, and inflammation observed.

TABLE 15.3

Study design for evaluating acellular biomaterials in healthy adult Lewis rat kidneys

| Biomaterial: | Time in vivo | |
| --- | --- | --- |
|  | 1 week | 4 weeks |
| PCL Beads | n = 1 | n = 1 |
| Gelatin Beads | n = 1 | ND |
| Gelatin Particles | n = 1 | n = 1 |
| HA/Gelatin Particles | n = 2 | ND |
| HA Particles | n = 1 | n = 1 |
| PLGA Particles | n = 1 | ND |
| PLGA Beads | n = 1 | ND |

Results

Response of Mammalian Kidney Tissue to Injection of Biomaterials into the Renal Parenchyma.

Biomaterials were analyzed for potential use in renal cell/biomaterial composites by direct injection into healthy rat kidneys (Table 15.3). Tissue responses were evaluated by measuring the degree of histopathology parameters (inflammation, fibrosis, necrosis, calcification/mineralization) and biocompatibility parameters (biomaterial degradation, neo-vascularization, and neo-tissue formation) at 1 and 4 weeks post-injection.

Figure 19A:
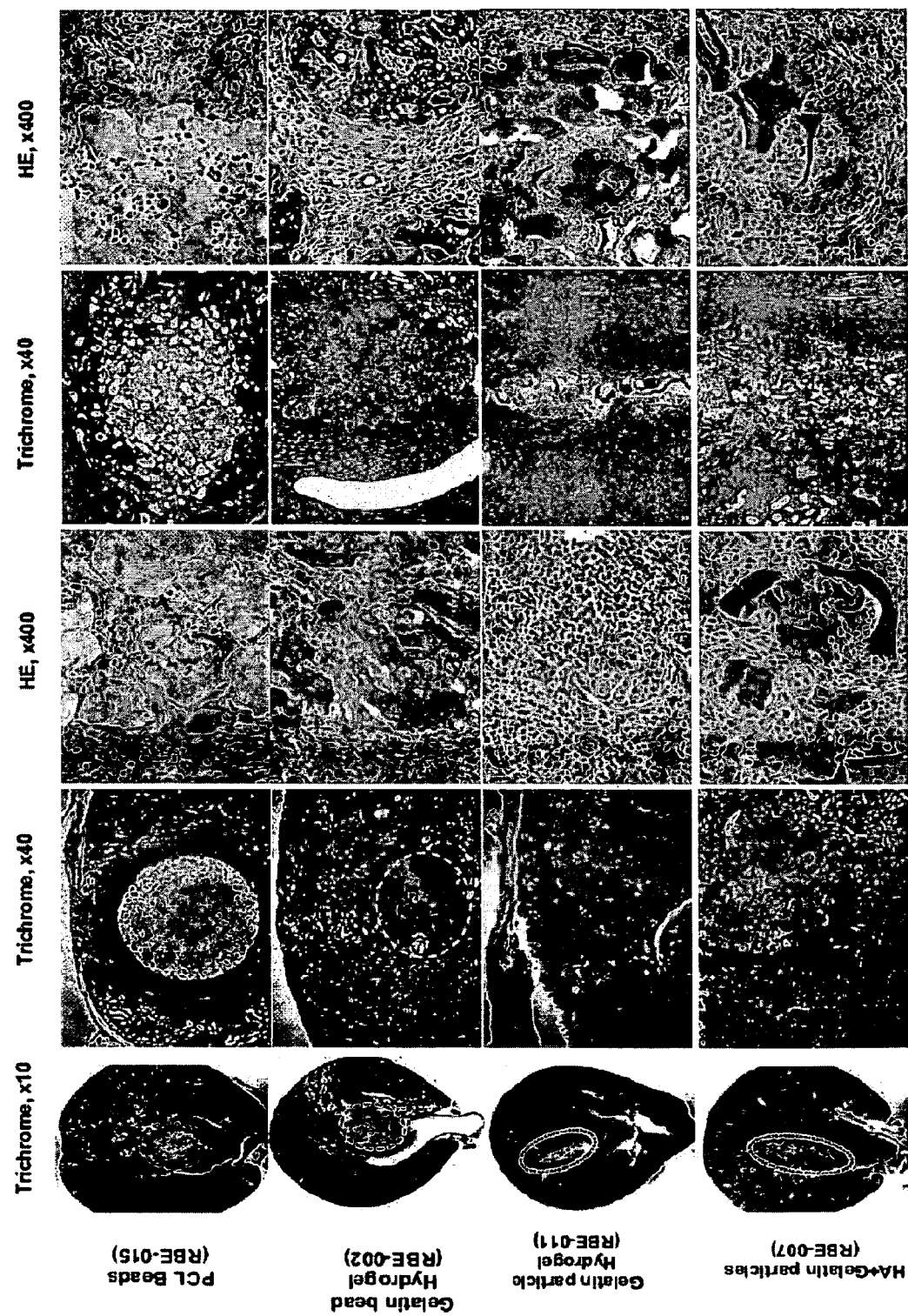
FIG. 19A-C shows in vivo evaluation of biomaterials at 1 week and 4 weeks post-implantation.
Figure 19B:
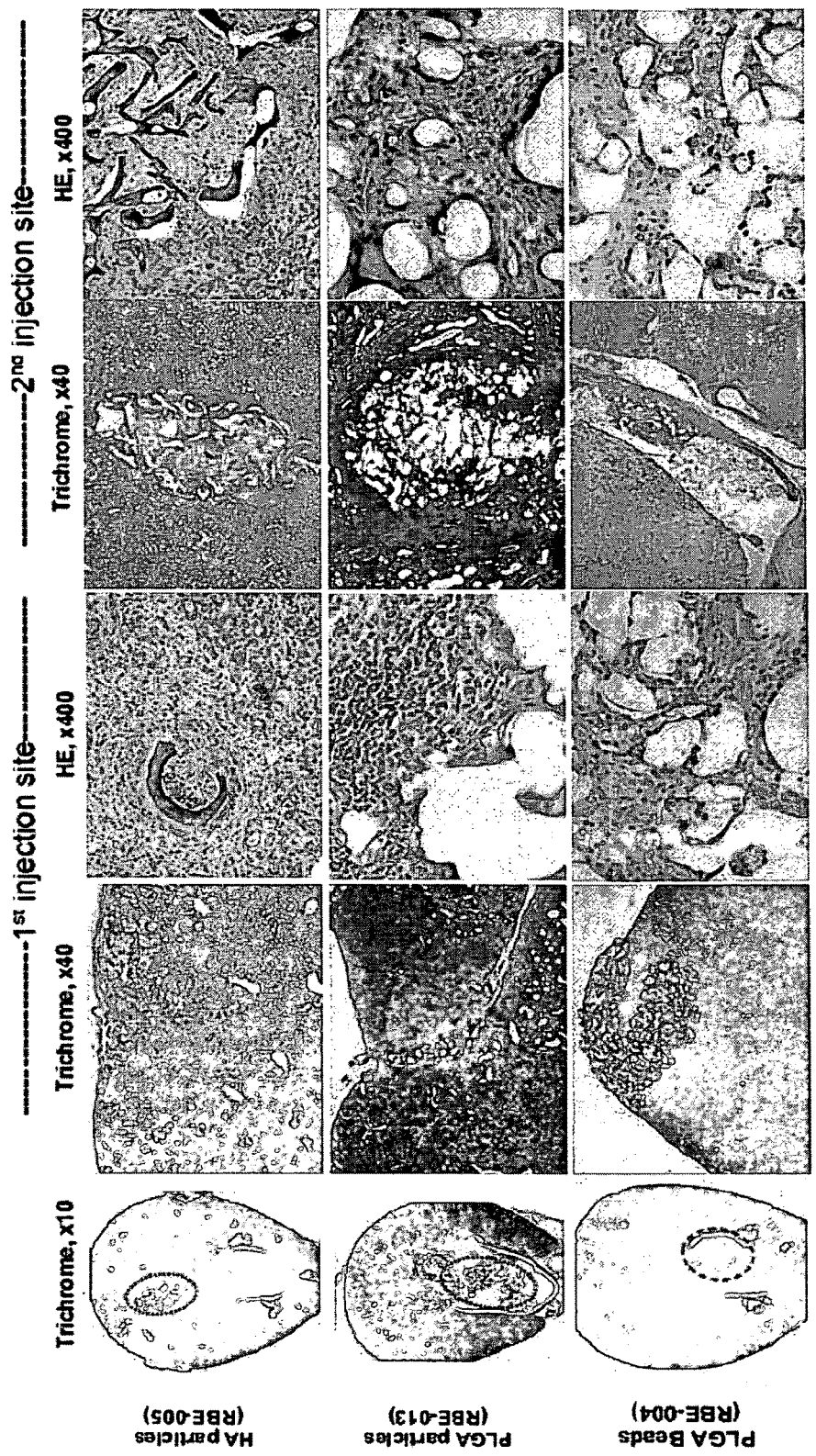

FIG. 19A-B shows in viva evaluation of biomaterials at 1 week post-implantation. Trichrome X10 low power image of kidney cross section showing biomaterial aggregate. Trichrome X40: Close-up of biomaterial aggregate. H&E X400: High magnification image of biomaterial aggregate to evaluate extent of cell/tissue infiltration. Each kidney was injected at two locations as described in Materials and Methods. At 1 week post-implantation, the host tissue responses elicited by each biomaterial tested were generally similar; however, gelatin hydrogels appeared to elicit less intense histopathological and more biocompatible responses.

Figure 19C:
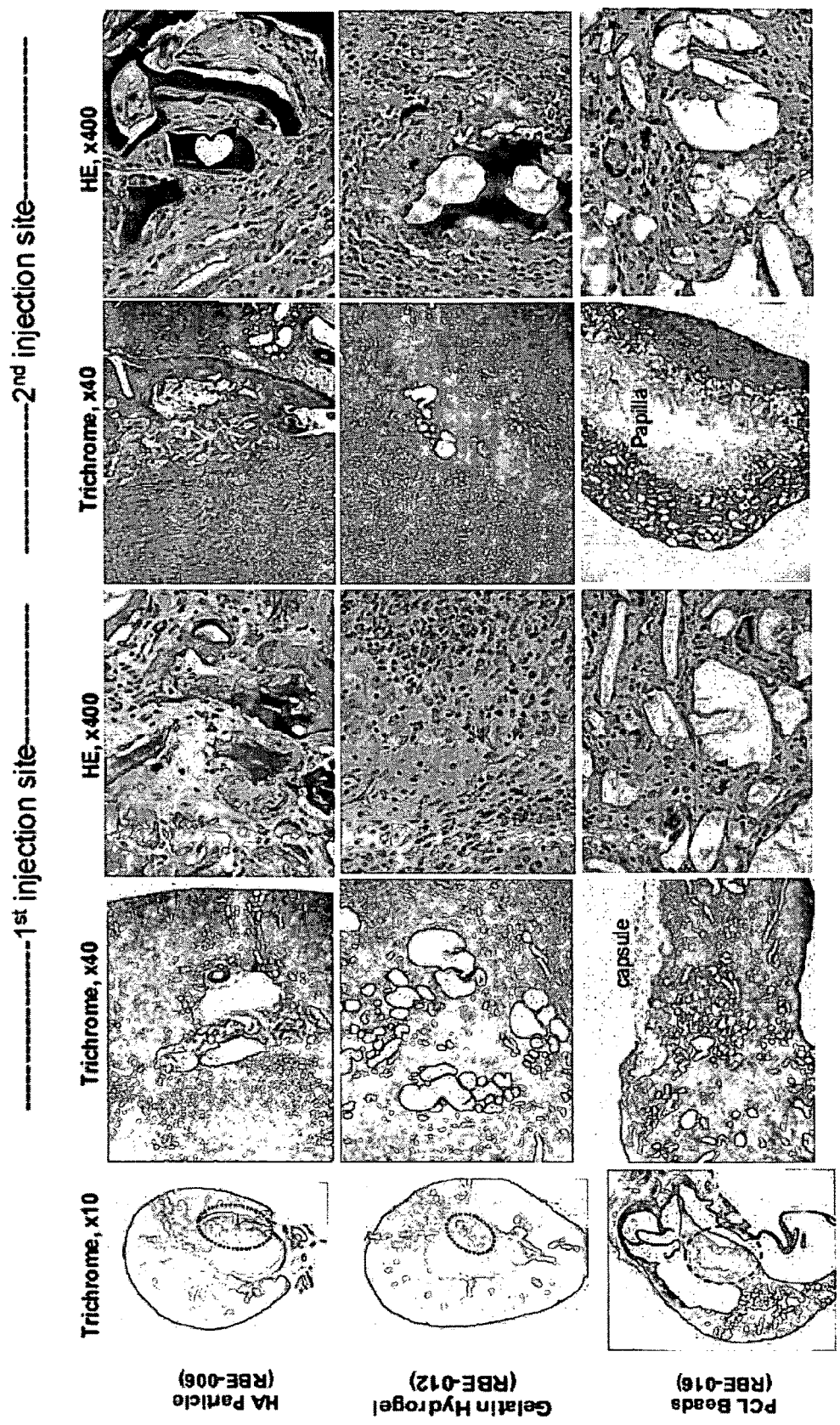

FIG. 19C shows in viva evaluation of biomaterials at 4 weeks post-implantation. At 4 weeks post-implantation, the severity of histopathology parameters in tissues injected with HA or gelatin particles were qualitatively reduced compared to 1 week post-implantation. Gelatin particles were nearly completely resorbed and less giant cell reaction was observed than in tissues that received HA particles. In most cases where biomaterials were injected via the medullary injection trajectory (e.g., deeper into the medulla/pelvis), undesirable outcomes including obstruction leading to hydronephrosis, inflammatory reactions of greater severity, and renal arteriolar and capillary micro-embolization leading to infarction was observed (data not shown).

Assessing Functional Phenotype of Therapeutically-Relevant Renal Cell Populations with Biomaterials.

Therapeutically-relevant renal cell populations (UNFX) that extended survival and increased renal function in a rodent model of chronic kidney disease after direct injection into renal parenchyma have been characterized (Presnell et al. WO/2010/056328; Kelley et al. supra 2010) and methods for their isolation, characterization, and expansion have been developed and translated across multiple species (Presnell et al. 2010 supra). To assess whether UNFX cells adhere to, remain viable, and retain a predominantly tubular, epithelial phenotype when incorporated into NKA Constructs, transcriptomic, secretomic, proteomic, and confocal immunofluorescence microscopy analyses were conducted on NKA Constructs produced from UNFX cells and various biomaterials.

Adherence and Viability.

Canine-derived UNFX cells were seeded with gelatin beads, PCL beads, PLGA beads, HA particles, and HA/gelatin particles as described (3 NKA Constructs per biomaterial). Cell distribution and viability were assessed one day after seeding by live/dead staining FIG. 20A-D shows live/dead staining of NKA constructs seeded with canine UNFX cells (A=gelatin beads; B=PCL beads; C=HA/gelatin particles; D=HA particles). Green indicates live cells; red indicates dead cells. (A) Gelatin beads; (B) PCL beads; (C) HA/gelatin particles; and (D) HA particles. Viable cells may be observed on all hydrogel-based NKA Constructs.

UNFX cells adhered robustly to naturally-derived, hydrogel-based biomaterials such as gelatin beads and HA/gelatin particles (black arrows in A, D), but showed minimal adherence to synthetic PCL (B) or PLGA beads (not shown). Cells did not adhere to HA particles (C) but showed evidence of bioresponse (i.e., spheroid formation). Functional viability of the seeded UNFX cells on hydrogel-based NKA Constructs was confirmed by assaying for leucine aminopeptidase, a proximal tubule-associated hydrolase (data not shown).

Transcriptomic Profiling.

The gene expression profiles of human UNFX cells in hydrogel-based NKA Constructs (3 NKA Constructs per biomaterial) and parallel 2D cultures of UNFX cells were compared by quantitative transcriptomic analysis.

Figure 20E:
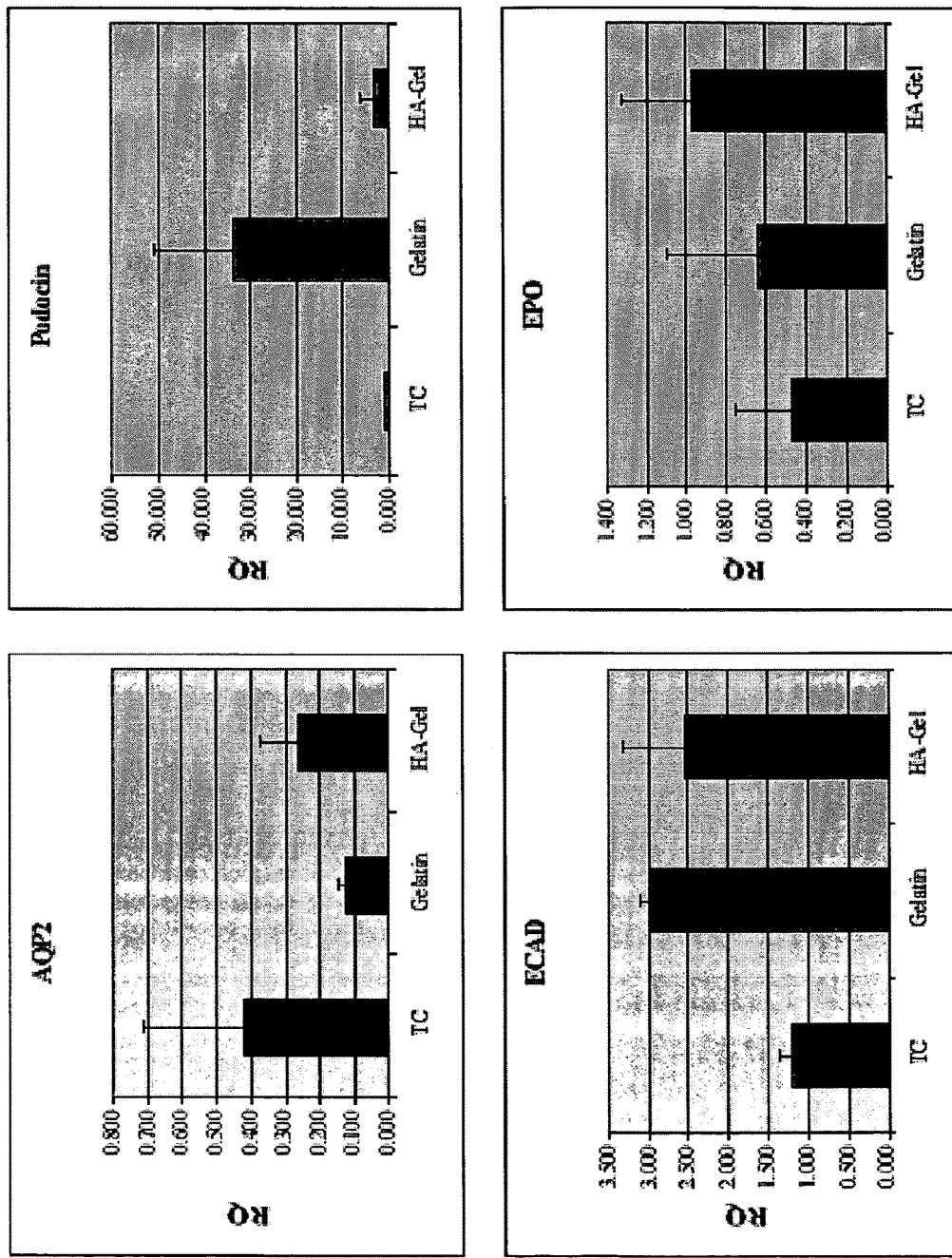
FIG. 20E-G shows transcriptomic profiling of NKA constructs.
Figure 20F:
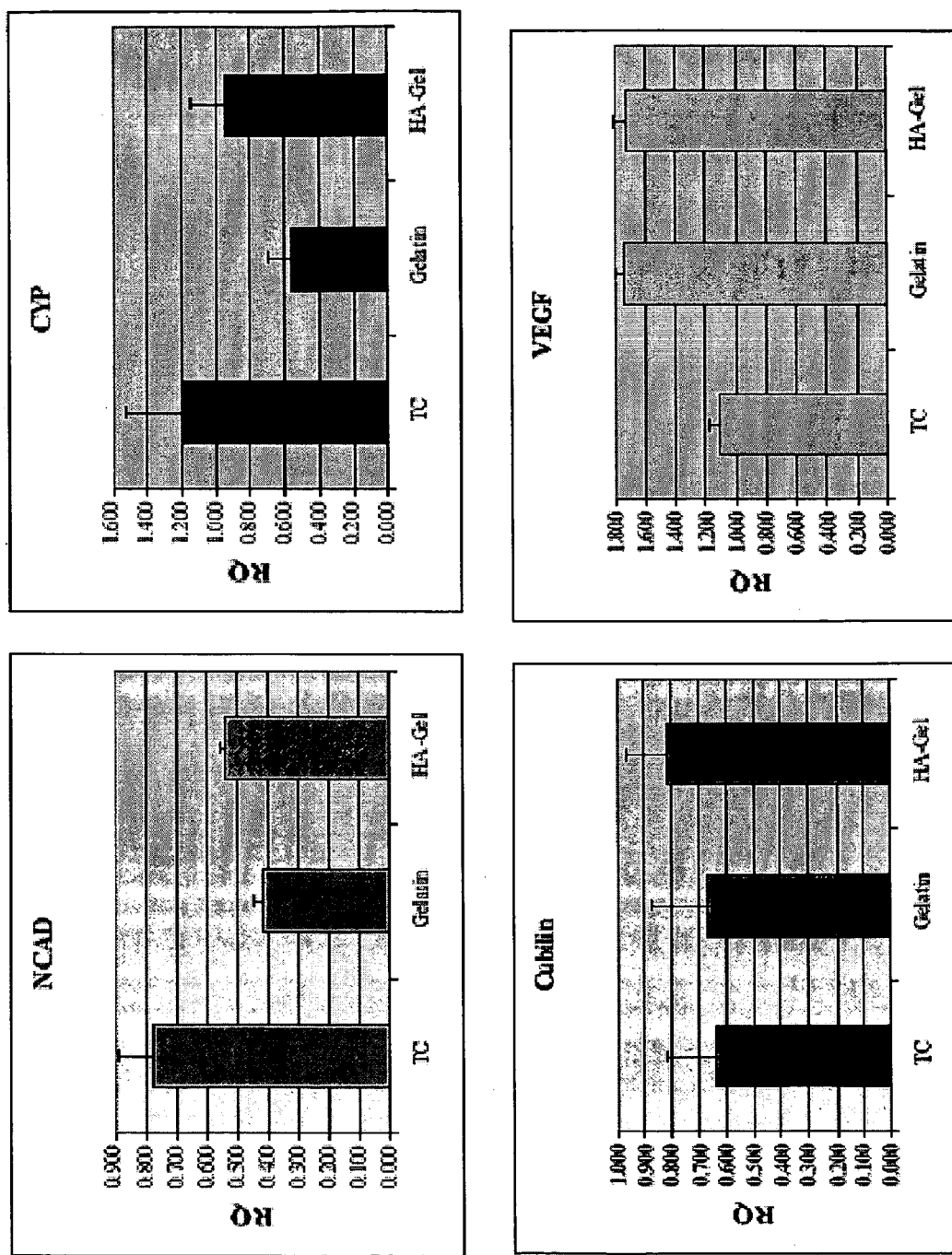
Figure 20G:
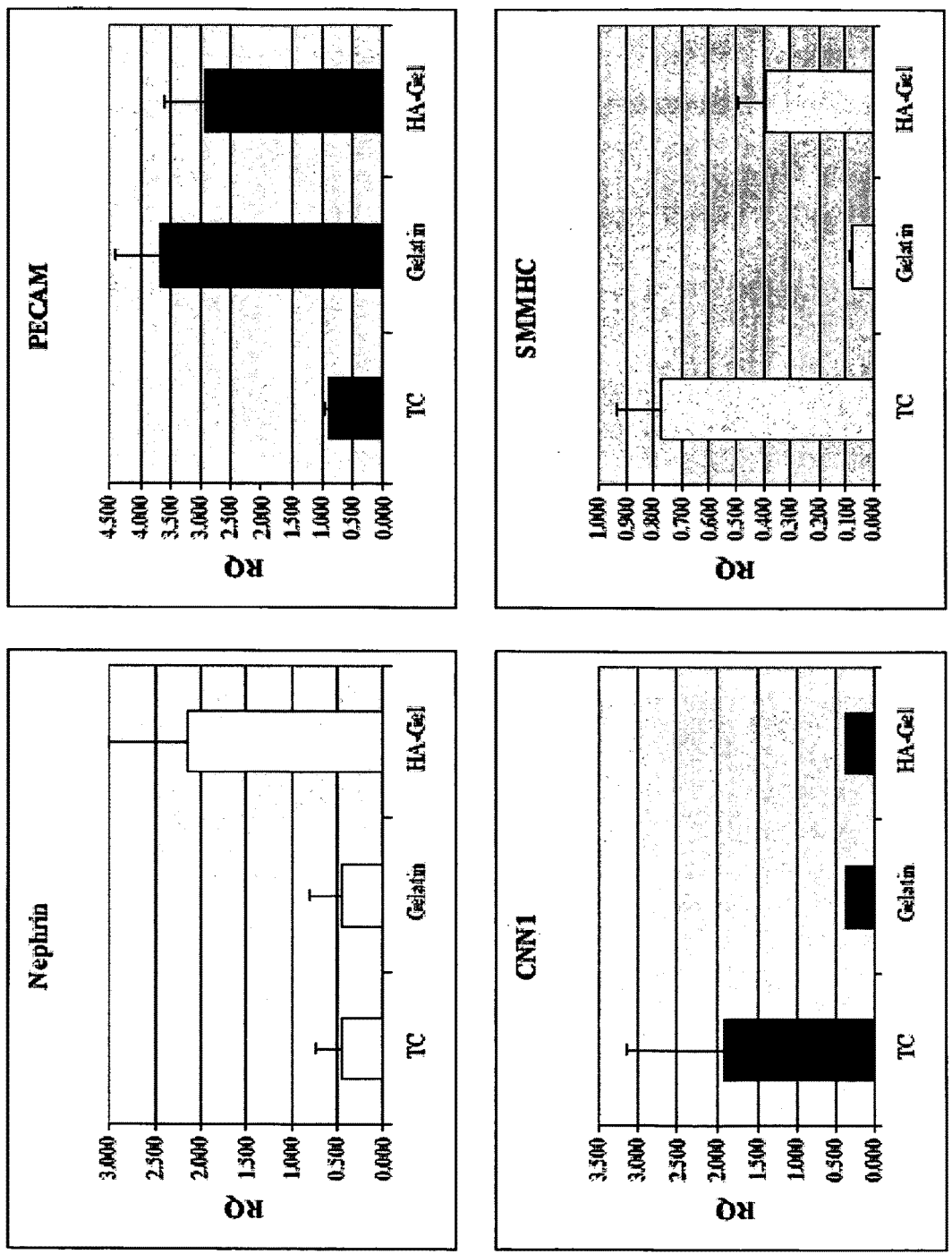

FIG. 20E-G shows transcriptomic profiling of NKA constructs. TC: primary human UNFX cells cultured in 2D. Gelatin: NKA Construct composed of human UNFX cells and gelatin hydrogel. HA-Gel: NKA Construct composed of human UNFX cells and HA/gelatin particles. qRT-PCR data presented in graphical and tabular format. Transcripts examined fell into four principal categories: (i) Tubular: aquaporin 2 (AQ2), E-cadherin (ECAD), erythropoietin (EPO), N-cadherin (NCAD), Cytochrome P450, Family 24, Subfamily A, Polypeptide 1—aka Vitamin D 24-Hydroxylase (CYP), cubilin, nephrin; (ii) Mesenchymal: calponin (CNN1), smooth muscle myosin heavy chain (SMMHC); (iii) Endothelial: vascular endothelial growth factor (VEGF), platelet endothelial cell adhesion molecule (PECAM); and (iv) Glomerular. podocin. Overall, tubular marker expression was comparable between hydrogel-based NKA Constructs and 2D UNFX cultures. Similarly, endothelial markers (VEGF and PECAM) were comparable. In contrast, the glomerular marker podocin exhibited significant variation among NKA Constructs. Podocin levels in HA/gelatin-based NKA Constructs were most comparable with those observed in 2D UNFX cultures. Interestingly, mesenchymal marker (CNN1 and SMMHC) expression was significantly down-regulated (p<0.05) in hydrogel-based NKA Constructs relative to 2D UNFX cultures, suggesting that fibroblastic sub-populations of UNFX may not propagate as well in the hydrogel-based NKA Constructs in the renal media formulation.

Secretomic Profiling.

NKA Constructs were produced with human UNFX and B2 cells and gelatin or HA/gelatin hydrogel (one NKA Construct per biomaterial per cell type=4 NKA Constructs total).

Figure 21A:
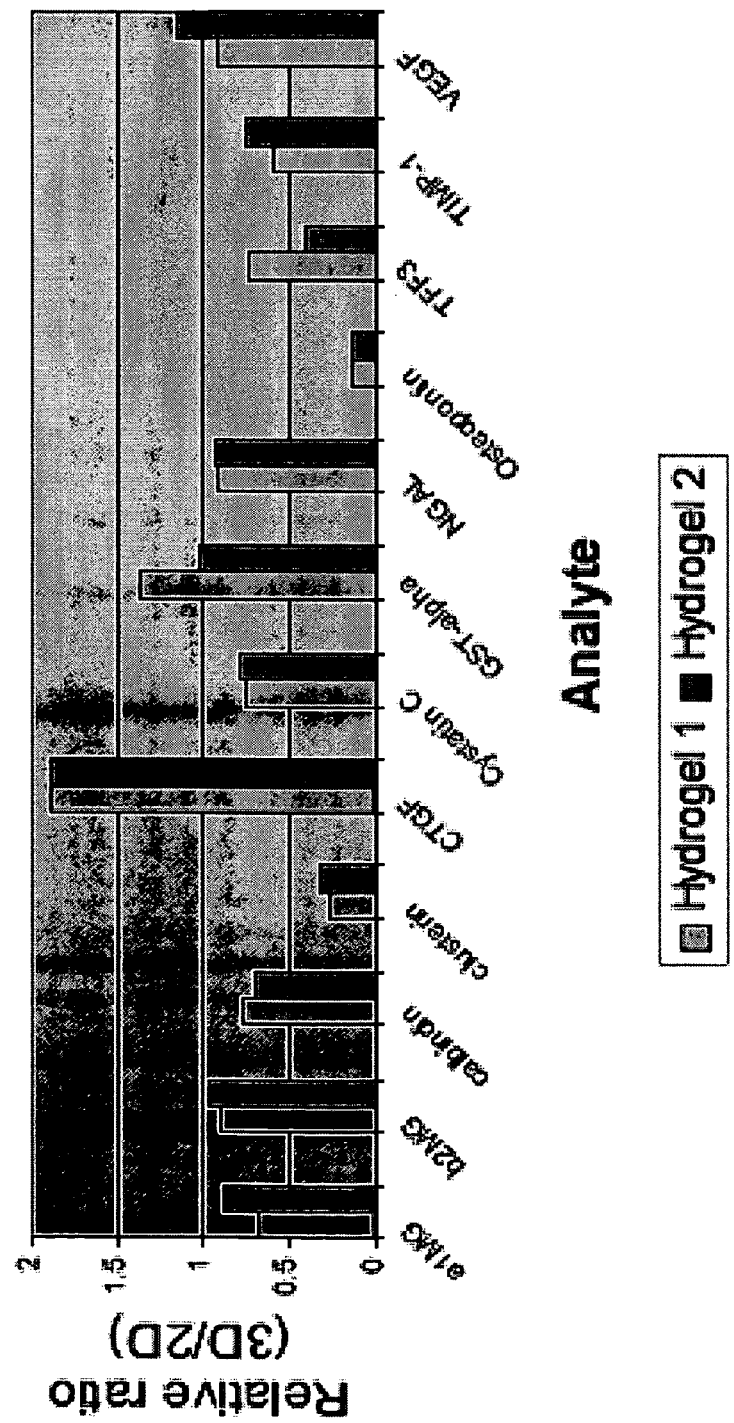
FIG. 21A-B shows the secretomic profiling of NKA Constructs.
Figure 21B:
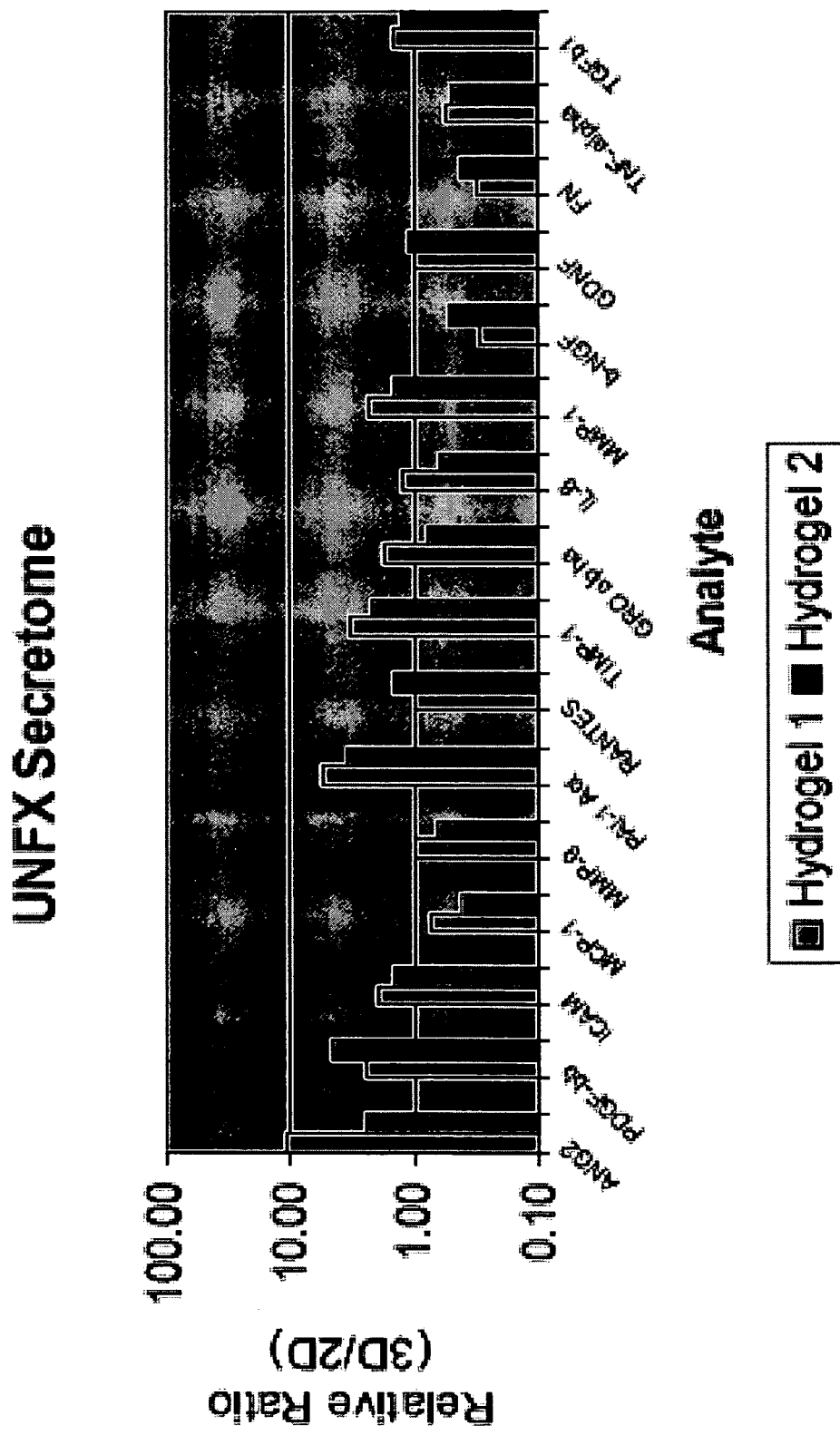

FIG. 21A-B shows the secretomic profiling of NKA Constructs. Data is presented as a 3D:2D ratio. NKA Constructs were produced from human UNFX or B2 cells and gelatin (Hydrogel 1) or HA/gelatin (Hydrogel 2) hydrogels as described in Materials and Methods. Secretomic profiling was performed on conditioned media from NKA Constructs matured for 3 days and compared with parallel 2D cultures of human UNFX or B2 cells by calculating the ratio of analyte expression of NKA Constructs (three-dimensional, or 3D, culture) to 2D culture (3D:2D ratio). For each of the three NKA Constructs seeded with UNFX cells, the 3D:2D ratios were at or close to 1, suggesting that the seeding process and 3 days of maturation on these biomaterials had little impact on the secretomic profile of UNFX cells. For NKA Constructs seeded with B2 cells, a similar result of a 3D:2D ratio at or near 1 was observed, providing additional evidence that the seeding process and 3 days of maturation on these biomaterials had little impact on the secretomic profile of therapeutically-relevant renal cells.

Proteomic Profiling.

Proteomic profiles of a given cell or tissue are produced by separating total cellular proteins using 2D gel electrophoresis and have been used to identify specific biomarkers associated with renal disease (Vidal et al. Clin Sci (Lond) 109(5):421-430; 2005).

Figure 22A:
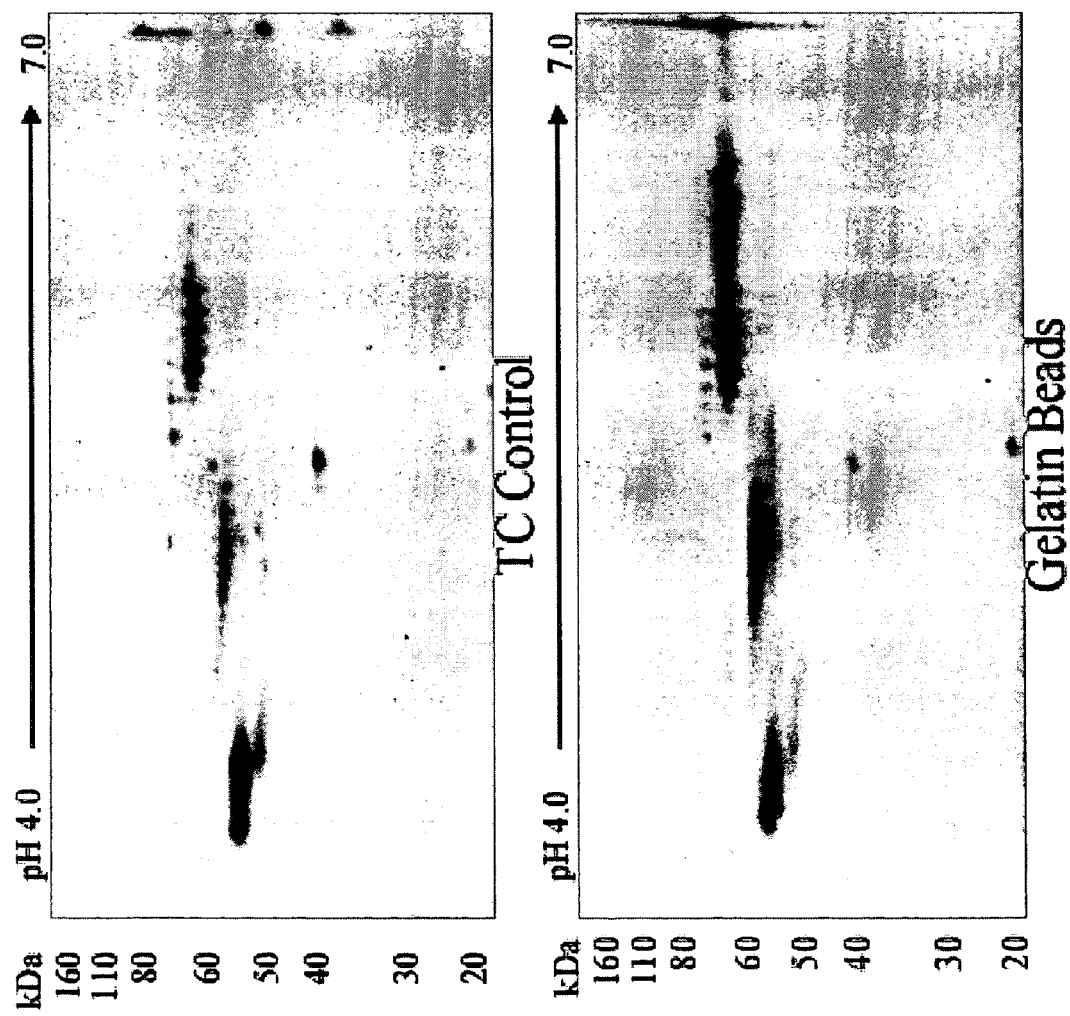
FIG. 22A-B shows proteomic profiling of NKA Constructs.
Figure 22B:
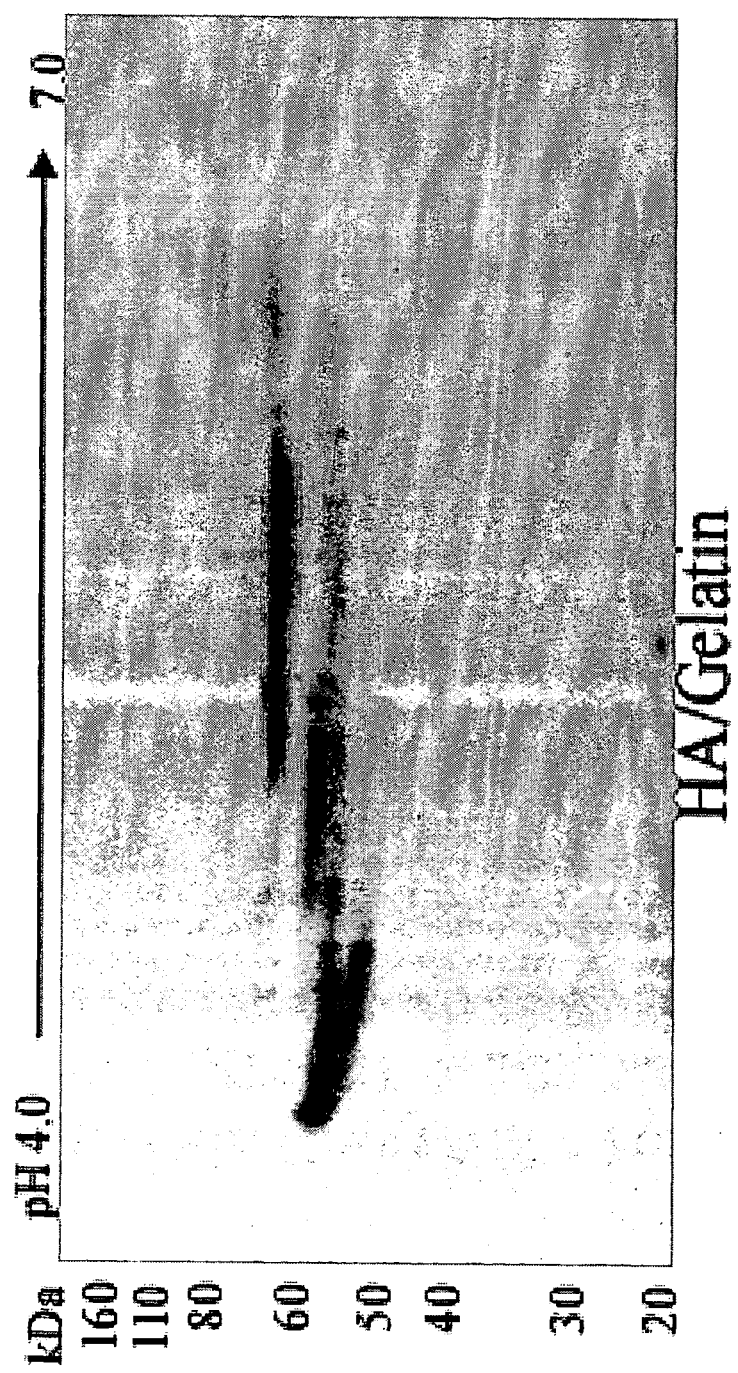

FIG. 22A-B shows proteomic profiling of NKA Constructs. NKA Constructs were produced with human UNFX cells and biomaterials as indicated. Proteins in total protein extracts were separated by 2D gel electrophoresis as described in Materials and Methods. In this experiment, proteomic profiling was used to compare protein expression in human UNFX cells in NKA Constructs (gelatin or HA/gelatin hydrogel-based, 3 NKA Constructs per biomaterial) and in 2D tissue culture. The proteome profiles of total protein isolated from NKA Constructs or 2D cultures of UNFX cells were essentially identical, providing additional evidence that the seeding process and 3 days maturation on these biomaterials had little impact on the proteomes expressed by UNFX cells.

Confocal Microscopy.

Figure 23B:
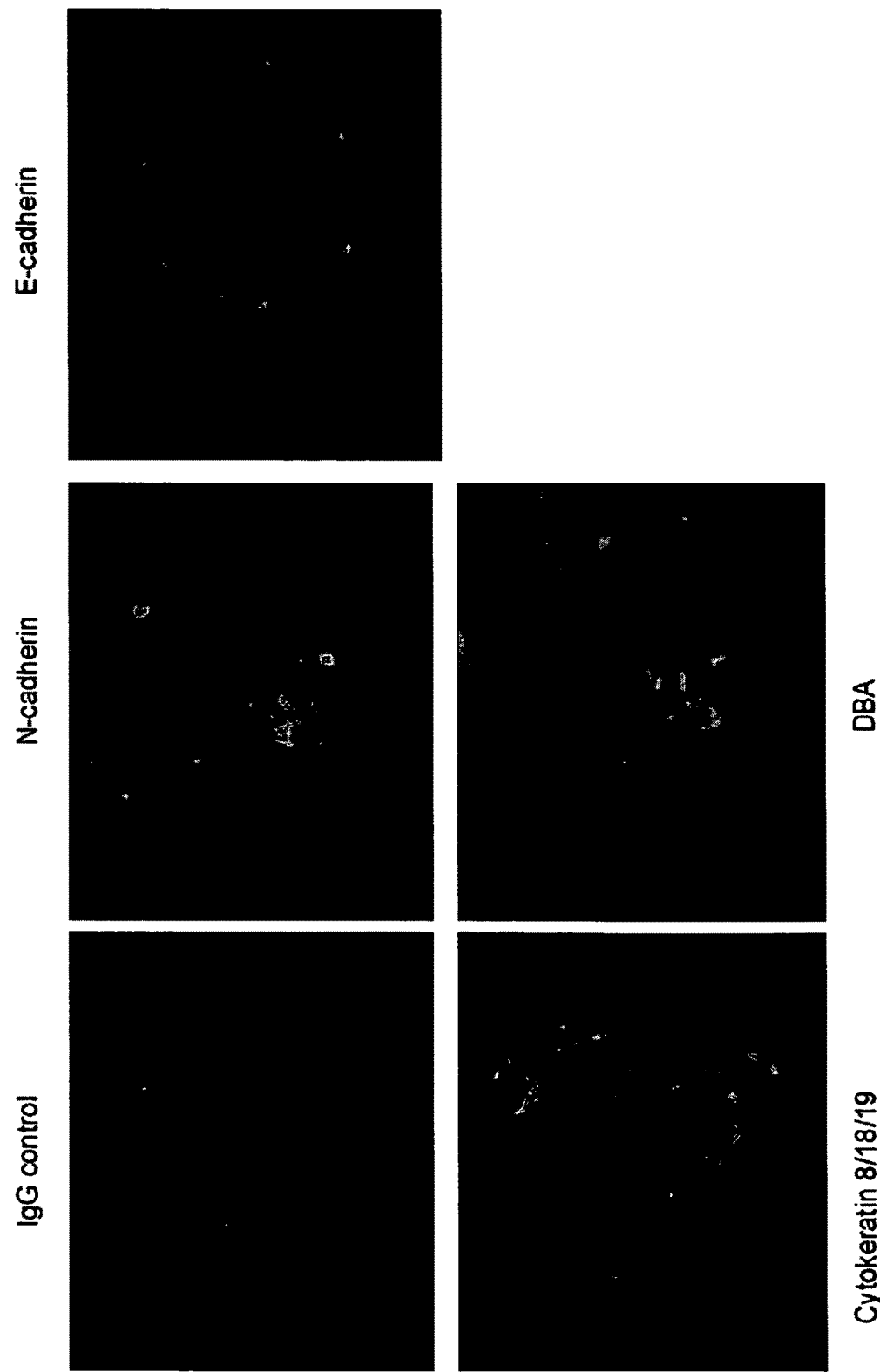
Figure 23C:
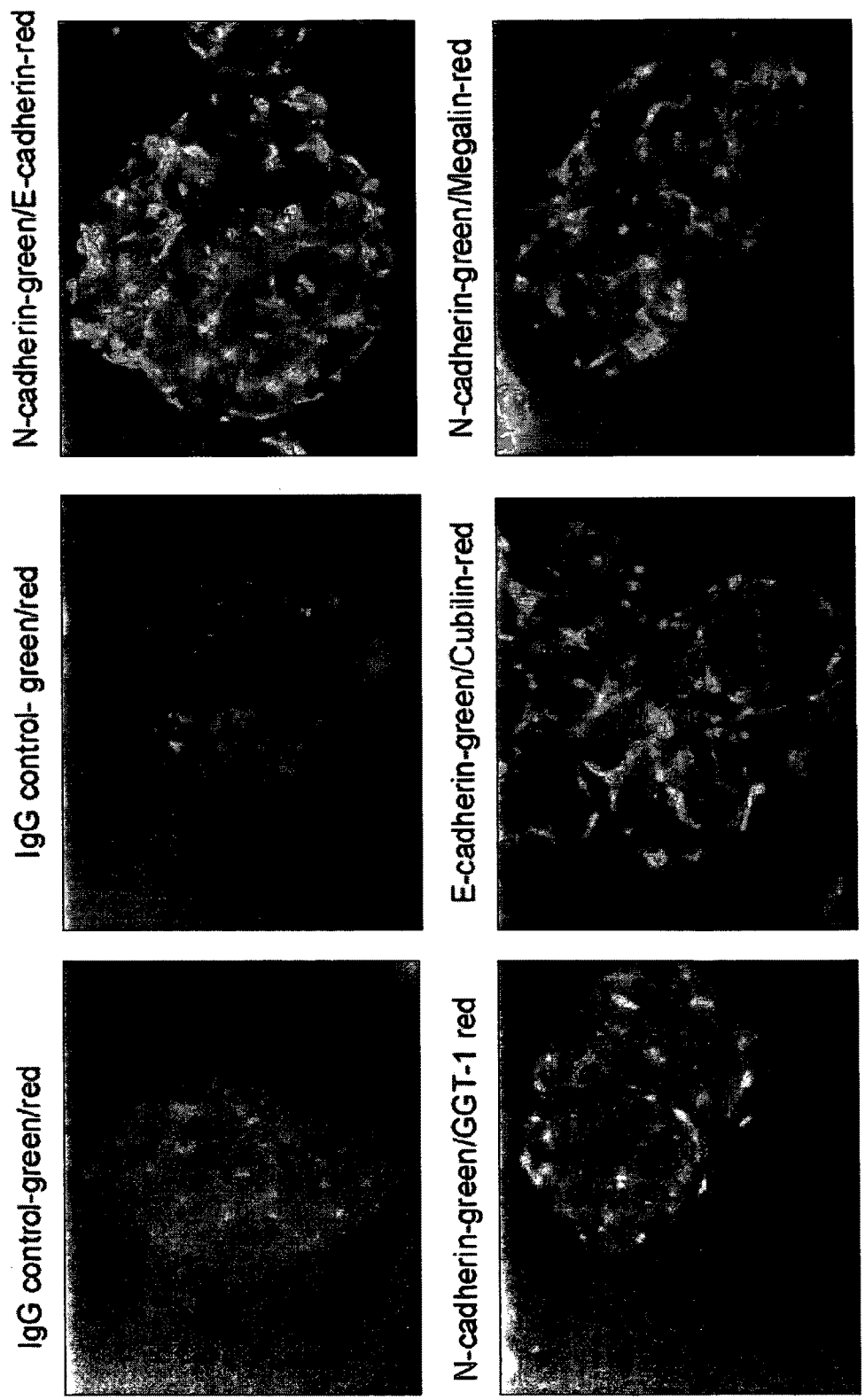

Retention of the tubular epithelial phenotype of rat and human B2 cells (Presnell et al. 2010 supra) in NKA Constructs was evaluated by confocal imaging of established biomarkers: FIG. 23A-C shows confocal microscopy of NKA Constructs. Confocal microscopy of NKA Constructs produced with human (A) or rat (B, C) B2 cells and gelatin hydrogel. (A) E-cadherin (red—solid white arrows), DBA (green—dashed green arrows) and gelatin hydrogel bead is visible with DIC optics. (B) DNA visualized with DAPI staining (blue—solid white arrows) and each of the following markers in green (dashed white arrows): IgG control, N-cadherin, E-cadherin, cytokeratin 8/18/18, DBA. (C) double-labeling images of markers and colors as indicated. E-cadherin and DBA in human NKA Constructs and E-cadherin, DBA, N-cadherin, cytokeratin 8/18/19, gamma glutamyl transpeptidase (GGT-1), and megalin in rat NKA Constructs. Optical sectioning of confocal images also allowed evaluation of the extent of cell infiltration into the biomaterial after seeding and 3 days of maturation. B2 cells in human and rat NKA Constructs exhibited expression of multiple tubular epithelial markers. Optical sectioning revealed minimal cell infiltration of the hydrogel construct, with cells generally confined to the surface of the biomaterial.

In Vivo Responses to Implantation of NKA Construct Prototypes.

Based on the in vivo responses to biomaterial injection into renal parenchyma and the in vitro phenotype and functional characterization of UNFX and B2 cells in NKA Constructs described above, gelatin hydrogel was selected to evaluate the in vivo response to NKA Construct injection into renal parenchyma in healthy Lewis rats. NKA Constructs were produced from syngeneic B2 cells and implanted into two animals, which were sacrificed at 1, 4, and 8 weeks post-implantation. All animals survived to scheduled necropsy when sections of renal tissues were harvested, sectioned, and stained with Trichrome, hematoxylin and eosin (H&E), and Periodic Acid Schiff (PAS).

Figure 24A:
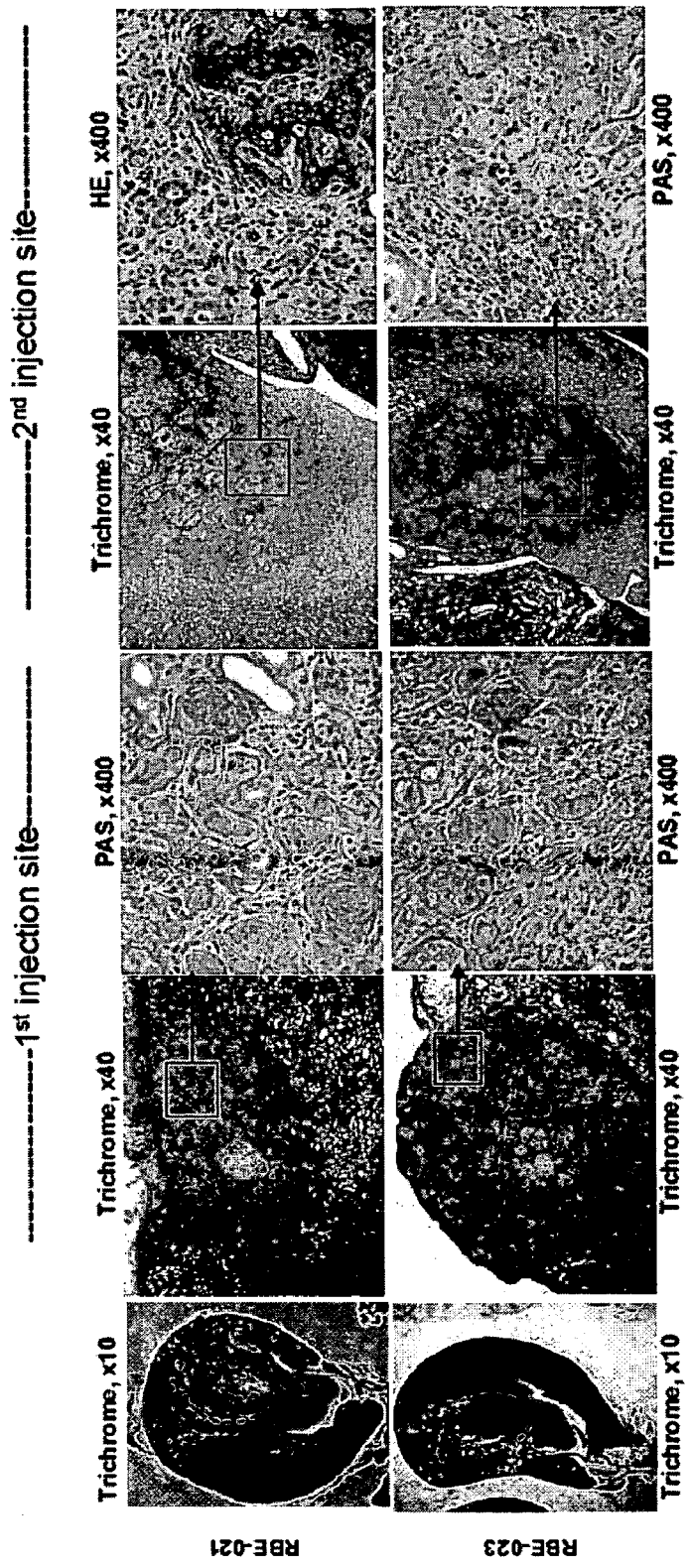
FIG. 24A-B shows in vivo evaluation of NKA Constructs at 1 week and 4 weeks post-implantation.
Figure 24B:
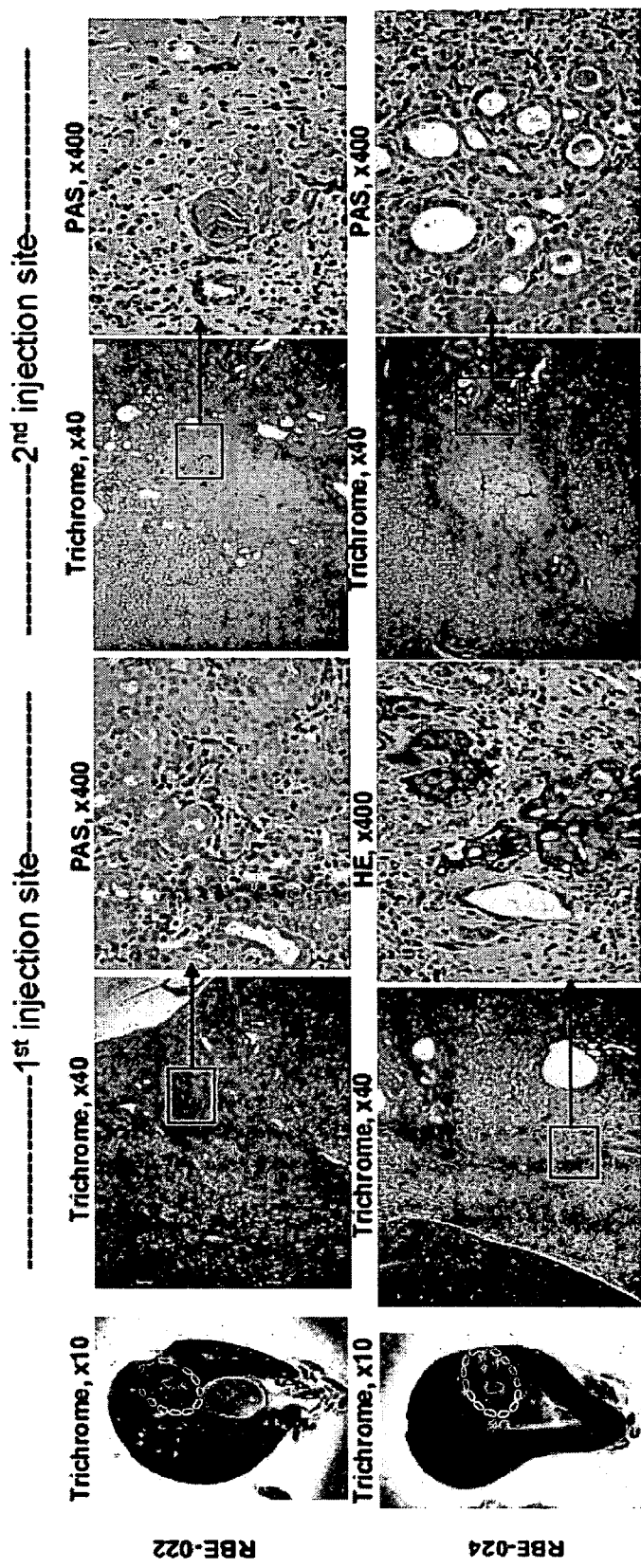
Figure 25:
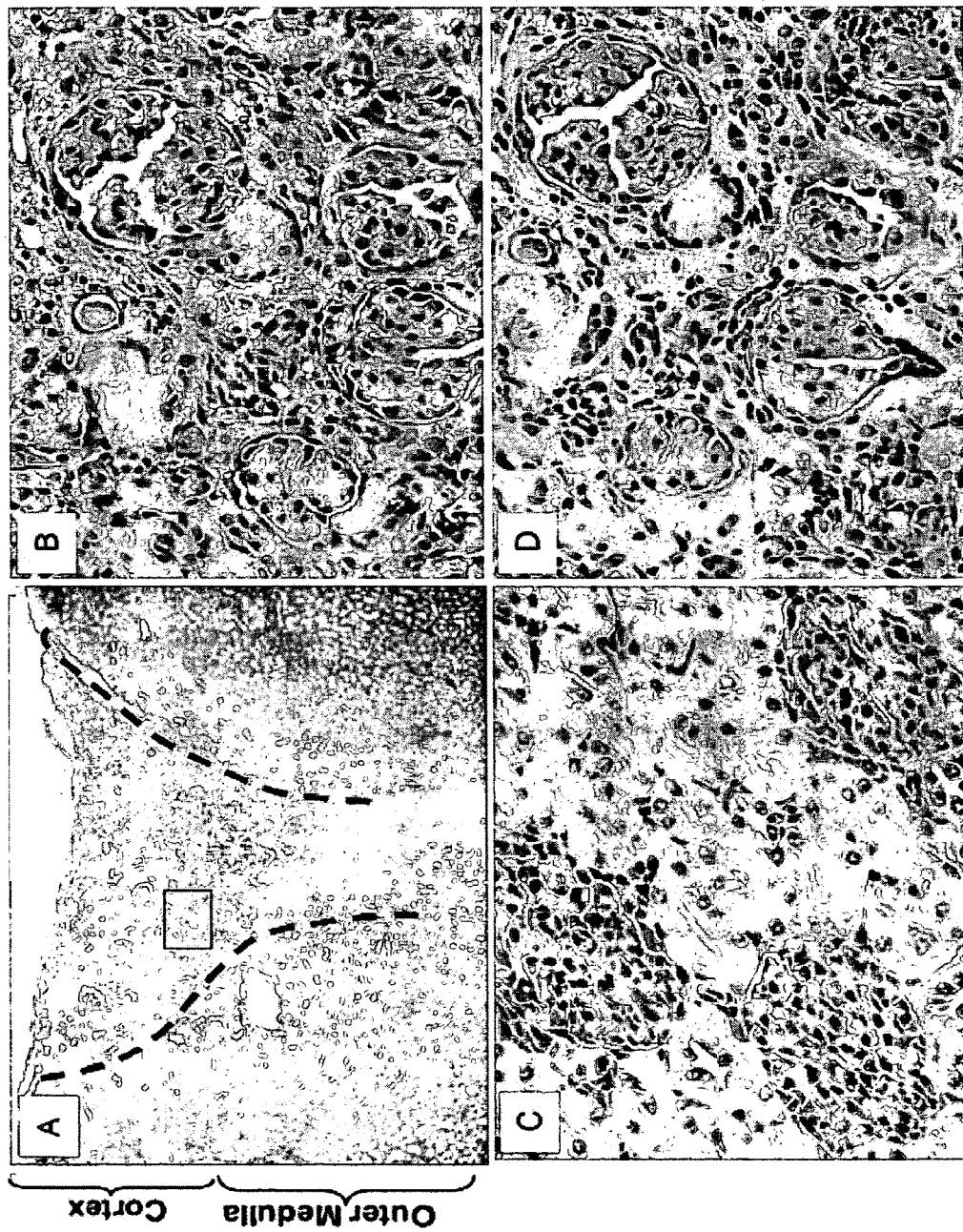
FIG. 25A-D shows in vivo evaluation of NKA Construct at 8 weeks post-implantation.

FIG. 24A-B shows in vivo evaluation of NKA Constructs at 1 and 4 weeks post-implantation. Trichrome X10 low power image of kidney cross section showing biomaterial aggregate. Trichrome X40: Close-up of biomaterial aggregate. H&E/PAS X400: High magnification image of biomaterial aggregate to evaluate extent of cell/tissue infiltration. Each kidney was injected at two locations as described in Materials and Methods.

FIG. 24A shows in vivo evaluation of NKA Constructs at 1 week post-implantation. At 1 week post injection, gelatin beads were present as focal aggregates (left panel, circled area) of spherical and porous material staining basophilic and surrounded by marked fibro-vascular tissue and phagocytic multi-nucleated macrophages and giant cells. Fibrovascular tissue was integrated within the beads and displayed tubular epithelial components indicative of neo-kidney tissue formation. Additionally, tubular and vasculoglomerular structures were identified by morphology (PAS panels).

FIG. 24B shows in vivo evaluation of NKA Constructs at 4 weeks post-implantation. By 4 weeks post-injection, the hydrogel was completely resorbed and the space replaced by progressive renal regeneration and repair with minimal fibrosis (note the numerous functional tubules within circled area of 4-week Trichrome panel).

FIG. 25A-D shows in vivo evaluation of NKA Construct at 8 weeks post-implantation. Trichrome X10 low power image of kidney cross section showing biomaterial aggregate. Trichrome X40: Close-up of biomaterial aggregate. H&E/PAS X400: High magnification image of biomaterial aggregate to evaluate extent of cell/tissue infiltration. (A) Moderate chronic inflammation (macrophages, plasma cells and lymphocytes), moderate numbers of hemosiderin-laden macrophages (chronic hemorrhage due to injection) with marked fibrovascular response (blue stained by Masson's trichrome—black arrows); (B) Higher magnification (trichrome stained, ×400) of boxed area of (A) showing regenerative response induction consistent with neo-kidney tissue formation (C) Representative of adjacent (normal) kidney parenchyma showing typical cortical glomeruli morphology HE, ×400); (D) HE stained section, ×400 comparing new glomeruli morphology observed in treatment area vs. FIG. 154C.

FIG. 25A-D shows in vivo evaluation of NKA Construct at 8 weeks post-implantation. At 8 weeks post-implantation, evidence of neo-kidney like tissue formation was observed, consistent with induction of early events in nephrogenesis. Comparison of the area of regenerative induction (B, D) with adjacent cortical parenchyma (C) showed presence of multiple S-shaped bodies and newly formed glomeruli.

Effect of Conditioned Media from NKA Constructs on TGF-β Induced EMT in HK2 Cells.

The development of tubulo-interstitial fibrosis during the progression of CKD is associated with TGF-β mediated EMT of tubular epithelial cells (Zeisberg et al. Am J Pathol 160(6):2001-2008; 2002). Also, attenuation of TGF-β pathways was observed in vivo in a rodent model of progressive CKD where survival was extended and renal function improved by treatment with UNFX and B2 cells (Presnell et al. WO/2010/056328). The human proximal tubular cell line HK2 has been well established as an in vitro model system to test the stimulatory or inhibitory effects of small molecules or proteins on TGF-β induced EMT (Dudas et al. Nephrol Dial Transplant 24(5):1406-1416; 2009; Hills et al. Am J Physiol Renal Physiol 296(3):F614-621; 2009). To investigate a potential mechanism by which NKA Constructs might affect renal tissue responses post-implantation, conditioned medium collected from NKA Constructs produced with UNFX cells and hydrogel was evaluated in the HK2 EMT assay system.

FIG. 26 shows conditioned medium from NKA Constructs attenuates TGF-β induced EMT in HK2 cells in vitro. EMT is monitored by quantitating the relative expression of ECAD (epithelial) and CNN1 (mesenchymal) markers. HK2 cells were cultured in 50:50 media (Control and TGFB Control samples) or conditioned medium (CM) from 2D cultures of human UNFX cells (TC) or NKA Constructs produced from human UNFX cells and either Gelatin or HA/Gelatin as indicated. To induce EMT, 10 ng/ml TGF-β was added to each sample (except Control) for 3 days prior to assay. When HK2 cells were cultured in 50:50 media (Control), ECAD (epithelial marker) was expressed at higher levels than CNN1 (mesenchymal marker). When TGF-β is added to the media for 3 days (TGFB Control), ECAD expression was significantly down-regulated with a concomitant up-regulation of CNN1, consistent with induction of an EMT event. Conditioned medium from 2D UNFX cell cultures significantly ($p<0.05$ for both ECAD and CNN1) attenuated the EMT response of HK2 cells to TGF-β (TC CM). Conditioned medium from NKA Constructs (Gelatin CM and HA/Gelatin CM) also attenuated the EMT response to TGF-β; however the overall effect was less than that observed with conditioned medium from 2D UNFX cell cultures (significant—$p<0.05$—for ECAD with both NKA Constructs and trending toward control though not statistically significant for CNN1). Additional mesenchymal markers were screened and yielded similar results (data not shown). These data suggest that NKA Constructs could potentially affect TGF-β pathways associated with tubulo-interstitial fibrosis in vivo in a manner similar to that observed with cell-based treatment (Presnell et al. WO/2010/056328). These data also suggest that the in vitro EMT assay has potential application for screening/optimizing/monitoring the biotherapeutic efficacy of NKA Constructs if in vivo responses can be demonstrated to have a statistically significant association with in vitro EMT responses, thereby potentially reducing the need for time consuming and expensive in vivo assays.

This study investigated the responses of mammalian renal parenchyma to implantation of synthetic and natural biomaterials, both acellular and as bioactive renal cell/biomaterial composites (i.e., NKA Constructs). A combination of in vitro functional assays and in vivo regenerative outcomes were analyzed to functionally screen candidate biomaterials for potential incorporation into a NKA construct prototype. Implantation of acellular hydrogel-based biomaterials into renal parenchyma (FIG. 19) was typically associated with minimal fibrosis or chronic inflammation and no evidence of necrosis by 4 weeks post-implantation. Moderate cellular/tissue in-growth and neo-vascularization was observed, with minimal remnant biomaterial. Based on these in vivo data, hydrogel-based biomaterials were selected to produce NKA Constructs with which to evaluate in vitro biofunctionality and in vivo regenerative potential. In vitro confirmation of material biocompatibility was provided through live/dead analysis of NKA Constructs (FIG. 20). Gelatin-containing hydrogels were associated with robust adherence of primary renal cell populations. Phenotypic and functional analysis of NKA Constructs produced from bioactive primary renal cell populations (UNFX or B2) and hydrogel biomaterials was consistent with continued maintenance of a tubular epithelial cell phenotype. Transcriptomic, secretomic, proteomic, and confocal microscopy analyses of NKA Construct confirmed no significant differences relative to primary renal cells seeded in 2D culture. Finally, implantation of hydrogel-based NKA construct into the renal parenchyma of healthy adult rodents was associated with minimal inflammatory and fibrotic response and regeneration of neo-kidney like tissue by 8 weeks post-implantation.

Taken together, these data provide evidence suggesting that a regenerative response was induced in vivo by NKA Constructs. These studies represent the first in vivo, intra-renal investigations of the biological response of mammalian kidney to implantation of a therapeutically-relevant primary renal cell/biomaterial composite. Observed results are suggestive that NKA Constructs have the potential to both facilitate regeneration of neo-kidney tissue and attenuate non-regenerative (e.g., reparative healing) responses.

Bioresponse of Mammalian Kidney to Implantation of Polymeric Materials.

In another study, host tissue responses to intra-renal injection of natural and synthetic biomaterials in rodent kidney were investigated to evaluate candidate biomaterials for forming cell/biomaterial composites with bioactive renal cell populations (Presnell et al. supra 2010). Methods: Natural biomaterials included gelatin and hyaluronic acid (HA). Synthetic biomaterials included polycaprolactone (PCL) and poly-lactic-co-glycolic acid (PLGA). Candidate biomaterials were evaluated in two discrete physical conformations: homogenous, spherical beads or heterogenous and non-uniform particles. PCL and PLGA beads were prepared using a modified double emulsion (water/oil/water) solvent extraction method. Gelatin beads were purchased (Cultispher-S®, Sigma-Aldrich, St. Louis, Mo.). PLGA particles were prepared using a solvent casting porogen leaching technique; gelatin and HA particles were prepared from cross-linked, lyophilized foam. Two injections of 35 µl of loosely packed biomaterials were delivered to the left kidney parenchyma of 3 month old Lewis rats. Histopathologic evaluation of formalin-fixed sections of kidney tissue at 1 and 4 weeks post-injection was conducted using a semi-quantitative grading severity scale from 0 (absent) to 4 (marked) of inflammation, tissue/cellular in-growth, neo-vascularization, material degradation, and fibro-cellular responses. Overall scores were calculated as the ratio of % positive to % negative response (the higher the overall score the superior outcome).

Results.

Histopathologic evaluation performed on biomaterial candidates—representative 40× images of kidneys harvested 1 week post-implantation, sections stained with Masson's Trichrome (data not shown). Materials composed of polymers of natural origin, such as gelatin and HA were associated with milder fibro-cellular response and chronic inflammation, and greater cellular in-growth, neo-vascularization, biomaterial degradation, and necessary inflammation required for tissue healing and integration when compared to the synthetic biomaterials, such as PLGA and PCL (organized fibrous encapsulation). Summary of histopathologic evaluation scoring. Scores were averaged by material composition (mean±SD). The synthetic materials (PLGA and PCL) scored the lowest, and gelatin materials generally scored higher than HA materials. This trend is most pronounced at the 4 week time point. Due to factors unrelated to the material injections, not all the samples tested at 1 week were available for analysis at 4 weeks. The number of samples that are included in the gelatin, HA, and synthetic groups are 3, 4, 3 at 1 week and 2, 3, 1 at 4 weeks, respectively.

Biomaterials of natural origin (e.g., gelatin or HA) delivered by injection to healthy renal parenchyma elicited tissue responses were less pathologic at 4 weeks post-injection than those of synthetic origin as measured by semi-quantitative histopathologic evaluation.

Example 16—Hypoxic Exposure of Cultured Human Renal Cells Induces Mediators of Cell Migration and Attachment and Facilitates the Repair of Tubular Cell Monolayers In Vitro The role of oxygen tension in the isolation and function of a selected population of renal epithelial cells (B2) with demonstrated therapeutic function in models of chronic kidney disease (CKD) was investigated. This study examined whether low oxygen exposure during processing alters composition and function of selected human selected renal cells (SRCs) or bioactive renal cells (BRCs). Upon exposure to 2% Oxygen, the following was observed: an alteration of the distribution of cells across a density gradient (see Presnell et al. WO 10/056328 incorporated herein by reference in its entirety), improvement in overall post-gradient yield, modulation of oxygen-regulated gene expression (previously reported in Kelley et al. supra (2010)), increased expression of erythropoietin, VEGF, HIF1-alpha, and KDR (VEGFR2). In-process exposure to low oxygen enhances the ability of selected bioactive renal cells to repair/regenerate damaged renal tubules.

Figure 27:
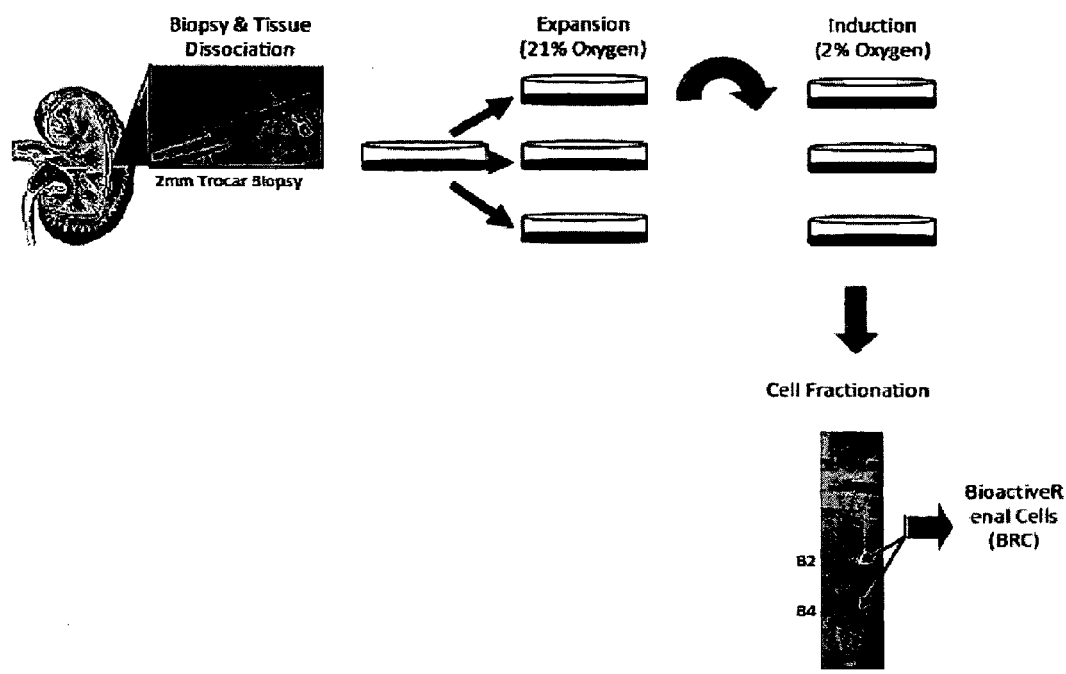
FIG. 27 depicts the procedure for exposing cells to low oxygen during processing.
Figure 28:
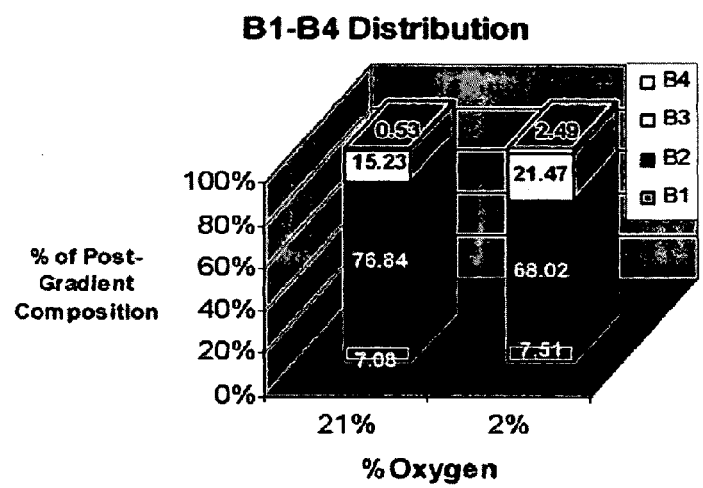
FIG. 28 shows that upon exposure to 2% Oxygen, the following was observed: alters distribution of cells across a density gradient, improves overall post-gradient yield

FIG. 27 depicts the procedure for exposing cells to low oxygen during processing. FIG. 28 shows that upon exposure to 2% Oxygen, the following was observed: alters distribution of cells across a density gradient, improves overall post-gradient yield. Hypoxic exposure (<3%) increased recovery of cultured human CKD-derived renal cells from iodixanol-based density gradients relative to atmospheric oxygen tension (21%) (96% vs. 74%) and increased the relative distribution of selected cells (B2) into high-density (>9% iodixanol) fractions (21.6% vs. 11.2%).

Competitive in vitro assays demonstrated that B2 cells pre-exposed for 24 hours to hypoxic conditions were more proficient in repairing damaged renal proximal tubular monolayer cultures than B2 cells cultured at 21% oxygen tension, with 58.6%±3% of the repair occurring within two hours of injury.

Figure 29B:
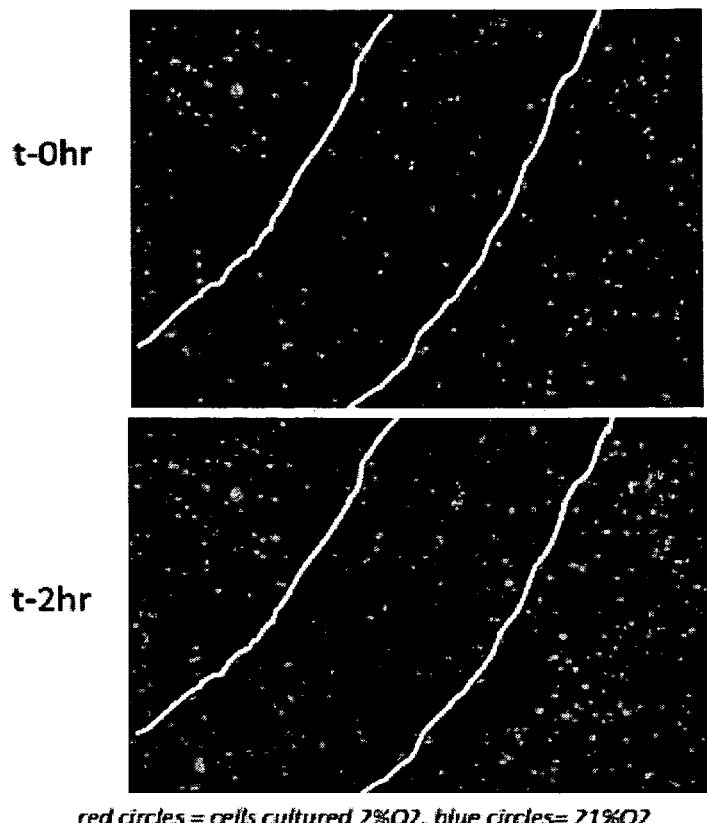
FIG. 29B shows results of a Quantitative Image Analysis (BD Pathway 855 BioImager).
Figure 29C:
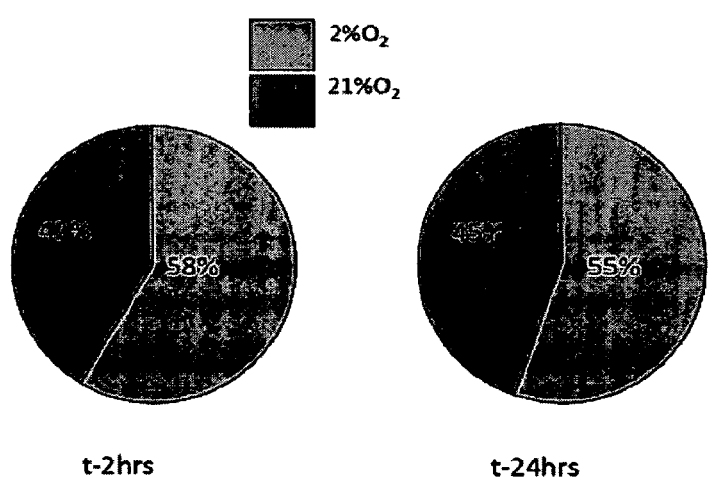
FIG. 29C shows cells induced with 2% oxygen to be more proficient at repair of tubular epithelial monolayers.

FIG. 29A depicts an assay developed to observe repair of tubular monolayers in vitro. 1. Cells are labeled with fluorescent dyes (2% oxygen, 21% oxygen, and HK2 tubular cells). 2. The tubular cell monolayer was established and wounded. 3. Oxygen-exposed labeled cells are added (2% and 21% exposed cells). They are seeded equally at 20,000/cm2. Culturing is in serum-free media at 5% O2 for 24 hrs. 4. Cells that repair wounding are quantified. FIG. 29B—Quantitative Image Analysis (BD Pathway 855 BioImager)—red circles=cells cultured 2% O2, blue circles=21% O2. FIG. 29C—it was observed that 2% oxygen-induced cells attached more rapidly (2 hrs) and sustained a mild advantage for 24 hrs. Cells induced with 2% oxygen were more proficient at repair of tubular epithelial monolayers.

FIG. 30A depicts an assay developed to observe repair of tubular monolayers in vitro. 1. Cells were labeled with fluorescent dyes. 2. The tubular cell monolayer was established on the bottom of 8 μm pore size transwell inserts and wounded. 3. The inserts are flipped and oxygen-exposed labeled cells are added (2% and 21% exposed cells). They are seeded equally at 50,000/cm2. Culturing is in serum-free media at 5% O2 for 24 hrs. 4. Cells that repair wounding are quantified.

FIG. 30B shows that the induction of cells with 2% Oxygen enhanced the migration and wound repair compared to un-induced (21% oxygen). FIG. 30C plots the % of migrated cells against the migration time. The average number of cells and average percentage of cells are provided in Table 16.1.

Hypoxia also induced mRNA expression of CXCR4, MMP9, ICAM1, and dystroglycan; genes that mediate cell migration and attachment. Focal accumulation of MMP9 and an increase in Connexin 43 aggregates on the cells' plasma membrane was confirmed by immunocytochemistry.

Figure 31A:
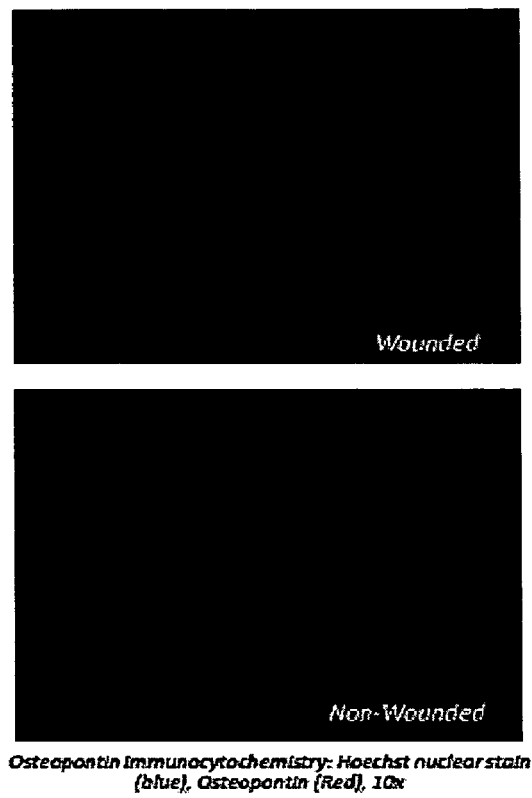
FIG. 31A shows that osteopontin is secreted by tubular cells and is upregulated in response to injury (Osteopontin Immunocytochemistry: Hoechst nuclear stain (blue), Osteopontin (Red), 10×). Osteopontin is upregulated by injury in established tubular cell monolayers as shown by immunofluorescence (FIG. 31A) and ELISA (FIG. 31B).
Figure 31B:
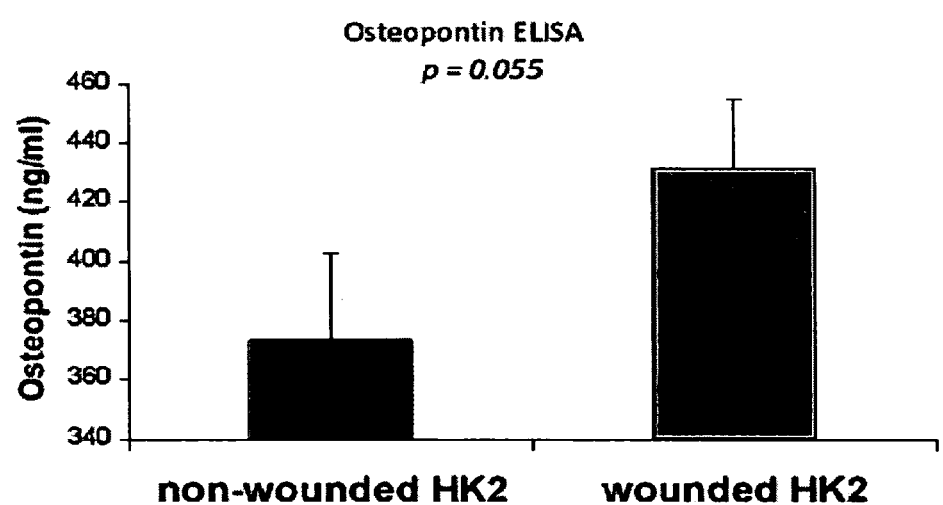

FIG. 31A shows that osteopontin is secreted by tubular cells and is upregulated in response to injury (Osteopontin Immunocytochemistry: Hoechst nuclear stain (blue), Osteopontin (Red), 10×). Osteopontin is a secreted phosphorylated glycoprotein (Kelly et al. J Am Soc Soc Nephrol, 1999). Osteopontin is expressed in kidney tubules and is involved in adhesion and migration. Osteopontin is upregulated by injury in established tubular cell monolayers as shown by immunofluorescence (FIG. 31A) and ELISA (FIG. 31B).

TABLE 16.1

|  | 3 hr | | 24 hr | |
| --- | --- | --- | --- | --- |
| N = 3 | Average # cells | Average % | Average # cells | Average % |
| 2% $O_2$ | 26.33 | 61.51% | 117.67 | 60.35% |
| 21% $O_2$ | 16.67 | 38.49% | 76.33 | 39.65% |

Quantitative image analysis using Sample PCI

Figure 32A:
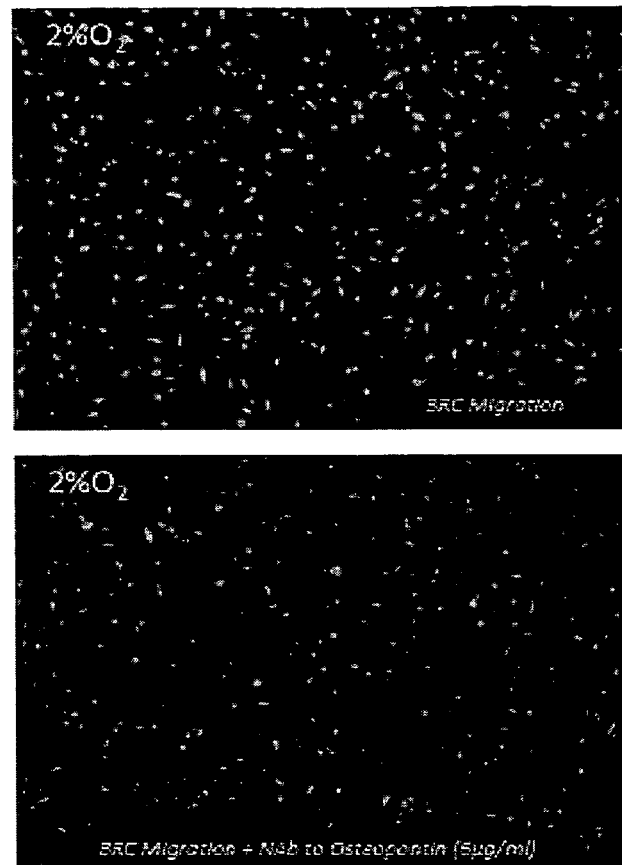
FIG. 32A shows that the migratory response of cells is mediated in part by osteopontin (Green=migrated cells (5×)).
Figure 32B:
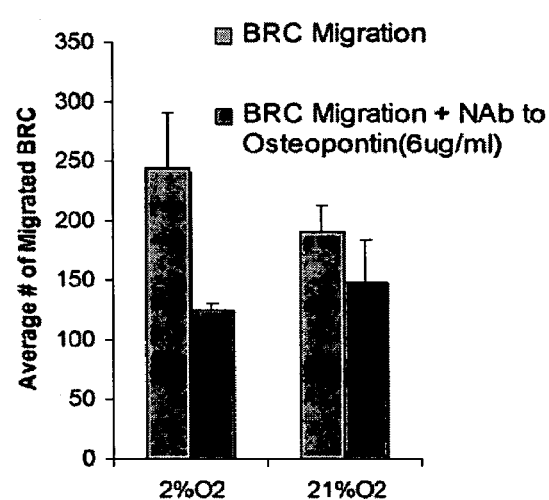
FIG. 32B shows that neutralizing antibodies (NAb) to osteopontin reduce renal cell migration response by 50%.

FIG. 32A shows that the migratory response of cells is mediated in part by osteopontin (Green=migrated cells (5×)). FIG. 32B shows that neutralizing antibodies (NAb) to osteopontin reduce renal cell migration response by 50%.

Figure 33:
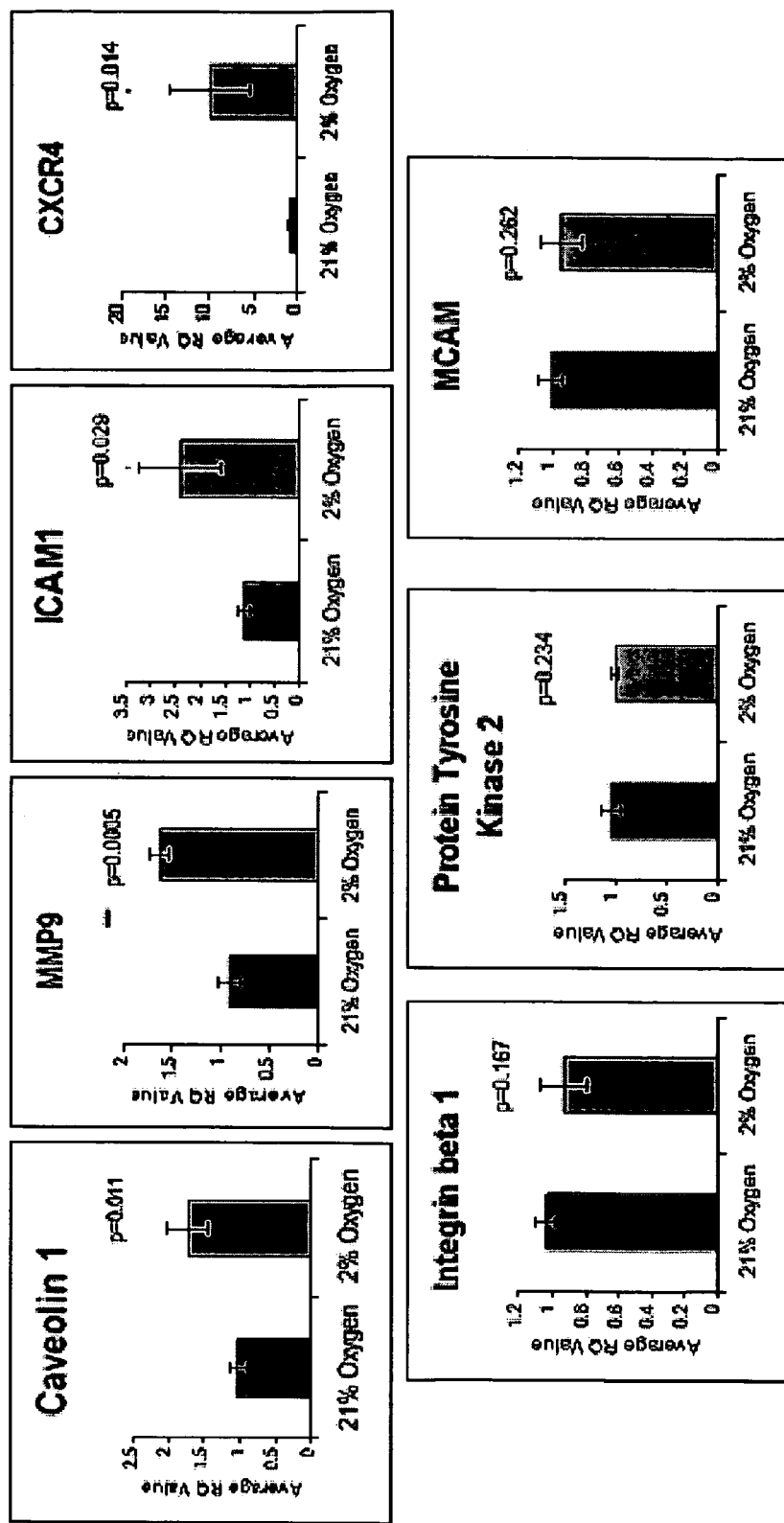
FIG. 33 shows that low-oxygen induction of cells modulates expression of tissue remodeling genes.

FIG. 33 shows that low-oxygen induction of cells modulates expression of tissue remodeling genes. Caveolin 1 is a scaffolding protein involved in modulation of integrin signaling. MMP9 is a metalloproteinase that facilitates migration through extracellular matrix degradation. ICAM1 is an intercellular adhesion molecule associated with epithelial cell motility. CXCR4 is a chemokine surface receptor that mediates cell migration.

Figure 34:
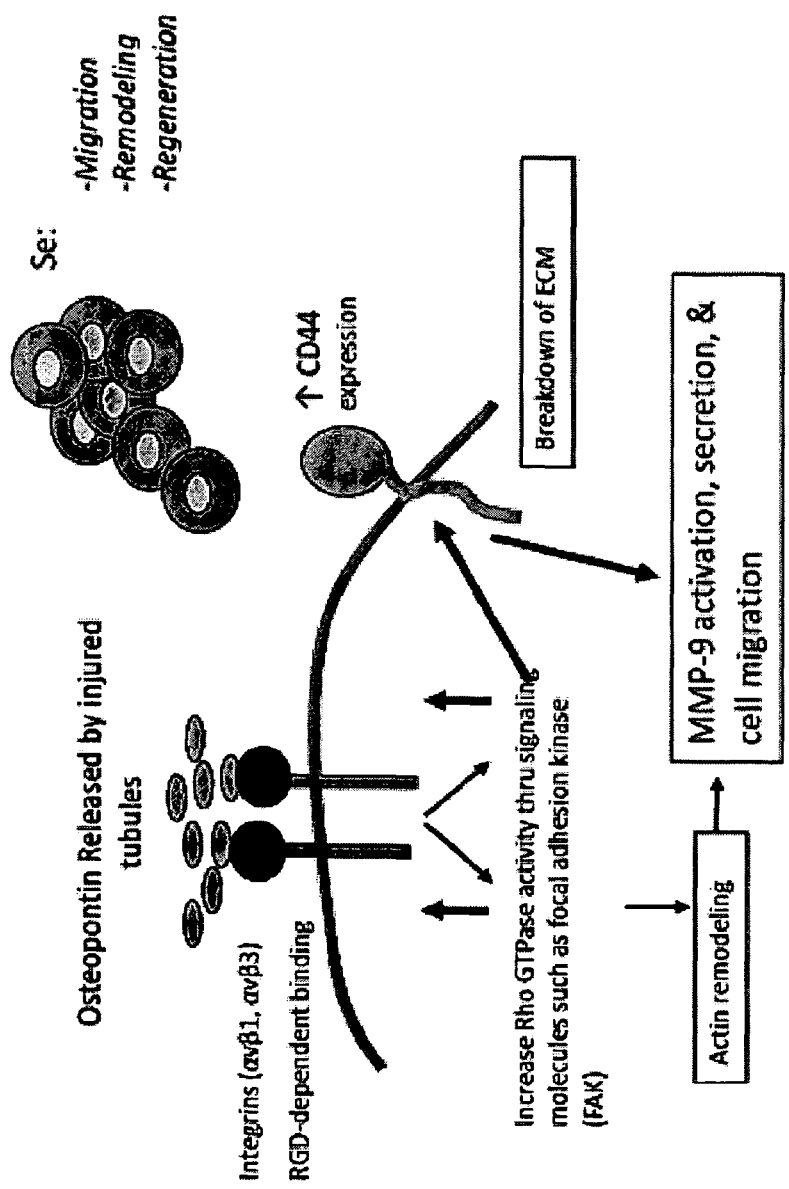
FIG. 34 depicts a putative mechanism for low oxygen augmentation of bioactivity of cells leading to renal regeneration.

FIG. 34 depicts a putative mechanism for low oxygen augmentation of bioactivity of cells leading to renal regeneration.

Taken together, these results suggest that hypoxic exposure facilitates the isolation of a specific renal cell subpopulation with demonstrated bioactivity for repair of tubular injury in vitro, and thus may potentially enhance the ability of these cells to migrate and engraft into diseased tissue after in vivo delivery. The SRCs demonstrated the ability to stabilize renal function and enhance survival in a rodent model of progressive CKD. The low oxygen levels (2% O2) provided the following: enhanced post-culture recovery of selected regenerative cells; enhanced cellular attachment and monolayer repair in response to tubular injury; and stimulated cellular migration in response to tubular injury. In addition, cellular migration and attachment were mediated in part by osteopontin in vitro, low-oxygen upregulated integrins, secreted proteins, and cell adhesion molecules which mediate tissue remodeling, migration, and cell-cell communication.

Example 17—Urine-Derived Microvesicles

An analysis of the miRNAs and proteins contained within the luminal contents of kidney derived microvesicles shed into the urine was performed to determine whether they might be used as biomarkers for assessing regenerative outcome. As excess microvesicles are shed into the extracellular space, some fuse with neighboring cells while others are excreted into the urine (Thou et al. 2008. Kidney Int. 74(5):613-621). These urinary microvesicles now become excellent biomarkers for assay development in order to better understand treatment outcomes.

The ZSF1 rodent model of metabolic disease with chronic progressive renal failure was used. B2+B4 cells were injected into the renal parenchyma of ZSF1 animals. Healthy animals and PBS vehicle were used as controls. Urine-derived vesicles were analyzed at different time points as summarized below.

Figure 35:
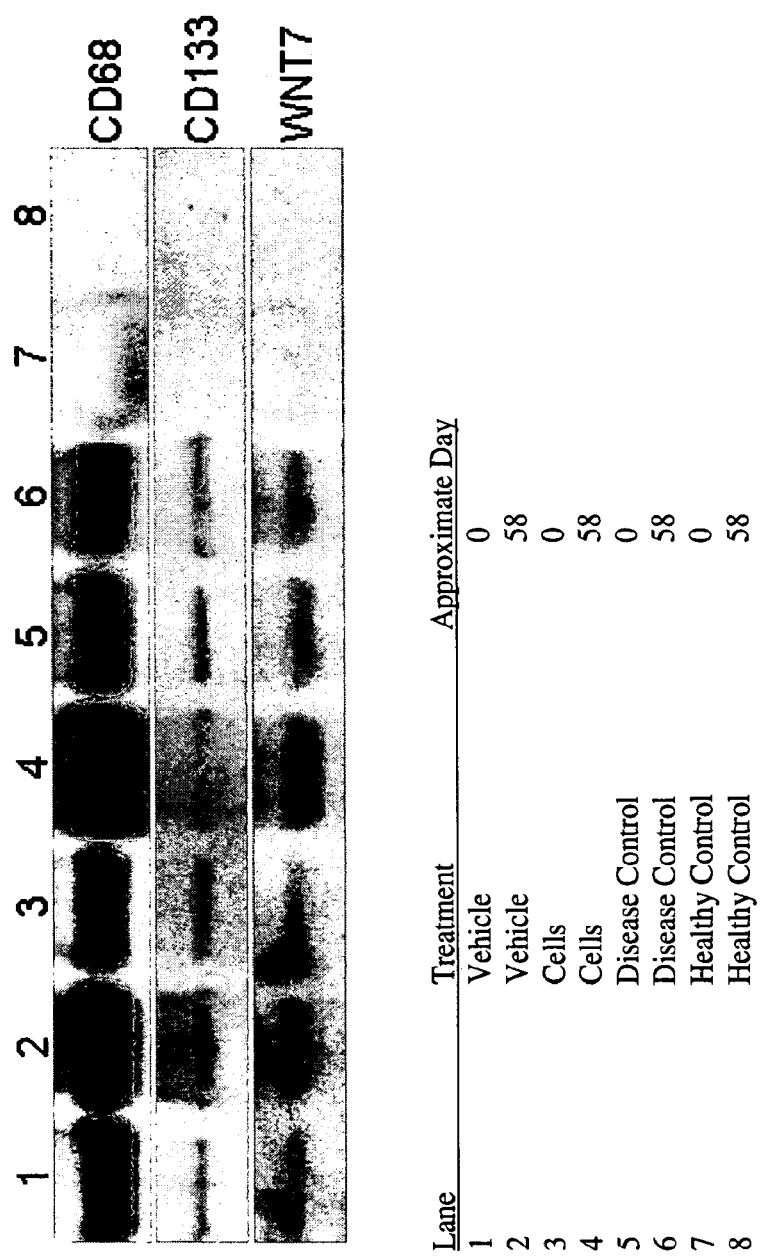
FIG. 35 shows detection of microvesicles via a Western blot.

1: ZSF1 animal—PBS vehicle injected; urine collected 197 days after injection
2: ZSF1 animal—PBS vehicle injection; urine collected 253 days after injection
3: ZSF1 animal—B2+B4 fraction injected; urine collected 197 days after injection
4: ZSF1 animal—B2+B4 fraction injected; urine collected 253 days after injection
5. ZSF1 animal—no injection; urine collected on day 197 of the study
6. ZSF1 animal—no injection; urine collected on day 253 of the study
7. Healthy animal—no injection; urine collected on day 197 of the study
8. Healthy animal—no injection; urine collected on day 253 of the study Urine was collected from the test animals on day 197 and about 253 days after treatment. Microvesicles were recovered from the urine by standard methods known in the art (for example, see Zhou et al. Kidney Int. 2008 September; 74(5): 613-621). As shown by standard Western blotting in FIG. 35, microvesicles recovered from the urine of treated animals (lanes 3-4) showed an increase in proteins associated with progenitor cells (CD133 & WNT7A) when compared to either vehicle treated (lanes 1-2) or untreated controls (lanes 5-8). In fact, microvesicles were only recovered from the urine of diseased animals (lanes 1-6), not healthy controls (lanes 7-8), as indicated by expression of the microvesicle specific protein CD63 (FIG. 35). The CD133-containing microvesicles appear to be prominosomes shed from kidney cells. Both CD133 and WNT7A have been associated with regeneration and stem cell division (Romagnani P and Kalluri R. 2009. Fibrogenesis Tissue Repair. 2(1):3; Lie et al. 2005. Nature. 437(7063):1370-5; Willert et al. 2003. Nature. 423(6938):448-52; Li et al. 2009. Am J Physiol Renal Physiol. 297(6):F1526-33). Taken together, this supports targeting proteins expressed in microvesicles as biomarkers for assay development designed to monitor regeneration.

miRNA Microarrays and RT-PCR.

Microarray and RT-PCR analysis of miRNA from urine-derived vesicles was performed by standard methods known in the art (for example, see Wang et al. supra 2010). In addition to proteins, miRNAs were found within the contents of the isolated microvesicles. Table 17.1 provides examples of miRNAs that were found to be increased with treatment.

TABLE 17.1

| miRNA   | RQ value | miRNA      | RQ value | miRNA    | RQ value |
|---------|----------|------------|----------|----------|----------|
| miR-15b | 6.5206   | miR-21     | 6.4755   | miR-30a  | 6.0002   |
| miR-30a*| 2.4666   | miR-30b-5p | 9.8833   | miR-30c  | 6.1688   |
| miR-30d | 5.9176   | miR-30d*   | 4.1482   | miR-30e  | 8.0836   |
| miR-30e*| 2.1622   | miR-141    | 5.1515   | miR-146a | 2.3054   |
| miR-151 | 3.4462   | miR-200a   | 9.3340   | miR-200c | 8.0278   |
| miR-429 | 9.7136   |            |          |          |          |

The change in miRNA was analyzed in ZSF1 animals treated with B2+B4 over time (day 197 and day 253). A fold change was observed for the following miRNAs:

| | | |
|---|---|---|
| miR-370 | let-7e* | miR-322* |
| miR-362 | miR-345-3p | miR-7a |
| miR-1224 | miR-193 | miR-532-3p |
| miR-22 | miR-207 | miR-29a |
| miR-598-5p | miR-501 | miR-130b |
| miR-540 | miR-125b-3p | miR-328 |
| miR-300-3p | miR-154 | miR-345-5p |
| miR-206 | miR-375 | miR-29c |
| miR-222 | miR-298 | miR-215 |
| miR-433 | miR-671 | miR-138* |
| let-7b | miR-21 | miR-182 |
| let-7c | let-7e | miR-147 |
| miR-497 | let-7f | miR-664 |
| let-7b* | miR-125a-5p | miR-339-5p |
| miR-24-2* | miR-194 | miR-743b |
| miR-770 | miR-152 | miR-96 |
| miR-124 | miR-128 | miR-203 |
| miR-485 | miR-423 | miR-130a |
| miR-760-5p | miR-92b | miR-346 |
| miR-296 | miR-139-3p | miR-674-3p |
| miR-764 | miR-667 | miR-140* |
| miR-221 | miR-98 | miR-192 |
| miR-883 | miR-181d | miR-409-3p |
| miR-15b | miR-500 | miR-106b* |
| miR-143 | miR-103 | let-7d |
| let-7a | miR-99b* | miR-28* |
| miR-339-3p | miR-935 | miR-219-2-3p |
| miR-484 | miR-674-5p | miR-148b-3p |
| miR-742 | miR-743a | miR-23b |
| miR-101b | miR-352 | raiR-195 |
| miR-425 | miR-326 | miR-30d |
| miR-31 | miR-181c | miR-301b |
| miR-29b | miR-504 | miR-320 |
| miR-652 | miR-598-3p | miR-30e |
| miR-322 | miR-490 | miR-350 |
| miR-429 | miR-675 | miR-34a |
| miR-291a-5p | miR-10a-5p | miR-219-1-3p |
| miR-26a | miR-184 | miR-543 |
| miR-141 | miR-100 | miR-210 |
| miR-185 | miR-874 | miR-30a* |
| miR-27b | miR-200a | miR-365 |
| miR-200c | miR-30c | miR-378 |
| miR-431 | miR-99b | miR-196b |
| miR-16 | miR-212 | miR-27a* |
| miR-23a | let-7i | miR-361 |
| miR-330* | miR-30a | miR-10b |
| miR-344-5p | miR-199a-5p | miR-466c |
| miR-347 | miR-25 | miR-342-3p |
| miR-125b* | miR-99a* | miR-216a |

-continued

| | | |
|---|---|---|
| miR-30b-5p | miR-28 | miR-101a* |
| miR-218 | miR-30d* | miR-24 |
| miR-99a | miR-151* | miR-151 |
| miR-488 | miR-344-3p | miR-205 |
| miR-493 | miR-126* | miR-17-5p |
| miR-9* | miR-145 | miR-134 |
| miR-92a | miR-20b-5p | miR-296* |
| miR-125b-5p | miR-294 | miR-26b* |
| miR-183 | miR489 | miR-30e* |
| miR-708 | miR-483 | miR-382 |
| miR-191 | miR-132 | miR-410 |
| miR-181b | miR-505 | miR-327 |
| miR-186 | miR-7a* | miR-133b |
| miR-872 | let-7i* | miR-142-3p |
| miR-188 | miR-21* | miR-324-5p |
| miR-22* | miR-331 | miR-125a-3p |
| miR-27a | miR-434 | let-7d* |
| miR-7b | miR-106b | miR-19b |
| miR-223 | miR-20a | miR-148b-5p |
| miR-374 | miR-34c | miR-107 |
| miR-127 | miR-871 | miR-34c* |
| miR-26b | miR-93 | miR-672 |
| miR-25* | miR-9 | miR-873 |
| miR-330 | miR-532-5p | miR-351 |
| miR-146a | miR-181a | miR-292-5p |
| miR-295 | miR-760-3p | miR-343 |
| miR-196a | miR-140 | miR-449a |
| miR-34b | miR-29a* | miR-323 |
| miR-129 | miR-138 | miR-29b-2* |
| miR-196c | miR-193* | miR-539 |
| miR-17-3p | miR-10a-3p | miR-465 |
| miR-133a | miR-877 | miR-214 |
| miR-19a | miR-29c* | miR-541 |
| miR-211 | miR-503 | miR-761 | miRNA levels were analyzed in ZSF1 animals treated with B2+B4 (day 253) and compared to the miRNA levels in ZSF1 animals treated with PBS vehicle (day 253). A fold change was observed for the following miRNAs:

| | | |
|---|---|---|
| miR-24 | miR-16 | miR-10b |
| miR-195 | let-7d* | miR-365 |
| miR-871 | miR-30e | miR-431 |
| miR-30b-5p | miR-200c | miR-29c |
| miR-19b | miR-292-5p | miR-15b |
| miR-99a | miR-152 | miR-21 |
| miR-429 | let-7i | miR-125b-5p |
| let-7f | miR-351 | miR-30c |
| miR-200a | miR-434 | miR-30a |
| miR-324-5p | miR-26b | miR-503 |
| miR-10a-5p | miR-489 | miR-26a |
| miR-148b-3p | miR-186 | miR-30d |
| miR-100 | miR-191 | miR-743b |
| miR-9 | miR-148b-5p | let-7b |
| let-7e | miR-138* | miR-133a |
| miR-23a | miR-370 | miR-345-5p |
| miR-322* | miR-465 | miR-342-3p |
| miR-96 | miR-129 | miR-34a |
| miR-106b | miR-344-3p | miR-7a |
| miR-23b | miR-374 | miR-291a-5p |
| miR-27b | miR-10a-3p | miR-34c |
| miR-29a | miR-352 | miR-300-3p |
| let-7a | miR-181a | miR-219-1-3p |
| miR-425 | let-7i* | miR-30a* |
| miR-20a | miR-134 | miR-125a-5p |
| miR-22* | miR-196a | miR-323 |
| miR-98 | miR-203 | miR-327 |
| miR-25 | let-7c | miR-883 |
| miR-194 | miR-151 | miR-541 |
| let-7d | miR-20b-5p | miR-708 |
| miR-141 | miR-26b* | miR-196c |
| miR-7a* | miR-140 | miR-216a |
| miR-107 | miR-128 | miR-146a |
| miR-93 | miR-222 | miR-27a* |
| miR-742 | miR-29a* | miR-223 |
| miR-505 | miR-872 | miR-106b* |

-continued

| | | |
|---|---|---|
| miR-19a | miR-328 | miR-466c |
| miR-17-5p | miR-760-3p | miR-490 |
| miR-743a | miR-295 | miR-326 |
| miR-182 | miR-151* | miR-664 |
| miR-378 | miR-138 | miR-29b |
| miR-761 | miR-211 | miR-30e* |
| miR-103 | miR-339-5p | miR-532-3p |
| miR-221 | miR-382 | miR-199a-5p |
| miR-212 | miR-497 | miR-154 |
| miR-27a | miR-184 | miR-127 |
| miR-30d* | miR-375 | miR-667 |
| miR-92a | miR-500 | miR-132 |
| miR-140* | miR-501 | miR-126* |
| miR-322 | miR-347 | miR-99b |
| miR-181b | miR-338 | miR-125a-3p |
| miR-296* | miR-671 | miR-181d |
| miR-339-3p | miR-34c* | miR-543 |
| miR-28* | miR-92b | let-7b* |
| miR-24-2* | miR-29b-2* | miR-99b* |
| miR-345-3p | miR-298 | miR-463 |
| miR-330* | miR-139-3p | miR-146b |
| miR-504 | miR-342-5p | miR-343 |
| miR-449a | miR-877 | miR-205 |
| miR-210 | miR-99a* | miR-23a* |
| miR-188 | miR-129* | miR-674-5p |
| miR-410 | miR-181c | miR-214 |
| miR-101a* | miR-21* | miR-540 |
| miR-147 | miR-25* | miR-133b |
| miR-192 | miR-143 | miR-29c* |
| miR-296 | miR-770 | miR-758 |
| miR-196b | miR-652 | miR-362 |
| miR-433 | miR-183 | miR-34b |
| miR-17-3p | miR-22 | miR-409-3p |
| miR-350 | miR-485 | miR-185 |
| miR-142-3p | miR-935 | miR-344-5p |
| miR-423 | miR-532-5p | miR-294 |
| miR-101b | miR-764 | miR-31 |
| miR-219-2-3p | miR-193 | miR-125b-3p |
| let-7e* | miR-672 | miR-204* |
| miR-484 | miR-325-5p | miR-361 |
| miR-1224 | miR-760-5p | miR-711 |
| miR-320 | miR-346 | miR-215 |
| miR-675 | miR-301a | miR-301b |
| miR-105 | miR-488 | miR-206 |
| miR-874 | miR-539 | miR-370 |
| miR-130a | miR-873 | miR-124 |
| miR-193* | miR-218 | miR-130b | miRNA levels were analyzed in ZSF1 animals treated with B2+B4 (day 197) and compared to the miRNA levels in ZSF1 animals treated with PBS vehicle (day 197). A fold change was observed for the following miRNAs:

| | | |
|---|---|---|
| miR-143 | miR-24-2* | miR-98 |
| miR-370 | miR-26b | miR-434 |
| miR-351 | miR-375 | miR-339-5p |
| let-7a | let-7f | miR-296 |
| miR-152 | miR-206 | miR-667 |
| miR-141 | miR-29a | miR-181b |
| let-7c | miR-100 | miR-324-5p |
| miR-222 | miR-29c | miR-30e |
| miR-362 | miR-16 | miR-10a-5p |
| miR-200a | miR-96 | miR-125a-5p |
| miR-188 | miR-151 | miR-29b |
| miR-429 | miR-125a-3p | miR-28* |
| miR-505 | miR-195 | miR-106b* |
| miR-21 | miR-210 | miR-30a |
| let-7e | miR-742 | miR-423 |
| miR-182 | miR-30d | miR-19b |
| let-7b | miR-194 | miR-500 |
| let-7i | miR-433 | miR-92a |
| miR-200c | miR-23b | miR-291a-5p |
| miR-99a | miR-124 | miR-181d |
| miR-221 | miR-101b | miR-320 |
| miR-30b-5p | miR-497 | miR-345-3p |
| let-7d | miR-425 | miR-764 |

-continued

| | | |
|---|---|---|
| miR-103 | miR-347 | miR-191 |
| miR-148b-3p | miR-19a | miR-10b |
| miR-26a | miR-431 | miR-298 |
| miR-186 | miR-17-5p | miR-92b |
| miR-22 | miR-24 | miR-322 |
| miR-330* | miR-205 | miR-181a |
| miR-484 | miR-196b | miR-219-1-3p |
| miR-339-3p | miR-126* | miR-30d* |
| miR-106b | miR-20b-5p | miR-301b |
| miR-25 | miR-128 | let-7e* |
| miR-326 | miR-22* | miR-196a |
| miR-129 | miR-196c | miR-9 |
| miR-31 | miR-192 | miR-27a* |
| miR-34a | miR-151* | miR-488 |
| miR-652 | miR-134 | miR-183 |
| miR-15b | miR-214 | miR-26b* |
| miR-130a | miR-674-5p | miR-138 |
| miR-378 | miR-125b-5p | miR-382 |
| miR-30c | miR-365 | miR-760-3p |
| let-7d* | miR-532-3p | let-7i* |
| miR-874 | miR-29c* | miR-184 |
| miR-485 | miR-7a | miR-25* |
| miR-93 | miR-147 | miR-34c |
| miR-671 | miR-27a | miR-30a* |
| miR-99b* | miR-181c | miR-466c |
| miR-139-3p | miR-99b | miR-28 |
| miR-27b | miR-125b-3p | miR-142-3p |
| miR-21* | miR-193 | miR-107 |
| miR-328 | miR-342-3p | miR-148b-5p |
| miR-185 | miR-215 | miR-331 |
| miR-743b | miR-132 | miR-218 |
| miR-127 | miR-532-5p | miR-30e* |
| miR-345-5p | miR-203 | miR-330 |
| miR-140* | miR-130b | miR-344-5p |
| miR-20a | miR-449a | miR-493 |
| miR-374 | miR-7a* | miR-17-3p |
| miR-664 | miR-219-2-3p | miR-7b |
| miR-877 | miR-23a | miR-34b |
| miR-193* | miR-483 | miR-503 |
| miR-216a | miR-223 | miR-873 |
| miR-99a* | miR-361 | |

The miRNAs listed in Table 17.1 provide examples of miRNAs that have been implicated in processes relative to tissue regeneration. miR-15b has been implicated in regulating apoptosis through BCL-2 and caspase regulation (Guo et al. 2009. J Hepatol. 50(4):766-78) as well as cell cycle progression through the regulation of cyclins (Xia et al. 2009. Biochem Biophys Res Commun. 380(2):205-10). miR-21 was shown to inhibit apoptosis by modulating survival pathways MAPK/ERK. The miR-30 family of miRNAs is critical for podocyte structure and function suggesting that an increase may be necessary for glomerulargenisis. miR-141, 200a, 200c and 429 are all involved in modulating epithelial to mesenchymal transition (EMT) in response to TGF-β signaling possibly reducing fibrosis (Saal et al. 2009. Curr. Opin. Nephrol. Hypertens. 18:317-323). miR-146a and 151 have been implicated in NFκB modulation thus potentially reducing the inflammatory response in vivo (Taganov et al. 2006. Proc Natl Acad Sci USA. 103(33):12481-6; Griffiths-Jones et al. 2006. NAR. 34 Database Issue: D140-D144). Collectively, these miRNAs regulate processes related to a successful regenerative outcome; thus making them candidate biomarkers for assay development. Overall, this data supports the concept that urinary microvesicles and/or their luminal contents are viable targets for regenerative assays as they contain proteins and miRNAs capable of modulating multiple pathways including: TGFβ-1, NFκB, apoptosis, cell division and pluripotency in addition to providing practitioners with a non-invasive means of monitoring treatment.

What is claimed is:

1. A method of providing a regenerative effect to a native kidney comprising in vivo contacting the native kidney with a composition comprising human secreted vesicles produced by an enriched renal cell population, wherein the vesicles comprise exosomes comprising a secreted paracrine factor that attenuates Plasminogen Activation Inhibitor-1 (PAI-1) signaling and/or Transforming Growth Factor Beta (TGFβ) signaling, and wherein the regenerative effect is a reduction in renal fibrosis.

2. The method of claim 1, wherein the paracrine factor inhibits Plasminogen Activation Inhibitor-1 (PAI-1).

3. The method of claim 1, wherein the paracrine factor is an miRNA.

4. The method of claim 1, wherein the paracrine factor is an miRNA that inhibits Plasminogen Activation Inhibitor-1 (PAI-1).

5. The method of claim 3, wherein the miRNA is extra-vesicular.

6. The method of claim 1 wherein the products are secreted from a renal cell construct comprising an enriched renal cell population directly seeded on or in a scaffold.

7. The method of claim 6 wherein the scaffold comprises a biocompatible material.

8. The method of claim 7 wherein the biocompatible material is a hydrogel.

9. The method of claim 8 wherein the hydrogel is gelatin.

10. The method of claim 1 wherein the regenerative effect is a reduction in epithelial-mesenchymal transition (EMT).

11. The method of claim 1 wherein the population comprises a first cell population, B2, comprising an enriched population of tubular cells having a density between about 1.045 g/mL and about 1.052 g/mL.

12. The method of claim 1 wherein the population comprises an admixture of human renal cells comprising a first cell population, B2, and a second cell population, wherein B2 comprises an enriched population of tubular cells having a density between about 1.045 g/mL and about 1.052 g/mL and wherein the second cell population comprises a B4 cell population having a density between about 1.063 g/mL and about 1.091 g/mL or a B3 cell population having a density between about 1.052 g ml and about 1.063 g/ml.

13. The method of claim 12 wherein the second cell population is a B4 cell population having a density between about 1.063 g/mL and about 1.091 g/mL.

14. The method of claim 12 wherein the second cell population is a B3 cell population having a density between about 1.052 g ml and about 1.063 g/ml.

15. The method of claim 13 wherein the admixture further comprises a third cell population, wherein the third cell population comprises a B3 cell population having a density between about 1.052 g ml and about 1.063 g/ml.

16. The method of claim 1 wherein the enriched renal cell population is non-autologous to the native kidney.

17. The method of claim 1 wherein the enriched renal cell population is autologous to the native kidney.

* * * * *